(12) United States Patent
Gallei

(10) Patent No.: US 9,187,731 B2
(45) Date of Patent: Nov. 17, 2015

(54) PRRS VIRUS INDUCING TYPE I INTERFERON IN SUSCEPTIBLE CELLS

(75) Inventor: Andreas Gallei, Hannover (DE)

(73) Assignee: Boehringer Ingelheim Vetmedica GmbH, Ingelheim am Rhein (DE)

( * ) Notice: Subject to any disclaimer, the

(56) References Cited

U.S. PATENT DOCUMENTS

| | | | |
|---|---|---|---|
| 6,391,314 B1 | 5/2002 | Allan et al. | |
| 6,455,245 B1 | 9/2002 | Wensvoort et al. | |
| 6,495,138 B1 | 12/2002 | van Nieuwstadt et al. | |
| 6,498,008 B2 | 12/2002 | Collins et al. | |
| 6,500,662 B1 | 12/2002 | Calvert et al. | |
| 6,592,873 B1 | 7/2003 | Paul et al. | |
| 6,641,819 B2 | 11/2003 | Mengeling et al. | |
| 6,660,513 B2 | 12/2003 | Mengeling et al. | |
| 6,773,908 B1 | 8/2004 | Paul et al. | |
| 6,806,086 B2 | 10/2004 | Wensvoort et al. | |
| 6,841,364 B2 | 1/2005 | Yuan et al. | |
| 6,855,315 B2 | 2/2005 | Collins et al. | |
| 6,982,160 B2 | 1/2006 | Collins et al. | |
| 7,018,638 B2 | 3/2006 | Chu et al. | |
| 7,081,342 B2 | 7/2006 | Mengeling et al. | |
| 7,109,025 B1 | 9/2006 | Eloit et al. | |
| 7,122,347 B2 | 10/2006 | Verheije et al. | |
| 7,132,106 B2 | 11/2006 | Calvert et al. | |
| 7,169,394 B2 | 1/2007 | Chu et al. | |
| 7,211,379 B2 | 5/2007 | Ellis et al. | |
| 7,232,680 B2 | 6/2007 | Calvert et al. | |
| 7,264,804 B2 | 9/2007 | Collins et al. | |
| 7,273,617 B2 | 9/2007 | Yuan et al. | |
| 7,312,030 B2 | 12/2007 | van Rijn et al. | |
| 7,335,361 B2 | 2/2008 | Liao et al. | |
| 7,335,473 B2 | 2/2008 | Wensvoort et al. | |
| 7,368,117 B2 | 5/2008 | Fetzer et al. | |
| 7,618,797 B2 | 11/2009 | Calvert et al. | |
| 7,632,636 B2 | 12/2009 | Roof et al. | |
| 7,691,389 B2 | 4/2010 | Calvert et al. | |
| 7,722,878 B2* | 5/2010 | Vaughn et al. | 424/186.1 |
| 7,897,343 B2 | 3/2011 | Wensvoort et al. | |
| 8,110,390 B2 | 2/2012 | Faaberg et al. | |
| 2002/0012670 A1 | 1/2002 | Elbers et al. | |
| 2002/0098573 A1 | 7/2002 | Meulenberg et al. | |
| 2002/0172690 A1 | 11/2002 | Calvert et al. | |
| 2003/0049274 A1 | 3/2003 | Meulenberg et al. | |
| 2003/0118608 A1 | 6/2003 | Wensvoort et al. | |
| 2003/0157689 A1 | 8/2003 | Calvert et al. | |
| 2003/0219732 A1 | 11/2003 | van Rijn et al. | |
| 2004/0009190 A1 | 1/2004 | Elbers et al. | |
| 2004/0132014 A1 | 7/2004 | Wensvoort et al. | |
| 2004/0197872 A1 | 10/2004 | Meulenberg et al. | |
| 2004/0213805 A1 | 10/2004 | Verheije | |
| 2004/0224327 A1 | 11/2004 | Meulenberg et al. | |
| 2004/0253270 A1 | 12/2004 | Meng et al. | |
| 2006/0063151 A1 | 3/2006 | Roof et al. | |
| 2006/0205033 A1 | 9/2006 | Meulenberg et al. | |
| 2006/0240041 A1 | 10/2006 | Meulenberg et al. | |
| 2006/0286123 A1 | 12/2006 | Fetzer et al. | |
| 2007/0003570 A1 | 1/2007 | Murtaugh et al. | |
| 2007/0042000 A1 | 2/2007 | Mengeling et al. | |
| 2009/0148474 A1 | 6/2009 | Roof et al. | |
| 2010/0003278 A1 | 1/2010 | Roof et al. | |
| 2010/0028860 A1 | 2/2010 | Roof et al. | |
| 2010/0129398 A1 | 5/2010 | Klinge et al. | |
| 2011/0104201 A1 | 5/2011 | Mengeling et al. | |
| 2011/0117129 A1 | 5/2011 | Roof et al. | |
| 2011/0195088 A1 | 8/2011 | Roof et al. | |
| 2012/0189655 A1 | 7/2012 | Wu et al. | |
| 2013/0028931 A1* | 1/2013 | Gallei | 424/204.1 |
| 2013/0183329 A1 | 7/2013 | Zhang et al. | |
| 2014/0314808 A1* | 10/2014 | Fetzer et al. | 424/204.1 |

FOREIGN PATENT DOCUMENTS

| | | | |
|---|---|---|---|
| EP | 208672 A1 | 1/1987 | |
| EP | 0440219 A1 | 8/1991 | |
| EP | 0529584 A2 | 3/1993 | |
| EP | 587780 A1 | 3/1994 | |
| EP | 0595436 A2 | 5/1994 | |
| EP | 0610250 A1 | 8/1994 | |
| EP | 676467 A2 | 10/1995 | |
| EP | 732340 A2 | 9/1996 | |
| EP | 0835929 A1 | 4/1998 | |
| EP | 0835930 A1 | 4/1998 | |
| EP | 0839912 A1 | 5/1998 | |
| EP | 1018557 A2 | 7/2000 | |
| FR | 2602791 A1 | 2/1988 | |
| GB | 2282811 A | 4/1995 | |
| GB | 2289279 A | 11/1995 | |
| JP | 62/198626 A | 9/1987 | |
| WO | 8803410 A1 | 5/1988 | |
| WO | 8908701 A1 | 9/1989 | |
| WO | 9221375 A1 | 12/1992 | |
| WO | 9303760 A1 | 3/1993 | |
| WO | 9306211 A1 | 4/1993 | |
| WO | 9307898 A1 | 4/1993 | |
| WO | 9314196 A1 | 7/1993 | |
| WO | 9418311 A1 | 8/1994 | |
| WO | 9528227 A1 | 10/1995 | |
| WO | 9531550 A1 | 11/1995 | |
| WO | 9604010 A1 | 2/1996 | |
| WO | 9606619 A1 | 3/1996 | |
| WO | 9636356 A1 | 11/1996 | |
| WO | 9640932 A1 | 12/1996 | |
| WO | 9700696 A1 | 1/1997 | |
| WO | 9731651 A1 | 9/1997 | |
| WO | 9731652 A1 | 9/1997 | |
| WO | 9818933 A1 | 5/1998 | |
| WO | 9835023 A1 | 8/1998 | |
| WO | 9850426 A1 | 11/1998 | |
| WO | 9855625 A1 | 12/1998 | |
| WO | 9855626 A2 | 12/1998 | |
| WO | 0053787 A1 | 9/2000 | |
| WO | 0065032 A1 | 11/2000 | |
| WO | 0159077 A1 | 8/2001 | |
| WO | 0190363 A1 | 11/2001 | |
| WO | 02060921 A2 | 8/2002 | |
| WO | 02095040 A1 | 11/2002 | |
| WO | 03062407 A1 | 7/2003 | |
| WO | 2006002193 A2 | 1/2006 | |
| WO | 2006034319 A2 | 3/2006 | |
| WO | 2006074986 A2 | 7/2006 | |
| WO | 2007002321 A2 | 1/2007 | |
| WO | 2007064742 A2 | 6/2007 | |
| WO | 2008109237 A2 | 9/2008 | |
| WO | 2008121958 A1 | 10/2008 | |
| WO | 2010025109 A1 | 3/2010 | |
| WO | 20110128415 A1 | 10/2011 | |

OTHER PUBLICATIONS

Kroese (Journal of General Virology. 2008; 89: 494-499).*
Gao et al. (Archives of Virology. 2004; 149: 1341-1351).*
Beura et al. (Virology. 2012; 433: 431-439).*
Cano et al., "Impact of a modfied-live porcine reproductive and respiratory syndrome virus vaccine intervention on a population of pigs infected with a heterologous isolate". Vaccine, vol. 25, 2007, pp. 4382-4391.
UniProt: Accession No. C9E449. "SubName: Full=M protein; SubName: Full= Membrane protein". Nov. 3, 2009.
UniProt: Accession No. D0VEE4. "SubName: Full=Unglycosylated membrane protein". Dec. 15, 2009.
UniProt: Accession No. Q6TLB4. "SubName: Full= Membrane protein M". Jul. 5, 2004.
Lopez et al., "Role of neutralizing antibodies in PRRSV protective immunity". Veterinary Immunology and Immunopathology, vol. 102, 2004, pp. 155-163.
Meier et al., "Gradual development of the interferon-g response of swine to porcine reproductive and respiratory syndrome virus infection or vaccination". Virology, vol. 309, 2003, pp. 18-31.
Miller et al., "Interferon type I response in porcine reproductive and respiratory syndrome virus-infected MARC-145 cells". Archives of Virology, vol. 149, 2004, pp. 2453-2463.
Shi et al., "Endoribonuclease activities of porcine reproductive and respiratory syndrome virus nsp11 was essential for nsp11 to inhibit IFN-β induction". Molecular Immunology, vol. 48, 2011, pp. 1568-1572.
Shi et al., "The Nonstructural Protein 1 Papain-Like Cysteine Protease Was Necessary for Porcine Reproductive and Respiratory

(56) References Cited

OTHER PUBLICATIONS

Syndrome Virus Nonstructural Protein 1 to Inhibit Interferon-β Induction". DNA and Cell Biology, vol. 30, No. 6, 2011, pp. 355-362.
Allende et al., "Porcine Reproductive and Respiratory Syndrome Virus: Description of Persistence in Individual Pigs upon Experimental Infection† ". Journal of Virology, vol. 74, No. 22, Nov. 2000, pp. 10834-10837.
Ansari et al., "Influence of N-Linked Glycosylation of Porcine Reproductive and Respiratory Syndrome Virus GP5 on Virus Infectivity, Antigenicity, and Ability to Induce Neutralizing Antibodies." Journal of Virology, vol. 80, No. 8, Apr. 2006, pp. 3994-4004.
Kim et al., "Modulation of type I interferon induction by porcine reproductive and respiratory syndrome virus and degradation of CREB-binding protein by non-structural protein 1 in MARC-145 and HeLa cells". Virology, vol. 402, 2010, pp. 315-326.
Kroese et al., "The nsp1α and nsp1β papain-like autoproteinases are essential for porcine reproductive and respiratory syndrome virus RNA synthesis". Journal of General Virology, vol. 89, 2008, pp. 494-499.
Li et al., "The cysteine protease domain of porcine reproductive and respiratory syndrome virus non-structural protein 2 antagonizes interferon regulatory factor 3 activation". Journal of General Virology, vol. 91, 2010, pp. 2947-2958.
Xiao et al., "The Level of Virus-Specific T-Cell and Macrophage Recruitment in Porcine Reproductive and Respiratory Syndrome Virus Infection in Pigs Is Independent of Virus Load". Journal of Virology, vol. 78, No. 11, Jun. 2004, pp. 5923-5933.
Xue et al., "The Crystal Structure of Porcine Reproductive and Respiratory Syndrome Virus Nonstructural Protein Nsp1b Reveals a Novel Metal-Dependent NucleaseÑ". Journal of Virology, vol. 84, No. 13, Jul. 2010, pp. 6461-6471.
Song et al., "Nonstructural protein 1? subunit-based inhibition of Nf-?B activation and suppression of interferon-? production by porcine reproductive and respiratory syndrome virus". Virology, vol. 407, 2010, pp. 268-280.
Sun et al., "Crystal Structure of Porcine Reproductive and Respiratory Syndrome Virus Leader Protease Nsp1aÑ". Journal of Virology, vol. 83, No. 21, Nov. 2009, pp. 10931-10940.
Brockmeier et al., "Genomic sequence and virulence comparison of four Type 2 porcine reproductive and respiratory syndrome virus strains". Virus Research, vol. 169, No. 1, 2012, pp. 212-221.
Leng et al., "Evaluation of the Efficacy of an Attenuated Live Vaccine against Highly Pathogenic Porcine Reproductive and Respiratory Syndrome Virus in Young Pigs". Clinical and Vaccine Immunology, vol. 19, No. 8, Aug 2012, pp. 1199-1206.
Charerntantanakul et al., "Porcine reproductive and respiratory syndrome virus vaccines: Immunogenicity, efficacy and safety aspects". World Journal of Virology, vol. 1, No. 1, Feb. 2012, pp. 23-30.
Collins et al., "Laboratory diagnosis of porcine reproductive and respiratory syndrome (PRRS) virus infection". Swine Health and Production, vol. 4, No. 1, Feb. 1996, pp. 33-35.
UniProt: Accession No. J9Qll1. "SubName: Full=Unglycosylated membrane protein". Nov. 28, 2012, 1 page.
UniProt: Accession No. J9QIW4. "SubName: Full=Polyprotein 1ab". Nov. 28, 2012, pp. 1-3.
UniProt: Accession No. J9QHK0. "SubName: Full=Nucleocapsid protein". Nov. 28, 2012, 1 page.
UniProt: Accession No. B4ZUF3. "SubName: Full=Envelope glycoprotein". Sep. 23, 2008, 1 page.
Database EMBL Accession No. EU759247, "Porcine respiratory and reproductive syndrome virus isolate PRRSV2000000079 envelope glycoprotein gene, complete cds". Aug. 10, 2008, 1 page.
Database EMBL Accession No. EF488739, "Porcine respiratory and reproductive syndrome virus isolate MN184C, complete genome". Apr. 19, 2007, pp. 1-4.
Mardassi et al., "Structural Gene Analysis of a Quebec Reference Strain of Porcine Reproductive and Respiratory Syndrome Virus (PRRSV)". Corona- and Related Viruses, Edited by P.J. Talbot and G.A. Levy, Plenum Press, New York, 1995, pp. 277-281.

Wassenaar et al., "Alternative Proteolytic Processing of the Arterivirus Replicase ORF1a Polyprotein: Evidence that NSP2 Acts as a Cofactor for the NSP4 Serine Protease". Journal of Virology, vol. 71, No. 12, Dec. 1997, pp. 9313-9322.
Webster et al., "Chemotherapy and Vaccination: a Possible Strategy for the Control of Highly Virulent Influenza Virus". Journal of Virology, vol. 55, No. 1, 1985, pp. 173-176.
Welch et al., "Construction and evaluation of genetically engineered replication-defective porcine reproductive and respiratory syndrome virus vaccine candidates". Veterinary Immunology and Immunopathology, vol. 102, 2004, pp. 277-290.
Wensvoort et al., "'Blue ear' disease in pigs". Veterinary Record, vol. 128, No. 24, Jun. 1991, p. 574.
Wensvoort et al., "'Lelystad agent'—the cause of abortus blauw (mystery swine disease)". Tijdschr Diergeneeskd, vol. 116, No. 13, Jul. 1991, pp. 675-676.
Wensvoort et al., "An Enzyme Immunoassay Employing Monoclonal Antibodies and Detecting Specifically Antibodies to Classical Swine Fever Virus". Veterinary Microbiology, vol. 17, 1988, pp. 129-140.
Wensvoort et al., "Antigenic Comparison of Lelystad Virus and Swine Infertility and Respiratory Syndrome (SIRS) Virus". Journal of Veterinary Diagnostic Investigation, vol. 4, 1992, pp. 134-138.
Wensvoort et al., "Bovine viral diarrhoea virus infections in piglets born to sows vaccinated against swine fever with contaminated vaccine". Research in Veterinary Science, vol. 45, 1988, pp. 143-148.
Wensvoort et al., "Characterization of Porcine and Some Ruminant Pestiviruses by Cross-neutralization" vol. 20, 1989, pp. 291-306.
Wensvoort et al., "Lelystad virus, the cause of porcine epidemic abortion and respiratory syndrome: a review of mystery swine disease research in Lelystad". Veterinary Microbiology, vol. 33, Nos. 1-4, Nov. 1992, pp. 185-193.
Wensvoort et al., "Mystery Swine Disease in the Netherlands the Isolation of Lelystad Virus". The Veterinary Quarterly, vol. 13, No. 3, 1991, pp. 121-130.
Wensvoort et al., "Production of Monoclonal Antibodies Against Swine Fever Virus and Their Use in Laboratory Diagnosis". Veterinary Microbiology, vol. 12, 1986, pp. 101-108.
Wensvoort et al., "The Porcine Reproductive and Respiratory Syndrome; Characteristics and diagnosis of the causative virus". Veterinary Biotechnology Newsletter, vol. 3, 1993, pp. 113-120.
Wesley et al., "Differentiation of vaccine (strain RespPRRS) and field strains of porcine reproductive and respiratory syndrome virus by restriction enzyme analysis". Proceedings of the American Association on Swine Practitioners, Nashville, TN, USA, 1996, pp. 141-143.
Westenbrink et al., "An enzyme-linked immunosorbent assay for detection of antibodies to porcine parvovirus". Journal of Virological Methods, vol. 23, 1989, pp. 169-178.
Wieczorek-Krohmer et al., "Porcine reproductive and respiratory syndrome virus (PRRSV): Monoclonal antibodies detect common epitopes on two viral proteins of European and U.S. isolates". Veterinary Microbiology, vol. 51, Nos. 3-4, Aug. 1996, pp. 257-266.
Witte, K.H. "The Situation of 'Epidemic Late Abortion of Swine' in the State of Northrhine-Westphalia". Workshop Seminar, Apr. 1991.
Woode, et al., "Porcine Rotavirus Infection". Diseases of Swine, Fifth Edition, Chapter 26, The Iowa State University Press, Ames, Iowa, 1981, pp. 310-322.
Woods et al., "Antigenicity of Inactivated Swine Influenza Virus Concentrated by Centrifugation". Research Communications in Chemical Pathology and Pharmacology, vol. 13, No. 1, 1976, pp. 129-132.
Woods et al., "Experimental challenge of pregnant gilts with swine influenza virus after vaccination". Research Communications in Chemical Pathology and Pharmacology, vol. 15, No. 4, Dec. 1976, pp. 787-795.
Woods et al., "Investigation of Four Outbreaks of Acute Respiratory Disease in Swine and Isolation of Swine Influenza Virus". Health Laboratory Science, vol. 5, No. 4, Oct. 1968, pp. 218-224.
Wootton et al., "Structure-function of the ORF7 protein of porcine reproductive and respiratory syndrome virus in the viral capsid assembly". Proceedings of the International Symposium on PRRS and Aujeszky's Disease, Ploufragan, France, Jun. 21-24, 1999, pp. 37-38.

(56) References Cited

OTHER PUBLICATIONS

Yamane et al., "Annual Examination of Influenza Virus Infection Among Pigs in Miyagi Prefecture, Japan: The Appearance of Hsw1N1 Virus". Acta Virologica, vol. 23, 1979, pp. 240-248.
Yang et al., "Comparative sequence analysis of open reading frames 2 to 7 of the modified live vaccine virus and other North American isolates of the porcine reproductive and respiratory syndrome virus". Archives of Virology, vol. 143, 1998, pp. 601-612.
Yoon et al., "A modified serum neutralization test for the detection of antibody to porcine reproductive and respiratory syndrome virus in swine sera". Journal of Veterinary Diagnostic Investigation, vol. 6, No. 3, Jul. 1994, pp. 289-292.
Yoon et al., "Failure to Consider the Antigenic Diversity of Porcine Reproductive and Respiratory Syndrome (PRRS) Virus Isolates May Lead to Misdiagnosis". Journal of Veterinary Diagnostic Investigation, vol. 7, Jul. 1995, pp. 386-387.
Yoon et al., "Isolation of a Cytopathic Virus from Weak Pigs on Farms with a History of Swine Infertility and Respiratory Syndrome". Journal of Veterinary Diagnostic Investigation, vol. 4, Apr. 1992, pp. 139-143.
Yu et al., "Specific Binding of Host Cellular Proteins to Multiple Sites within the 39 End of Mouse Hepatitis Virus Genomic RNA". Journal of Virology, vol. 69, No. 4, Apr. 1995, pp. 2016-2023.
Yuan et al., "Complete genome comparison of porcine reproductive and respiratory syndrome virus parental and attenuated strains". Virus Research, vol. 74, 2001, pp. 99-110.
Yuan et al., "Erratum to 'Complete genome comparison of porcine reproductive and respiratory syndrome virus parental and attenuated strains'[Virus Research 74 (2001) 99-110]". Virus Research, vol. 79, 2001, p. 187.
Yuan et al., "Molecular characterization of a highly pathogenic strain of PRRSV associated with porcine High Fever syndrome in China". 2007 International Porcine Reproductive and Respiratory Syndrome (PRRS) Symposium, Chicago, Illinois, Nov.-Dec. 2007, Poster 70.
Yuan et al., American Society for Virology, 16th Annual Meeting, Bozeman, Montana, Jul. 19-23, 1997, Abstract P29-5, p. 229.
Zeijst, et al., "The Genome of Equine Arteritis Virus". Virology, vol. 68, 1975, pp. 418-425.
Zhou et al., "Generation of cytotoxic and humoral immune responses by nonreplicative recombinant Semliki Forest virus". Proceedings of the National Academy of Sciences, vol. 92, Mar. 1995, pp. 3009-3013.
Zimmerman et al., "General overview of PRRSV: A perspective from the United States". Veterinary Microbiology, vol. 55, Nos. 1-4, Apr. 1997, pp. 187-196.
International Search Report and Written Opinion for PCT/EP2012/064893 mailed Oct. 24, 2012.
Fang et al., "A Full-Length cDNA Infectious Clone of North American Type 1 Porcine Reproductive and Respiratory Syndrome Virus: Expression of Green Fluorescent Protein in the Nsp2 Region". Journal of Virology, vol. 80, No. 23, Dec. 2006, pp. 11447-11455.
Huang et al., "Novel strategies and approaches to develop the next generation of vaccines against porcine reproductive and respiratory syndrome virus (PRRSV)". Virus Research, vol. 154, 2010, pp. 141-149.
Thanawongnuwech et al., "Taming PRRSV: Revisiting the control strategies and vaccine design". Virus Research, vol. 154, No. 1-2, 2010, pp. 133-140.
Nam et al. "Complete genomic characterization of a European type 1 porcine reproductive and respiratory syndrome virus isolate in Korea". Archives of Virology, vol. 154, No. 4, 2009, pp. 629-638.
"Dutch Team Isolates Mystery Pig Disease Agent", Animal Pharm, vol. 230, Abstract No. 00278268, Jun. 21, 1991, p. 21.
"For purification of viral RNA from Plasma, Serum, Cell-free body fluids, Cell-Culture supernatants". QIAamp® Viral RNA Mini Kit Handbook, QIAGEN, Jan. 1999, Cat #52906, pp. 1-35.
"Frontiers closing to mystery disease pigs". Animal Pharm., No. 228, May 24, 1991, p. 2.

"Revision of the taxonomy of the Coronavirus, Torovirus, and Arterivirus genera". Archives of Virology, vol. 135, 1994, pp. 227-239.
Abstracts of Papers Presented at the 71st Annual Meeting of the Conference of Research Workers in Animal Disease, No.'s 1-6, Nov. 5-6, 1990, 2 pages.
Aksenova et al., "Cultivation of the rabies virus in the continuous kidney cell line 4647 from the green marmoset". Vopr. Virusol., vol. 30, No. 2, 1985, pp. 180-182. (See Axenova for English Abstract).
Albina et al., "Immune responses in pigs infected with porcine reproductive and respiratory syndrome virus (PRRSV)". Veterinary Immunology and Immunopathology, vol. 61, 1998, pp. 49-66.
Allan et al., "Experimental infection of colostrum deprived piglets with porcine circovirus 2 (PCV2) and procine reproductive and respiratory syndrome virus (PRRSV) potentiates PCV2 replication". 2000, Archives of Virology, vol. 145, pp. 2421-2429.
Allende et al., "Mutations in the genome of porcine reproductive and respiratory syndrome virus responsible for the attenuated phenotype". Archives of Virology, vol. 145, No. 6, Jun. 2000, pp. 1149-1161.
Allende et al., "North American and European porcine reproductive and respiratory syndrome viruses differ in non-structural protein coding regions". Journal of General Virology, vol. 80, 1999, pp. 307-315.
Altschul et al., "Basic Local Alignment Search Tool". Journal of Molecular Biology, vol. 215, 1990, pp. 403-410.
Andreyev et al., "Genetic variation and phylogenetic relationships of 22 porcine reproductive and respiratory syndrome virus (PRRSV) field strains based on sequence analysis of open reading frame 5". Archives of Virology, vol. 142, 1997, pp. 993-1001.
Ashworth et al., "Antibody-dependent cell-mediated cytotoxicity (ADCC) in Aujeszky's disease". Archives of Virology, vol. 59, No. 4, 1979, pp. 307-318.
Axenova, T.A. "Propagation of Rabies Vaccine Virus in Continuous Green Monkey Kidney Cells 4647". Vopr. Virusol., vol. 30, No. 2, 1985, p. 182. (English Abstract of Aksenova Reference.).
Backstrom et al., "Respiratory Diseases of Swine". Veterinary Clinics of North America: Large Animal Practice, vol. 4, No. 2, Nov. 1982, pp. 259-276.
Barfoed et al., "DNA vaccination of pigs with open reading frame 1-7 of PRRS virus". Vaccine, vol. 22, 2004, pp. 3628-3641.
Baric et al., "Interactions between Coronavirus Nucleocapsid Protein and Viral RNAs: Implications for Viral Transcription". Journal of Virology, vol. 62, No. 11, Nov. 1988, pp. 4280-4287.
Baric et al., "Subgenomic Negative-Strand RNA Function during Mouse Hepatitis Virus Infection". Journal of Virology, vol. 74, No. 9, May 2000, pp. 4039-4046.
Bautista et al., "Comparison of Porcine Alveolar Macrophages and CL 2621 for the Detection of Porcine Reproductive and Respiratory Syndrome (PRRS) Virus and Anti-PRRS Antibody". Journal of Veterinary Diagnostic Investigation, vol. 5, No. 2, Apr. 1993, pp. 163-165.
Bautista et al., "Serologic Survey for Lelystad and VR-2332 Strains of Porcine Respiratory and Reproductive Syndrome (PRRS) Virus in US Swine Herds". Journal of Veterinary Diagnostic Investigation, vol. 5, No. 4, Oct. 1992, pp. 612-614.
Beale, AJ, "Vaccines and antiviral drugs". Principles of bacteriology, virology and immunity, vol. 3, Ch. 86, 1984, pp. 147-161.
Beare et al., "Further Studies in Man of Man of HSw1N1 Influenza Viruses". Journal of Medical Virology, vol. 5, 1980, pp. 33-38.
Beghi et al., "Guillain-Barré Syndrome: Clinicoepidemiologic Features and Effect of Influenza Vaccine". Archives of Neurology, vol. 42, No. 11, 1985, pp. 1053-1057.
Benfield et al., "Characterization of swine infertility and respiratory syndrome (SIRS) virus (isolate ATCC VR-2332)". Journal of Veterinary Diagnostic Investigation, vol. 4, 1992, pp. 127-133.
Benfield et al., "Etiologic Agent of Swine Infertility and Respiratory Syndrome in the United States". 72st Annual Meeting of the Conference of Research Workers in Animal Disease, Chicago, IL, Nov. 11-12, 1991, p. 48, Abstract No. 268.
Benfield et al., "Properties of SIRS Virus Isolate ATCC VR-2332 in the United States and Preliminary Characterization of a Monoclonal

(56) References Cited

OTHER PUBLICATIONS

Antibody to this Virus". American Association of Swine Practitioners Newsletter, vol. 4, No. 4, Jul./Aug. 1992, pp. 19-21.

Berendt et al., "Evaluation of Commercially Prepared Vaccines for Experimentally Induced Type/A/New Jersey/8/76 Influenza Virus Infections in Mice and Squirrel Monkeys". The Journal of Infectious Diseases, vol. 136, Dec. 1977, pp. S712-S718.

Berendt et al., "Reaction of Squirrel Monkeys to Intratracheal Inoculation with Influenza/A/New Jersey/76 (Swine) Virus". Infection and Immunity, vol. 16, No. 2, May 1977, pp. 476-479.

Beura et al., "Porcine Reproductive and Respiratory Syndrome Virus Nonstructural Protein 1β Modulates Host Innate Immune Response by Antagonizing IRF3 Activation". Journal of Virology, Volo. 84, No. 3, Feb. 2010, pp. 1574-1584.

Bilodeau et al., "'Porcine Reproductive and Respiratory Syndrome' in Quebec". The Veterinary Record, Aug. 3, 1991, p. 102.

Blackburn et al., "Use of human influenza vaccine to protect against blue-eared pig disease". Veterinary Record, vol. 129, No. 1, Jul. 1991, p. 19.

Bohl et al., "Isolation and Serotyping of Porcine Rotaviruses and Antigenic Comparison with Other Rotaviruses". Journal of Clinical Microbiology, vol. 19, No. 2, Feb. 1984, pp. 105-111.

Bouillant et al., "Viral Susceptibility of a Cell Line Derived from the Pig Oviduct". Canadian Journal of Comparative Medicine, vol. 39, 1975, pp. 450-456.

Boursnell et al., "Sequence of the membrane protein gene from avian coronavirus IBV". Virus Research, vol. 1, 1984, pp. 303-313.

Boursnell et all., "Completion of the Sequence of the Genome of the Coronavirus Avian Infectious Bronchitis Virus". Journal of General Virology, vol. 68, 1987, pp. 57-77.

Bowie et al., "Deciphering the Message of Protein Sequences: Tolerance to Amino Acid Substitutions". Science, vol. 247, 1990, pp. 1306-1310.

Boyer et al., "Infectious Transcripts and cDNA Clones of RNA Viruses". Virology, vol. 198, No. 2, Feb. 1994, pp. 415-426.

Bramel-Verheije et al., "Expression of a Foreign Epitope by Porcine Reproductive and Respiratory Syndrome Virus". Virology, vol. 278, 2000, pp. 380-389.

Bredenbeek et al., "The primary structure and expression of the second open reading frame of the polymerase gene of the coronavirus MHV-A59; a highly conserved polymerase is expressed by an efficient ribosomal frameshifting mechanism". Nucleic Acids Research, vol. 18, No. 7, 1990, pp. 1825-1832.

Brenner et al., "A Negative Staining Method for High Resolution Electron Microscopy of Viruses". Biochimica Et Biophysica Acta, vol. 34, 1959, pp. 103-110.

Brinton-Darnell et al., "Structure and chemical-physical characteristics of lactate dehydrogenase-elevating virus and its RNA". Journal of Virology, vol. 16, No. 2, Aug. 1975, pp. 420-433.

Brinton-Darnell, M. "Lactate Dehydrogenase-Elevating, Equine Arteritis and Lelystad Viruses". Encyclopedia of Virology, vol. 2, 1999, pp. 763-771.

Bruner, D.W., "Table XXXII. Characteristics of Viral Respiratory Infections in Swine" Hagan's Infectious Diseases of Domestic Animals: With Special Reference to Etiology, Diagnosis, and Biologic Therapy, Sixth Edition, Comstock Publishing Associations, a division of Cornell University Press, Ithaca and London, 1973, 5 pages.

Brüggemann et al., "Immunoglobulin V region variants in hybridoma cells. I. Isolation of a variant with altered idiotypic and antigen binding specificity". The EMBO Journal, vol. 1, No. 5, 1982, pp. 629-634.

Buck, K. W., "Comparison of the Replication of Positive-Stranded RNA Viruses of Plants and Animals". Advances in Virus Research, vol. 47, 1996, pp. 159-251.

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue". The Journal of Cell Biology, vol. 111, 1990, pp. 2129-2138.

Burroughs, et al., "Relationship of San Miguel Sea Lion Virus to Other Members of the Calicivirus Group". Intervirology, vol. 10, 1978, pp. 51-59.

Cabasso et al., "Propagation of Infectious Canine Hepatitis Virus in Tissue Culture". Proceedings of the Society for Experimental Biology and Medicine, vol. 85, 1954, pp. 239-245.

Caeiro et al., "In vitro DNA replication by cytoplasmic extracts from cells infected with African swine fever virus". Virology, vol. 179, No. 1, Nov. 1990, pp. 87-94.

Callebaut et al., "Antigenic Differentiation between Transmissible Gastroenteritis Virus of Swine and a Related Porcine Respiratory Coronavirus". Journal of General Virology, vol. 69, 1988, pp. 1725-1730.

Dildrop et al., "Immunoglobulin V region variants in hybridoma cells. II. Recombination between V genes". The EMBO Journal, vol. 1, No. 5, 1982, pp. 635-640.

Dreher, T.W., "Functions of the 3'-Untranslated Regions of Positive Strand RNA Viral Genomes". Annual Review of Phytopathology, vol. 37, 1999, pp. 151-174.

Drew et al., "Production, characterization and reactivity of monoclonal antibodies to porcine reproductive and respiratory syndrome virus". Journal of General Virology, vol. 76, 1995, pp. 1361-1369.

Drew, T., "Porcine Reproductive and Respiratory Syndrome Virus: A Review". Apr. 1996, 3 pages.

Duan et al., "Identification of a putative Receptor for Porcine Reproductive and Respiratory Syndrome Virus on Porcine Alveolar Macrophages". Journal of Virology, vol. 72, No. 5, May 1998, pp. 4520-4523.

Duran et al. "Recombinant Baculovirus Vaccines Against Porcine Reproductive and Respiratory Syndrome (PRRS)". Abstracts PRRS, Aug. 9 to 10, 1995, Copenhagen, Denmark, 2 pages.

Dykhuizen et al., "Determining the Economic Impact of the 'New' Pig Disease", Porcine Reproductive and Respiratory Syndrome, A Report on the Seminar Held in Brussels on Nov. 4-5, 1991 and Organized by the European Commission, pp. 53-60.

Easterday, B.C., "Swine Influenza". Diseases of Swine, Sixth Edition, Iowa State University Press, 1986, pp. 244-315. (Part One of Two-pp. 244-285). This NPL is too large for EFS submission. Therefore filing in two parts.

Easterday, B.C., "Swine Influenza". Diseases of Swine, Sixth Edition, Iowa State University Press, 1986, pp. 244-315. (Part Two of Two-pp. 286-315). This NPL is too large for EFS submission. Therefore filing in two parts.

Easterday, et al., "Swine Influenza". In Diseases of Swine (8th Edition), BE Straw, S D'Allaire, WI. Mengeling, DJ Taylor, eds., Ames: Iowa State University Press, 1999, pp. 277-290.

Edwards et al., "Oligodeoxyribonucleotide ligation to single-stranded cDNAs: a new tool for cloning 5' ends of mRNAs and for constructing cDNA libraries by in vitro amplification". Nucleic Acids Research, vol. 19, No. 19, 1991, pp. 5227-5232.

Ehresmann et al., "RNA synthesized in calicivirus-infected cells is atypical of picornaviruses". Journal of Virology, vol. 22, No. 2, May 1977, pp. 572-576.

Ellis, R.W., "New Technologies for Making Vaccines". Vaccines, Chapter 29, Plotkin et al Eds., WB Saunders Company, Philadelphia, PA, 1988, pp. 568-575.

Enjuanes et al., "Isolation and Properties of the DNA of African Swine Fever (ASF) Virus". Journal of General Virology, vol. 32, No. 3, Sep. 1976, pp. 479-492.

*Enzo Biochem Inc.* v. *Gen-Probe Incorporated et al.*, No. 01-01230; Decided Jul. 15, 2002.

Estes et al., "Simian rotavirus SA11 replication in cell cultures". Journal of Virology, vol. 31, No. 3, Sep. 1979, pp. 810-815.

Fang et al., "Heterogeneity in nsp2 of European-like porcine reproductive and respiratory syndrome viruses isolated in the United States". Virus Research, vol. 100, 2004, pp. 229-235.

Fenner et al., "Immunization against Viral Diseases", Veterinary Virology, Ch. 14, 1992, pp. 265-271.

Fenner et al., "Viral Genetics and Evolution", Veterinary Virology, Ch. 5, 1992, pp. 89-95.

Ferrari et al., "Isolation of Cytopathic Strains of Rotavirus from Pigs". Microbiologica, vol. 9, No. 3, Jul. 1986, pp. 287-294.

(56) References Cited

OTHER PUBLICATIONS

Flint et al., "Virus Cultivation, Detection, and Genetics". Virology, Molecular Biology, Pathogenesis, and Control, Ch. 2, 2000, pp. 40-42.
Foss et al., "Adjuvant Danger Signals Increase the Immune Response to Porcine Reproductive and Respiratory Syndrome Virus". Viral Immunology, vol. 15, No. 4, 2002, pp. 557-566.
Frolov et al., "Alphavirus-based expression vectors: Strategies and applications". Proceedings of the National Academy of Sciences, vol. 93, Oct. 1996, pp. 11371-11377.
Fu et al., "Detection and survival of group A rotavirus in a piggery". Veterinary Record, vol. 125, 1989, pp. 576-578.
Fukuhara et al., "Evidence for endocytosis-independent infection by human rotavirus". Archives of Virology, vol. 97, Nos. 1-2, 1987, pp. 93-99.
Funkhouser et al., "Mutations in the 5'-noncoding, 2C and P3 Regions of the Genome Increase the Efficiency of Hepatitis A Virus Growth in MRC-5 Cells". Vaccines, vol. 94, Cold Springs Harbor Laboratory Press, 1994, pp. 345-349.
Gao et al., "Genomic characterization of two Chinese isolates of Porcine respiratory and reproductive syndrome virus". Archives of Virology, vol. 149, 2004, pp. 1341-1351.
Garwes, D.J., "Transmissible gastroenteritis". Veterinary Record, vol. 122, 1988, pp. 462-463.
Geisbert et al., "Use of Immunoelectron Microscopy to Show Ebola Virus During the 1989 United States Epizootic". Journal of Clinical Pathology, vol. 43, No. 10, Oct. 1990, pp. 813-816.
Girard et al., "Experimentally induced porcine proliferative and necrotising pneumonia with an influenza A virus". The Veterinary Record, vol. 130, Mar. 1992, pp. 206-207.
Godeny et al., "Map location of lactate dehydrogenase-elevating virus (LDV) capsid protein (Vpl) gene", Virology, vol. 177, No. 2, Aug. 1990, pp. 768-771.
Godeny et al., "The 3' Terminus of Lactate Dehydrogenase-Elevating Virus Genome RNA Does Not Contain Togavirus or Flavivirus Conserved Sequences", Virology, vol. 72, 1989, pp. 647-650.
Goldfield et al., "Influenza in New Jersey in 1976: Isolations of Influenza A/New Jersey/76 Virus at Fort Dix". The Journal of Infectious Diseases, vol. 136, Supp. 3, 1977, pp. S347-S355.
Goldstein, et al., "Evaluation of Three Cell Culture Systems as Substrates for Influenza Virus Assay". Applied Microbiology, vol. 19, No. 4, Apr. 1970, pp. 580-582.
Gong et al., "Characterization of RNA synthesis during a one-step growth curve and of the replication mechanism of bovine viral diarrhoea virus". Journal of General Virology, vol. 77, 1996, pp. 2729-2736.
Gorcyca et al., RespPRRS: A new tool for the prevention and control of PRRS in pigs. Proceedings of the American Association of Swine Practitioners, Omaha, Nebraska, Mar. 1995, pp. 1-22.
Gourreau et al., "Diffusion du virus de la grippe du porc (H1N1=Hsw1N1) en France". Annales de l'Institut Pasteur/Virologie, vol. 132, No. 2, Apr.-Jun. 1981, pp. 287-294.
Goyal, S., "Porcine Reproductive and Respiratory Syndrome", Journal of Veterinary Diagnostic Investigation, vol. 5, No. 4, 1993, pp. 656-664.
Gravell et al., "Differences among isolates of simian hemorrhagic fever (SHF) virus". Proceedings of the Society for Experimental Biology and Medicine, vol. 181, No. 1, 1986, pp. 112-119.
Graves, J.H., "Swine Vesicular Disease". Diseases of Swine, Fifth Edition, Chapter 23, The Iowa State University Press, Ames, Iowa, 1958, pp. 288-293.
Grebennikova et al., "Genomic characterization of virulent, attenuated, and revertant passages of a North American porcine reproductive and respiratory syndrome virus strain". Virology, vol. 321, 2004, pp. 383-390.
Greiner et al., "Quantitative relationship of systemic virus concentration on growth and immune response in pigs". Journal of Animal Science, vol. 78, 2000, pp. 2690-2695.
Grizzard et al., "Experimental production of respiratory tract disease in cebus monkeys after intratracheal or intranasal infection with influenza A/Victoria/3/75 or influenza A/New Jersey/76 virus". Infection and Immunity, vol. 21, No. 1, Jul. 1978, pp. 201-205.
Grouse, L.D., "Swine Flue Sequelae"., Journal of the American Medical Association, vol. 243, No. 24, 1980, p. 2489.
Grunert et al., "Sensitivity of Influenza A/New Jersey/8/76 (HswINI) Virus to Amantadine-HCl". Journal of Infectious Diseases, vol. 136, No. 2, 1977, pp. 297-300.
Guan et al., "Requirement of a 5?-Proximal Linear Sequence on Minus Strands for Plus-Strand Synthesis of a Satellite RNA Associated with Turnip Crinkle Virus". Virology, vol. 268, No. 2, Mar. 2000, pp. 355-363.
Gubler et al., "A simple and very efficient method for generating cDNA libraries". Gene, vol. 25, 1983, pp. 263-269.
Gustafson, D.P., "Pseudorabies". Diseases of Swine, Fifth Edition, Ch. 14, The Iowa State University Press, Ames, Iowa, 1981, pp. 209-223.
Halbur et al., "Comparative pathogenicity of nine US porcine reproductive and respiratory syndrome virus (PRRSV) isolates in a five-week-old cesarean-derived, colostrum-deprived pig model". Journal of Veterinary Diagnostic Investigation, vol. 8, 1996, pp. 11-20.
Halbur et al., "Effects of different US isolates of porcine reproductive and respiratory syndrome virus (PRRSV) on blood and bone marrow parameters of experimentally infected pigs". Veterinary Record, vol. 151, 2002, pp. 344-348.
Carrascosa et al., "Relationship of San Miguel Sea Lion Virus to Other Members of the Calicivirus Group". Journal of Virological Methods, vol. 3, No. 6, Jan. 1982, pp. 303-310.
Carvajal et al., "Evaluation of a Blocking ELISA Using Monoclonal Antibodies for the Detection of Porcine Epidemic Diarrhea Virus and Its Antibodies". Journal of Veterinary Diagnostic Investigation, vol. 7, No. 1, Jan. 1995, pp. 60-64.
Cavanagh, D., "Nidovirales: a new order comprising Coronaviridae and Arteriviridae". Archives of Virology, vol. 142, No. 3, 1997, pp. 629-633.
Chang et al., "A cis-Acting Function for the Coronavirus Leader in Defective Interfering RNA Replication". Journal of Virology, vol. 68, No. 12, Dec. 1994, pp. 8223-8231.
Chang et al., "Evolution of Porcine Reproductive and Respiratory Syndrome Virus during Sequential Passages in Pigs". Journal of Virology, vol. 76, No. 10, May 2002, pp. 4750-4763.
Chao et al., "Monoclonal Antibodies to Metacyclic Stage Antigens of Trypanosoma Cruzi" The American Journal of Tropical Medicine and Hygiene, vol. 34, No. 4, Jul. 1985, pp. 694-701.
Charley, B., "Interaction of influenza virus with swine alveolar macrophages: Influence of anti-virus antibodies and cytochalasin B". Annales de l'Instiut Pasteur. Virologie, vol. 134, No. 1, Jan. 1983, pp. 51-59.
Chasey et al., "Replication of Atypical Ovine Rotavirus in Small Intestine and Cell Culture". Journal of General Virology, vol. 67, No. 3, Mar. 1986, pp. 567-576.
Chen et al., "Determination of the 5' end of the lactate dehydrogenase-elevating virus genome by two independent approaches". Journal of General Virology, vol. 75, 1994, pp. 925-930.
Chen et al., "Identification of two auto-cleavage products of nonstructural protein 1 (nsp1) in porcine reproductive and respiratory syndrome virus infected cells: nsp1 function as interferon antagonist". Virology, vol. 398, 2010, pp. 87-97.
Christianson et al., "Experimental Reproduction of a Newly Described Viral Disease, Swine Infertility and Respiratory Syndrome (SIRS), in Pregnant Sows". 72nd Annual Meeting of the Conference of Research Workers in Animal Disease, Chicago, IL, Nov. 11 & 12, 1991, p. 48, Abstract No. 269.
Christianson et al., "Experimental reproduction of swine infertility and respiratory syndrome in pregnant sows". American Journal of Veterinary Research, vol. 53, No. 4, Apr. 1992, pp. 485-488.
Christianson et al., "Porcine reproductive and respiratory syndrome: A review"., Journal of Swine Health and Production, vol. 2, No. 2, Mar. and Apr. 1994, pp. 10-28.
Christianson et al., "Swine Infertility and Respiratory Syndrome". Pig Veterinary Journal, vol. 27, No. 9, Apr. 1991, pp. 9-12.
Chutivongse et al., "One-year study of the 2-1-1 intramuscular postexposure rabies vaccine regimen in 100 severely exposed Thai

(56) References Cited

OTHER PUBLICATIONS patients using rabies immune globulin and Vero cell rabies vaccine". Vaccine, vol. 9, No. 8, Aug. 1991, pp. 573-576.
Clark et al., "Trypsin enhancement of rotavirus infectivity: mechanism of enhancement". Journal of Virology, vol. 39, No. 3, Sep. 1981, pp. 816-822.
Collins et al., "Experimental Transmission of Swine Reproductive Failure Syndrome (Mystery Swine Disease) in Gnotobiotic Piglets". 71st Annual Meeting of the Conference of Research Workers in Animal Disease, Chicago, IL, Nov. 5-6, 1990, Abstract No. 2.
Collins et al., "Isolation of swine infertility and respiratory syndrome virus (isolate ATCC VR-2332) in North America and experimental reproduction of the disease in gnotobiotic pigs". Journal of Veterinary Diagnostic Investigation, vol. 4, 1992, pp. 117-126.
Collins et al., "Production of infectious human respiratory syncytial virus from cloned cDNA confirms an essential role for the transcription elongation factor from the 5' proximal open reading frame of the M2 mRNA in gene expression and provides a capability for vaccine development". Proceedings of the National Academy of Sciences, vol. 92, Dec. 1995, pp. 11563-11567.
Collins et al., "Respiratory Disease in a Swine Herd Experiencing a Reproductive Failure Syndrome". Minnesota Swine Conference for Veterinarians, Sep. 16-18, 1990, pp. 206-207.
Collins et al., "Swine Diagnostic Pathology". Allen D. Leman Swine Conference, College of Veterinary Medicine, University of Minnesota, Sep. 18-22, 1998, pp. 1-4.
Collins et al., "Swine Infertility and Respiratory Syndrome (Mystery Swine Disease)". Minnesota Swine Conference for Veterinarians, St. Paul, MN, Sep. 15-17, 1991, pp. 200-205.
Collins, J.E., "Newly Recognized Respiratory Syndromes in North American Swine Herds". American Association of Swine Practitioners Newsletter, vol. 3, No. 7, Sep.-Oct. 1991, pp. 7, 10-11.
Conner et al., "Isolation and characteristics of an equine reovirus type 3 and an antibody prevalence survey to reoviruses in horses located in New York State". Veterinary Microbiology, vol. 9, No. 1, Feb. 1984, pp. 15-25.
Conzelmann et al., "Molecular Characterization of Porcine Reproductive and Respiratory Syndrome Virus, a Member of the Arterivirus Group". Virology, vol. 193, 1993, pp. 329-339.
Cooper et al., "Porcine Reproductive and Respiratory Syndrome: NEB-1 PRRSV Infection did not Potentiate Bacterial Pathogens". Journal of Veterinary Diagnostic Investigation, vol. 7, No. 3, Jul. 1995, pp. 313-320.
Corn et al., "Isolation of Vesicular Stomatitis Virus New Jersey Serotype from Phlebotomine Sand Files in Georgia". The American Journal of Tropical Medicine and Hygiene, vol. 42, No. 5, May 1990, pp. 476-482.
Dacso, et al., "Sporadic occurrence of zoonotic swine influenza virus infections". Journal of Clinical Microbiology, vol. 20, No. 4, Oct. 1984, pp. 833-835.
Darwich et al., "Genetic and immunobiological diversities of porcine reproductive and respiratory syndrome genotype I strains". Veterinary Microbiology, vol. 150, 2011, pp. 49-62.
Database WPIL Week 8702, Derwent Publications Ltd., London, GB; AN 87-009295 [2] & EP, A,208672 (Regional Wallonne-Chiron Corp, Wallonne Regional) Jan. 14, 1987.
Database WPIL Week 8741, Derwent Publications Ltd., London, GB; AN 87-286929 [41] & EP, A,62, 198626 (Za Bieseibutsu Kagaku Ken) Sep. 2, 1987.
Database WPIL Week 8821, Derwent Publications Ltd., London, GB; AN 88-147502 [21] & WO,A,8 803 410 (Inst Pasteur) May 19, 1988.
De Mazancourt et al., "Antibody response to the rubella virus structural proteins in infants with the congenital rubella syndrome". Journal of Medical Virology, vol. 19, No. 2, Jun. 1986, pp. 111-122.
De Vries et al., "Genetic Manipulation of Equine Arteritis Virus Using Full-Length cDNA Clones: Separation of Overlapping Genes and Expression of a Foreign Epitope". Virology, vol. 270, No. 1, 2000, pp. 84-97.

De Vries et al., "The Genome Organization of the Nidovirales: Similarities and Differences between Arteri-, Toro-, and Coronaviruses". Seminars in Virology, vol. 8, 1997, pp. 33-47.
De Vries, et al., "All subgenomic mRNAs of equine arteritis virus contain a common leader sequence". Nucleic Acids Research, vol. 18, No. 11, 1990, pp. 3241-3247.
Dea et al., "Antigenic Variability among North American and European Strains of Porcine Reproductive and Respiratory Syndrome Virus as Defined by Monoclonal Antibodies to the Matrix Protein". Journal of Clinical Microbiology, vol. 34, No. 5, Jun. 1996, pp. 1488-1493.
Dea et al., "Antigenic variant of swine influenza virus causing proliferative and necrotizing pneumonia in pigs". Journal of Veterinary Diagnostic Investigation, vol. 4, No, 4, 1992, pp. 380-392.
Dea et al., "Caracteristiques d'Isolats des virus influenza et de l'encephalomyocardite associes au Syndrome Reproducteur et Respiratoire Porcine (S.R.R.P.) au Quebec.sup.a," Le Medecin Veterinaire Du Quebec, vol. 21, No. 4, Nov. 1991, pp. 170-175.
Dea et al., "Current knowledge on the structural proteins of porcine reproductive and respiratory syndrome (PRRS) virus: comparison of the North American and European isolate". Archives of Virology, vol. 145, No. 4, Apr. 2000, pp. 659-688.
Dea et al., "Isolation of encephalomyocarditis virus among stillborn and post-weaning pigs in Quebec". Archives of Virology, vol. 117, Nos. 1-2, 1991, pp. 121-128.
Dea et al., "Swine reproductive and respiratory syndrome in Quebec: Isolation of an enveloped virus serologically-related to Lelystad virus". Canadian Veterinary Journal, vol. 33, No. 12, Dec. 1992, pp. 801-808.
Dea et al., "Virus Isolations from Farms in Quebec Experiencing Severe Outbreaks of Respiratory and Reproductive Problems". Proceedings of the Mystery Swine Disease Committee Meeting, Denver, CO, Oct. 6, 1990, pp. 67-72.
Del Val et al., "Glycosylated components of African swine fever virus particles". Virology, vol. 152, No. 1, Jul. 1986, pp. 39-49.
Den Boon et al., "Equine Arteritis Virus Is Not a Togavirus but Belongs to the Coronaviruslike Superfamily". Journal of Virology, vol. 65, No. 6, 1991, pp. 2910-2920.
Den Boon et al., "Processing and Evolution of the N-Terminal Region of the Arterivirus Replicase ORF1a Protein: Identification of Two Papainlike Cysteine Proteases". Journal of Virology, vol. 69, No. 7, Jul. 1995, pp. 4500-4505.
Deng et al., "An improved procedure for utilizing terminal transferase to add homopolymers to the 3' termini of DNA". Nucleic Acids Research, vol. 9, No. 16, 1981, pp. 4173-4188.
Derbyshire, J.B. "Porcine Enterovirus Infections". Diseases of Swine, Fifth Edition, Chapter 20, 1981, pp. 265-270.
Devereux et al., "A Comprehensive Set of Sequence Analysis Programs for VAX". Nucleic Acids Research, vol. 12, No. 1, 1984, pp. 387-395.
Dianzani et al., "Is Human Immunodeficiency Virus RNA Load Composed of Neutralized Immune Complexes". The Journal of Infectious Diseases, vol. 185, 2002, pp. 1051-1054.
Potgieter et al., "Isolation of Swine Influenza Virus in Oklahoma". Journal of the American Veterinary Medical Association, vol. 171, No. 8, 1977, pp. 758-760.
Potts et al., "Peroxidase-labeled primary antibody method for detection of pestivirus contamination in cell cultures". Journal of Virological Methods, vol. 26, No. 1, Oct. 1989, pp. 119-124.
Quaife, T. "Mystery Agent Isolated! Isolation of the etiological agent behind mystery swine disease is a major breakthrough". Swine Practitioner, Mystery Disease: Part 8, Nov. 1991, pp. 4-7.
Reed et al., "A Simple Method of Estimating Fifty Per Cent Endpoints"., The American Journal of Hygiene, vol. 27, No. 3, May 1938, pp. 493-497.
Reed et al., "Persistent Respiratory Virus Infection in Tracheal Organ Cultures". British Journal of Experimental Pathology, vol. 50, 1969, pp. 378-388.
Rice et al., "Production of Infectious RNA Transcripts from Sindbis Virus cDNA Clones: Mapping of Lethal Mutations, Rescue of a Temperature-Sensitive Marker, and In Vitro Mutagenesis to Generate Defined Mutants". Journal of Virology, vol. 61, No. 12, Dec. 1987, pp. 3809-3819.

(56) References Cited

OTHER PUBLICATIONS

Roberts et al., "Abortion in Swine". Veterinary Ostetrics and Genital Diseases, Edwards Brothers, Inc., Ann Arbor, 1986, pp. 180-192.

Roof et al., "Efficacy of Modified Live Virus Porcine Reproductive and Respiratory Virus Vaccines Against Heterologous Respiratory Challenge". 4th International Symposium on Emerging and Re-emerging Pig Diseases, Rome, Jun. 28-Jul. 2, 2003, pp. 117-118.

Ropp et al., "Characterization of Emerging European-Like Porcine Reproductive and Respiratory Syndrome Virus Isolates in the United States"., Journal of Virology, vol. 78, No. 7, Apr. 2004, pp. 3684-3703.

Rossow et al., "Experimental porcine reproductive and respiratory syndrome virus infection in one-, four-, and 10- week-old pigs". Journal of Veterinary Diagnostic Investigation, vol. 6, 1993, pp. 3-12.

Rossow, K.D., "Porcine Reproductive and Respiratory Syndrome". Veterinary Pathology, vol. 35, 1998, pp. 1-20.

Roth et al., "Influenza virus hemagglutinin expression is polarized in cells infected with recombinant SV40 viruses carrying cloned hemagglutinin DNA". Cell, vol. 33, No. 2, Jun. 1983, pp. 435-443.

Roth et al., "The large external domain is sufficient for the correct sorting of secreted or chimeric influenza virus hemagglutinins in polarized monkey kidney cells". The Journal of Cell Biology, vol. 104, Mar. 1987, pp. 769-782.

Rottier et al., "Predicted Membrane Topology of the Coronavirus Protein E1". Biochemistry, vol. 25, 1986, pp. 1335-1339.

Rovira et al., "Experimental Inoculation of Conventional Pigs with Porcine Reproductive and Respiratory Syndrome virus and Porcine Circovirus 2", J. Virol, jApril 2002, vol. 76, No. 7, pp. 3232-3239.

Sagripanti et al., "The Cap Structure of Simian Hemorrhagic Fever Virion RNA". Virology, vol. 151, 1986, pp. 143-150.

Saif et al., "Serial propagation of porcine group C rotavirus (pararotavirus) in a continuous cell line and characterization of the passaged virus". Journal of Clinical Microbiology, vol. 26, No. 7, Jul. 1988, pp. 1277-1282.

Saif, L.J., "Coronavirus Immunogens". Veterinary Microbiology, vol. 37, No. 3-4, Nov. 1993, pp. 285-297.

Sarnow, P. "Role of 3'-End Sequences in Infectivity of Poliovirus Transcripts Made In Vitro". Journal of Virology, vol. 63, No. 1, Jan. 1989, pp. 467-470.

Sawicki et al., "Coronavirus Transcription: Subgenomic Mouse Hepatitis Virus Replicative Intermediates Function in RNA Synthesis". Journal of Virology, vol. 64, No. 3, Mar. 1990, pp. 1050-1056.

Schmidt et al., "Infection of Influenza A Viruses of Tracheal Organ Cultures Derived from Homologous and Heterologous Hosts". The Journal of Infectious Diseases, vol. 129, No. 1, 1974, pp. 28-36.

Scott, F.W., "Immunization against feline coronaviruses". Advances in Experimental Medicine and Biology, vol. 218, 1987, pp. 569-576.

Seal et al., "Analysis of the Serologic Relationship among San Miguel Sea Lion Virus and Vesicular Exanthema of Swine Virus Isolates. Application of the Western Blot Assay for Detection of Antibodies in Swine Sera to these Virus Types". Journal of Veterinary Diagnostic Investigation, vol. 7, No. 2, Apr. 1995, pp. 190-195.

Seal et al., "Isolation of caliciviruses from skunks that are antigenically and genotypically related to San Miguel sea lion virus Original Research". Virus Research, vol. 37, No. 1, Jun. 1995, pp. 1-12.

Seneca, H., "Influenza: epidemiology, etiology, immunization and management". Journal of American Geriatrics Society, vol. 28, No. 6, Jun. 1980, pp. 241-250.

Sethna et al., "Coronavirus subgenomic minus-strand RNAs and the potential for mRNA replicons". Proceedings of the National Academy of Sciences, vol. 86, Jul. 1989, pp. 5626-5630.

Setzer et al., "Size Heterogeneity in the 3' End of Dihydrofolate Reductase Messenger RNAs in Mouse Cells". Cell, vol. 22, Nov. 1980, pp. 361-370.

Shaw et al., "Experimental rotavirus infection in three-week-old pigs". American Journal of Veterinary Research, vol. 50, No. 11, Nov. 1989, pp. 1961-1965.

Shen et al., "Determination of the complete nucleotide sequence of a vaccine strain of porcine reproductive and respiratory syndrome virus and identification of the Nsp2 gene with a unique insertion". Archives of Virology, vol. 145, No. 5, May 2000, pp. 871-883.

Shibata et al., "Detection of Human Papilloma Virus in Paraffin-Embedded Tissue Using the Polymerase Chain Reaction". The Journal of Experimental Medicine, vol. 167, No. 1, Jan. 1988, pp. 225-230.

Shieh et al., "The 5'-End Sequence of the Murine Coronavirus Genome: Implications of Multiple Fusion Sites in Leader-Primed Transcription". Virology, vol. 156, 1987, pp. 321-330.

Shin et al., "Assessment of Porcine Reproductive and Respiratory Syndrome Virus RNA Load in Sera and Tissues during Acute Infection". Journal of Veterinary Science, vol. 3, No. 2, 2002, pp. 75-85.

Shope et al., "The Susceptibility of Swine to the Virus of Human Influenza". Annual Meeting of the Society of American Bacteriologists in New York, 1936, pp. 791-801.

Shortridge et al., "Geographical Distribution of Swine (HSw1N1) and Hong Kong (H3N2) Influenza Virus Variants in Pigs in Southeast Asia". Intervirology, vol. 11, No. 1, 1979, pp. 9-15.

Skiadopoulos et al., "Identification of Mutations Contributing to the Temperature-Sensitive, Cold-Adapted, and Attenuation Phenotypes of the Live-Attenuated Cold-Passage 45 (cp45) Human Parainfluenza Virus 3 Candidate Vaccine". Journal of Virology, vol. 73, No. 2, Feb. 1999, pp. 1374-1381.

Smith et al., "Isolation of Swine Influenza Virus from Autopsy Lung Tissue of Man". New England Journal of Medicine, vol. 294, Mar. 1976, pp. 708-710.

Smith et al., "San Miguel Sea Lion Virus Isolation, Preliminary Characterization and Relationship to Vesicular Exanthema of Swine Virus". Nature, vol. 244, Jul. 1973, pp. 108-110.

Snijder et al., "A 3'-Coterminal Nested Set of Independently Transcribed mRNAs Is Generated during Berne Virus Replication". Journal of Virology, vol. 64, No. 1, Jan. 1990, pp. 331-338.

Snijder et al., "Identification of a Novel Structural Protein of Arteriviruses". Journal of Virology, vol. 73, No. 8, Aug. 1999, pp. 6335-6345.

Snijder et al., "Non-structural proteins 2 and 3 interact to modify host cell membranes during the formation of the arterivirus replication complex". Journal of General Virology, vol. 83, 2001, pp. 985-994.

Snijder et al., "Proteolytic Processing of the Replicase ORF1a Protein of Equine Arteritis Virus". Journal of Virology, vol. 68, No. 9, Sep. 1994, pp. 5755-5764.

Snijder et al., "The carboxyl-terminal part of the putative Berne virus polymerase is expressed by ribosomal frameshifting and contains sequence motifs which indicate that toro- and coronaviruses are evolutionarily related". Nucleic Acids Research, vol. 18, No. 15, Aug. 1990, pp. 4535-4542.

Snijder et al., "The molecular biology of arteriviruses". Journal of General Virology, vol. 79, 1998, pp. 961-979.

Snijder et al., "Toroviruses: replication, evolution and comparison with other members of the coronavirus-like superfamily". Journal of General Virology, vol. 74, 1993, pp. 2305-2316.

Spaan et al., "Coronaviruses: Structure and Genome Expression". Journal of General Virology, vol. 69, 1988, pp. 2939-2952.

Stephen et al., "Swine Influenza Virus Vaccine: Potentiation in Rhesus Monkeys in Antibody Responses by a Nuclease Resistant Derivative of Ply I-Poly C". U.S. Army Medical Research Institute of Infectious Diseases, Fort Detrick, Frederick, MD 21701, 1976, 10 pages.

Stephen et al., "Swine influenza virus vaccine: potentiation of antibody responses in rhesus monkeys". Science, vol. 197, No. 4310, 1977, pp. 1289-1290.

Stevenson et al., "Endemic Porcine Reproductive and Respiratory Syndrome Virus Infection of Nursery Pigs in Two Swine Herds without Current Reproductive Failure". Journal of Veterinary Diagnostic Investigation, vol. 5, 1993, pp. 432-434.

Stim, T.B., "Arbovirus Plaquing in Two Simian Kidney Cell Lines". Journal of General Virology, vol. 5, No. 3, Oct. 1969, pp. 329-338.

Suarez et al., "Direct detection of the porcine reproductive and respiratory syndrome (PRRS) virus by reverse polymerase chain reaction (RT-PCR)". Archives of Virology, vol. 135, No. 1-2, 1994, pp. 89-99.

(56) References Cited

OTHER PUBLICATIONS

NCBI: Accession No. AF159149. "Porcine reproductive and respiratory syndrome virus isolate MLV RespPRRS/Repro, complete genome." Aug. 28, 2000.
NCBI: Accession No. AF176348. "Porcine reproductive and respiratory syndrome virus isolate PA8 complete genome." Sep. 3, 2002.
NCBI: Accession No. AF184212. "Porcine reproductive and respiratory syndrome virus strain SP, complete genome." Sep. 28, 2000.
NCBI: Accession No. AF325691. "Porcine reproductive and respiratory syndrome virus isolate NVSL 977985 IA 1-4-2, complete genome." Feb. 11, 2001.
NCBI: Accession No. AF331831. "Porcine reproductive and respiratory syndrome virus BJ-4, complete genome." Jan. 15, 2001.
NCBI: Accession No. M96262. "Lelystad virus, complete genome." Nov. 8, 2000.
NCBI: Accession No. M96262.2. "Lelystad virus, complete genome." Nov. 8, 2000.
NCBI: Accession No. NC_001639. Lactate dehydrogenase-elevating virus, complete genome. Dec. 8, 2008.
NCBI: Accession No. NC_001961. "Porcine reproductive and respiratory syndrome virus, complete genome." Jan. 12, 2004.
NCBI: Accession No. NC_002533. "Lelystad virus, complete genome." Nov. 11, 2000.
NCBI: Accession No. NC_002534. "Lactate dehydrogenase-elevating virus, complete genome." Dec. 29, 2003.
NCBI: Accession No. U15146. "Lactate dehydrogenase-elevating virus Plagemann strain, complete genome." Jan. 26, 1996.
NCBI: Accession No. U87392 AF030244 000153. "Porcine reproductive and respiratory syndrome virus strain VR-2332, complete genome." Nov. 17, 2000.
Nelsen et al., "Porcine Reproductive and Respiratory Syndrome Virus Comparison: Divergent Evolution on Two Continents". Journal of Virology, vol. 73, No. 1, Jan. 1999, pp. 270-280.
Nelson et al., "Differentiation of U.S. and European Isolates of Porcine Reproductive and Respiratory Syndrome Virus by Monoclonal Antibodies". Journal of Clinical Microbiology, vol. 31, No. 12, Dec. 1993, pp. 3184-3189.
Nelson et al., "High affinity interaction between nucleocapsid protein and leader/intergenic sequence of mouse hepatitis virus RNA". Journal of General Virology, vol. 81, 2000, pp. 181-188.
Nielsen et al., "Generation of an Infectious Clone of VR-2332, a Highly Virulent North American-Type Isolate of Porcine Reproductive and Respiratory Syndrome Virus". Journal of Virology, vol. 77, No. 6, Mar. 2003, pp. 3702-3711.
Nishimura et al., "Replication and Synthesis of Japanese Encephalitis Virus Ribonucleic Acids in Vero Cells". Japanese Journal of Microbiology, vol. 15, No. 4, 1971, pp. 309-316.
Nodelijk et al., "A quantitative assessment of the effectiveness of PRRSV vaccination in pigs under experimental conditions". Vaccine, vol. 19, 2000, pp. 3636-3644.
Nuttall, P.A., "Growth Characteristics of Two Strains of Bovine Virus Diarrhoea Virus". Archives of Virology, vol. 66, 1980, pp. 365-369.
Office Action in CA 2,650,236 dated Feb. 9, 2011.
Oirschot et al., "Development of an ELISA for detection of antibodies to glycoprotein I of Aujeszky's disease virus: a method for the serological differentiation between infected and vaccinated pigs". Journal of Virological Methods, vol. 22, 1988, pp. 191-206.
Ojeh et al., "Isolation, characterisation and serial propagation of a Nigerian strain of porcine group A rotavirus in a monkey kidney cell line (MA104)". Discovery and Innovation, vol. 8, No. 2, Jun. 1996, pp. 159-164.
Oleksiewicz et al., "Epitope Mapping Porcine Reproductive and Respiratory Syndrome Virus by Phage Display: the nsp2 Fragment of the Replicase Polyprotein Contains a Cluster of B-Cell Epitopes". Journal of Virology, vol. 75, No. 7, Apr. 2001, pp. 3277-3290.
Oleksiewicz et al., "Semen from Boars Infected with Porcine Reproductive and Respiratory Syndrome Virus (PRRSV) Contains Antibodies Against Structural as Well as Nonstructural Viral Proteins". Veterinary Microbiology, vol. 81, 2001, pp. 109-125.
Olsthoorn et al., "A conformational switch at the 3' end of a plant virus RNA regulates viral replication". The EMBO Journal, vol. 18, No. 17, 1999, pp. 4856-4864.
Opriessnig et al., "Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and Two Recent Field Isolates of PRRSV". Journal of Virology, vol. 76, No. 23, Dec. 2002, pp. 11837-11844.
Opriessnig et al., "Use of an Experimental Model to Test the Efficacy of Planned Exposure to Live Porcine Reproductive and Respiratory Syndrome Virus". Clinical and Vaccine Immunology, vol. 14, No. 12, Dec. 2007, pp. 1572-1577.
Ostrowski et al., "Identification of Neutralizing and Nonneutralizing Epitopes in the Porcine Reproductive and Respiratory Syndrome Virus GP5 Ectodomain". Journal of Virology, vol. 76, No. 9, May 2002, pp. 4241-4250.
Pan et al., "Replication of African swine fever virus in cell cultures". American Journal of Veterinary Research, vol. 41, No. 9, Sep. 1980, pp. 1357-1367.
Parratt et al., "Radioimmunoassay of Antibody and its Clinical Applications". John Wiley & Sons, Chichester, 1982, p. 43.
Parsley et al., "Poly (rC) binding protein 2 forms a ternary complex with the 5'-terminal sequences of poliovirus RNA and the viral 3CD proteinase". RNA, vol. 3, 1997, pp. 1124-1134.
Patriarca, et al., "Lack of Significant Person-to-Person Spread of Swine Influenza-Like Virus Following Fatal Infection in an Immunocomprised Child". American Journal of Epidemiology, vol. 119, No. 2, 1984, pp. 152-158.
Paul et al., "Porcine Reproductive and Respiratory Syndrome: An Overview". Journal of Clinical Veterinary Medicine, vol. 11, No. 12, Nov. 1993, pp. 1-16.
Pearson et al., "Improved tools for biological sequence comparison". Proceedings of the National Academy of Sciences, vol. 85, Apr. 1988, pp. 2444-2448.
Pedersen et al., "Open Reading Frame 1a-Encoded Subunits of the Arterivirus Replicase Induce Endoplasmic Reticulum-Derived Double-Membrane Vesicles Which Carry the Viral Replication Complex". Journal of Virology, vol. 73, No. 3, Mar. 1999, pp. 2016-2026.
Pejsak et al., "Clinical signs and economic losses caused by porcine reproductive and respiratory syndrome virus in a large breeding farm". Veterinary Microbiology, vol. 44, 1997, pp. 317-322.
Peng et al., "Analysis of Second-Site Revertants of a Murine Coronavirus Nucleocapsid Protein Deletion Mutant and Construction of Nucleocapsid Protein Mutants by Targeted RNA Recombination". Journal of Virology, vol. 69, No. 6, Jun. 1995, pp. 3449-3457.
Penzes et al., "Characterization of a Replicating and Packaged Defective RNA of Avian Coronavirus Infectious Bronchitis Virus". vol. 203, No. 2, Sep. 1994, pp. 286-293.
Percy et al., "Expression of a Foreign Protein by Influenza A Virus". Journal of Virology, vol. 68, No. 7, Jul. 1994, pp. 4486-4492.
Pesch et al., "New insights into the genetic diversity of European porcine reproductive and respiratory syndrome virus (PRRSV)". Veterinary Microbiology, vol. 107, 2005, pp. 31-48.
Pirtle et al., "Morphologic Heterogeneity of a Strain of Swine Influenza Virus (A/Swine/Wisconsin/1/68, Hsw1N1) Propagated at Different Temperatures". American Journal of Veterinary Research, vol. 36, No. 1, 1975, pp. 1783-1787.
Plagemann et al., "Lactate Dehydrogenase-Elevating Virus, Equine Arteritis Virus, and Simina Hemorrhagic Fever Virus: A New Group of Positive-Strand RNA Viruses". Advances in Virus Research, vol. 41, 1991, pp. 99-192.
Pol et al., "Pathological, ultrastructural, immunohistochemical changes caused by Lelystad virus in experimentally induced infections of mystery swine disease (synonym: porcine epidemic abortion and respiratory syndrome (PEARS))". Veterinary Quarterly, vol. 13, No. 3, Jul. 1991, pp. 137-143.
Polson et al., "An evaluation of the financial impact of Porcine Reproductive and Respiratory Syndrome (PRRS) in nursery pigs". Proceedings of the 13th International Pig Veterinary Society Congress, Jun. 1994, p. 31.
Polson et al., "Financial Implications of Mystery Swine Disease (MSD)". 1993, pp. 8-28.

(56) References Cited

OTHER PUBLICATIONS

Polson, DD, "Answers to Your Questions on PRRS". NOBL Laboratories, 1993, 18 pages.

Polson, DD, "RespPRRS a PRRS Vaccine Review", NOBL Laboratories, 1993, 22 pages.

Porcine Reproductive and Respiratory Syndrome: A Report on the Seminar Held in Brussels on Nov. 4-5, 1991 and Organized by the European Commission.

Poser, C.M., "Swine Influenza Vaccination: Truth and Consequences". Archives of Neurology, vol. 42, No. 11, 1985, pp. 1090-1092.

Meng et al., "Characterization of a High-Virulence US Isolate of Porcine Reproductive and Respiratory Syndrome Virus in a Continuous Cell Line, ATCC CRL11171". Journal of Veterinary Diagnostic Investigation, vol. 8, No. 3, Jul. 1996, pp. 374-381.

Meng et al., "Molecular cloning and nucleotide sequencing of the 3'-terminal genomic RNA of the porcine reproductive and respiratory syndrome virus". Journal of General Virology, vol. 75, 1994, pp. 1795-1801.

Meng et al., "Phylogenetic analyses of the putative M (ORF 6) and N (ORF 7) genes of porcine reproductive and respiratory syndrome virus (PRRSV): implication for the existence of two genotypes of PRRSV in the U.S.A. and Europe". Archives of Virology, vol. 140, No. 4, 1995, pp. 745-755.

Meng, X.J., "Heterogeneity of porcine reproductive and respiratory syndrome virus: implications for current vaccine efficacy and future vaccine development". Veterinary Microbiology, vol. 74, 2000, pp. 309-329.

Mengeling et al., "An update of research at the National Animal Disease Center on current field strains of Porcine Reproductive and Respiratory Syndrome (PRRS) virus". Allen D. Leman Swine Conference, 1997, pp. 138-145.

Mengeling et al., "Clinical consequences of exposing pregnant gilts to strains of porcine reproductive and respiratory syndrome (PRRS) virus isolated from field cases of "atypical" PRRS". American Journal of Veterinary Research, vol. 59, No. 12, Dec. 1998, pp. 1540-1544.

Mengeling et al., "Clinical Effects of porcine reproductive and respiratory syndrome virus on pigs during the early postnatal interval". American Journal of Veterinary Research, vol. 59, No. 1, Jan. 1998, pp. 52-55.

Mengeling et al., "Comparative safety and efficacy of attenuated single-strain and multi-strain vaccines for porcine reproductive and respiratory syndrome". Veterinary Microbiology, vol. 93, 2003, pp. 25-38.

Mengeling et al., "Comparison among strains of porcine reproductive and respiratory syndrome virus for their ability to cause reproductive failure". American Journal of Veterinary Research, vol. 57, No. 6, Jun. 1996, pp. 834-839.

Mengeling et al., "Mystery Pig Disease: Evidence and Considerations for its Etiology". Proceedings of the Mystery Swine Disease Committee Meeting, Oct. 6, 1990, Denver, Colorado, Livestock Conservation Institute, Madison, WI, USA, pp. 88-90.

Mengeling et al., "Strain specificity of the immune response of pigs following vaccination with various strains of porcine reproductive and respiratory syndrome virus". Veterinary Microbiology, vol. 93, 2003, pp. 13-24.

Meredith, MJ, "Porcine Reproductive and Respiratory Syndrome (PRRS)", Pig Disease Information Center, 1st North American Edition, University of Cambridge, Aug. 1994, pp. 1-57.

Mettenleiter et al., "Isolation of a viable herpesvirus (pseudorabies virus) mutant specifically lacking all four known nonessential glycoproteins". Virology, vol. 179, No. 1, Nov. 1990, pp. 498-503.

Meulenberg et al., "An infectious cDNA clone of Porcine Reproductive and Respiratory Syndrome Virus". Coronaviruses and Arteriviruses (Advances in Experimental Medicine and Biology, vol. 440), Ch. 24, 1998, pp. 199-206.

Meulenberg et al., "Characterization of Proteins Encoded by ORFs 2 to 7 of Lelystad Virus". Virology, vol. 206, No. 1, Jan. 1995, pp. 155-163.

Meulenberg et al., "Identification and Characterization of a Sixth Structural Protein of Lelystad Virus: The Glycoprotein GP2Encoded by ORF2 Is Incorporated in Virus Particles". Virology, vol. 225, No. 1, Nov. 1996, pp. 44-51.

Meulenberg et al., "Infectious Transcripts from Cloned Genome-Length cDNA of Porcine Reproductive and Respiratory Syndrome Virus". Journal of Virology, vol. 72, No. 1, Jan. 1998, pp. 380-387.

Meulenberg et al., "Lelystad Virus, the Causative Agent of Porcine Epidemic Abortion and Respiratory Syndrome (PEARS), is Related to LDV and EAV". Virology, vol. 192, 1993, pp. 62-72.

Meulenberg et al., "Localization and Fine Mapping of Antigenic Sites on the Nucleocapsid Protein N of Porcine Reproductive and Respiratory Syndrome Virus with Monoclonal Antibodies". Virology, vol. 252, 1998, pp. 106-114.

Meulenberg et al., "Molecular characterization of Lelystad virus". Veterinary Microbiology, vol. 55, 1997, pp. 197-202.

Meulenberg et al., "Nucleocapsid Protein N of Lelystad Virus: Expression by Recombinant Baculovirus, Immunological Properties, and Suitability for Detection of Serum Antibodies". Clinical and Diagnostic Laboratory Immunology, vol. 2, No. 6, Nov. 1995, pp. 652-656.

Meulenberg et al., "Posttranslational Processing and Identification of a Neutralization Domain of the GP4 Protein Encoded by ORF4 of Lelystad Virus". Journal of Virology, vol. 71, No. 8, Aug. 1997, pp. 6061-6067.

Meulenberg et al., "Subgenomic RNAs of Lelystad virus contain a conserved leader-body junction sequence". Journal of General Virology, vol. 74, 1993, pp. 1697-1701.

Molenkamp et al., "Isolation and Characterization of an Arterivirus Defective Interfering RNA Genome". Journal of Virology, vol. 74, No. 7, 2000, pp. 3156-3165.

Molenkamp et al., "The arterivirus replicase is the only viral protein required for genome replication and subgenomic mRNA transcription". Journal of General Virology, vol. 81, No. 10, 2000, pp. 2491-2496.

Montagnon, B.J., "Polio and rabies vaccines produced in continuous cell lines: a reality for Vero cell line". Dev Biol Stand., vol. 70, 1989, pp. 27-47.

Moore, C., "Porcine Proliferative and Necrotyzing Pneumonia Clinical Findings". Presented at American Association of Swine Practitioners, 22nd Annual Meeting, Mar. 3-5, 1991, pp. 443-453.

Moormann et al., "Hog cholera virus: identification and characterization of the viral RNA and the virus specific RNA synthesized in infected swine kidney cells". Virus Research, vol. 11, 1988, pp. 281-291.

Moormann et al., "Infectious RNA Transcribed from an Engineered Full-Length cDNA Template of the Genome of a Pestivirus". Journal of Virology, vol. 70, No. 2, Feb. 1996, pp. 763-770.

Moormann et al., "Molecular cloning and nucleotide sequence of hog cholera virus strain brescia and mapping of the genomic region encoding envelope protein E1". Virology, vol. 177, No. 1, Jul. 1990, pp. 184-198.

Morin et al., "Severe proliferative and necrotizing pneumonia in pigs: A newly recognized disease". Canadian Veterinary Journal, vol. 31, Dec. 1990, pp. 837-839.

Morozov et al., "Sequence analysis of open reading frames (ORFs) 2 to 4 of a U.S. isolate of porcine reproductive and respiratory syndrome virus". Archives of Virology, vol. 140, No. 7, 1995, pp. 1313-1319.

Morrison et al., "Brief Communications Serologic evidence incriminating a recently isolated virus (ATCC VR-2332) as the cause of swine infertility and respiratory syndrome (SIRS)". Journal of Veterinary Diagnostic Investigation, vol. 4, No. 2, Apr. 1992, pp. 186-188.

Morrison et al., "Sero-epidemiologic Investigation of Swine Infertility and Respiratory Syndrome (SIRS)". 72st Annual Meeting of the Conference of Research Workers in Animal Disease, Chicago, IL, Nov. 11-12, 1991, p. 55, Abstract No. 309.

Mountz et al., "The in vivo generation of murine IgD-secreting cells is accompanied by deletion of the Cμ gene and occasional deletion of the gene for the Cd1 domain". The Journal of Immunology, vol. 145, No. 5, Sep. 1990, pp. 1583-1591.

(56) References Cited

OTHER PUBLICATIONS

Mukamoto et al., "Immunogenicity in Aujeszky's disease virus structural glycoprotein gVI (gp50) in swine". Veterinary Microbiology, vol. 29, No. 2, Oct. 1991, pp. 109-121.
Murakami, et al., "Difference in growth behavior of human, swine, equine, and avian influenza viruses at a high temperature". Archives of Virology, vol. 100, Nos. 3-4, 1988, pp. 231-244.
Murphy et al., "Immunization Against Virus" in Virology, 2nd Edition, vol. 1, Fields, et al., eds. Raven Press, NY, 1990, pp. 469-502.
Murphy et al., "Virus Taxonomy". Chapter 2 in Fields Virology, 2nd. Edition, Fields, et al., eds, Raven Press, New York, 1990, pp. 9-35.
Murtaugh et al., "Comparison of the structural protein coding sequences of the VR-2332 and Lelystad virus strains of the PRRS virus". Archives of Virology, vol. 140, No. 8, 1995, pp. 1451-1460.
Murtaugh et al., "Genetic Variation in the PRRS Virus". Coronaviruses and Arteriviruses, Plenum Press, New York, 1998, pp. 787-794.
Murtaugh et al., "Immunological Responses of Swine to Porcine Reproductive and Respiratory Syndrome Virus Infection". Viral Immunology, vol. 15, No. 4, 2002, pp. 533-547.
Murtaugh et al., "Role of Viral Proteases in PRRS Immunity, Project Period Sep. 1, 1997-Dec. 31, 2002, no cost extension Jan. 1, 2003-Jun. 30, 2003". Final Report: Aug. 30, 2003, Department of Veterinary Pathology, University of Minnesota, St. Paul, MN and Boehringer Ingelheim Vetmedica, Inc., Ames, IA, 2003, pp. 1-38.
Murtaugh, "Allen D Lehman Swine Conference: the Evolution of the Swine veterinary profession: The PRRS Virus". University of Minnesota, Veterinary Continuing Education and Extension, vol. 20, 1993, pp. 43-47.
Myers et al., "Propagation of avian rotavirus in primary chick kidney cell and MA104 cell cultures". Avian Diseases, vol. 33, No. 3, Jul.-Sep. 1989, pp. 578-581.
Nakamura et al., "Studies on Swine Influenza III. Propagation of Swine Influenza Virus in Explants of Respiratory Tract Tissues from Fetal Pigs". The Cornell Veterinarian, vol. LX, No. 1, Jan. 1970, pp. 27-35.
Narayanan et al., "Characterization of the Coronavirus M Protein and Nucleocapsid Interaction in Infected Cells". Journal of Virology, vol. 74, No. 17, Sep. 2000, pp. 8127-8134.
NCBI: Accession No. AE005172. "Arabidopsis thaliana chromosome 1, top arm complete sequence." Dec. 14, 2000.
NCBI: Accession No. AF046869. "Porcine reproductive and respiratory syndrome virus isolate 16244B, Feb. 18, 1997 (Nebraska) pass.3, complete genome." Mar. 17, 1999.
NCBI: Accession No. AF066183. "Porcine reproductive and respiratory syndrome virus RespPRRS MLV, complete genome." Feb. 22, 2001.
Wesley et al., "Differentiation of a porcine reproductive and respiratory syndrome virus vaccine strain from North American field strains by restrction fragment length polymorphism analysis of ORF 5". Journal of Veterinary Diagnostic Investigation, vol. 10, 1998, pp. 140-144.
Buddaert et al., "In Vivo and In Vitro Interferon (IFN) Studies with the Porcine Reproductive and Respiratory Syndrome Virus (PRRSV)". Coronaviruses and Arteriviruses: Advances in Experimental Medicine and Biology, vol. 440, Plenum Press, New York, 1998, pp. 461-467.
Haller et al., "The Interferon Response Circuit in Antiviral Host Defense". Verh. K. Acad. Geneeskd. Belg., vol. 71, 2009, pp. 73-86.
Shi et al., "Porcine reproductive and respiratory syndrome virus (PRRSV) could be sensed by professional beta interferon-producing system and had mechanisms to inhibit this action in MARC-145 cells". Virus Research, vol. 153, 2010, pp. 151-156.
Suarez et al., "Phylogenetic relationships of European strains of porcine reproductive and respiratory syndrome virus (PRRSV) inferred from DNA sequences of putative ORF-5 and ORF-7 genes". Virus Research, vol. 42, Nos. 1-2, Jun. 1996, pp. 159-165.
Sumiyoshi et al., "Infectious Japanese Encephalitis Virus RNA Can Be Synthesized from In Vitro-Ligated cDNA Templates". Journal of Virology, vol. 66, No. 9, Sep. 1992, pp. 5425-5431.

Tahara et al., "Coronavirus Translational Regulation: Leader Affects mRNA Efficiency". Virology, vol. 202, No. 1, Aug. 1994, pp. 621-630.
Tao et al., "Host Range Restriction of Parainfluenza Virus Growth Occurs at the Level of Virus Genome Replication". Virology, vol. 220, 1996, pp. 69-77.
Tauraso et al., "Simian Hemorrhagic Fever: III. Characterization of a Viral Agent". The American Journal of Tropical Medicine and Hygiene, vol. 17, No. 3, May 1968, pp. 422-431.
Terpstra et al., "Experimental reproduction of porcine epidemic abortion and respiratory syndrome (mystery swine disease) by infection with Lelystad virus: Koch's postulates fulfilled". The Veterinary Quarterly, vol. 13, No. 3, Jul. 1991, pp. 131-136.
Thacker, B., "Clinical Manifestations of PRRS Virus". 2003 PRRS Compendium: Second Edition, National Pork Board, Des Moines, IA, 2003, pp. 7-15.
Thanawongnuwech et al., "Effects of Low (Modified-live Virus Vaccine) and High (VR-2385)-Virulence Strains of Porcine Reproductive and Respiratory Syndrome Virus on Pulmonary Clearance of Copper Particles in Pigs". Veterinary Pathology, vol. 35, 1998, pp. 398-406.
Theil et al., "Isolation and Serial Propagation of Turkey Rotaviruses in a Fetal Rhesus Monkey Kidney (MA104) Cell Line". Avian Diseases, vol. 30, No. 1, 1985, pp. 93-104.
Theil et al., "Partial characterization of a bovine group A rotavirus with a short genome electropherotype". Journal of Clinical Microbiology, vol. 26, No. 6, Jun. 1988, p. 1094-1099.
Thomson et al., "Ontario. Proliferative and necrotizing pneumonia (PNP) of swine: the Ontario situation". Canadian Veterinary Journal, vol. 32, May 1991, p. 313.
Thouless et al., "Isolation of two lapine rotaviruses: Characterization of their subgroup, serotype and RNA electropherotypes". Archives of Virology, vol. 89, Nos. 1-4, 1986, pp. 161-170.
Tian et al. "Emergence of Fatal PRRSV Variants: Unparalleled Outbreaks of Atypical PRRS in China and Molecular Dissection of the Unique Hallmark". PLoS One, vol. 2, No. 6, e526, 2007, pp. 1-10.
Timony, P.J. "Equine Viral Arteritis", Manual of Standards for Diagnostic Tests and Vaccines, 1992, pp. 493-500.
Tobita et al., "Plaque Assay and Primary Isolation of influenza A Viruses in an Established Line of Canine Kidney Cells (MDCK) in the Presence of Trypsin". Medical Microbiology and Immunology, vol. 162, No. 1, Dec. 1975, pp. 9-14.
Todd et al., "Development of an adjuvant-active nonionic block copolymer for use in oil-free subunit vaccines formulations". Vaccine, vol. 15, No. 5, 1997, pp. 564-570.
Travassos et al., "Carajas and Maraba Viruses, Two New Vesiculoviruses Isolated from Phlebotomine Sand Flies in Brazil". American Journal of Tropical Medicine and Hygiene, vol. 33, No. 5, Sep. 1984, pp. 999-1006.
Tsunemitsu et al., "Isolation, characterization, and serial propagation of a bovine group C rotavirus in a monkey kidney cell line (MA104)". Journal of Clinical Microbiology, vol. 29, No. 11, Nov. 1991, pp. 2609-2613.
Ulmer et al., "Enhancement of DNA vaccine potency using conventional aluminum adjuvants". Vaccine, vol. 18, 2000, pp. 18-28.
Urasawa et al., "Sequential Passages of Human Rotavirus in MA-104 Cells". Microbiology and Immunology, vol. 25, No. 10, 1981, pp. 1025-1035.
Van Alstine, W.G., "Mystery Swine Disease in the United States". The New Pig Disease: Porcine Respiration and Reproductive Syndrome. A Report on the Seminar/Workshop Held in Brussels by the European Commission (Directorate-General for Agriculture), Apr. 29-30, 1991, pp. 65-70.
Van Alstine, W.G., "Past Diagnostic Approaches and Findings and Potentially Useful Diagnostic Strategies". Proceedings Mystery Swine Disease Committee Meeting, Oct. 6, 1990, pp. 52-58.
Van Berlo et al., "Equine Arteritis Virus-Infected Cells Contain Six Polyadenylated Virus-Specific RNAs". Virology, vol. 118, 1982, pp. 345-352.
Van Der Linden et al., "Virological kinetics and immunological responses to a porcine reproductive and respiratory syndrome virus infection of pigs at different ages". Vaccine, vol. 21, 2003, pp. 1952-1957.

(56) References Cited

OTHER PUBLICATIONS

Van Der Meer et al., "ORF1a-Encoded Replicase Subunits Are Involved in the Membrane Association of the Arterivirus Replication Complex". Journal of Virology, vol. 72, No. 8, 1998, pp. 6689-6698.
Van Der Most et al., "A Domain at the 3' End of the Polymerase Gene Is Essential for Encapsidation of Coronavirus Defective Interfering RNAs". Journal of Virology, vol. 65, No. 6, Jun. 1991, pp. 3219-3226.
Van Dinten et al., "An infectious arterivirus cDNA clone: Identification of a replicase point mutation that abolished discontinuous mRNA transcription". Proceedings of the National Academy of Sciences, vol. 94, Feb. 1997, pp. 997-996.
Van Dinten et al., "Processing of the Equine Arteritis Virus Replicase ORF1b Protein: Identification of Cleavage Products Containing the Putative Viral Polymerase and Helicase Domains". Journal of Virology, vol. 70, No. 10, Oct. 1996, pp. 6625-6633.
Van Dinten et al., "Proteolytic Processing of the Open Reading Frame 1b-Encoded Part of Arterivirus Replicase Is Mediated by nsp4 Serine Protease and Is Essential for Virus Replication". Journal of Virology, vol. 73, No. 3, Mar. 1999, pp. 2027-2037.
Van Marle et al., "Arterivirus discontinuous mRNA transcription is guided by base pairing between sense and antisense transcription-regulating sequences". Proceedings of the National Academy of Sciences, vol. 96, 1999, pp. 12056-12061.
Van Marle et al., "Characterization of an Equine Arteritis Virus Replicase Mutant Defective in Subgenomic mRNA Synthesis". Journal of Virology, vol. 73, No. 7, Jul. 1999, pp. 5274-5281.
Van Marle et al., "Regulation of Coronavirus mRNA Transcription". Journal of Virology, vol. 69, No. 12, Dec. 1995, pp. 7851-7856.
Van Nieuwstadt et al., "Infection with porcine respiratory coronavirus does not fully protect pigs against intestinal transmissable gastroenteritis virus". The Veterinary Record, vol. 125, No. 3, 1989, pp. 58-60.
Van Nieuwstadt et al., "Proteins Encoded by Open Reading Frames 3 and 4 of the Genome of Lelystad Virus (Arteriviridae) Are Structural Proteins of the Virion". Journal of Virology, vol. 70, No. 7, Jul. 1996, pp. 4767-4772.
Van Nieuwstadt et al., "Use of two enzyme-linked immunosorbent assays to monitor antibody responses in swine with experimentally induced infection with porcine epidemic diarrhea virus". American Journal of Veterinary Research, vol. 42, Jul. 1991, pp. 1044-1050.
Van Zijl et al., "Live Attenuated Pseudorabies Virus Expressing Envelope Glycoprotein E1 of Hog Cholera Virus Protects Swine Against Both Pseudorabies and Hog Cholera". Journal of Virology, vol. 65, No. 5, May 1991, pp. 2761-2765.
Vennema et al., "Nucleocapsid-independent assembly of coronavirus-like particles by co-expression of viral envelope protein genes". The EMBO Journal, vol. 15, No. 8, 1996, pp. 2020-2028.
Verheije et al., "Kissing Interaction between 3' Noncoding and Coding Sequences Is Essential for Porcine Arterivirus RNA Replication". Journal of Virology, vol. 76, No. 3, Feb. 2002, pp. 1521-1526.
Verheije et al., "Safety and protective efficacy of porcine reproductive and respiratory syndrome recombinant virus vaccines in young pigs". Vaccine, vol. 21, 2003, pp. 2556-2563.
Veterinary Bulletin, vol. 58, No. 11, 1988, Nos. 6903-6909, p. 932.
Veterinary Bulletin, vol. 60, No. 3, 1990, Nos. 1536-1551, pp. 255-256.
Vieira et al., "New pUC-derived cloning vectors with different selectable markers and DNA replication origins". Gene, vol. 100, 1991, pp. 189-194.
VIIIth International Symposium on Nidoviruses (Corona and Arteriviruses), May 20-25, 2000, 32 pages.
Visser, Nicolaas, "Declaration of Dr. N. Visser". Nov. 14, 1995, pp. 1-11.
Von Busse, F.W., Epidemiologic Studies on Porcine Reproductive and Respiratory Syndrome (PRRS). Tierarztliche Umschau, Dec. 1991, pp. 708-717 (Abstract in English p. 711).
Von Ohlinger et al., "Der Seuchenhafte Spatabort beim Schwein Ein Beitrag zur Atiologie des Porcine Reproductive and Respiratory Syndrome (PRRS)". Tierarztl, vol. 46, 1991, pp. 703-708.

Waltner-Toews et al., "A Field Trial to Evaluate the Efficacy of a Combined Rotavirus-Coronavirus/Escherichia coli vaccine in Dairy Cattle"., Canadian Journal of Comparative Medicine, vol. 49, No. 1, 1985, pp. 1-9.
Wang et al., "Attenuation of porcine reproductive and respiratory syndrome virus strain MN184 using chimeric construction with vaccine sequence". Virology, vol. 371, 2008, pp. 418-429.
Ward et al., "Efficiency of human rotavirus propagation in cell culture". Journal of Clinical Microbiology, vol. 19, No. 6, Jun. 1984, pp. 748-753.
Wardley et al., "The Host Response to African Swine Fever Virus". Progress of Medical Virology, vol. 34, 1987, pp. 180-192.
Tian et al., "An attenuated live vaccine based on highly pathogenic porcine reproductive and respiratory syndrome virus (HP-PRRSV) protects piglets against HP-PRRS". Veterinary Microbiology, vol. 138, 2009. pp. 34-40.
Zhou et al., "The 30-Amino-Acid Deletion in the Nsp2 of highly Pathogenic Porcine Reproductive and Respiratory Syndrome Virus Emerging in China is Not Related to Its Virulence". Journal of Virology, vol. 83, No. 10, May 2009, pp. 5156-5167.
Wang et al., "Immune responses in piglets infected with highly pathogenic porcine reproductive and respiratory syndrome virus". Veterinary Immunology and Immunopathology, vol. 142, 2011, pp. 170-178.
Yu et al., "Genomic Sequencing Reveals Mutations Potentially Related to the Overattenuation of a Highly Pathogenic Porcine Reproductive and Respiratory Syndrome Virus". Clinical and Vaccine Immunology, vol. 20, No. 4, Apr. 2013, pp. 613-619.
Chen et al., "Synthetic B- and T-cell epitope peptides of porcine reproductive and respiratory syndrome virus with Gp96 as adjuvant induced humoral and cell-mediated immunity". Vaccine, vol. 31, 2013, pp. 1838-1847.
Li et al., "Emergency vaccination alleviates highly pathogenic porcine reproductive and respiratory syndrome virus infection after contact exposure". BMC Veterinary Research, vol. 9, No. 26, 2013, pp. 1-6.
Liesner et al., "Efficacy of Ingelvac® PRRS MLV against highly pathogenic PRRSV: a summary of three challenge trials". Virology & Viral Diseases-PRRS, 22nd International Pig Veterinary Society Congress, Korea, 2012, p. 958.
Greiner et al., "Quantitative Effect of Porcine Reproductive Respiratory Syndrome Virus on Pig Growth and Immune Response"., 1999, Swine Research Report, Paper 5, 1998, 4 pages.
Halbur et al., "Variable Pathogenicity of Nine Porcine Reproductive and Respiratory Syndrome Virus (PRRSV) Isolates". Conference of Research Workers in Animal Diseases, Abstracts of Papers, Chicago, Illinois, paper #222, Nov. 1993.
Halbur et al., "Viral Pneumonia in Neonatal and Nursery pigs. Experimental Work with SIRS Agent and Evidence of Another New Viral Agent". Agri-Practice, vol. 12, No. 1, Jan.-Feb. 1991, pp. 23-34.
Hao et al., "Polymorphic genetic characterization of the ORF7 gene of porcine reproductive and respiratory syndrome virus (PRRSV) in China". Virology Journal, vol. 8, No. 73, 2011, pp. 1-9.
Harlow & Lane, Editors, "Antibodies, A Laboratory Manual". Cold Spring Harbor: Cold Spring Harbor Laboratory, New York, 1988, pp. 423, 464-468.
Haynes et al., "Temporal and Morphologic Characterization of the Distribution of Porcine Reproductive and Respiratory Syndrome Virus (PRRSV) by In Situ Hybridization in Pigs Infected with Isolates of PRRSV that Differ in Virulence". Veterinary Pathology, vol. 34, 1997, pp. 39-43.
Heath, et al., "The Behaviour of Some Influenza Viruses in Tissue Cultures of Kidney Cells of Various Species". Archiv. f. Virusforschung Bd. VIII, HS, 1958, pp. 577-591.
Hedger et al., "Swine Vesicular Disease Virus". Virus Infections of Porcines, Elsevier Science Publishers, B.V., 1989, pp. 241-250.
Hennen, J., "Statistical methods for longitudinal research on bipolar disorders". Bipolar Disorders, vol. 5, 2003, pp. 156-168.
Hill, Howard, "Overview and History of Mystery Swine". Proceedings of the Mystery Swine Disease Committee Meeting, Denver, CO, Oct. 6, 1990, pp. 29-40.

(56) References Cited

OTHER PUBLICATIONS

Hirsch et al., "Ultrastructure of Human Leukocytes After Simultaneous Fixation with Glutaraldehyde and Osmium Tetroxide and "Postfixation" in Uranyl Acetate". The Journal of Cell Biology, vol. 38, 1968, pp. 615-627.
Hofmann et al., "Propagation of the virus of porcine epidemic diarrhea in cell culture". Journal of Clinical Microbiology, vol. 26, No. 11, Nov. 1988, pp. 2235-2239.
Hofmann et al., "Quantitation, biological and physicochemical properties of cell culture-adapted porcine epidemic diarrhea coronavirus (PEDV)". Veterinary Microbiology, vol. 20, No. 2, Jun. 1989, pp. 131-142.
Honda et al., "A Serological Comparison of 4 Japanese Isolates of Porcine Enteroviruses with the International Reference Strains". The Japanese Journal of Veterinary Science, vol. 52, No. 1, 1990, pp. 49-54.
Horowitz et al., "Anti-schistosome monoclonal antibodies of different isotypes—correlation with cytotoxicity". The EMBO Journal, vol. 2, No. 2, 1983, pp. 193-198.
Horsfall et al., "General Principles of Animal Virus Multiplication". Viral and Rickettsial Infections of Man, Fourth Edition, J.B. Lippincott Company, Philadelphia, 1965, pp. 239-241.
Horzinek et al., "Studies on the Substructure of Togaviruses: II. Analysis of Equine Arteritis Rubella, Bovine Viral Diarrhea, and Hog Cholera Viruses". Archiv Für die gesamte Virusforschung, vol. 33, 1971, pp. 306-318.
Hoshino et al., "Isolation and characterization of an equine rotavirus". Journal of Clinical Microbiology, vol. 18, No. 3, Sep. 1983, pp. 585-591.
Hoshino et al., "Serotypic Similarity and Diversity of Rotaviruses of Mammalian and Avian Origin as Studied by Plaque-Reduction Neutralization". The Journal of Infectious Diseases, vol. 149, No. 5, May 1984, pp. 694-702.
Hsue et al., "Characterization of an Essential RNA Secondary Structure in the 3' Untranslated Region of the Murine Coronavirus Genome". Journal of Virology, vol. 74, No. 15, Aug. 2000, pp. 6911-6921.
Huang et al., "Polypyrimidine Tract-Binding Protein Binds to the Complementary Strand of the Mouse Hepatitis Virus 39 Untranslated Region, Thereby Altering RNA Conformation". Journal of Virology, vol. 73, No. 11, Nov. 1999, pp. 9110-9116.
Hurrelbrink et al., "Attenuation of Murray Valley Encephalitis Virus by Site-Directed Mutagenesis of the Hinge and Putative Receptor-Binding Regions of the Envelope Protein". Journal of Virology, vol. 75, No. 16, Aug. 2001, pp. 7692-7702.
Hwang et al., "A 68-Nucleotide Sequence within the 39 Noncoding Region of Simian Hemorrhagic Fever Virus Negative-Strand RNA Binds to Four MA104 Cell Proteins". Journal of Virology, vol. 72, No. 5, May 1998, pp. 4341-4351.
Hyllseth, B., "Structural Proteins of Equine Arteritis Virus". Archiv Für die gesamte Virusforschung, vol. 30, 1973, pp. 177-188.
Iltis et al., "Persistent Varicella-Zoster virus infection in a human rhabdomyosarcoma cell line and recovery of a plaque variant". Infection and Immunity, vol. 37, No. 1, Jul. 1982, pp. 350-358.
Imagawa et al., "Isolation of Foal Rotavirus in MA-104 Cells". Bulleting of Equine Research Institute, vol. 18, 1981, pp. 119-128.
Izeta et al., "Replication and Packaging of Transmissible Gastroenteritis Coronavirus-Derived Synthetic Minigenomes". Journal of Virology, vol. 73, No. 2, Feb. 1999, pp. 1535-1545.
Jackwood et al., "Replication of Infectious Bursal Disease Virus in Continuous Cell Lines". Avian Diseases, vol. 31, No. 2, Apr.-Jun. 1987, pp. 370-375.
Johnson et al., "Feline panleucopaenia virus. IV. Methods for obtaining reproducible in vitro results". Research in Veterinary Science, vol. 8, No. 2, Apr. 1967, pp. 256-264.
Johnson et al., "Pathogenic and humoral immune responses to porcine reproductive and respiratory syndrome virus (PRRSV) are related to viral load in acute infection". Veterinary Immunology and Immunopathology, vol. 102, No. 3, PRRS Immunology and Immunopathology Special Issue, Dec. 2004, pp. 233-247.
Johnston et al., "Genetic to genomic vaccination". Vaccine, vol. 15, No. 8, 1997, pp. 808-809.
Joo et al., "Encephalomyocarditis Virus As a Potential Cause for Mystery Swine Disease", Livestock Conservation Institute, Proceedings of the Mystery Swine Disease Committee Meeting, Denver, CO, Oct. 6, 1990, pp. 62-66.
Jun et al., "Comparison of Dynamics in Viremia Levels in Chickens Inoculated with Marek's Disease Virus Strains of Different Pathotypes". Virologica Sinica, vol. 16, No. 1, Mar. 2001, pp. 59-63.
Jusa et al., "Effect of heparin on infection of cells by porcine reproductive and respiratory syndrome virus". American Journal of Veterinary Research, vol. 58, No. 5, May 1997, pp. 488-491.
Just et al., "A/New Jersey/76 influenza vaccine trial in seronegative schoolchildren: Comparison of a subunit vaccine with a whole-virus vaccine". Medical Microbiology and Immunology, vol. 164, No. 4, 1978, pp. 277-284.
Kang et al., "Primary Isolation and Identification of Avian Rotaviruses from Turkeys Exhibiting Signs of Clinical Enteritis in a Continuous MA-104 Cell Line". Avian Diseases, vol. 30, 1986, pp. 494-499.
Kapur et al., "Genetic variation in porcine reproductive and respiratory syndrome virus isolates in the midwestern United States". Journal of General Virology, vol. 77, 1996, pp. 1271-1276.
Kasza et al., "Establishment, viral susceptibility and biological characteristics of a swine kidney cell line SK-6". Research in Veterinary Science, vol. 13, No. 1, Jan. 1972, pp. 46-51.
Kasza et al., "Isolation and Characterization of a Rotavirus from Pits". Veterinary Record, vol. 87, 1970, pp. 681-686.
Katz et al., "Antigenic differences between European and American isolates of porcine reproductive and respiratory syndrome virus (PRRSV) are encoded by the carboxyterminal portion of viral open reading frame 3". Veterinary Microbiology, vol. 44, No. 1, Apr. 1995, pp. 65-76.
Keffaber, K., "Reproductive Failure of Unknown Etiology"., AASP Newsletter, vol. 1, No. 2, Sep.-Oct. 1989, pp. 1, 4-5, 8-10.
Keffaber, K.K., "Swine Reproductive Failure of Unknown Etiology". The George A. Young Swine Conference & Annual Nebraska SPF Swine Conference, Aug. 13-14, 1990, pp. 55-67.
Key et al., "Genetic variation and phylogenetic analyses of the ORF5 gene of acute porcine reproductive and respiratory syndrome virus isolates". Veterinary Microbiology, vol. 83, 2001, pp. 249-263.
Kim et al., "Analysis of cis-Acting Sequences Essential for Coronavirus Defective Interfering RNA Replication". Virology, vol. 197, No. 1, Nov. 1993, pp. 53-63.
Kim et al., "Different Biological Characteristics of Wild-Type Porcine Reproductive and Respiratory Syndrome Viruses and Vaccine Viruses and Identification of the Corresponding Genetic Determinants". Journal of Clinical Microbiology, vol. 46, No. 5, May 2008, pp. 1758-1768.
Kim et al., "Enhanced replication of porcine reproductive and respiratory syndrome (PRRS) virus in a homogeneous subpopulation of MA-104 cell line". Archives of Virology, vol. 133, 1993, pp. 477-483.
Kimman et al., "Challenges for porcine reproductive and respiratory syndrome virus (PRRSV) vaccinology". Vaccine, vol. 27, No. 28, Jun. 2009, pp. 3704-3718.
Klein et al., "Deletion of the IgH enhancer does not reduce immunoglobulin heavy chain production of a hybridoma IgD class switch variant". The EMBO Journal, vol. 3, No. 11, Nov. 1984, pp. 2473-2476.
Klinge et al, "Age-dependent resistance to Porcine reproductive and respiratory syndrome virus replication in swine". Virology Journal, vol. 6, No. 177, Oct. 2009.
Klinge et al., "PRRSV replication and subsequent immune responses in swine of various ages". Abstract of Poster No. 56, International Porcine Reproductive and Respiratory Syndrome (PRRS) Symposium, PRRS and PRRSV-Related Diseases: Prevention and Control Strategies, Chicago, IL, Nov. 30-Dec. 1, 2007.
Klovins et al., "A Long-range Pseudoknot in Qb RNA is Essential for Replication". Journal of Molecular Biology, vol. 294, 1999, pp. 875-884.
Klump et al., "Complete Nucleotide Sequence of Infectious Coxsackievirus B3 cDNA: Two Initial 5' Uridine Residues Are

(56) References Cited

OTHER PUBLICATIONS

Regained during Plus-Strand RNA Synthesis". Journal of Virology, vol. 64, No. 4, Apr. 1990, pp. 1573-1583.
Klupp et al., "Sequence and expression of the glycoprotein gH gene of pseudorabies virus". Virology, vol. 182, No. 2, Jun. 1991, pp. 732-741.
Knowles et al., "Classification of porcine enteroviruses by antigenic analysis and cytopathic effects in tissue culture: Description of 3 new serotypes". Archives of Virology, vol. 62, No. 3, 1979, pp. 201-208.
Kolodziej et al., "Epitope tagging and protein surveillance". Methods in Enzymology, vol. 194, 1991, pp. 508-519.
Kouvelos et al., "Comparison of Bovine, Simian and Human Rotavirus Structural Glycoproteins". Journal of General Virology, vol. 65, Jul. 1984, pp. 1211-1214.
Kreutz, L.C., "Cellular membrane factors are the major determinants of porcine reproductive and respiratory syndrome virus tropism". Virus Research, vol. 53, 1998, pp. 121-128.
Kundin, W.D., "Hong Kong A-2 Influenza Virus Infection among Swine during a Human Epidemic in Taiwan". Nature, vol. 228, Nov. 1970, p. 857.
Kuo et al., "A Nested Set of Eight RNAs Is Formed in Macrophages Infected with Lactate Dehydrogenase-Elevating Virus", Journal of Virology, vol. 65, No. 9, Sep. 1991, pp. 5118-5123.
Kusanagi et al., "Isolation and Serial Propagation of Porcine Epidemic Diarrhea Virus in Cell Cultures and Partial Characterization of the Isolate". Journal of Veterinary Medical Science, vol. 54, No. 2, 1992, pp. 313-318.
Kutsuzawa et al., "Isolation of Human Rotavirus Subgroups 1 and 2 in Cell Culture". Journal of Clinical Microbiology, vol. 16, No. 4, Oct. 1982, pp. 727-730.
Kwang et al., "Cloning, expression, and sequence analysis of the ORF4 gene of the porcine reproductive and respiratory syndrome virus MN-1b". Journal of Veterinary Diagnostic Investigation, vol. 6, No. 3, Jul. 1994, pp. 293-296.
Labarque et al., "Effect of cellular changes and onset of humoral immunity on the replication of porcine reproductive and respiratory syndrome virus in the lungs of pigs". Journal of General Virology, vol. 81, 2000, pp. 1327-1334.
Labarque et al., "Respiratory tract protection upon challenge of pigs vaccinated with attenuated porcine reproductive and respiratory syndrome virus vaccines". Veterinary Microbiology, vol. 95, 2003, pp. 187-197.
Lai et al., "Coronavirus: how a large RNA viral genome is replicated and transcribed". Infectious Agents and Disease, vol. 3, Nos. 2-3, 1994, pp. 98-105.
Lai et al., "Coronavirus: organization, replication and expression of genome". Annual Review of Microbiology, vol. 33, 1990, pp. 303-333.
Lai et al., "Infectious RNA transcribed from stably cloned full-length cDNA of dengue type 4 virus". Proceedings of the National Academy of Sciences, vol. 88, Jun. 1991, pp. 5139-5143.
Lazar et al., "Transforming Growth Factor a: Mutation of Aspartic Acid 47 and Leucine 48 Results in Different Biological Activities". Molecular and Cellular Biology, vol. 8, No. 3, Marc. 1988, pp. 1247-1252.
Leitner et al., "DNA and RNA-based vaccines: principles, progress and prospects". Vaccine, vol. 18, 2000, pp. 765-777.
Levy et al., "Freeze-drying is an effective method for preserving infectious type C retroviruses". Journal of Virological Methods, vol. 5, Nos. 3-4, Nov. 1982, pp. 165-171.
Liljestrom et al., "A New Generation of Animal Cell Expression Vectors Based on the Semliki Forest Virus Replicon". Nature Biotechnology, vol. 9, 1991, pp. 1356-1361.
Lin et al., "Deletion Mapping of a Mouse Hepatitis Virus Defective Interfering RNA Reveals the Requirement of an Internal and Discontiguous Sequence fro Replication". Journal of Virology, vol. 67, No. 10, Oct. 1993, pp. 6110-6118.
Lin et al., "Identification of the cis-Acting Signal for Minus-Strand RNA Synthesis of a Murine Coronavirus: Implications for the Role of Minus-Strand RNA in RNA Replication and Transcription". Journal of Virology, vol. 68, No. 12, Dec. 1994, pp. 8131-8140.
Lin et al., "The 3' Untranslated Region of Coronavirus RNA Is Required for Subgenomic mRNA Transcription from a Defective Interfering RNA". Journal of Virology, vol. 70, No. 10, Oct. 1995, pp. 7236-7240.
Liu et al., "A Specific Host Cellular Protein Binding Element Near the 3? End of Mouse Hepatitis Virus Genomic RNA". Virology, vol. 232, No. 1, May 1997, pp. 74-85.
Loula, T., "Clinical Presentation of Mystery Pig Disease in the Breeding Herd and Suckling Piglets". Proceedings of the Mystery Swine Disease Committee Meeting, Denver, CO, Oct. 6, 1990, pp. 37-40.
Loula, T., "Mystery Pig Disease", Agri-Practice, vol. 12, No. 1, Jan.-Feb. 1991, pp. 29-34.
Luo et al., "Antiviral activity of type I and type III interferons against porcine reproductive and respiratory syndrome virus (PRRSV)". Antiviral Research, vol. 91, 2011, pp. 91-101.
Luytjes et al., "Replication of Synthetic Defective Interfering RNAs Derived from Coronavirus Mouse Hepatitis Virus-A59". Virology, vol. 216, No. 1, Feb. 1996, pp. 174-183.
Lv et al., "An infectious cDNA clone of a highly pathogenic porcine reproductive and respiratory syndrome virus variant associated with porcine high fever syndrome". Journal of General Virology, vol. 89, 2008, pp. 2075-2079.
Madec et al., "Consequences pathologiques d'un episode grippal severe (virus swine A/H1N1 dans les conditions naturelles chez la truie non immune en debut de gestation". Comparative Immunology, Microbiology and Infectious Diseases, vol. 12, Nos. 1-2, 1989, pp. 17-27.
Madin, S.H. "Vesicular Exanthema Virus". Virus Infections of Porcines, Elsevier Science Publishers B.V., 1989, pp. 267-271.
Makabe et al., "Hemagglutination with Ovine Rotavirus". Archives of Virology, vol. 90, 1986, pp. 153-158.
Makino et al., "Leader sequences of murine coronavirus mRNAs can be freely reassorted: Evidence for the role of free leader RNA in transcription". Proceedings of the National Academy of Sciences, vol. 83, Jun. 1986, pp. 4204-4208.
Makino et al., "Primary Structure and Translation of a Defective Interfering RNA of Murine Coronavirus". Virology, vol. 166, 1988, pp. 550-560.
Mardassi et al., "Identification of major differences in the nucleocapsid protein genes of a Québec strain and European strains of porcine reproductive and respiratory syndrome virus". vol. 75, No. 3, Mar. 1994, pp. 681-685.
Mardassi et al., "Molecular analysis of the ORFs 3 to 7 of porcine reproductive and respiratory syndrome virus, Québec reference strain". Archives of Virology, vol. 140, No. 8, 1995, pp. 1405-1418.
Mason, P.W., "Maturation of Japanese encephalitis virus glycoproteins produced by infected mammalian and mosquito cells". Virology, vol. 169, No. 2, Apr. 1989, pp. 354-364.
Masters et al., "Functions of the coronavirus nucleocapsid protein". Coronaviruses and Their Diseases, Plenum Press, New York, 1990, pp. 235-238.
Masurel, N., "Swine Influenza Virus and the Recycling of Influenza-A Viruses in Man". The Lancet, Jul. 31, 1976, pp. 244-247.
Matanin et al., "Purification of the major envelop protein GP5 of porcine reproductive and respiratory syndrome virus (PRRSV) from native virions". Journal of Virological Methods, vol. 147, 2008, pp. 127-135.
McAuliffe et al., "Codon Substitution Mutations at Two Positions in the L Polymerase Protein of Human Parainfluenza Virus Type 1 Yield Viruses with a Spectrum of Attenuation In Vivo and Increased Phenotypic Stability In Vitro". Journal of Virology, vol. 78, No. 4, Feb. 2004, pp. 2029-2036.
McCullough et al., "9. Experimental Transmission of Mystery Swine Disease", The New Pig Disease Porcine Respiration and Reproductive Syndrome, A report on the seminar/workshop held in Brussels on Apr. 29-30, 1991, pp. 46-52.
McDaniel, H.A., "African Swine Fever". Diseases of Swine, 5th Edition, Chapter 18, The Iowa State University Press, Ames, Iowa, 1981, pp. 237-245.

(56) References Cited

OTHER PUBLICATIONS

McFerran, J.B., "Reovirus Infection". Diseases of Swine, Fifth Edition, Chapter 28, The Iowa State University Press, Ames, Iowa, 1981, pp. 330-334.

McIntosh, "Diagnostic Virology". Fields Virology, Ch. 17, Second Edition, vol. 1, 1990, pp. 411-437.

McKinney, W.P., "Fatal Swine Influenza Pneumonia During Late Pregnancy". Archives of Internal Medicine, vol. 150, No. 1, Jan. 1990, pp. 213-215.

McQueen et al., "Influenza in animals". Advances in Veterinary Science, vol. 12, 1968, pp. 285-336.

Meikeljohn et al., "Respiratory Virus Vaccine Evaluation and Surveillance". Semi-Annual Contract Progress Report to the National Institute of Allergy and Infectious Diseases, Sep. 15, 1965 to Mar. 15, 1966, 21 pgs.

Melchers et al., "Cross-talk between orientation-dependent recognition determinants of a complex control RNA element, the enterovirus oriR". RNA, vol. 6, 2000, pp. 976-987.

Mendez et al., "Molecular Characterization of Transmissible Gastroenteritis Coronavirus Defective Interfering Genomes: Packaging and Heterogeneity". Virology, vol. 217, 1996, pp. 495-507.

\* cited by examiner

FIG. 1

| | | |
|---|---|---|
| EU LoN94-13 nsp1Beta | SSVYRWKKFVVFTDSSPNGRPRMMWTPESDDSADLEALPPELERQVEILIRSFPAHHPVS | 60 |
| delta nsp1 IX-10 nsp1Beta | .............................██.............................. | 58 |
| delta nsp1 XVII-1 nsp1Beta | ..............................███............................. | 57 |
| delta nsp1 XVIII-12 nsp1Beta | ..............................████............................ | 56 |
| delta nsp1 XIX-2 nsp1Beta | .............................█████............................ | 55 |
| delta nsp1 XX-9 nsp1Beta | ............................██████............................ | 54 |
| EU LoN94-13 nsp1Beta | LADWELAESPENGFSFSTYHSGGYLVQNPDVFDSKCWLSCFLDQPIEVRLYEDYLANAFG | 120 |
| delta nsp1 IX-10 nsp1Beta | ............................................................ | 118 |
| delta nsp1 XVII-1 nsp1Beta | ............................................................ | 117 |
| delta nsp1 XVIII-12 nsp1Beta | ............................................................ | 116 |
| delta nsp1 XIX-2 nsp1Beta | ............................................................ | 115 |
| delta nsp1 XX-9 nsp1Beta | ............................................................ | 114 |
| EU LoN94-13 nsp1Beta | YQTKWGVSGKYLQRRLQVNGIRAVIDPDGPIHVEALSCPQSWIRHLTLDDDVTPGFVRLT | 180 |
| delta nsp1 IX-10 nsp1Beta | ............................................................ | 178 |
| delta nsp1 XVII-1 nsp1Beta | ............................................................ | 177 |
| delta nsp1 XVIII-12 nsp1Beta | ............................................................ | 176 |
| delta nsp1 XIX-2 nsp1Beta | ............................................................ | 175 |
| delta nsp1 XX-9 nsp1Beta | ............................................................ | 174 |
| EU LoN94-13 nsp1Beta | SLRIVPNTEPTTLRIFRFGAHKWYG | 205 |
| delta nsp1 IX-10 nsp1Beta | ......................... | 203 |
| delta nsp1 XVII-1 nsp1Beta | ......................... | 202 |
| delta nsp1 XVIII-12 nsp1Beta | ......................... | 201 |
| delta nsp1 XIX-2 nsp1Beta | ......................... | 200 |
| delta nsp1 XX-9 nsp1Beta | ......................... | 199 |

FIG. 2

```
                              nsp1Alpha
             EU LoN94-13  MSGTFSRCMCTPAARVFWNAGQVYCTRCLSARSLLPPELQDIDLAAIGLFYKPKDKLHWK 60

EU Lelystad nsp1Beta  ------------------------------------------------------------

US GD-XH (3MTV_A) nsp1Beta  ------------------------------------------------------------

US VR-2332 nsp1Beta  ------------------------------------------------------------
                              nsp1Alpha
             EU LoN94-13  VPIGIPQVECTPSGCCWLSGIFPLARMTSGNHNFLQRLVKVADVLYRDGCLTSRHLRELQ 120

EU Lelystad nsp1Beta  ------------------------------------------------------------

US GD-XH (3MTV_A) nsp1Beta  ------------------------------------------------------------

US VR-2332 nsp1Beta  ------------------------------------------------------------
                              nsp1Alpha
             EU LoN94-13  VYERGCSWYPITGPVPGMGLYANSMHVSDQPFPGATHVLTNSPLPQQACRQPFCPFEEAH 180

EU Lelystad nsp1Beta  ------------------------------------------------------------

US GD-XH (3MTV_A) nsp1Beta  ------------------------------------------------------------

US VR-2332 nsp1Beta  ------------------------------------------------------------
                                           deletion site
                              nsp1Beta
             EU LoN94-13  SSVYRWKKFVVFTDSSPNGR--PRMMWTPESDDSADLEALPPELERQVEILIRSFPAHHP 238

EU Lelystad nsp1Beta  ................L....--S............A..V................... 58
                                           P23R24
                              NTD                                                    LKD
    US GD-XH (3MTV_A) nsp1Beta  ad..digrga.myvaggkvswa..ggn------evkf.pv.k...klvanr.ht...p..v 54

US VR-2332 nsp1Beta  AT..DIGHDA.MYVAERKVSWA..GGD------EVKF..V.G...KLIANR.RT...P..T 54
                              nsp1Beta
             EU LoN94-13  VSLADWELAESPENGFSFSTYHSGGYLVQNPDVFDSKCWLSCFLDQPIEVRLYEDYLANA 298

EU Lelystad nsp1Beta  .D......T..........N.S..C.H..........G.........G.SV...CH.EH..D. 118
                              LKD                                      PCP Beta
    US GD-XH (3MTV_A) nsp1Beta  .dmskftfi-t.gs.v.mrveyqy.c.padt-.pegn..wrllds!.p..qyk.irh..q 112

US VR-2332 nsp1Beta  .DMSKFAFT-A.GC.V.MRVERQH.C.PADT-.PEGN..W.L.DLL.L..QNK.IRH..Q 112
                              nsp1Beta
             EU LoN94-13  FGYQTKWGVSGKYLQRRLQVNGIRAVIDPDGPIHVEALSCPQSWIRHLTLDDDVT-PGFV 357

EU Lelystad nsp1Beta  .........H...........R.....V................................ 177
                              PCP Beta
    US GD-XH (3MTV_A) nsp1Beta  ......h..p..............l....t.th...vlqyf.vke......k.veepsl...e 172

US VR-2332 nsp1Beta  ......H..................L...T.LN...V.QYF.VKE......K.AGEPSYS..E 172
                              nsp1Beta                             nsp2
             EU LoN94-13  RLTSLRIVPNTEPTT---LRIFRFGAHKWYGAAGK 389

EU Lelystad nsp1Beta  .................------S..............---- 205
                              PCP Beta    CTE
    US GD-XH (3MTV_A) nsp1Beta  d.lrl.ve...s.lagkdek.....s........---- 203

US VR-2332 nsp1Beta  D.LRI.VE...S.LADKEEK.....S........---- 203
```

US 9,187,731 B2

PRRS VIRUS INDUCING TYPE I INTERFERON IN SUSCEPTIBLE CELLS

SEQUENCE LISTING

The instant application contains a Sequence Listing which has been submitted in ASCII format via EFS-Web and is hereby incorporated by reference in its entirety. Said ASCII copy, created on Sep. 4, 2014 is named 01-2739-US-1-UP-SEQ.txt and is 243,336 bytes in size.

FIELD OF THE INVENTION

The present invention belongs to the field of vaccines and medicaments for the prophylaxis and treatment of infectious diseases. In particular, it relates to attenuated live viruses useful as vaccine or medicament for preventing or treating Porcine Reproductive and Respiratory Syndrome (PRRS), a viral disease affecting swine.

BACKGROUND OF THE INVENTION

Porcine reproductive and respiratory syndrome virus (PRRSV) is a member of the virus family Arteriviridae and belongs, together with the Coronaviridae, to the virus order Nidovirales. PRRSV is an enveloped virus with a single-stranded, positive-sense RNA genome of about 15 kilobases comprising nine open reading frames (ORFs), namely ORF1a, ORF1ab, ORF2a, ORF 2ab, and ORFs 3 through ORF7. ORFs 1a and 1ab encode large polyproteins that are processed into the viral nonstructural proteins (nsp) by auto- and transcleavages of viral proteases nsp1, nsp2, and nsp4 (Snijder and Meulenberg, 1998).

There are two distinct viral PRRSV genotypes causing similar clinical symptoms that diverge by about 40% on nucleotide sequence level, genotype I (EU) and genotype II (US). The North American (US) prototype strain is VR-2332, while the European (EU) prototype strain is Lelystad virus.

PRRSV is considered one of the economically most important infectious agents in pigs causing late-term reproductive failure in sows and respiratory disease in growing pigs. Often, PRRSV infection is complicated by secondary bacterial infections being attributed to the immunosuppressive nature of the virus. Also, PRRSV viremia lasts for weeks, and virus then still can be detected in lymphoid organs for several months, demonstrating difficulties or failure of the host's immune response to clear the virus (Allende et al., 2000).

The specific immune response to PRRSV infection is characterized by delayed induction of neutralizing antibodies (Lopez and Osorio, 2004) and short cell-mediated immune response (Xiao et al., 2004). It is commonly accepted that these effects can in part be attributed, along with presentation of decoy epitopes (Ostrowski et al., 2002; Ansari et al., 2006) and glycan shielding of viral envelope proteins (Ansari et al., 2006), to the viral inhibition of the host's innate immune system. It has been demonstrated that PRRSV infection does not or only weakly or delayedly induce production of type I interferon (IFN) (interferon α and interferon β; (Miller et al., 2004)) or type II IFN, (interferon γ; (Meier et al., 2003)) in susceptible cell lines (swine pulmonary alveolar macrophages, monkey kidney cells MARC-145) and/or pigs (Buddaert et al., 1998).

Thus, there is a need for novel vaccines and medications effecting a rapid induction of neutralizing antibodies and interferon responses for the prophylaxis and treatment of PRRSV infection.

BRIEF DESCRIPTION OF THE FIGURES

FIG. 1: Sequence alignment of nsp1β protein sequences from parental EU PRRSV strain LoN94-13 and from vaccine candidates (SEQ ID NOS 7 and 21-25, respectively, in order of appearance).

FIG. 2: Sequence alignment of nsp1β proteins from PRRSV strains (SEQ ID NOS 82, 8 and 83-84, respectively, in order of appearance).

DETAILED DESCRIPTION

Figure 3A:
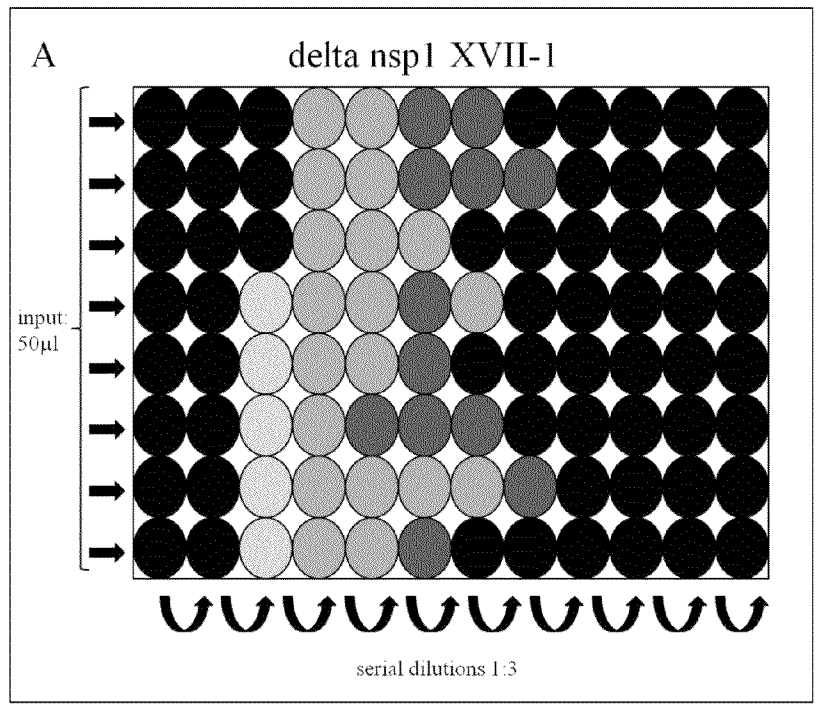
FIG. 3: PRRSV-specific immunofluorescence of virus stock titrations. (A) delta nsp1 XVII-1; (B) delta nsp1 XVIII-12. Black, negative fluorescence; light grey, few positive cells; grey, foci of positive cells; dark grey, complete cell monolayer positive.

IFNs play an important role in establishing an effective adaptive immune response against viral infections, and many viruses therefore have developed strategies and counteractions against onset of the host's innate immune system (Haller and Weber, 2009). In the interest to identify the anticipated PRRSV IFN antagonist(s), extensive screening analyses based on cell lines stably expressing genes of interest or on cells transfected with protein-expressing plasmids have identified several PRRSV nonstructural proteins (nsps) including nsp1 (see below), nsp2 (Beura et al., 2010; Li et al., 2010), nsp4 (Beura et al., 2010), and nsp11 (Beura et al., 2010; Shi et al., 2011a) to be involved in blocking the induction of type I IFN.

nsp1 is located at the N-terminus of the PRRSV ORF1a-derived polyprotein 1a and is processed into two multifunctional subunits, nsp1α and nsp1β, each of which contains a papain-like cysteine protease (PCP) domain essential for self-release from the viral polyprotein (den Boon et al., 1995; Chen et al., 2010). nsp1α contains an N-terminal zinc-finger domain and the PCPα protease domain, while nsp1β contains PCPβ. For both nsp1 subunits, nsp1α and nsp1β, the three-dimensional crystal structure has been resolved (Sun et al., 2009; Xue et al., 2010). According to these analyses, nsp1β consists of an N-terminal domain (NTD), a linker domain (LKD), the PCP domain (PCP beta), and a C-terminal extension (CTE); (Xue et al., 2010), see FIG. 2. C-terminal, nsp1β-mediated cleavage of nsp1 from nsp2 occurs at site WYG (SEQ ID NO: 70)/AGR (SEQ ID NO: 71) for PRRSV US strains (Kroese et al., 2008) or is predicted at site WYG (SEQ ID NO: 70)/AAG (SEQ ID NO: 72) for PRRSV EU strains (Chen et al., 2010), while nsp1α/nsp1β cleavage occurs at site ECAM (SEQ ID NO: 73)/AxVYD (SEQ ID NO: 74) for PRRSV US strains or is predicted at site EEAH (SEQ ID NO: 75)/SxVYR (SEQ ID NO: 76) for PRRSV EU strains (Chen et al., 2010).

Several studies on protein level demonstrated to the mechanistic detail that PRRSV nsp1 and/or its autocleavage-derived subunits nsp1α and/or nsp1β inhibit type I IFN production by interfering with IFN transcription (Song et al., 2010; Kim et al., 2010; Chen et al., 2010; Beura et al., 2010). In addition, it has been demonstrated that nsp1β interferes with the cellular response to interferon (interferon signaling); (Chen et al., 2010). Moreover, it was demonstrated that PRRSV infection inhibits IFNα and/or IFNβ production in PRRSV infected cells in vitro (Kim et al., 2010; Beura et al., 2010), the sub-cellular localization of nsp1 (subunits) was determined (Song et al., 2010; Chen et al., 2010), and mechanistic aspects of type I IFN inhibition that were obtained by others from single protein expression experiments were confirmed in cells infected with PRRSV (Shi et al., 2010). Finally, a nsp1 mutagenesis study based on nsp1 protein expression investigated effects on viral IFN inhibition (Shi et al., 2011b), showing that mutations that inactivated papain-like cysteine protease activity of nsp1α made nsp1 lose its IFN antagonism activity, whereas mutations that inactivated papain-like cysteine protease activity of nsp1β did not influence the IFN antagonism activity of nsp1.

However, a viable PRRSV strain that induces IFN production and/or does not interfere with IFN signaling after infection of susceptible cells and/or the host, in particular a PRRSV strain comprising a genomic mutation in its nsp1 gene, has not been described yet.

It is thus an aim of the present invention to make available such a viable PRRS virus inducing the IFN response of a cell, in particular of a host cell, wherein said PRRS virus may serve as an effective vaccine or medicament for the prophylaxis or treatment of the Porcine reproductive and respiratory syndrome in swine.

The solution to the above technical problem is achieved by the description and the embodiments characterized in the claims.

Thus, the invention in its different aspects and embodiments is implemented according to the claims.

The invention is based on the surprising finding of a Porcine Reproductive and Respiratory Syndrome (PRRS) virus which is able to induce the interferon type I response of a cell, in particular of a host cell.

Hence, one aspect of the invention concerns a PRRS virus (PRRSV) which is able to induce the interferon type I production and secretion by a cell infected by said virus, wherein the PRRS virus according to the invention in particular is able to induce or induces the interferon type I production and secretion by an interferon competent cell infected by said virus.

As used herein, it is understood that the terms "interferon type I", "IFN type I", "type I interferon" and "type I IFN" are equivalent.

Interferon type I production and secretion by a cell, as described herein, particularly means that interferon type I is made and released by a cell in response to the infection of the PRRS virus according to the invention. In this regard, interferon type I, as mentioned herein, is preferably interferon-α and/or interferon-β.

The infection of a cell by the PRRS virus according to the invention in particular includes attachment of the virus to the cell, entry of the virus into the cell, disassembly of the virion, and preferably replication and transcription of the viral genome, expression of viral proteins, and assembly and release of new infectious viral particles.

The cell, as mentioned herein, is a primary or secondary susceptible cell, preferably a mammalian cell, in particular a porcine or a simian cell, more preferably said cell is a porcine macrophage or a MA-104 cell or a MARC-145 cell or a Vero cell.

It is further understood that the PRRS virus according to the invention is able to induce in vitro and/or in vivo the interferon type I production and secretion by a cell infected by said virus.

Preferably, the PRRS virus according to the invention is a live PRRS virus and/or a modified-live PRRS virus and/or an attenuated PRRS virus.

The term "attenuated PRRS virus", as described herein, is in particular directed to a PRRS virus which is attenuated in vitro and/or in vivo, more particular in susceptible cell lines and/or the host.

The term "host", as used herein, is in particular directed to animals infectable with PRRS virus, in particular swine, more particular pigs, such as domestic pigs.

As mentioned herein, "attenuated" particularly relates to a reduced virulence of a pathogen, in particular of a wild type PRRS virus, wherein "virulence" is understood to be the degree of pathogenicity, and wherein "pathogenicity" is directed to the ability of the pathogen to produce clinical symptoms in the host, such as elevated body temperature.

In particular preferably, the PRRS virus according to the invention has or shows increased sensitivity to type I INF when compared to wild type PRRSV, wherein the term "sensitivity to type I INF" is understood as reduced viral infectivity when IFNβ is present, preferably in a sufficient amount for significantly reducing viral infectivity of wild type PRRSV, in the medium surrounding the virus at the time of infection.

The term "wild type PRRS virus" or "wild type PRRSV", respectively, as used herein, is in particular directed to an infectious pathogenic PRRS virus, which is particularly capable of causing PRRS in swine. In one particular preferred embodiment, the term "wild type PRRS virus" is directed to a PRRS virus whose genome comprises a RNA sequence or consists of a RNA polynucleotide, wherein said RNA sequence or RNA polynucleotide is a RNA copy of a polynucleotide selected from the group consisting of SEQ ID NO: 13, SEQ ID NO: 14 and SEQ ID NO: 15.

In one embodiment, the PRRS virus according to the invention is a PRRS virus mutant, in particular comprising, in comparison with the genome of a wild type PRRSV strain, a mutation in a gene encoding a protein of said virus.

In a preferred embodiment, the PRRS virus according to the invention comprises a mutation in the gene encoding the nsp1 protein of said virus. Thus, the invention preferably concerns a PRRS virus which is able to induce the interferon type I production and secretion by an infected cell as a result of a mutation in the gene encoding the nsp1 protein, wherein said mutation is preferably a mutation as mentioned hereinafter.

Hence, the invention particularly concerns a PRRS virus comprising, in comparison with the genome of a wild type strain, a mutation in the gene encoding the nsp1 protein. Accordingly, the mutation as described herein is preferably a mutation in comparison with the sequence of the corresponding wild type gene encoding the nsp1 protein.

The invention is thus preferably directed to a PRRS virus; in particular a wild type PRRS virus, wherein a mutation, preferably a mutation as mentioned hereinafter, has been implemented in the genome of said virus resulting in a non-natural nsp1 protein or in the lack of nsp1 protein of said virus.

In the context of the invention it is understood, that the mutation as described herein may be implemented to any PRRS virus, such as to a PRRS virus selected from the group consisting of wild type PRRS virus, attenuated PRRS virus, modified-life PRRS virus, PRRS virus mutant and combinations thereof. In one example, the mutation as described herein may be implemented to an attenuated and/or live PRRS virus, for example to a PRRS virus selected from the group of the PRRS virus strains that have been deposited on 27 Oct. 2004 with the European Collection of Cell Cultures (ECACC), Porton Down, Salisbury, Wiltshire, SP4 OJG, Great Britain, under the Accession Numbers ECACC 04102703, ECACC 04102702, and ECACC 04102704. Hence, the mutation as described herein can be combined with one or more other mutations, preferably one or more other attenuating mutations, in a PRRS virus.

In the context of the invention, the term "PPRRS virus" is in particular equivalent with "PRRS virus strain".

The term "mutation" in the context of the invention is understood as a change in a genomic sequence, in particular in the RNA sequence of a PRRS virus. Since viruses that use RNA as their genetic material have rapid mutation rates, the term "mutation", as mentioned herein, is particularly directed to a genetically engineered change in a genomic sequence, such as by site directed mutagenesis, which in particular results in a virus growing to titers significantly lower than wild type PRRS virus in interferon competent cells and/or in the infected host, when propagated under the same conditions. Moreover, in another preferred embodiment the mutation described herein can also be caused by natural mutation and subsequent isolation of the PRRS virus according to the invention, wherein said isolated virus includes the mutation described herein.

Preferably, the mutation, as described herein, comprises or consists of one or more point mutations and/or one or more genomic deletions and/or one or more insertions.

The term "nsp1 protein", as used herein, is directed to the PRRSV nonstructural protein 1.

The nsp1 protein is preferably a polypeptide having at least 70%, preferably at least 80%, more preferably at least 90%, still more preferably at least 95% or in particular 100% sequence identity with a polypeptide selected from the group consisting of SEQ ID NO:1 and SEQ ID NO:2 if the PRRS virus according to the invention is a genotype I PRRS virus, or the nsp1 protein is preferably a polypeptide having at least 70%, preferably at least 80%, more preferably at least 90%, still more preferably at least 95% or in particular 100% sequence identity with the polypeptide set forth in SEQ ID NO:3 if the PRRS virus according to the invention is a genotype II PRRS virus.

In one aspect, the PRRS virus according to the invention preferably also may comprise a mutation in the gene encoding the nsp1 protein selected from the group consisting of SEQ ID NOs 1-3.

It is hence understood that the PRRS virus according to the invention is a genotype I PRRS virus or a genotype II PRRS virus. It is further understood that the terms "genotype I" and "genotype II" are equivalent to the terms "genotype 1" and "genotype 2" or to the terms "type 1" and "type 2", as frequently used in the literature in the context of PRRSV.

Sequence identity in the context of the invention is understood as being based on pairwise determined similarity between nucleotide or protein sequences. The determination of percent identity between two sequences is preferably accomplished using a mathematical algorithm, in particular the well-known Smith-Waterman algorithm (Smith and Waterman, M. S. (1981) J Mol Biol, 147(1):195-197). For purposes of the present invention, percent sequence identity of an amino acid sequence is determined using the Smith-Waterman homology search algorithm using an affine 6 gap search with a gap open penalty of 12 and a gap extension penalty of 2, BLOSUM matrix 62. The Smith-Waterman homology search algorithm is taught in Smith and Waterman (1981) Adv. Appl. Math 2:482-489, herein incorporated by reference. A variant may, for example, differ from the reference nsp1, nsp1α, nsp1β or NTD molecule by as few as 1 to 15 amino acid residues, as few as 1 to 10 amino acid residues, such as 6-10, as few as 5, as few as 4, 3, 2, or even 1 amino acid residue. Alternatively, percent identity of a nucleotide sequence is determined using the Smith-Waterman homology search algorithm using a gap open penalty of 25 and a gap extension penalty of 5. Such a determination of sequence identity can be performed using, for example, the DeCypher Hardware Accelerator from TimeLogic Version G, or the sequence identity is determined with the software CLC MAIN WORKBENCH 4.1.1 (CLC BIO).

The term "having 100% sequence identity", as used herein, is understood to be equivalent to the term "being identical".

In another preferred embodiment, the mutation in the PRRS virus according to the invention comprises or consists of one or more point mutations and/or one or more genomic deletions and/or one or more insertions.

In a further preferred embodiment, the PRRS virus according to the invention comprises a mutation in the gene sequences encoding the nsp1α subunit of the nsp1 protein and/or the nsp1β subunit of the nsp1 protein of said virus.

The term "nsp1α", as mentioned herein, is thus directed to the PRRSV nsp1α subunit of the nsp1 protein, and the term "nsp1β", as used herein, is hence directed to the PRRSV nsp1β subunit of the nsp1 protein.

The nsp1α is preferably a polypeptide having at least 70%, preferably at least 80%, more preferably at least 90%, still more preferably at least 95% or in particular 100% sequence identity with a polypeptide selected from the group consisting of SEQ ID NO:4 and SEQ ID NO:5 if the PRRS virus according to the invention is a genotype I PRRS virus, or the nsp1α is preferably a polypeptide having at least 70%, preferably at least 80%, more preferably at least 90%, still more preferably at least 95% or in particular 100% sequence identity with the polypeptide set forth in SEQ ID NO:6 if the PRRS virus according to the invention is a genotype II PRRS virus.

The nsp1β is preferably a polypeptide having at least 70%, preferably at least 80%, more preferably at least 90%, still more preferably at least 95% or in particular 100% sequence identity with a polypeptide selected from the group consisting of SEQ ID NO:7 and SEQ ID NO:8 if the PRRS virus according to the invention is a genotype I PRRS virus, or the nsp1β is preferably a polypeptide having at least 70%, preferably at least 80%, more preferably at least 90%, still more preferably at least 95% or in particular 100% sequence identity with the polypeptide set forth in SEQ ID NO:9 if the PRRS virus according to the invention is a genotype II PRRS virus.

In a particular preferred embodiment, the PRRS virus according to the invention comprises a mutation in the gene sequence encoding the N-terminal domain (NTD) of the nsp1β of said virus. The term "NTD", as mentioned herein, is thus directed to the N-terminal domain of the PRRSV nsp1β subunit.

The NTD is preferably a polypeptide or has a polypeptide sequence, respectively, having at least 60%, particularly at least 70%, preferably at least 80%, more preferably at least 90%, still more preferably at least 95% or in particular 100% sequence identity with a polypeptide or a polypeptide sequence, respectively, selected from the group consisting of SEQ ID NO:10 and SEQ ID NO:11 if the PRRS virus according to the invention is a genotype I PRRS virus, or the NTD is preferably a polypeptide or has polypeptide sequence, respectively, having at least 60%, particularly at least 70%, preferably at least 80%, more preferably at least 90%, still more preferably at least 95% or in particular 100% identity with the polypeptide or the polypeptide sequence, respectively, set forth in SEQ ID NO:12 if the PRRS virus according to the invention is a genotype II PRRS virus.

In a preferred embodiment, the NTD comprising the mutation has the sequence selected from the group consisting of the sequences

SXXYXXXXXVXFXDXXXXGXXMWXXXSXXSXXLEXLPXXLXXXXXXLXRS,

SXXYXXXXXVXFXDXXXXGXMWXXXSXXSXXLEXLPXXLXXXXXXLXRS,

SXXYXXXXXVXFXDXXXXMWXXXSXXSXXLEXLPXXLXXXXXXLXRS,

SXXYXXXXXVXFXDXXXXMWXXXSXXSXXLEXLPXXLXXXXXXLXRS,

SXXYXXXXXVXFXDXXXMWXXXSXXSXXLEXLPXXLXXXXXXLXRS,

SXXYXXXXXVXFXDXXMWXXXSXXSXXLEXLPXXLXXXXXXLXRS, as set forth in SEQ ID NOs:36-41, if the PRRS virus according to the invention is a genotype I PRRS virus, or the NTD comprising the mutation preferably has the sequence selected from the group consisting of the sequences

AXVYDIGXXAVMXVAXXXXSWAGGXXXXFXXXXXXLXLXAXXXXXS,

AXVYDIGXXAVMXVAXXXXSWGGXXXXFXXXXXXLXLXAXXXXXS,

AXVYDIGXXAVMXVAXXXXSGGXXXXFXXXXXXLXLXAXXXXXS,

AXVYDIGXXAVMXVAXXXXGGXXXXFXXXXXXLXLXAXXXXXS,

AXVYDIGXXAVMXVAXXXGGXXXXFXXXXXXLXLXAXXXXXS,

AXVYDIGXXAVMXVAXXGGXXXXFXXXXXXLXLXAXXXXXS, as set forth in SEQ ID NOs: 42-47, if the PRRS virus according to the invention is a genotype II PRRS virus.

Thus, the PRRS virus according to the invention preferably comprises a gene sequence encoding a NTD selected from the sequences

SXXYXXXXXVXFXDXXXXGXXMWXXXSXXSXXLEXLPXXLXXXXXXLXRS,

SXXYXXXXXVXFXDXXXXGXMWXXXSXXSXXLEXLPXXLXXXXXXLXRS,

SXXYXXXXXVXFXDXXXXMWXXXSXXSXXLEXLPXXLXXXXXXLXRS,

SXXYXXXXXVXFXDXXXXMWXXXSXXSXXLEXLPXXLXXXXXXLXRS,

SXXYXXXXXVXFXDXXXMWXXXSXXSXXLEXLPXXLXXXXXXLXRS,

SXXYXXXXXVXFXDXXMWXXXSXXSXXLEXLPXXLXXXXXXLXRS, as set forth in SEQ ID NOs:36-41, if the PRRS virus according to the invention is a genotype I PRRS virus, or the PRRS virus according to the invention preferably comprises a gene sequence encoding a NTD selected from the sequences

AXVYDIGXXAVMXVAXXXXSWAGGXXXXFXXXXXXLXLXAXXXXXS,

AXVYDIGXXAVMXVAXXXXSWGGXXXXFXXXXXXLXLXAXXXXXS,

AXVYDIGXXAVMXVAXXXXSGGXXXXFXXXXXXLXLXAXXXXXS,

AXVYDIGXXAVMXVAXXXXGGXXXXFXXXXXXLXLXAXXXXXS,

AXVYDIGXXAVMXVAXXXGGXXXXFXXXXXXLXLXAXXXXXS,

AXVYDIGXXAVMXVAXXGGXXXXFXXXXXXLXLXAXXXXXS.

as set forth in SEQ ID NOs: 42-47, if the PRRS virus according to the invention is a genotype II PRRS virus.
In one exemplary embodiment, the NTD comprising the mutation may, for instance, have the sequence selected from the group consisting of the sequences

SSVYRWKKFVVFTDSSXNGRMMWTPESDDSAXLEXLPPELERQVEILIRS,

SSVYRWKKFVVFTDSSXNGMMWTPESDDSAXLEXLPPELERQVEILIRS,

SSVYRWKKFVVFTDSSXNMMWTPESDDSAXLEXLPPELERQVEILIRS,

SSVYRWKKFVVFTDSSXMMWTPESDDSAXLEXLPPELERQVEILIRS,

SSVYRWKKFVVFTDSSMMWTPESDDSAXLEXLPPELERQVEILIRS,

SSVYRWKKFVVFTDSMMWTPESDDSAXLEXLPPELERQVEILIRS, as set forth in SEQ ID NOs:48-53, if the PRRS virus according to the invention is a genotype I PRRS virus, or the NTD comprising the mutation may, for instance, have the sequence selected from the group consisting of the sequences

ATVYDIGXXAVMYVAXXXKVSWAGGXEVKFEXVPXELKLXANRLXTS,

ATVYDIGXXAVMYVAXXXKVSWGGXEVKFEXVPXELKLXANRLXTS,

ATVYDIGXXAVMYVAXXXKVSGGXEVKFEXVPXELKLXANRLXTS,

ATVYDIGXXAVMYVAXXXKVGGXEVKFEXVPXELKLXANRLXTS,

ATVYDIGXXAVMYVAXXKGGXEVKFEXVPXELKLXANRLXTS,

ATVYDIGXXAVMYVAXXGGXEVKFEXVPXELKLXANRLXTS, as set forth in SEQ ID NOs: 54-59, if the PRRS virus according to the invention is a genotype II PRRS virus.

Thus, in one exemplary embodiment, the PRRS virus according to the invention may, for instance, comprise a gene sequence encoding a NTD selected from the sequences

SSVYRWKKFVVFTDSSXNGRMMWTPESDDSAXLEXLPPELERQVEILIRS,

SSVYRWKKFVVFTDSSXNGMMWTPESDDSAXLEXLPPELERQVEILIRS,

SSVYRWKKFVVFTDSSXNMMWTPESDDSAXLEXLPPELERQVEILIRS,

SSVYRWKKFVVFTDSSXMMWTPESDDSAXLEXLPPELERQVEILIRS,

SSVYRWKKFVVFTDSSMMWTPESDDSAXLEXLPPELERQVEILIRS,

SSVYRWKKFVVFTDSMMWTPESDDSAXLEXLPPELERQVEILIRS, as set forth in SEQ ID NOs:48-53, if the PRRS virus according to the invention is a genotype I PRRS virus, or the PRRS virus according to the invention may, for instance, comprise a gene sequence encoding a NTD selected from the sequences

ATVYDIGXXAVMYVAXXXKVSWAGGXEVKFEXVPXELKLXANRLXTS,

ATVYDIGXXAVMYVAXXXKVSWGGXEVKFEXVPXELKLXANRLXTS,

ATVYDIGXXAVMYVAXXXKVSGGXEVKFEXVPXELKLXANRLXTS,

ATVYDIGXXAVMYVAXXXKVGGXEVKFEXVPXELKLXANRLXTS,

ATVYDIGXXAVMYVAXXKGGXEVKFEXVPXELKLXANRLXTS,

ATVYDIGXXAVMYVAXXGGXEVKFEXVPXELKLXANRLXTS, as set forth in SEQ ID NOs: 54-59, if the PRRS virus according to the invention is a genotype II PRRS virus.

It is thus understood that a genotype I PRRS virus, as mentioned herein, is in particular a virus whose genome comprises a gene sequence coding for a polypeptide having at least 70%, preferably at least 80%, more preferably at least 90%, still more preferably at least 95% or in particular 100% sequence identity with a polypeptide selected from the group consisting of SEQ ID NO:1, SEQ ID NO:2, SEQ ID NO:4, SEQ ID NO:5, SEQ ID NO:7 and SEQ ID NO:8, or is in particular a virus whose genome comprises a gene sequence coding for a polypeptide having at least 60%, particularly at least 70%, preferably at least 80%, more preferably at least 90%, still more preferably at least 95% or in particular 100% sequence identity with a polypeptide selected from the group consisting of SEQ ID NO:10 and SEQ ID NO:11.

Preferably, the genotype I PRRS virus, as mentioned herein, comprises or consists of a RNA polynucleotide having at least 70%, preferably at least 80%, more preferably at least 90%, still more preferably at least 95% or in particular 100% sequence identity with a RNA polynucleotide complementary to a polynucleotide selected from the group consisting of SEQ ID NO: 13 and SEQ ID NO: 14.

It is further understood that a genotype II PRRS virus, as mentioned herein, is in particular a virus whose genome comprises a gene sequence coding for a polypeptide having at least 70%, preferably at least 80%, more preferably at least 90%, still more preferably at least 95% or in particular 100% sequence identity with a polypeptide selected from the group consisting of SEQ ID NO:3, SEQ ID NO:6 and SEQ ID NO:9, or is in particular a virus whose genome comprises a gene sequence coding for a polypeptide having at least 60%, particularly at least 70%, preferably at least 80%, more preferably at least 90%, still more preferably at least 95% or in particular 100% sequence identity with the polypeptide set forth in SEQ ID NO:12.

Preferably, the genotype II PRRS virus, as mentioned herein, comprises or consists of a RNA polynucleotide having at least 70%, preferably at least 80%, more preferably at least 90%, still more preferably at least 95% or in particular 100% sequence identity with a RNA polynucleotide complementary to the polynucleotide set forth in SEQ ID NO: 15.

In the following, the single letter code for amino acids is used for amino acid sequences, where additionally X signifies any genetically encoded amino acid residue.

Within the context of the invention it is in particular understood that the N-terminal domain (NTD) of nsp1β starts with the N-terminus of nsp1β, preferably starts with the amino acid sequence SXXY (SEQ ID NO: 60) if the PRRS virus is a genotype I PRRS virus or with the amino acid sequence AXVY (SEQ ID NO: 61) if the PRRS virus is a genotype II PRRS virus, and the NTD ends with the serine residue (S) within the amino sequence SFP of the nsp1β. Regarding the NTD domain of a genotype II PRRS virus it is in particular referred to the publication Xue et al. 2010, hereby incorporated by reference. Said amino acid sequences SXXY (SEQ ID NO: 60) or AXVY (SEQ ID NO: 61) and SFP (SEQ ID NO: 62) are especially conserved in the nsp1β of wild type PRRS viruses and are thus preferably used amino acid sequence motifs for defining the NTD domain according to the invention.

In a particular preferred embodiment, the PRRS virus according to the invention thus comprises a mutation in the gene sequence coding for the NTD, wherein the NTD preferably starts with motif SXXY (SEQ ID NO: 60) for PRRS virus type 1 strains or with motif AXVY (SEQ ID NO: 61) for PRRS virus type 2 strains and ends with the serine residue (S) within the conserved SFP (SEQ ID NO: 62) motif of the nsp1β subunit.

According to the invention, it is in particular preferred if said mutation is located within the part of the gene sequence coding for the NTD, where the amino acid stretches folding into β sheet secondary structures are encoded.

In one preferred aspect, the mutation, as described herein, thus comprises a deletion or replacement of a nucleotide triplet coding for an amino acid residue located within the first 24 N-terminal amino acid residues of the NTD sequence.

In particular, it is preferred if the mutation described herein comprises of a deletion or replacement of 2 to 7 or more, preferably consecutive, nucleotide triplets each coding for an amino acid residue located within the first 24 N-terminal amino acid residues of the NTD sequence.

In another preferred aspect, the mutation, as mentioned herein, comprises the deletion or replacement of a nucleotide triplet coding for an amino acid residue with a charged, preferably positively charged, side chain, in particular coding for an arginine residue.

Exemplarily, the mutation mentioned herein preferably consists of a deletion of 2, 3, 4, 5, 6 or 7 consecutive nucleotide triplets coding for the respective number (2, 3, 4, 5, 6 or 7) of consecutive amino acid residues located within the first 24 N-terminal amino acid residues of the NTD sequence, wherein this mutation comprises the deletion of a nucleotide triplet coding for an amino acid residue with a charged, preferably positively charged, side chain, in particular coding for an arginine residue.

The mutation, as described herein, preferably comprises or consists of a deletion or replacement of the nucleotide triplet coding for the first arginine residue (R) located at least 21 amino acid residues in C-terminal direction from the N-terminal amino acid residue of the nsp1β NTD and/or the mutation, as mentioned herein, comprises a deletion or replacement of the nucleotide triplet coding for the arginine residue (R) of the nsp1 amino acid sequence RXMW (SEQ ID NO: 63) if the PRRS virus is a genotype I PRRS virus or with the amino acid sequence RGG (SEQ ID NO: 64) of said virus if the PRRS virus is a genotype II PRRS virus and/or the mutation, as mentioned herein, comprises or consists of a deletion or replacement of the nucleotide triplet coding for the arginine residue (R) of the amino acid sequence RMM (SEQ ID NO: 65) or RGG (SEQ ID NO: 64) of the nsp1 protein.

According to the invention, the phrase "replacement of a nucleotide triplet" is understood as being a replacement of a nucleotide triplet of the wild type sequence by another nucleotide triplet coding for a different amino acid residue than the wild type sequence.

The phrase "deletion of nucleotide triplet" in the context of the invention is directed to a deletion of a nucleotide triplet resulting in the deletion of an amino acid residue in comparison with the wild type sequence.

In particular, said mutation further comprises a deletion or replacement of one nucleotide triplet coding for the amino acid residue flanking said arginine residue (R) in N-terminal direction, wherein said mutation preferably comprises or consists of a deletion or replacement of two consecutive nucleotide triplets coding for the amino acid residues PR (SEQ ID NO: 77).

More particular, said mutation further comprises a deletion or replacement of two, three, four, five, six, seven or more consecutive nucleotide triplets coding for two, three, four, five, six, seven or more amino acid residues flanking said arginine residue (R) in N-terminal direction.

Preferably, said mutation comprises a deletion or replacement of three consecutive nucleotide triplets coding for the amino acid sequence RXR (SEQ ID NO: 66) or APR (SEQ ID NO: 67) of the nsp1β, or wherein said mutation comprises a deletion or replacement of four consecutive nucleotide triplets coding for the amino acid residues GRXR (SEQ ID NO: 68) or WAPR (SEQ ID NO: 69) of the nsp1β.

As result, the PRRS virus according to the invention comprises in one embodiment a gene coding for a nsp1 protein selected from the group consisting of SEQ ID NO:16, SEQ ID NO:17, SEQ ID NO:18, SEQ ID NO:19 and SEQ ID NO:20, or comprises in another embodiment a gene sequence coding for a nsp1β selected from the group consisting of SEQ ID NO:21, SEQ ID NO:22, SEQ ID NO:23, SEQ ID NO:24 and SEQ ID NO:25, or comprises in a further embodiment a gene sequence coding for a NTD selected from the group consisting of SEQ ID NO:26, SEQ ID NO:27, SEQ ID NO:28, SEQ ID NO:29 and SEQ ID NO:30.

In yet another preferred embodiment, the mutation, as described herein comprises a deletion of the gene sequence encoding the (whole) nsp1 protein, encoding the (whole) nsp1α subunit, encoding the (whole) nsp1β subunit, or encoding a part, preferably at least seven consecutive amino acid residues, of or the (whole) NTD domain of the nsp1β subunit.

Yet another aspect of the invention is directed to a polynucleotide comprising or consisting of the genome of the PPRS virus according to the invention.

Further, the invention is also directed to a virus particle, wherein said virus particle comprises a polynucleotide which comprises or consists of the genome of the PPRS virus according to the invention or which comprises or consists of a DNA copy of the PPRS virus according to the invention.

Still further, the present invention provides a DNA-Vector comprising a copy of, or a cDNA sequence complementary to, respectively, a polynucleotide which comprises or consists of the genome of the PPRS virus according to the invention.

In one exemplary and non-limiting example the DNA vector, as mentioned herein, comprises a polynucleotide sequence selected from the group consisting of SEQ ID NO:31, SEQ ID NO:32, SEQ ID NO:33, SEQ ID NO:34 and SEQ ID NO:35.

Also, the present invention provides a cell comprising a polynucleotide, which comprises or consists of the genome of the PPRS virus according to the invention or which comprises or consists of a DNA copy of the PPRS virus according to the invention.

In one exemplary and non-limiting example the PRRS virus according to the invention, or the genome of the PRRS virus according to the invention, respectively, comprises a RNA sequence or consists of a RNA polynucleotide, wherein said RNA sequence or RNA polynucleotide is a RNA copy of a polynucleotide selected from the group consisting of SEQ ID NO: 31, SEQ ID NO: 32, SEQ ID NO: 33, SEQ ID NO: 34 and SEQ ID NO: 35.

Another aspect of the invention concerns the PRRS virus according to the invention for use as vaccine or medicament, in particular for use in the prophylaxis or treatment of Porcine Reproductive and Respiratory Syndrome preferably in swine. The present invention further provides a composition containing the PRRS virus according to the invention for use as a vaccine or as a medicament, in particular for use in the prophylaxis or treatment of Porcine Reproductive and Respiratory Syndrome preferably in swine.

In a preferred aspect, said vaccine or medicament is administered in two doses or preferably in one dose to an animal in need thereof. By the term "prophylaxis or therapy", as mentioned herein, it is meant that the prophylaxis is to administer a drug, in particular a vaccine, before exposure to PRRSV and the treatment is to administer a drug, in particular a medicament, after infection with PRRSV or onset of PRRS.

In particular, the vaccine, as mentioned herein, is a live vaccine and/or a modified live vaccine and/or an attenuated live or attenuated modified live vaccine.

The strains of the PRRS virus according to the invention can be grown and harvested by methods known in the art, e.g. by propagating in suitable cells like the simian cell line MA-104, Vero cells, or porcine alveolar macrophages. Preferably, vaccines according to the present invention are modified live vaccines comprising one or more of these strains alive in a suitable carrier, but inactivated virus may also be used to prepare killed vaccine (KV). Modified live vaccines (MLV) are typically formulated to allow administration of $10^1$ to $10^7$ viral particles per dose, preferably $10^3$ to $10^6$ particles per dose, more preferably $10^4$ to $10^6$ particles per dose (4.0-6.0 $\log_{10}$ $TCID_{50}$). KV may be formulated based on a pre-inactivation titre of $10^3$ to $10^{10}$ viral particles per dose. The vaccine may comprise a pharmaceutically acceptable carrier, for example a physiological salt-solution. The vaccine may or may not comprise an adjuvant. A suitable adjuvant may optionally also be used. For example, a suitable adjuvant that may be used a-tocopherol acetate which may be obtained under the trade name Diluvac Forte®. Alternatively, alum based adjuvants may be used.

A further aspect of the invention is thus directed to the use of the PRRS virus according to the invention for the preparation of a vaccine or medicament for the prophylaxis or treatment of Porcine Reproductive and Respiratory Syndrome, preferably in swine.

A vaccine according to the present invention may be presented in form of a freeze-dried preparation of the live virus, to be reconstituted with a solvent, to result in a solution for injection. The solvent may, for example, be water, physiological saline, a buffer, or an adjuvanting solvent. The solvent may additionally use adjuvants, for example a-tocopherol acetate. The reconstituted vaccine may then be injected into a pig, for example as an intramuscular or intradermal injection into the neck. For intramuscular injection, a volume of 2 ml may be applied, for an intradermal injection it is typically 0.2 ml. In a further aspect, the present invention therefore is a product, comprising in separate containers a freeze-dried composition of the virus, and a solvent for reconstitution, and optionally further containing a leaflet or label comprising instructions of use.

Yet another aspect of the invention thus concerns a method for the prophylaxis or treatment of Porcine Reproductive and Respiratory Syndrome comprising administering the PRRS virus according to the invention to an animal, preferably to a swine, more preferably to a pig, in particular preferably to a piglet or a sow.

A vaccine according to the present invention may not only comprise the PRRS virus according to the invention as antigen, but may include further components active against PRRS or other porcine viral or bacterial diseases, like porcine circovirus, classical swine fever virus or mycoplasma hyorhinis. Therefore, the invention further relates to a vaccine as described, characterized in that it contains at least one further antigen active against a porcine disease which is not PRRS.

Still another aspect of the invention thus concerns a medicament or vaccine comprising the PRRS virus according to the invention.

Still a further aspect of the invention is directed to a method of preparing a vaccine or medicament, in particular for the prophylaxis or treatment of Porcine Reproductive and Respiratory Syndrome preferably in swine, said method comprising the cultivation of the PRRS virus according to the invention in cell culture.

Moreover, the invention comprises a method of producing the PRRS virus according to the invention, said method comprising the mutagenesis of the gene coding for the nsp1 protein in the genome of a PRRS virus, and wherein the mutation, as described herein, is in particular introduced by genetic engineering in the genome of said virus, preferably by site directed mutagenesis.

Preferably, for any of the aforementioned methods, the above-mentioned DNA-vector is used and/or said methods comprise the detection of interferon type I, in particular interferon type I secretion, and/or of mRNA coding for interferon type I. Said detection in particular comprises the detection of interferon type I and/or of mRNA coding for interferon type I by a bioassay, wherein said bioassay is preferably selected from the group consisting of ELISA, PCR, GLISA, IFA, biosensoric measurement, Surface Plasmon Resonance (SPR) measurement, selective media, lateral flow, biochip measurement, immunomagnetic separation, electrochemiluminescence, chromogenic media, immunodiffusion, DNA hybridization, staining, colorimetric detection, luminescence, and combinations thereof.

In yet a further aspect, the invention provides an immunogenic composition containing the PRRS virus according to the invention.

As used herein, the term "immunogenic composition" in particular refers to a composition that will elicit an immune response in an animal that has been exposed to the composition. An immune response may include induction of antibodies and/or induction of a T-cell response.

Usually, an "immune response" includes but is not limited to one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number or severity of, or lack of one or more of the symptoms associated with the infection of the pathogen, in the delay of onset of viremia, in a reduced viral persistence, in a reduction of the overall viral load and/or in a reduction of viral excretion. Thus, an "immune response" in particular means but is not limited to the development in a subset of a cellular and/or antibody-mediated immune response to the composition or vaccine of interest.

In one aspect, the immunogenic composition of the invention is preferably a vaccine or medicament.

As used herein, the term "viremia" is particularly understood as a condition in which PRRS virus particles circulate in the bloodstream of an animal.

The term "animal", as mentioned herein, is in particular directed to swine, more particular to a pig, preferably a domestic pig.

In a preferred aspect, the immunogenic composition of the invention comprises an amount of $10^1$ to $10^7$ viral particles of the PRRS virus according to the invention per dose, preferably $10^3$ to $10^6$ particles per dose, more preferably $10^4$ to $10^6$ particles per dose.

In another preferred aspect, the immunogenic composition of the invention comprises an amount of the PRRS virus according to the invention which is equivalent to a virus titre of at least about $10^3$ $TCID_{50}$/mL per dose, preferably between $10^3$ to $10^5$ $TCID_{50}$/mL per dose In yet another preferred aspect, the immunogenic composition of the invention further contains one or more pharmaceutically acceptable carriers or excipients. Said one or more pharmaceutically acceptable carriers or excipients are preferably selected from the group consisting of solvents, dispersion media, adjuvants, stabilizing agents, diluents, preservatives, antibacterial and antifungal agents, isotonic agents, and adsorption delaying agents.

The present invention is further directed to the immunogenic composition of the invention for use in a method for
inducing an immune response against PRRSV, or
the prevention or reduction of PRRS, or
the prevention or reduction of PRRSV viremia and/or
preventing or reducing clinical symptoms, in particular the elevated body temperature, associated with PRRSV infection, or
the prevention or reduction of the elevated body temperature associated with the administration of an attenuated PRRSV vaccine to an animal.

As used herein, the term "inducing an immune response" to an antigen or composition is the development of a humoral and/or cellular immune response in an animal to an antigen present in the composition of interest.

The term "prevention" or "reduction" or "preventing" or "reducing", respectively, as used herein, means, but is not limited to a process which includes the administration of a PRRSV antigen, namely of the PRRSV according to the invention which is included in the composition of the invention, to an animal, wherein said PRRSV antigen, when administered to said animal elicits or is able to elicit an immune response in said animal against PRRSV. Altogether, such treatment results in reduction of the clinical symptoms of PRRS or of symptoms associated with PRRSV infection, respectively. More specifically, the term "prevention" or "preventing, as used herein, means generally a process of prophylaxis in which an animal is exposed to the immunogenic composition of the present invention prior to the induction or onset of the disease process (PRRS).

Herein, "reduction of PRRS" or "reduction of clinical symptoms associated with PRRSV infection" means, but is not limited to, reducing the number of infected subjects in a group, reducing or eliminating the number of subjects exhibiting clinical symptoms of infection, or reducing the severity of any clinical symptoms that are present in the subjects, in comparison to wild-type infection. For example, it should refer to any reduction of pathogen load, pathogen shedding, reduction in pathogen transmission, or reduction of any clinical sign symptomatic of PRRSV infection, in particular of elevated body temperature. Preferably these clinical symptoms are reduced in subjects receiving the composition of the present invention by at least 10% in comparison to subjects not receiving the composition and may become infected. More preferably, clinical symptoms are reduced in subjects receiving the composition of the present invention by at least 20%, preferably by at least 30%, more preferably by at least 40%, and even more preferably by at least 50%.

Also, the elevated body temperature usually associated with the administration of an attenuated PRRSV vaccine to an animal is reduced in subjects receiving the composition of the present invention by at least 10% in comparison to subjects receiving a conventional attenuated PRRSV vaccine. More preferably, the elevated body temperature usually associated with the administration of an attenuated PRRSV vaccine is reduced in subjects receiving the composition of the present invention by at least 20%, preferably by at least 30%, more preferably by at least 40%, and even more preferably by at least 50%.

Hence, a further advantage of the PRRS virus according to the invention is in particular the effect that its administration to an animal, e.g. for the prophylaxis or treatment of PRRS, results in a reduced increase of body temperature in the animal in comparison with a conventional attenuated PPRSV vaccine.

The term "conventional attenuated PRRSV vaccine", as mentioned herein, is in particular directed to any attenuated PRRSV useful as a vaccine, wherein said PRRSV does not have the characteristic features of the PRRS virus of the present invention, in particular is not able to induce the interferon type I production and secretion by a cell infected by said PRRSV.

The term "subject", as mentioned herein, in particular relates to an animal.

The term "body temperature", as used herein, in particular refers to the approximate average normal, internal temperature of an animal, for example about 38.5-39° C. in pigs, whereas the body temperature associated with a PRRSV infection may be elevated up to 41° C. in pigs.

The term "reduction of PRRSV viremia" means, but is not limited to, the reduction of PRRS virus entering the bloodstream of an animal, wherein the viremia level, i.e. the number of PRRSV RNA copies per mL of blood serum or the number of plaque forming colonies per deciliter of blood serum, is reduced in the blood serum of subjects receiving the composition of the present invention by at least 50% in comparison to subjects not receiving the composition and may become infected. More preferably the viremia level is reduced in subjects receiving the composition of the present invention by at least 90%, preferably by at least 99.9%, more preferably by at least 99.99%, and even more preferably by at least 99.999%.

The present invention further relates to the use of the PRRS virus according to the invention or of the immunogenic composition of the invention for the preparation of a vaccine or medicament for
- inducing an immune response against PRRSV, or
- treating or preventing PRRS, or
- preventing or reducing PRRSV viremia and/or
- preventing or reducing clinical symptoms, in particular the elevated body temperature, associated with PRRSV infection, or
- the prevention or reduction of the elevated body temperature associated with the administration of an attenuated PRRSV vaccine to an animal.

In particular, it is preferred if the vaccine or medicament, as mentioned herein, is to be administered in two doses or preferably in a single dose to an animal.

The present invention also provides a method of preparing an immunogenic composition, preferably a vaccine or medicament, more preferably a vaccine or medicament for
- inducing an immune response against PRRSV, or
- treating or preventing PRRS, or
- preventing or reducing PRRSV viremia and/or
- preventing or reducing clinical symptoms, in particular the elevated body temperature, associated with PRRSV infection, or
- the prevention or reduction of the elevated body temperature associated with the administration of an attenuated PRRSV vaccine to an animal, wherein said method comprises the step of mixing the PRRS virus according to the invention with one or more pharmaceutically acceptable carriers or excipients, and wherein said one or more pharmaceutically acceptable carriers or excipients are preferably selected from the group consisting of solvents, dispersion media, adjuvants, stabilizing agents, diluents, preservatives, antibacterial and antifungal agents, isotonic agents, and adsorption delaying agents.

In another aspect, the present invention further provides a method for
- inducing an immune response against PRRSV, or
- treating or preventing PRRS, or
- preventing or reducing PRRSV viremia and/or
- preventing or reducing clinical symptoms, in particular the elevated body temperature, associated with PRRSV infection, or
- the prevention or reduction of the elevated body temperature associated with the administration of an attenuated PRRSV vaccine to an animal, wherein said method comprises the step of administering the immunogenic composition of the invention to an animal in need thereof, and wherein preferably the immunogenic composition and/or the vaccine is administered in two doses or, more preferably, in a single dose.

EXAMPLES

In the examples five viable, genetically designed PRRSV mutant strains are described which are based on infectious EU PRRSV cDNA clone LoN94-13. These strains, delta nsp1 IX-10, delta nsp1 XVII-1, delta nsp1 XVIII-12, delta nsp1 XIX-2 and delta nsp1 XX-9 (henceforth referred to as vaccine candidates), harbor genomic deletions of two, three, four, five, or six codons in their predicted nsp1 genes, respectively, resulting in deletions of two (motif P21R22 (SEQ ID NO: 77)), three (motif R20P21R22 (SEQ ID NO: 78)), four (motif G19R20P21R22 (SEQ ID NO: 79)), five (motif N18G19R20P21R22 (SEQ ID NO: 80)), or six (motif (P17N18G19R20P21R22 (SEQ ID NO: 81)) amino acids in their predicted nsp1β proteins, respectively (FIG. 1).

Based on sequence alignments of parental strain LoN94-13 with PRRSV US and EU reference strains VR-2332 and Lelystad virus as well as with strain GD-XH, the deletions are located in the predicted nsp1β portion of nsp1 (FIG. 2). In more detail, the deletion site for all vaccine candidates is located in the N-terminal domain (NTD) of nsp1β and overlaps with amino acids P23R24 (SEQ ID NO: 77) of GD-XH nsp1β; (FIG. 2).

After transfection of synthetic transcripts of the vaccine candidates into BHK21 cells and transfer of cell culture supernatant from transfected BHK21 cells onto PRRSV-susceptible MA104 cells, plaque formation typical for PRRSV infection occurred. PRRSV-specificity and viability for each of the vaccine strains then was demonstrated by subsequent cell culture passages on MA104 cells and PRRSV-specific immunofluorescence using monoclonal antibody SDOW17 (Rural Technologies).

Figure 3B:
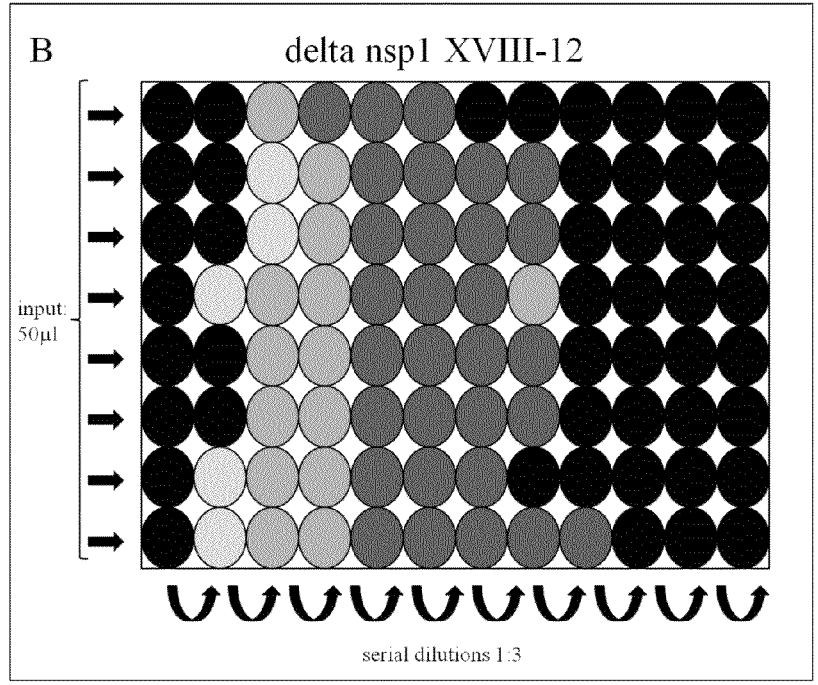

After endpoint dilution and generation of virus stocks each derived from material of a single virus plaque, virus titers of the obtained virus stocks were determined for each vaccine candidate by serial virus titrations on 96-well plates containing MA104 cells followed by PRRSV-specific immunofluorescence analyses six to seven days post infection. Unlike experience with titrations of virus stocks from parental PRRSV LoN94-13, the first serial dilutions of vaccine candidates delta nsp1 XVII-1 and delta nsp1 XVIII-12 did not demonstrate a cytopathic effect and virus plaque formation, while at higher dilutions of the virus stocks a cytopathic effect was detectable. Moreover, when respective titrations were investigated by immunofluorescence, cell culture wells of the first serial dilutions were negative for PRRSV infection for both vaccine candidates, while wells infected with higher dilutions of the virus stocks showed PRRSV-specific immunofluorescence, respectively (FIG. 3).

Figure 4:
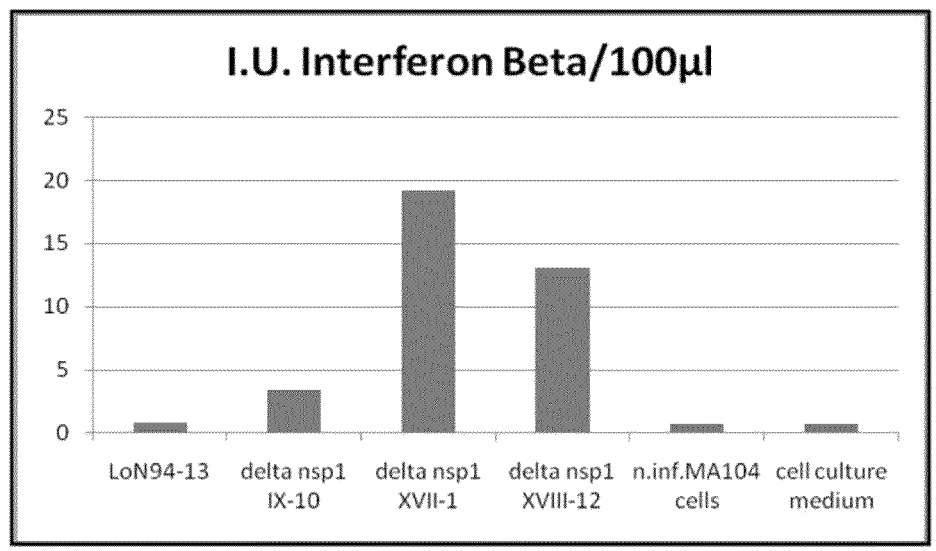
FIG. 4: Virus stocks of vaccine candidates contain IFNβ.

To determine whether the prepared vaccine candidate virus stocks contained type I IFN, a commercial ELISA specific for human IFNβ (Invitrogen) was used. MA104 cells are epithelial Green Monkey kidney cells. According to the ELISA manufacturer, this Invitrogen ELISA is also suited for the detection of primate IFNβ other than human. For each vaccine candidate's virus stock, 100 µl served as assay input, while a virus stock from parental strain LoN94-13, cell culture medium, and medium from noninfected cells served as controls. For quantification of the obtained results, a calibration curve was included using a positive control of the ELISA manufacturer. All samples were measured in duplicates. Unlike the negative controls, virus stocks of the vaccine candidates contained considerable levels of type I IFN, while the virus stock of the parental virus showed IFN levels as low as the negative controls (FIG. 4).

To confirm the results obtained and to assess kinetics of type I IFN production in cells infected with the vaccine candidates, a time course experiment was performed using MA104 cells infected at a multiplicity of infection (MOI) of 0.001, respectively. Parental strain LoN94-13 served as negative control. While there were only very little and unaltered levels of type I IFN near background detectable for infection with parental strain LoN94-13, vaccine candidates delta nsp1 XVII-1 and delta nsp1 XVIII-12 induced considerable and increasing amounts of up to about 18 I.U. IFNβ per 25 µl sample volume from two days post infection on (FIG. 5).

Figure 6:
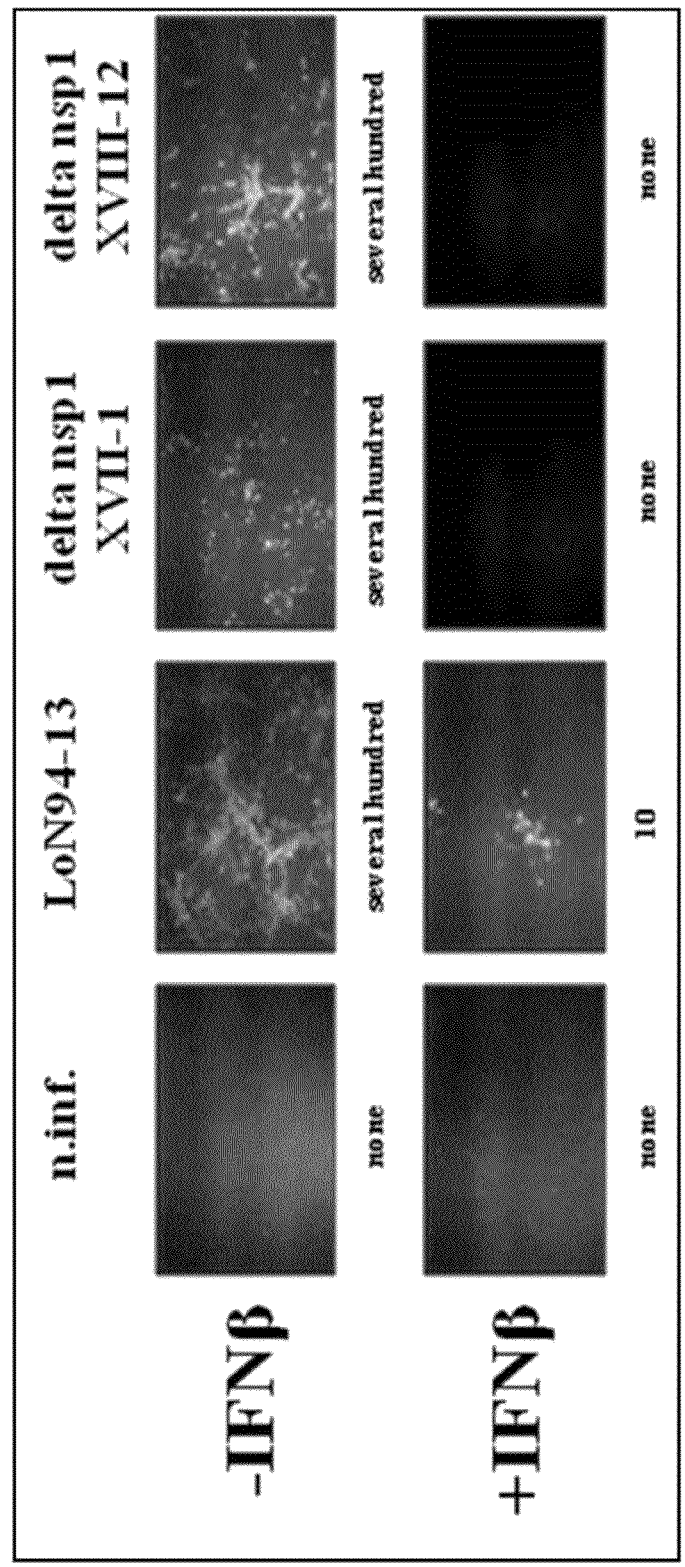
FIG. 6: Delta nsp1 mutants show increased sensitivity to type I IFN.

It was experimentally assessed whether vaccine candidates containing genomic deletions in nsp1 demonstrate an increased sensitivity to type I IFN (FIG. 6). $5 \times 10^5$ MA104 cells were seeded into a well of a six-well plate and were either not infected (n.inf.) or infected with 800 infectious virus particles of one of the virus strains given on top, respectively. Cells then were either inoculated with 120 I.U. human IFNβ (+IFNβ, bottom row), respectively, or not (−IFNβ, top row). Three days post infection, immunofluorescence analysis specific for the PRRSV capsid protein was performed using monoclonal antibody SDOW17 (Rural Technologies). The total numbers of foci of PRRSV-infected cells per well are given below, respectively.

This experiment demonstrated that inoculation with type I IFN reduced the number of PRRSV infection events in cells after inoculation with a defined number of infectious virus particles, reflecting reduced viral infectivity of PRRSV when IFN was added. This reduction was 80-fold for wild type virus LoN94-13 (FIG. 6). In addition, for infection with wild type virus, foci of infected cells were smaller than in the well not inoculated with IFN (FIG. 6). However, for vaccine strains delta nsp1 XVII-1 and delta nsp1 XVIII-12, viral infectivity was reduced to zero when INF was added (FIG. 6). Thus, these vaccine candidates not only induce production of type I IFN in infected cells (FIG. 4 and FIG. 5), but also demonstrate increased sensitivity to type I INF when compared to wild type PRRSV (FIG. 6). This is reflected by their dramatically reduced viral infectivity when IFNβ is present.

Figure 5:
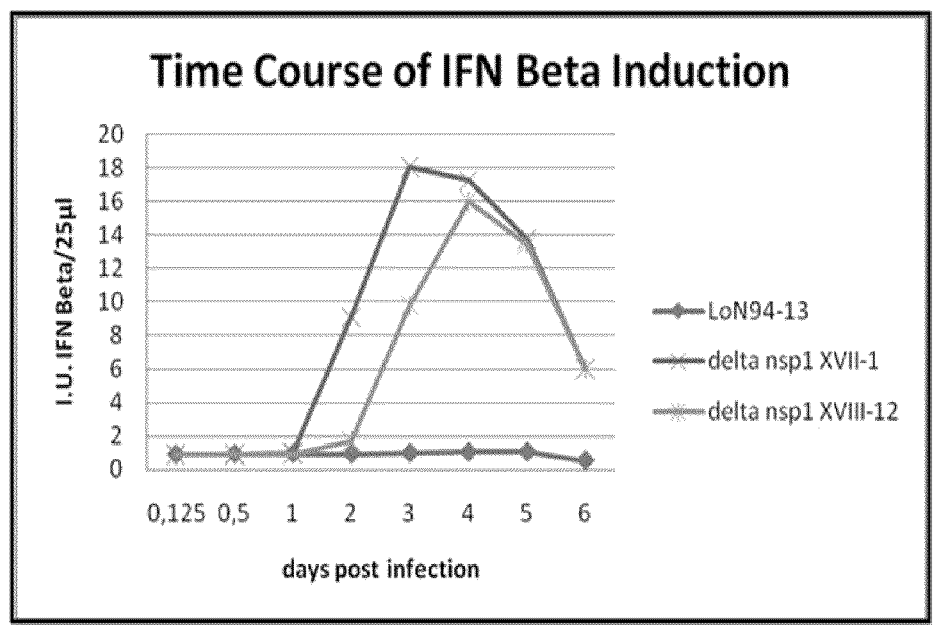
FIG. 5: Time course of IFNβ induction after infection of MA104 cells.

Interestingly, the cells infected for the time course experiment summarized in FIG. 5 not only produced considerable amounts of IFNβ, but at the end of the experiment at six days post infection, cells infected with vaccine candidates delta nsp1 XVII-1 and delta nsp1 XVIII-12 showed signs of recovery from usually lytical PRRSV infection. While cells infected with parental strain LoN94-13 were fully lysed, cells infected with the vaccine candidates grew in a partially (delta nsp1 XVIII-12) or completely intact monolayer (delta nsp1 XVII-1). For the latter, only weak signs of a PRRSV-induced cytopathic effect were still detectable. Thus, the interferon production of infected cells together with the observed sensitivity of vaccine candidates to type I IFN correlated with partial or almost complete recovery of infected cells over time. It is reasonable to expect that type I IFN induction by the vaccine candidates together with their increased sensitivity to type I IFN will contribute to a significantly attenuated viral phenotype in the natural host. In particular, expected features of the vaccine candidates' attenuation in pigs include stimulation of the innate and specific immunity, both humoral and cellular, and less shedding and/or shortened viremia of the vaccine viruses.

To assess whether the PRRSV vaccine candidates are attenuated in the host, an animal experiment in piglets was performed.

Three groups, each of ten animals, were infected at study day 0 either with wild-type parental EU PRRSV strain Lon94-13 (WT group), or with delta nsp1 XVIII-12 (nsp1 group), or were not infected (Ch control group). Infection was applied by intramuscular injection to the neck at dosages of $10^{6.56}$ TCID$_{50}$ for LoN94-13 or $10^{6.6}$ TCID$_{50}$ for delta nsp1 XVIII-12, respectively. 21 days post vaccination, all animals were challenged with a virulent EU PRRSV strain being heterologous to LoN94-13 by intramuscular injection and intranasal inoculation at a total dosage of $3 \times 10^{6.52}$ TCID$_{50}$. Animals were kept until the end of the experiment at day 31, ten days after challenge, and body temperatures were measured for all animals at days 0 (1 and 4 hours post vaccination), 1, 3, 5, 8, 10, 12, 14, 18, 20, 22, 24, 26, 28, and 31.

Mean body temperatures were determined for each animal for the time after vaccination but before challenge using measured body temperature data from all timepoints from day 0 through day 20. Subsequently, mean body temperatures were determined for each group (FIG. 7, (left-hand) columns). Error bars indicate standard deviations, respectively. Following the same procedure, mean body temperatures and standard deviations were determined for all groups for the time after challenge using measured body temperature data from all timepoints from day 22 through 31 (FIG. 7, (right-hand) columns).

The term "Significant(ly)" in the context of the following means either (i) p-values of 0.05 or lower as determined by the Dunnett test and obtained from comparing the nsp1 group with either the WT or the Ch control group for either of the two time periods investigated (before and after challenge) or (ii) p-values of 0.05 or lower when comparing the mean temperature change within a group and between the two time periods investigated (before and after challenge).

When comparing the determined mean body temperatures for the time after vaccination but before challenge (left hand columns) in between the three groups, animals from the WT group demonstrated a rise in body temperature of more than 0.4° C. when compared to animals from the noninfected Ch control group, thus demonstrating virulence of LoN94-13 in the infected host. In contrast, the nsp1 group showed a significant reduction in mean body temperature of more than 0.2° C. when compared to the WT group. Thus, since vaccination dosages were the same for the WT and the nsp1 group, the considerable reduction in increase of body temperature compared to WT demonstrates that the described mutation in the genome of delta nsp1 XVIII-12 has significantly reduced virulence of the WT parental strain LoN94-13 in the infected animal.

Figure 7:
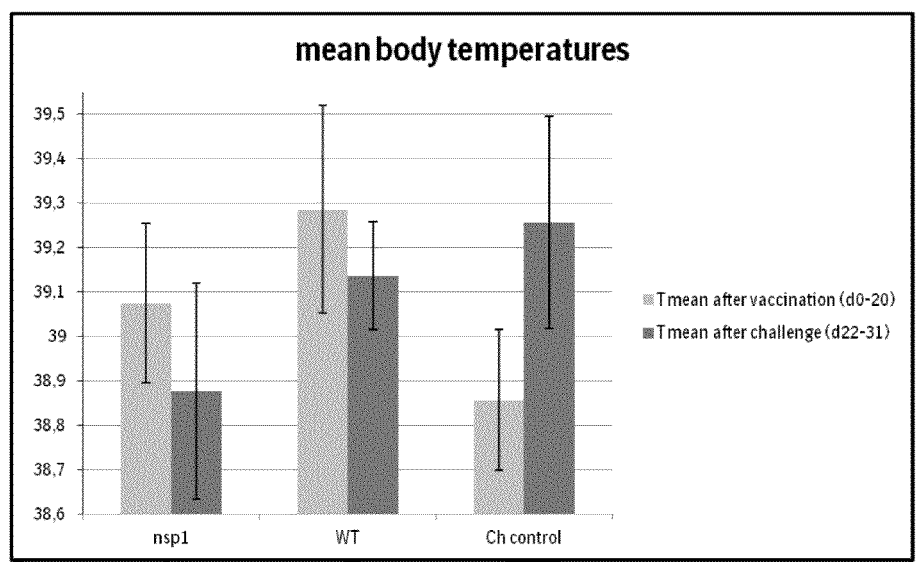
FIG. 7: Mean body temperatures of vaccinated groups before and after challenge.

The significant rise in the mean body temperature of the Ch control group from before challenge to after challenge of 0.4° C. demonstrates virulence of the heterologous EU PRRSV challenge strain. The mean temperature of the WT group after challenge was slightly lower than before challenge, but not significantly reduced (FIG. 7). In contrast, the mean body temperature of the nsp1 group after challenge was significantly reduced by almost 0.2° C. when compared to that before challenge. Moreover, the body temperature of the nsp1 group after challenge was significantly reduced by almost 0.4° C. when compared to the Ch control group after challenge. Also, mean body temperature of the nsp1 group after challenge was significantly lower that that of the WT group after challenge by more than 0.2° C. Taken together, this demonstrates that a measurable and significant degree of protection from signs of disease induced by the applied challenge virus was conferred to pigs by vaccination with delta nsp1 XVIII-12. Since parental PRRSV strain LoN94-13 did not confer significant protection, it is evident that the described mutation in the genome of delta nsp1 XVIII-12 is causative for the observed significant protective technical effect.

Analogous experiments, wherein the vaccination was performed with lower amounts ($10^5$ TCID$_{50}$) of delta nsp1 XVIII-12 showed results similar to the above described results (data not shown). Thus, in practice, a preferred amount of $10^3$ to $10^5$ TCID$_{50}$ is sufficient for vaccination.

Taken together, the invention described here represents the first known viable PRRSV (EU) strains that contain mutations (deletions) in the nsp1 gene (nsp1β) that induce type I IFN (IFNβ) production in susceptible cells (MA104) and that show increased sensitivity to type I IFN (IFNβ). Moreover, the animal data demonstrates that (i) vaccine candidate delta nsp1 XVIII-12 is significantly attenuated in the host when compared to its parental PRRSV strain LoN94-13 and that (ii) vaccine candidate delta nsp1 XVIII-12 confers significant protection from signs of disease induced by challenge with a heterologous PRRSV strain while parental strain LoN94-13 does not. Thus, the described vaccine candidates or the described mutations therein, either alone or combined with other attenuating mutations, may serve as promising life attenuated PRRSV vaccines.

IN THE SEQUENCE LISTING

SEQ ID NO: 1 corresponds to LoN94-13 complete nsp1 protein,
SEQ ID NO: 2 corresponds to Lelystad virus complete nsp1 protein,
SEQ ID NO: 3 corresponds to VR2332 complete nsp1 protein,
SEQ ID NO: 4 corresponds to LoN94-13 complete nsp1 Alpha,
SEQ ID NO: 5 corresponds to Lelystad virus complete nsp1 Alpha,
SEQ ID NO: 6 corresponds to VR2332 complete nsp1 Alpha,
SEQ ID NO: 7 corresponds to LoN94-13 complete nsp1 Beta,
SEQ ID NO: 8 corresponds to Lelystad virus complete nsp1 Beta,
SEQ ID NO: 9 corresponds to VR2332 complete nsp1 Beta,
SEQ ID NO: 10 corresponds to LoN94-13 nsp1 Beta NTD,
SEQ ID NO: 11 corresponds to Lelystad virus nsp1 Beta NTD,
SEQ ID NO: 12 corresponds to VR2332 nsp1 Beta NTD,
SEQ ID NO: 13 corresponds to LoN94-13 complete viral cDNA insert,
SEQ ID NO: 14 corresponds to Lelystad virus complete genome,
SEQ ID NO: 15 corresponds to VR2332 complete genome,
SEQ ID NO: 16 corresponds to delta nsp1 IX-10 complete nsp1 protein sequence,
SEQ ID NO: 17 corresponds to delta nsp1 XVII-1 complete nsp1 protein sequence,
SEQ ID NO: 18 corresponds to delta nsp1 XVIII-12 complete nsp1 protein sequence,
SEQ ID NO: 19 corresponds to delta nsp1 XIX-2 complete nsp1 protein sequence,
SEQ ID NO: 20 corresponds to delta nsp1 XX-9 complete nsp1 protein sequence,
SEQ ID NO: 21 corresponds to delta nsp1 IX-10 complete nsp1Beta protein sequence,
SEQ ID NO: 22 corresponds to delta nsp1 XVII-1 complete nsp1Beta protein sequence,
SEQ ID NO: 23 corresponds to delta nsp1 XVIII-12 complete nsp1Beta protein sequence,
SEQ ID NO: 24 corresponds to delta nsp1 XIX-2 complete nsp1Beta protein sequence,
SEQ ID NO: 25 corresponds to delta nsp1 XX-9 complete nsp1Beta protein sequence,
SEQ ID NO: 26 corresponds to delta nsp1 IX-10 nsp1Beta NTD protein sequence,
SEQ ID NO: 27 corresponds to delta nsp1 XVII-1 nsp1Beta NTD protein sequence,
SEQ ID NO: 28 corresponds to delta nsp1 XVIII-12 nsp1Beta NTD protein sequence,
SEQ ID NO: 29 corresponds to delta nsp1 XIX-2 nsp1Beta NTD protein sequence,
SEQ ID NO: 30 corresponds to delta nsp1 XX-9 nsp1Beta NTD protein sequence,
SEQ ID NO: 31 corresponds to delta nsp1 IX-10 complete viral cDNA insert sequence,
SEQ ID NO: 32 corresponds to delta nsp1 XVII-1 complete viral cDNA insert sequence,
SEQ ID NO: 33 corresponds to delta nsp1 XVIII-12 complete viral cDNA insert sequence,
SEQ ID NO: 34 corresponds to delta nsp1 XIX-2 complete viral cDNA insert sequence,
SEQ ID NO: 35 corresponds to delta nsp1 XX-9 complete viral cDNA insert sequence,
SEQ ID NO: 36 corresponds to a (type 1) nsp1 Beta NTD with mutation (deletion of 2 aa),
SEQ ID NO: 37 corresponds to a (type 1) nsp1 Beta NTD with mutation (deletion of 3 aa),
SEQ ID NO: 38 corresponds to a (type 1) nsp1 Beta NTD with mutation (deletion of 4 aa),
SEQ ID NO: 39 corresponds to a (type 1) nsp1 Beta NTD with mutation (deletion of 5 aa),
SEQ ID NO: 40 corresponds to a (type 1) nsp1 Beta NTD with mutation (deletion of 6 aa),
SEQ ID NO: 41 corresponds to a (type 1) nsp1 Beta NTD with mutation (deletion of 7 aa),
SEQ ID NO: 42 corresponds to a (type 2) nsp1 Beta NTD with mutation (deletion of 2 aa),
SEQ ID NO: 43 corresponds to a (type 2) nsp1 Beta NTD with mutation (deletion of 3 aa),
SEQ ID NO: 44 corresponds to a (type 2) nsp1 Beta NTD with mutation (deletion of 4 aa),
SEQ ID NO: 45 corresponds to a (type 2) nsp1 Beta NTD with mutation (deletion of 5 aa),
SEQ ID NO: 46 corresponds to a (type 2) nsp1 Beta NTD with mutation (deletion of 6 aa),
SEQ ID NO: 47 corresponds to a (type 2) nsp1 Beta NTD with mutation (deletion of 7 aa),
SEQ ID NO: 48 corresponds to a (type 1) nsp1 Beta NTD with mutation (deletion of 2 aa),
SEQ ID NO: 49 corresponds to a (type 1) nsp1 Beta NTD with mutation (deletion of 3 aa),
SEQ ID NO: 50 corresponds to a (type 1) nsp1 Beta NTD with mutation (deletion of 4 aa),
SEQ ID NO: 51 corresponds to a (type 1) nsp1 Beta NTD with mutation (deletion of 5 aa), SEQ ID NO: 52 corresponds to a (type 1) nsp1 Beta NTD with mutation (deletion of 6 aa),
SEQ ID NO: 53 corresponds to a (type 1) nsp1 Beta NTD with mutation (deletion of 7 aa),
SEQ ID NO: 54 corresponds to a (type 2) nsp1 Beta NTD with mutation (deletion of 2 aa),
SEQ ID NO: 55 corresponds to a (type 2) nsp1 Beta NTD with mutation (deletion of 3 aa),
SEQ ID NO: 56 corresponds to a (type 2) nsp1 Beta NTD with mutation (deletion of 4 aa),
SEQ ID NO: 57 corresponds to a (type 2) nsp1 Beta NTD with mutation (deletion of 5 aa),
SEQ ID NO: 58 corresponds to a (type 2) nsp1 Beta NTD with mutation (deletion of 6 aa),
SEQ ID NO: 59 corresponds to a (type 2) nsp1 Beta NTD with mutation (deletion of 7 aa).

REFERENCE LIST

Allende, R., Laegreid, W. W., Kutish, G. F., Galeota, J. A., Wills, R. W., Osorio, F. A., 2000. Porcine reproductive and respiratory syndrome virus: description of persistence in individual pigs upon experimental infection. J. Virol. 74, 10834-10837.

Ansari, I. H., Kwon, B., Osorio, F. A., Pattnaik, A. K., 2006. Influence of N-linked glycosylation of porcine reproductive and respiratory syndrome virus GP5 on virus infectivity, antigenicity, and ability to induce neutralizing antibodies. J. Virol. 80, 3994-4004.

Beura, L. K., Sarkar, S. N., Kwon, B., Subramaniam, S., Jones, C., Pattnaik, A. K., Osorio, F. A., 2010. Porcine reproductive and respiratory syndrome virus nonstructural protein 1beta modulates host innate immune response by antagonizing IRF3 activation. J. Virol. 84, 1574-1584.

Buddaert, W., Van, R. K., Pensaert, M., 1998. In vivo and in vitro interferon (IFN) studies with the porcine reproductive and respiratory syndrome virus (PRRSV). Adv. Exp. Med. Biol. 440, 461-467.

Chen, Z., Lawson, S., Sun, Z., Zhou, X., Guan, X., Christopher-Hennings, J., Nelson, E. A., Fang, Y., 2010. Identification of two auto-cleavage products of nonstructural protein 1 (nsp1) in porcine reproductive and respiratory syndrome virus infected cells: nsp1 function as interferon antagonist. Virology 398, 87-97.

den Boon, J. A., Faaberg, K. S., Meulenberg, J. J., Wassenaar, A. L., Plagemann, P. G., Gorbalenya, A. E., Snijder, E. J., 1995. Processing and evolution of the N-terminal region of the arterivirus replicase ORF1a protein: identification of two papainlike cysteine proteases. J. Virol. 69, 4500-4505.

Haller, O., Weber, F., 2009. The interferon response circuit in antiviral host defense. Verh. K. Acad. Geneeskd. Belg. 71, 73-86.

Kim, O., Sun, Y., Lai, F. W., Song, C., Yoo, D., 2010. Modulation of type I interferon induction by porcine reproductive and respiratory syndrome virus and degradation of CREB-binding protein by non-structural protein 1 in MARC-145 and HeLa cells. Virology 402, 315-326.

Kroese, M. V., Zevenhoven-Dobbe, J. C., Bos-de Ruijter, J. N., Peeters, B. P., Meulenberg, J. J., Cornelissen, L. A., Snijder, E. J., 2008. The nsp1alpha and nsp1 papain-like autoproteinases are essential for porcine reproductive and respiratory syndrome virus RNA synthesis. J. Gen. Virol. 89, 494-499.

Li, H., Zheng, Z., Zhou, P., Zhang, B., Shi, Z., Hu, Q., Wang, H., 2010. The cysteine protease domain of porcine reproductive and respiratory syndrome virus non-structural protein 2 antagonizes interferon regulatory factor 3 activation. J. Gen. Virol. 91, 2947-2958.

Lopez, O. J., Osorio, F. A., 2004. Role of neutralizing antibodies in PRRSV protective immunity. Vet. Immunol. Immunopathol. 102, 155-163.

Meier, W. A., Galeota, J., Osorio, F. A., Husmann, R. J., Schnitzlein, W. M., Zuckermann, F. A., 2003. Gradual development of the interferon-gamma response of swine to porcine reproductive and respiratory syndrome virus infection or vaccination. Virology 309, 18-31.

Miller, L. C., Laegreid, W. W., Bono, J. L., Chitko-McKown, C. G., Fox, J. M., 2004. Interferon type I response in porcine reproductive and respiratory syndrome virus-infected MARC-145 cells. Arch. Virol. 149, 2453-2463.

Ostrowski, M., Galeota, J. A., Jar, A. M., Platt, K. B., Osorio, F. A., Lopez, O. J., 2002. Identification of neutralizing and normeutralizing epitopes in the porcine reproductive and respiratory syndrome virus GP5 ectodomain. J. Virol. 76, 4241-4250.

Shi, X., Wang, L., Li, X., Zhang, G., Guo, J., Zhao, D., Chai, S., Deng, R., 2011a. Endoribonuclease activities of porcine reproductive and respiratory syndrome virus nsp11 was essential for nsp11 to inhibit IFN-beta induction. Mol. Immunol. 48, 1568-1572.

Shi, X., Wang, L., Zhi, Y., Xing, G., Zhao, D., Deng, R., Zhang, G., 2010. Porcine reproductive and respiratory syndrome virus (PRRSV) could be sensed by professional beta interferon-producing system and had mechanisms to inhibit this action in MARC-145 cells. Virus Res. 153, 151-156.

Shi, X., Zhang, G., Wang, L., Li, X., Zhi, Y., Wang, F., Fan, J., Deng, R., 2011b. The Nonstructural Protein 1 Papain-Like Cysteine Protease Was Necessary for Porcine Reproductive and Respiratory Syndrome Virus Nonstructural Protein 1 to Inhibit Interferon-beta Induction. DNA Cell Biol. 30, 355-362.

Snijder, E. J., Meulenberg, J. J., 1998. The molecular biology of arteriviruses. J. Gen. Virol. 79 (Pt 5), 961-979.

Song, C., Krell, P., Yoo, D., 2010. Nonstructural protein 1alpha subunit-based inhibition of NF-kappaB activation and suppression of interferon-beta production by porcine reproductive and respiratory syndrome virus. Virology 407, 268-280.

Sun, Y., Xue, F., Guo, Y., Ma, M., Hao, N., Zhang, X. C., Lou, Z., Li, X., Rao, Z., 2009. Crystal structure of porcine reproductive and respiratory syndrome virus leader protease Nsp1alpha. J. Virol. 83, 10931-10940.

Xiao, Z., Batista, L., Dee, S., Halbur, P., Murtaugh, M. P., 2004. The level of virus-specific T-cell and macrophage recruitment in porcine reproductive and respiratory syndrome virus infection in pigs is independent of virus load. J. Virol. 78, 5923-5933.

Xue, F., Sun, Y., Yan, L., Zhao, C., Chen, J., Bartlam, M., Li, X., Lou, Z., Rao, Z., 2010. The crystal structure of porcine reproductive and respiratory syndrome virus nonstructural protein Nsp1beta reveals a novel metal-dependent nuclease. J. Virol. 84, 6461-6471.

The invention claimed is:

1. A replication-competent Porcine Reproductive and Respiratory Syndrome (PRRS) virus comprising a deletion of at least three consecutive nucleotide triplets in the gene sequence encoding the N terminal domain (NTD) of the nsp1β subunit of the nsp1 protein of said virus, wherein the NTD starts with the N-terminus of nsp1β of amino acid sequence SXXY (SEQ ID NO: 60) and ends with the serine (S) residue within the amino acid sequence SFP (SEQ ID NO: 62), wherein said deletion of three consecutive nucleotide triplets comprises the first encoded arginine residue (R) located at least 21 amino acid residues located in the C-terminal direction from the NTD amino acid residue of nsp1β and two amino acid residues flanking said R residue in the N-terminal direction, and wherein the modified PRRS virus induces production and secretion of interferon type I by a cell infected with said virus.

2. The PRRS virus according to claim 1, wherein said modification comprises a deletion of three consecutive nucleotide triplets coding for the amino acid sequence RXR (SEQ ID NO: 66) of the nsp1β subunit, or wherein said mutation comprises a deletion of four consecutive nucleotide triplets coding for the amino acid residues GRXR (SEQ ID NO: 68) of the nsp1β subunit, wherein X is a genetically encoded amino acid residue.

3. The PRRS virus according to claim 1, wherein said PPRS virus has increased sensitivity to interferon type I.

4. The PRRS virus according to claim 1, wherein said PRRS virus is an attenuated PRRS virus.

5. The PRRS virus according to claim 1, wherein said PPRS virus is a genotype I.

6. The PRRS virus according to claim 1, wherein said interferon type I is Interferon-α, Interferon-β or combinations thereof.

7. The PRRS virus according to claim 1, wherein said cell is a mammalian cell, and wherein said mammalian cell is a cell of a primary or secondary cell line or a host cell.

8. The PRRS virus according to claim 7, wherein said mammalian cell is a porcine cell or a simian cell.

9. The PRRS virus according to claim 8, wherein said porcine cell is a porcine macrophage.

10. The PRRS virus according to claim 8, wherein said simian cell is a MA-104 or a MARC-145 cell.

11. A method for the treatment of Porcine Reproductive and Respiratory Syndrome comprising administering an effective amount of the PRRS virus of claim 1 to a swine, pig, piglet or a sow in need of said treatment.

12. A polynucleotide comprising the genome of the PRRS virus according to claim 1.

13. A DNA Vector comprising a copy of the polynucleotide of claim 12.

14. A virus particle comprising the polynucleotide of claim 12 or 13.

15. A cell comprising the polynucleotide of claim 12 or the DNA-vector of claim 13.

16. A method of preparing a PRRS virus composition comprising the cultivation of the PRRS virus according to claim 1 in cell culture.

17. A method for the detection of interferon type I, or of mRNA coding for interferon type I by the cell infected with the modified PRRS virus of claim 1, wherein the interferon type I and/or the mRNA coding for interferon type I is detected by a bioassay, wherein said bioassay is preferably selected from the group consisting of ELISA, PCR, GLISA, IFA, biosensoric measurement, Surface Plasmon Resonance (SPR) measurement, selective media, lateral flow, biochip measurement, immunomagnetic separation, electrochemiluminescence, chromogenic media, immunodiffusion, DNA hybridization, staining, colorimetric detection, luminescence, and combinations thereof.

18. An immunogenic composition comprising the PRRS virus according to claim 1.

19. The immunogenic composition according to claim 18, comprising an amount of $10^1$ to $10^7$ viral particles per dose.

20. The immunogenic composition according to claim 18, comprising an amount of $10^3$ to $10^6$ particles per dose.

21. The immunogenic composition according to claim 18, comprising an amount of $10^4$ to $10^6$ particles per dose.

22. The immunogenic composition according to claim 18, comprising an amount of said PRRS virus which is equivalent to a virus titre of at least about $10^3$ $TCID_{50}$/mL per dose.

23. The immunogenic composition according to claim 18, comprising an amount of said PRRS virus which is equivalent to a virus titre of between $10^3$ to $10^5$ $TCID_{50}$/mL per dose.

24. The immunogenic composition according to claim 18, further comprising one or more pharmaceutically acceptable carriers or excipients.

25. The immunogenic composition according to claim 24, wherein said one or more pharmaceutically acceptable carriers or excipients are selected from the group consisting of solvents, dispersion media, adjuvants, stabilizing agents, diluents, preservatives, antibacterial and antifungal agents, isotonic agents, and adsorption delaying agents.

26. A method for inducing an immune response against PRRSV comprising administering an effective amount of the immunogenic composition of claim 18 to an animal in need thereof.

27. The method of claim 26, wherein the immunogenic composition is administered in a single dose or in two doses.

* * * * *

SEQUENCE LISTING

<160> NUMBER OF SEQ ID NOS: 84

<210> SEQ ID NO 1
<211> LENGTH: 385
<212> TYPE: PRT
<213> ORGANISM: Porcine reproductive and respiratory syndrome virus

<400> SEQUENCE: 1

```
Met Ser Gly Thr Phe Ser Arg Cys Met Cys Thr Pro Ala Ala Arg Val
1               5                   10                  15

Phe Trp Asn Ala Gly Gln Val Tyr Cys Thr Arg Cys Leu Ser Ala Arg
            20                  25                  30

Ser Leu Leu Pro Pro Glu Leu Gln Asp Ile Asp Leu Ala Ala Ile Gly
        35                  40                  45

Leu Phe Tyr Lys Pro Lys Asp Lys Leu His Trp Lys Val Pro Ile Gly
    50                  55                  60

Ile Pro Gln Val Glu Cys Thr Pro Ser Gly Cys Cys Trp Leu Ser Gly
65                  70                  75                  80

Ile Phe Pro Leu Ala Arg Met Thr Ser Gly Asn His Asn Phe Leu Gln
                85                  90                  95

Arg Leu Val Lys Val Ala Asp Val Leu Tyr Arg Asp Gly Cys Leu Thr
            100                 105                 110

Ser Arg His Leu Arg Glu Leu Gln Val Tyr Glu Arg Gly Cys Ser Trp
        115                 120                 125

Tyr Pro Ile Thr Gly Pro Val Pro Gly Met Gly Leu Tyr Ala Asn Ser
    130                 135                 140

Met His Val Ser Asp Gln Pro Phe Pro Gly Ala Thr His Val Leu Thr
145                 150                 155                 160

Asn Ser Pro Leu Pro Gln Gln Ala Cys Arg Gln Pro Phe Cys Pro Phe
                165                 170                 175

Glu Glu Ala His Ser Ser Val Tyr Arg Trp Lys Lys Phe Val Val Phe
            180                 185                 190

Thr Asp Ser Ser Pro Asn Gly Arg Pro Arg Met Met Trp Thr Pro Glu
        195                 200                 205

Ser Asp Asp Ser Ala Asp Leu Glu Ala Leu Pro Pro Glu Leu Glu Arg
    210                 215                 220

Gln Val Glu Ile Leu Ile Arg Ser Phe Pro Ala His His Pro Val Ser
225                 230                 235                 240

Leu Ala Asp Trp Glu Leu Ala Glu Ser Pro Glu Asn Gly Phe Ser Phe
                245                 250                 255

Ser Thr Tyr His Ser Gly Gly Tyr Leu Val Gln Asn Pro Asp Val Phe
            260                 265                 270

Asp Ser Lys Cys Trp Leu Ser Cys Phe Leu Asp Gln Pro Ile Glu Val
        275                 280                 285

Arg Leu Tyr Glu Asp Tyr Leu Ala Asn Ala Phe Gly Tyr Gln Thr Lys
    290                 295                 300

Trp Gly Val Ser Gly Lys Tyr Leu Gln Arg Arg Leu Gln Val Asn Gly
305                 310                 315                 320

Ile Arg Ala Val Ile Asp Pro Asp Gly Pro Ile His Val Glu Ala Leu
                325                 330                 335

Ser Cys Pro Gln Ser Trp Ile Arg His Leu Thr Leu Asp Asp Asp Val
            340                 345                 350

Thr Pro Gly Phe Val Arg Leu Thr Ser Leu Arg Ile Val Pro Asn Thr
        355                 360                 365
```

```
Glu Pro Thr Thr Leu Arg Ile Phe Arg Phe Gly Ala His Lys Trp Tyr
            370                 375                 380

Gly
385

<210> SEQ ID NO 2
<211> LENGTH: 385
<212> TYPE: PRT
<213> ORGANISM: Porcine reproductive and respiratory syndrome virus

<400> SEQUENCE: 2

Met Ser Gly Thr Phe Ser Arg Cys Met Cys Thr Pro Ala Ala Arg Val
1               5                   10                  15

Phe Trp Asn Ala Gly Gln Val Phe Cys Thr Arg Cys Leu Ser Ala Arg
            20                  25                  30

Ser Leu Leu Ser Pro Glu Leu Gln Asp Thr Asp Leu Gly Ala Val Gly
        35                  40                  45

Leu Phe Tyr Lys Pro Arg Asp Lys Leu His Trp Lys Val Pro Ile Gly
    50                  55                  60

Ile Pro Gln Val Glu Cys Thr Pro Ser Gly Cys Cys Trp Leu Ser Ala
65                  70                  75                  80

Val Phe Pro Leu Ala Arg Met Thr Ser Gly Asn His Asn Phe Leu Gln
                85                  90                  95

Arg Leu Val Lys Val Ala Asp Val Leu Tyr Arg Asp Gly Cys Leu Ala
            100                 105                 110

Pro Arg His Leu Arg Glu Leu Gln Val Tyr Glu Arg Gly Cys Asn Trp
        115                 120                 125

Tyr Pro Ile Thr Gly Pro Val Pro Gly Met Gly Leu Phe Ala Asn Ser
    130                 135                 140

Met His Val Ser Asp Gln Pro Phe Pro Gly Ala Thr His Val Leu Thr
145                 150                 155                 160

Asn Ser Pro Leu Pro Gln Gln Ala Cys Arg Gln Pro Phe Cys Pro Phe
                165                 170                 175

Glu Glu Ala His Ser Ser Val Tyr Arg Trp Lys Lys Phe Val Val Phe
            180                 185                 190

Thr Asp Ser Ser Leu Asn Gly Arg Ser Arg Met Met Trp Thr Pro Glu
        195                 200                 205

Ser Asp Asp Ser Ala Ala Leu Glu Val Leu Pro Pro Glu Leu Glu Arg
    210                 215                 220

Gln Val Glu Ile Leu Ile Arg Ser Phe Pro Ala His His Pro Val Asp
225                 230                 235                 240

Leu Ala Asp Trp Glu Leu Thr Glu Ser Pro Glu Asn Gly Phe Ser Phe
                245                 250                 255

Asn Thr Ser His Ser Cys Gly His Leu Val Gln Asn Pro Asp Val Phe
            260                 265                 270

Asp Gly Lys Cys Trp Leu Ser Cys Phe Leu Gly Gln Ser Val Glu Val
        275                 280                 285

Arg Cys His Glu Glu His Leu Ala Asp Ala Phe Gly Tyr Gln Thr Lys
    290                 295                 300

Trp Gly Val His Gly Lys Tyr Leu Gln Arg Arg Leu Gln Val Arg Gly
305                 310                 315                 320

Ile Arg Ala Val Val Asp Pro Asp Gly Pro Ile His Val Glu Ala Leu
                325                 330                 335

Ser Cys Pro Gln Ser Trp Ile Arg His Leu Thr Leu Asp Asp Asp Val
            340                 345                 350
```

```
Thr Pro Gly Phe Val Arg Leu Thr Ser Leu Arg Ile Val Pro Asn Thr
            355                 360                 365

Glu Pro Thr Thr Ser Arg Ile Phe Arg Phe Gly Ala His Lys Trp Tyr
370                 375                 380

Gly
385

<210> SEQ ID NO 3
<211> LENGTH: 383
<212> TYPE: PRT
<213> ORGANISM: Porcine reproductive and respiratory syndrome virus

<400> SEQUENCE: 3

Met Ser Gly Ile Leu Asp Arg Cys Thr Cys Thr Pro Asn Ala Arg Val
1               5                   10                  15

Phe Met Ala Glu Gly Gln Val Tyr Cys Thr Arg Cys Leu Ser Ala Arg
            20                  25                  30

Ser Leu Leu Pro Leu Asn Leu Gln Val Ser Glu Leu Gly Val Leu Gly
        35                  40                  45

Leu Phe Tyr Arg Pro Glu Glu Pro Leu Arg Trp Th

```
                      325                 330                 335
Ile Arg His Leu Lys Leu Ala Gly Glu Pro Ser Tyr Ser Gly Phe Glu
            340                 345                 350

Asp Leu Leu Arg Ile Arg Val Glu Pro Asn Thr Ser Pro Leu Ala Asp
        355                 360                 365

Lys Glu Glu Lys Ile Phe Arg Phe Gly Ser His Lys Trp Tyr Gly
    370                 375                 380

<210> SEQ ID NO 4
<211> LENGTH: 180
<212> TYPE: PRT
<213> ORGANISM: Porcine reproductive and respiratory syndrome virus

<400> SEQUENCE: 4

Met Ser Gly Thr Phe Ser Arg Cys Met Cys Thr Pro Ala Ala Arg Val
1               5                   10                  15

Phe Trp Asn Ala Gly Gln Val Tyr Cys Thr Arg Cys Leu Ser Ala Arg
            20                  25                  30

Ser Leu Leu Pro Pro Glu Leu Gln Asp Ile Asp Leu Ala Ala Ile Gly
        35                  40                  45

Leu Phe Tyr Lys Pro Lys Asp Lys Leu His Trp Lys Val Pro Ile Gly
    50                  55                  60

Ile Pro Gln Val Glu Cys Thr Pro Ser Gly Cys Cys Trp Leu Ser Gly
65                  70                  75                  80

Ile Phe Pro Leu Ala Arg Met Thr Ser Gly Asn His Asn Phe Leu Gln
                85                  90                  95

Arg Leu Val Lys Val Ala Asp Val Leu Tyr Arg Asp Gly Cys Leu Thr
            100                 105                 110

Ser Arg His Leu Arg Glu Leu Gln Val Tyr Glu Arg Gly Cys Ser Trp
        115                 120                 125

Tyr Pro Ile Thr Gly Pro Val Pro Gly Met Gly Leu Tyr Ala Asn Ser
    130                 135                 140

Met His Val Ser Asp Gln Pro Phe Pro Gly Ala Thr His Val Leu Thr
145                 150                 155                 160

Asn Ser Pro Leu Pro Gln Gln Ala Cys Arg Gln Pro Phe Cys Pro Phe
                165                 170                 175

Glu Glu Ala His
            180

<210> SEQ ID NO 5
<211> LENGTH: 180
<212> TYPE: PRT
<213> ORGANISM: Porcine reproductive and respiratory syndrome virus

<400> SEQUENCE: 5

Met Ser Gly Thr Phe Ser Arg Cys Met Cys Thr Pro Ala Ala Arg Val
1               5                   10                  15

Phe Trp Asn Ala Gly Gln Val Phe Cys Thr Arg Cys Leu Ser Ala Arg
            20                  25                  30

Ser Leu Leu Ser Pro Glu Leu Gln Asp Thr Asp Leu Gly Ala Val Gly
        35                  40                  45

Leu Phe Tyr Lys Pro Arg Asp Lys Leu His Trp Lys Val Pro Ile Gly
    50                  55                  60

Ile Pro Gln Val Glu Cys Thr Pro Ser Gly Cys Cys Trp Leu Ser Ala
65                  70                  75                  80

Val Phe Pro Leu Ala Arg Met Thr Ser Gly Asn His Asn Phe Leu Gln
```

```
                    85                  90                  95
Arg Leu Val Lys Val Ala Asp Val Leu Tyr Arg Asp Gly Cys Leu Ala
                100                 105                 110

Pro Arg His Leu Arg Glu Leu Gln Val Tyr Glu Arg Gly Cys Asn Trp
            115                 120                 125

Tyr Pro Ile Thr Gly Pro Val Pro Gly Met Gly Leu Phe Ala Asn Ser
        130                 135                 140

Met His Val Ser Asp Gln Pro Phe Pro Gly Ala Thr His Val Leu Thr
145                 150                 155                 160

Asn Ser Pro Leu Pro Gln Gln Ala Cys Arg Gln Pro Phe Cys Pro Phe
                165                 170                 175

Glu Glu Ala His
            180

<210> SEQ ID NO 6
<211> LENGTH: 180
<212> TYPE: PRT
<213> ORGANISM: Porcine reproductive and respiratory syndrome virus

<400> SEQUENCE: 6

Met Ser Gly Ile Leu Asp Arg Cys Thr Cys Thr Pro Asn Ala Arg Val
1               5                   10                  15

Phe Met Ala Glu Gly Gln Val Tyr Cys Thr Arg Cys Leu Ser Ala Arg
            20                  25                  30

Ser Leu Leu Pro Leu Asn Leu Gln Val Ser Glu Leu Gly Val Leu Gly
        35                  40                  45

Leu Phe Tyr Arg Pro Glu Glu Pro Leu Arg Trp Thr Leu Pro Arg Ala
    50                  55                  60

Phe Pro Thr Val Glu Cys Ser Pro Ala Gly Ala Cys Trp Leu Ser Ala
65                  70                  75                  80

Ile Phe Pro Ile Ala Arg Met Thr Ser Gly Asn Leu Asn Phe Gln Gln
                85                  90                  95

Arg Met Val Arg Val Ala Ala Glu Leu Tyr Arg Ala Gly Gln Leu Thr
            100                 105                 110

Pro Ala Val Leu Lys Ala Leu Gln Val Tyr Glu Arg Gly Cys Arg Trp
        115                 120                 125

Tyr Pro Ile Val Gly Pro Val Pro Gly Val Ala Val Phe Ala Asn Ser
    130                 135                 140

Leu His Val Ser Asp Lys Pro Phe Pro Gly Ala Thr His Val Leu Thr
145                 150                 155                 160

Asn Leu Pro Leu Pro Gln Arg Pro Lys Pro Glu Asp Phe Cys Pro Phe
                165                 170                 175

Glu Cys Ala Met
            180

<210> SEQ ID NO 7
<211> LENGTH: 205
<212> TYPE: PRT
<213> ORGANISM: Porcine reproductive and respiratory syndrome virus

<400> SEQUENCE: 7

Ser Ser Val Tyr Arg Trp Lys Lys Phe Val Val Phe Thr Asp Ser Ser
1               5                   10                  15

Pro Asn Gly Arg Pro Arg Met Met Trp Thr Pro Glu Ser Asp Asp Ser
            20                  25                  30

Ala Asp Leu Glu Ala Leu Pro Pro Glu Leu Glu Arg Gln Val Glu Ile
```

```
                35                  40                  45
Leu Ile Arg Ser Phe Pro Ala His His Pro Val Ser Leu Ala Asp Trp
         50                  55                  60
Glu Leu Ala Glu Ser Pro Glu Asn Gly Phe Ser Phe Ser Thr Tyr His
 65                  70                  75                  80
Ser Gly Gly Tyr Leu Val Gln Asn Pro Asp Val Phe Asp Ser Lys Cys
                 85                  90                  95
Trp Leu Ser Cys Phe Leu Asp Gln Pro Ile Glu Val Arg Leu Tyr Glu
                100                 105                 110
Asp Tyr Leu Ala Asn Ala Phe Gly Tyr Gln Thr Lys Trp Gly Val Ser
            115                 120                 125
Gly Lys Tyr Leu Gln Arg Arg Leu Gln Val Asn Gly Ile Arg Ala Val
        130                 135                 140
Ile Asp Pro Asp Gly Pro Ile His Val Glu Ala Leu Ser Cys Pro Gln
145                 150                 155                 160
Ser Trp Ile Arg His Leu Thr Leu Asp Asp Val Thr Pro Gly Phe
                165                 170                 175
Val Arg Leu Thr Ser Leu Arg Ile Val Pro Asn Thr Glu Pro Thr Thr
            180                 185                 190
Leu Arg Ile Phe Arg Phe Gly Ala His Lys Trp Tyr Gly
        195                 200                 205

<210> SEQ ID NO 8
<211> LENGTH: 205
<212> TYPE: PRT
<213> ORGANISM: Porcine reproductive and respiratory syndrome virus

<400> SEQUENCE: 8

Ser Ser Val Tyr Arg Trp Lys Lys Phe Val Val Phe Thr Asp Ser Ser
 1               5                  10                  15
Leu Asn Gly Arg Ser Arg Met Met Trp Thr Pro Glu Ser Asp Asp Ser
                20                  25                  30
Ala Ala Leu Glu Val Leu Pro Pro Glu Leu Glu Arg Gln Val Glu Ile
            35                  40                  45
Leu Ile Arg Ser Phe Pro Ala His His Pro Val Asp Leu Ala Asp Trp
        50                  55                  60
Glu Leu Thr Glu Ser Pro Glu Asn Gly Phe Ser Phe Asn Thr Ser His
 65                  70                  75                  80
Ser Cys Gly His Leu Val Gln Asn Pro Asp Val Phe Asp Gly Lys Cys
                 85                  90                  95
Trp Leu Ser Cys Phe Leu Gly Gln Ser Val Glu Val Arg Cys His Glu
                100                 105                 110
Glu His Leu Ala Asp Ala Phe Gly Tyr Gln Thr Lys Trp Gly Val His
            115                 120                 125
Gly Lys Tyr Leu Gln Arg Arg Leu Gln Val Arg Gly Ile Arg Ala Val
        130                 135                 140
Val Asp Pro Asp Gly Pro Ile His Val Glu Ala Leu Ser Cys Pro Gln
145                 150                 155                 160
Ser Trp Ile Arg His Leu Thr Leu Asp Asp Val Thr Pro Gly Phe
                165                 170                 175
Val Arg Leu Thr Ser Leu Arg Ile Val Pro Asn Thr Glu Pro Thr Thr
            180                 185                 190
Ser Arg Ile Phe Arg Phe Gly Ala His Lys Trp Tyr Gly
        195                 200                 205
```

-continued

```
<210> SEQ ID NO 9
<211> LENGTH: 203
<212> TYPE: PRT
<213> ORGANISM: Porcine reproductive and respiratory syndrome virus

<400> SEQUENCE: 9

Ala Thr Val Tyr Asp Ile Gly His Asp Ala Val Met Tyr Val Ala Glu
1               5                   10                  15

Arg Lys Ile Ser Trp Ala Pro Arg Gly Gly Asp Glu Val Lys Phe Glu
            20                  25                  30

Ala Val Pro Gly Glu Leu Arg Leu Ile Ala Asn Arg Leu Arg Thr Ser
        35                  40                  45

Phe Pro Pro His His Thr Val Asp Met Ser Lys Phe Ala Phe Thr Ala
    50                  55                  60

Pro Gly Cys Gly Val Ser Met Arg Val Glu Arg Gln His Gly Cys Leu
65                  70                  75                  80

Pro Ala Asp Thr Val Pro Glu Gly Asn Cys Trp Trp Ser Leu Phe Asp
                85                  90                  95

Ser Leu Pro Leu Glu Val Gln Asn Lys Glu Ile Arg His Ala Asn Gln
            100                 105                 110

Phe Gly Tyr Gln Thr Lys His Gly Val Ser Gly Lys Tyr Leu Gln Arg
        115                 120                 125

Arg Leu Gln Val Asn Gly Leu Arg Ala Val Thr Asp Leu Asn Gly Pro
    130                 135                 140

Ile Val Val Gln Tyr Phe Ser Val Lys Glu Ser Trp Ile Arg His Leu
145                 150                 155                 160

Lys Leu Ala Gly Glu Pro Ser Tyr Ser Gly Phe Glu Asp Leu Leu Arg
                165                 170                 175

Ile Arg Val Glu Pro Asn Thr Ser Pro Leu Ala Asp Lys Glu Glu Lys
            180                 185                 190

Ile Phe Arg Phe Gly Ser His Lys Trp Tyr Gly
        195                 200

<210> SEQ ID NO 10
<211> LENGTH: 52
<212> TYPE: PRT
<213> ORGANISM: Porcine reproductive and respiratory syndrome virus

<400> SEQUENCE: 10

Ser Ser Val Tyr Arg Trp Lys Lys Phe Val Val Phe Thr Asp Ser Ser
1               5                   10                  15

Pro Asn Gly Arg Pro Arg Met Met Trp Thr Pro Glu Ser Asp Asp Ser
            20                  25                  30

Ala Asp Leu Glu Ala Leu Pro Pro Glu Leu Glu Arg Gln Val Glu Ile
        35                  40                  45

Leu Ile Arg Ser
    50

<210> SEQ ID NO 11
<211> LENGTH: 52
<212> TYPE: PRT
<213> ORGANISM: Porcine reproductive and respiratory syndrome virus

<400> SEQUENCE: 11

Ser Ser Val Tyr Arg Trp Lys Lys Phe Val Val Phe Thr Asp Ser Ser
1               5                   10                  15

Leu Asn Gly Arg Ser Arg Met Met Trp Thr Pro Glu Ser Asp Asp Ser
```

```
                    20                  25                  30

Ala Ala Leu Glu Val Leu Pro Pro Glu Leu Glu Arg Gln Val Glu Ile
            35                  40                  45

Leu Ile Arg Ser
        50

<210> SEQ ID NO 12
<211> LENGTH: 48
<212> TYPE: PRT
<213> ORGANISM: Porcine reproductive and respiratory syndrome virus

<400> SEQUENCE: 12

Ala Thr Val Tyr Asp Ile Gly His Asp Ala Val Met Tyr Val Ala Glu
1               5                   10                  15

Arg Lys Ile Ser Trp Ala Pro Arg Gly Gly Asp Glu Val Lys Phe Glu
            20                  25                  30

Ala Val Pro Gly Glu Leu Arg Leu Ile Ala Asn Arg Leu Arg Thr Ser
        35                  40                  45

<210> SEQ ID NO 13
<211> LENGTH: 15116
<212> TYPE: DNA
<213> ORGANISM: Porcine reproductive and respiratory syndrome virus

<400> SEQUENCE: 13
atgatgtgta gggtattccc cctacataca cgacactact agtgtttgtg taccttggag      60
gcgtgggtac agccccgccc cacccccttgg cccctgttct agcccaacag gtatccttct    120
ctctcggggc gagtgtgccg cctgctgctc ccttgcagcg ggaaggacct cccgagtatt     180
cccggagagc acctgcttta cgggatctcc acccttttaac catgtctggg acgttctccc   240
ggtgcatgtg caccccggct gctcgggtat tttggaacgc cggccaagtc tattgcacac    300
ggtgtctcag tgcgcggtct cttctcccctc cggaacttca ggacattgac ctcgccgcaa   360
ttggcttgtt ttacaagcct aaagacaagc ttcactggaa agtccctatc ggcatccctc    420
aggtggagtg tactccatcc gggtgttgtt ggctctcagg cattttcccc ttagcgcgca    480
tgacctccgg caatcacaac ttcctacaac gacttgtgaa agttgccgat gtgttgtacc    540
gtgatggttg cttaacttct cgacaccttc gtgaactcca gtttacgag cgtggctgca    600 gctggtaccc aatcacgggg ccagtgcccg ggatgggttt gtacgcaaat tccatgcacg   660
tatctgacca gccgttccct ggtgccaccc atgtgttgac gaactcgcct ttgcctcaac   720
aagcttgtcg gcagccgttc tgcccatttg aggaggctca ttctagcgtg tacaggtgga   780
aaaaatttgt ggtcttcacg gactcctccc caacggtcg gcctcgcatg atgtggacgc    840
cggaatccga tgattcagcc gacctagagg cgctaccgcc tgagctagaa cgtcaggtcg    900
aaatcctcat tcggagtttt cctgcccatc accctgtcag cctggccgac tgggagctcg    960
ctgagtcccc tgagaacggt ttttccttca gcacgtacca ttctggtggt tatcttgtcc   1020
aaaaccccga cgtgtttgac agcaagtgct ggctctcctg tttcttggat cagccgatcg   1080
aagtgcgcct ctatgaggat tatctggcta acgctttcgg ttaccaaacc aagtggggcg   1140
tgtctggtaa gtacctccag cgcaggcttc aagtcaacgg tattcgtgct gtaatcgatc   1200
ctgatggccc cattcacgtt gaagcgctgt cttgccccca atcttggatc aggcacctga   1260
ctctggacga tgacgtcacc ccaggattcg ttcgcctaac atccctccgc attgtgccga   1320
acacagagcc cactactctc cgaatctttc ggtttggagc gcataagtgg tatggcgctg   1380
```

```
ccggcaaacg ggctcgtgcc aagcgtgccg ctaaaagtga aagggtccg gctcccactc    1440 ccaaggttgc cccgccagcc cccacctgcg gaattgttac ctactctcca ccaacagacg    1500
ggtcttgcgg ttggcacgtc cttgccgcca taatgaaccg aatgatgaac ggtgacttca    1560
tgtcccctct ggcccagtac aacagaccag aggatgattg gcttctgat tacgatcttg     1620 cccaggcgat tcaatgtctg cggttgcctg ctaccatagt tcggaatcgt gcctgtccca    1680
acgccaagta cctcataaaa ctcaacgag tccactggga ggtagaggtg aggtcaggga     1740
tggcccctcg ctcccttccc cgcgagtgcg tagtcggcgt tgttccgaa ggctgtgccg     1800 catcgcctta cccagaaaac gggctaccta acgagcgtt tgaggccttg gcgtctgctt     1860
acagactacc ttccgattgt gtcagttctg gtattgctga cttttcttgct aaccccctc    1920 aggaattctg gactcttgac aaaatgttga cctccccgtc accggagcgg tctggttttt    1980
ccagtctgta caaattgcta ttagaggttg tcccgcagaa atgcggagcc acggaagggg    2040
ctttcaccta tgctgttgag agaatgctga aggattgccc gagctccgaa caggccatgg    2100
cccttctggc aaaaattaaa gttccatcct caaaggcccc gtctgtgtcc ctggacgagt    2160
gtttccctac ggatgtttca gccgatttcg aaccagcatc tcaggagagg tcccaaaatt    2220
ccagcgctgc tgttgtcctg cattcaccga atgcaaaaga gttcgaggaa gcagctccag    2280
gggaagttca ggagggtggc cacaaggccg tccactctgc actccctgcc ggggggtccta   2340 acaataagca ggcacagctg gttgccggtg agcaactgaa gctcggcggt tgtggttcgg    2400
tagttgggaa tgcacatgaa ggtgttctgg tcccacctgg tccaattaat ttgacaagcg    2460
gggatttacc ctcctcaggc tccatgaaag aagtatgct caatagccgg gaggacgaac     2520
cactggattt gtcccaacca gcaacagctg tcacaacgac tcttatggga gagctaacac    2580
ccgactacct aggttctgat actggtgccc tccccgtcac cgtccgaaaa tttgtcccga    2640
cggggcctat actccgtcat gttgagcact gcagcacggg gtcgggcgat agcagttcgc    2700
ctttggatct gtctggtgcg caaaccccgg accagccttt aaatctgtcc ctggcggctt    2760
ggccagtgag gaccaccgcg tctgatcctg gctgggtcca cggtagacgc gagcctgtct    2820
ttgtaaagcc tcgagatgtt ttctctgatg gcgattcagc ccttcagttc ggggagcttt    2880
ctgaatccag ctctgtcatc gagtttgatc gggcaaaaga tgctcaggtg gctgacgccc    2940
ctgtcggtct gacgacttcg gacgaggccc tctccgcagt cgatcctttc gagttttccg    3000
aactcaagcg cccacgtttc tccgcacaag ccttaattga ccgaggcggc ccacttgccg    3060
atgtccatgc aaaaataaag aaccgggtat atgaacagtg cctccaagct tgtgagcccg    3120
gtagtcgcgc aaccccagct accagggagt ggctcgacaa aatgtgggag agagtggaca    3180
tgaaaacctg gcgctgcacc tcacagttcc aagctggtca cattcttgcg tccctcaaat    3240
tcctccctga catgattcaa gacacaccgc ctcctgttcc caggaagaac cgagccagtg    3300
ataaagctgg cctgaaacaa ctagtggcac agtgggatag gagattgagt tcaacccccc    3360
ccccaaaacc ggttgggccg gtacttgacc gggtcgatcc tccgcctacg ggtacccggc    3420
aagaagacgt caccccctcc gatgggccac cccatgcgcc ggatggtcga gtgagtacgg    3480
gtgggagttg gaaaggcctt atgctttccg gcacccgtct cacggggtcc atcagtcatc    3540
gcctcatgac atgggttttt gaagttgtct cccatctccc agcttttatg ctcacacttt    3600
tctcgccgcg gggctctatg gctccaggcg attgggtttt tgcaggtgtt gttttacttg    3660
ctctcctgct ctgtcgttct tacccaatat tcgggtgcct tcccttattg ggtgtctttt    3720
ctggtactgt gcggcgtgtt cgtctgggtg ttttttggctc ttggatggct tttgctgtat    3780
```

```
ttttattctc gactccatcc aacccagtcg gttcttcttg taaccacgat tcgccggagt    3840
gtcatgctga gcttctggct cttgagcagc gccaactttg ggaacctgtg cgcggccttg    3900
tggtcggccc atcgggcctc ttatgtgtca ttcttggcaa gttactcggt gggtcacgtt    3960
atctctggca tgttctccta cgtctatgcc tgcttgcaga tttggccctt tctcttgttt    4020
atgtggtgtc ccaggggcgt tgtcacaagt gttggggaaa gtgtataagg acagctcctg    4080
ctgaggtggc ttttaatgta tttcctttct cgcgcgccac ccgtagttct cttgtatcct    4140
tatgtgatcg attccaaacg ccaaaaggag ttgatcccgt gcacttggcg acaggttggc    4200
gcgggtgctg gcgtggtgag agtcctatcc atcaaccaca ccaaaagccc atagcttacg    4260
ccaatttgga tgaaaagaag atatctgccc aaacggttgt tgctgtccca tacgatccca    4320
atcaggctat caaatgtctg aaagttctgc aggcgggagg ggctatcgtg gatcagccta    4380
cgcctgaggt cgttcgtgtg tccgagatcc ccttctcagc cccattttc ccaaaagttc    4440 cagtcaaccc agattgtagg gtcgtggtgg attcggacac ttttgtggct gcggttcgtt    4500
gtggttattc gacatcacaa ctggtcctgg gccagggcaa cttgccaag ttaaatcaaa    4560 cccccccag gaactctatc tccaccaaag cgactggtgg ggcctcttat acttttgctg    4620
tggctcaagt gtctgtgtgg accttgttc atttcgtcct cggtctttgg ctcacgtcac    4680
ctcaagtgtg tggtcgagga accgctgacc catggtgttc aagtccattt tcatatccta    4740
cctatggccc cggggttgtg tgctcctctc gactttgtgt gtctgctgac ggggtcaccc    4800
ttccattgtt ctcagccgtg gcacaactct ctggtaggga ggtggggatt tttatttag    4860 tgctcgtctc ctttattgcc ttggcccacc gcatggctct taaggcagac atgttagtag    4920 tcttttggc tctttgtgct tatgcctggc ccatgagctc ctggttgatc tgcttctttc    4980
ctatactctt gaggtgggtt acccttcacc ctctcactat gctttgggtg cattcattct    5040
tgatgttttg tctcccagca gccggcgtcc tctcactggg gataactggc ctcctctggg    5100
caatcggccg ctttactcag gttgccggaa tcattacacc ttatgatatc caccagtaca    5160
cctctgggcc acgtggtgca gccgctgtgg ccacagcccc agaaggcact tacatggccg    5220
ccgtccggag agctgcttta accgggcgga ctttaatctt caccccgtcc gcagttggat    5280
cccttctcga aggtgctttc aggactcata aaccctgcct taacaccgtg aatgtcgtag    5340
gctcctccct tggttccgga ggggttttca ccattgacgg aaaaaaatt gtcgtcactg    5400 ctgcccatgt gctgaacggc gacacagcta gagtcaccgg tgattcctac aaccgcatgc    5460
acactttcaa gactaatggt gactatgcct ggtcccatgc tgataactgg cagggcgctg    5520
cccctgtggt caaggttgcg aaagggtatc gcggtcgtgc ctactggcaa acatcaactg    5580
gtgtcgagcc tggtgttatt gggaatgggt tcgccttctg tttcaccaac tgcggcgatt    5640
cggggtcacc cgttatctca gaatctggtg atcttatcgg aatccacacc ggttcaaaca    5700
aacttggttc tggtcttgtg acaaccctg aaggggagac ctgtaccatc agagaaacca    5760
agctttctga cctttccaga catttcgcag gcccaagcgt tcctcttggg gacatcaaat    5820
tgagtccggc catcatccct gatgtgacat ccattccgag tgacttggca tcgctcctag    5880
cttccgtccc tgtaatggaa ggcggcctct cgaccgttca acttttgtgt gtcttttcc    5940 tcctctggcg catgatgggc catgcctgga cgcccattgt tgccgtgggc ttctttttgc    6000
tgaatgaaat tctccagca gttttggttc gagccgtgtt ttcttttgca ctctttgtgc    6060
ttgcatgggc caccccctgg tctgcacaag tgttgatgat tagacttctc acggcatctc    6120
```

```
tcaaccgcaa caaactttct cttgcgttct acgcactcgg aggtgttgtt ggtttggctg    6180
ctgaaatcgg acttttgct ggtaaattgt ctgaattgtc tcaagctctt tcgacatact    6240
gtttcttacc tagggtcctt gctatgacca gctgtgttcc catcatcatc attggtggac    6300
tccatgccct cggtgtgatt ctgtggttat tcaaataccg gtgcctccac aacatgctgg    6360
ttggtgatgg aagcttttca agcgctttct tcctacggta ttttgcagag ggcaatctca    6420
ggagaggtgt ttcacagtcc tgtggcatga gtaacgagtc cctgacggct gctttggctt    6480
gcaagttgtc acaggctgac cttgatttt tgtccagctt aacgaacttc aagtgctttg    6540
tatctgcttc aaacatgaaa aatgctgccg ccagtacat tgaagcagct tatgccaggg    6600
ccctgcgtca agagttggcc tctttagtcc agattgacaa aatgaaagga ttttgtcca    6660 agctagaggc ctttgctgaa acggccactc cgtccctcga cgtaggtgac gtgattgttc    6720
tacttggaca acatcctcac ggatccgttc tcgatattaa tgtggggact gaaaggaaaa    6780
ctgtatccgt gcaagagacc cggagcctag gcggctccaa gttcagtgtt tgtactgttg    6840
tgtcaaacac acccgtggac gccttagccg gtattccact ccagacacca acccccctt    6900 tcgagaatgg cccgcgtcat cgcagcgagg aggacgatct taaagtcgag aggatgaaga    6960
aacactgcgt gtccctcggc ttccacaaca ttaacgtaa agtttactgc aagatttggg    7020
acaagtctac cggtgacgcc tttacactg atgattcccg gtacacccaa gactatgctt    7080
ttcaggacag gtcagctgac tatagagaca gggactacga gggtgtgcaa accgcccccc    7140
aacagggatt tgatccaaag tctgaaaccc ctgttggtac cgttgtgatc ggcggtatta    7200
cgtacaacag gtatttggtc aaaggtaagg aggttctggt tcccaagcct gacaactgcc    7260
ttgaagctgc caagctgtcc cttgagcaag ctctcgctgg gatgggccaa acttgtgacc    7320
ttacagctgc cgaggtggaa aagctaaagc gcatcattgg tcaacttcaa ggattgacca    7380
ctgagcaggc tttaaactgt tagccgccag cggcttgacc cgctgtggcc gcggcggcct    7440
agttgtaact gaaacggcgg taaaaattgt caaataccac agcagaactt ttaccttagg    7500
ctctttagac ctaaaagtca cttccgaggt ggaggtgaag aagtcaaccg agcagggcca    7560
cgctgttgtg gcaaacttgt gttctggtgt cgtcttgatg agacctcacc caccgtccct    7620
tgtcgacgtt cttctgaaac ccggacttga cataacaccc ggcattcaac cagggcatgg    7680
ggccgggaat atgggcgtgg acggttccat ttgggatttt gaaaccgcac ccacaaaggc    7740
tgaactcgag ttatccaagc aaataattca agcatgtgaa gtcaggcgcg gggatgcccc    7800
gaacctccag ctcccttaca agctctatcc tgttagaggg gatcctgagc ggcataaagg    7860
ccacctcatc aataccaggt ttggagactt accttacaaa actcctcaag acaccaagtc    7920
cgcaatccac gcggcttgtt gcctgcaccc caacggggcc ccgtgtctg atggtaaatc    7980 cacactaggt accactcttc aacatggctt cgagctttat gtccctactg tgccctatag    8040
tgtcatggag taccttgatt cacgcccaga caccccttt atgtgcacta aacacggcac    8100
ttccaaggct gctgcagagg acctccaaaa atacgaccta tccacccaag gatttgtcct    8160
gcctggggtc ctacgcctag tgcgcaggtt catctttggc acattggca aggcaccgcc    8220 attgttcctc ccatcaactt atcccgccaa gaactccatg gcaggtatta atggtcagag    8280
gttcccaaca aaggatgttc aaagtatacc tgaaattgat gaaatgtgtg cccgcgccgt    8340
caaggagaat tggcaaactg tgacaccttg cacccctcaag aaacagtatt gttctaggcc    8400
caaaaccagg accatcctgg gcactaacaa cttcatagcc ttggctcata gatcggcgct    8460
cagtggtgtt acccaggcat tcatgaagaa ggcttggaag tccccaatag ccttagggaa    8520
```

```
aaacaaattc aaggagctgc attgcactgt cgctggcagg tgcctcgagg ccgacttggc    8580
ttcctgtgac cgcagcaccc ctgccattgt gaggtggttc actacccacc tcctatatga    8640
acttgcagga tgtgaagaat atctacctag ctatgtgctt aactgttgcc atgaccttgt    8700
ggcgacgcag gatggtgctt tcacaaaacg cggtggcctg tcgtctggag acccagtcac    8760
cagtgtgtcc aacactgtgt actcactggt gatttatgcc cagcacatgg tactatctgc    8820
cctgaaaatg ggtcatgaaa ttggcctcaa gttcctcgaa gaacaactca aatttgagga    8880
ccttcttgaa atccagccta tgttagtata ctctgatgat cttgtcttgt acgcagaaaa    8940
gcccaccttc cccaactatc attggtgggt cgagcatctt gacctgatgt tgggctttaa    9000
aacggaccca agaaaaaccg tcataactga taaacccagt ttcctcgggt gcagaatcga    9060
agcagggcga cagctagtcc ccaatcgcga ccgcatcctg gctgctcttg catatcacat    9120
gaaggcgcag aacgcctcag agtattatgc gtctgctgcc gcaatcctga tggattcatg    9180
tgcttgcatt gaccacgatc ctgaatggta tgaggacctc atctgtggca ttgcccgatg    9240
cgctcgcctg gacggttata gctttccagg tccggcattt ttcatgtcca tgtgggagaa    9300
gctgaggagt cataatgaag ggaagaaatt ccgccactgc ggcatctgcg acgccaaagc    9360
cgactacgcg gctgcttgtg ggcttgattt gtgtttgttt cattcgcact ttcaccaaca    9420
ctgccctgtc actctgagct gcggtcacca tgccggttcg aaggaatgtt cgcagtgtca    9480
gtcacctgtt ggggccggca gatcccctct tgatgctgtg ctggaacaaa ttccatacaa    9540
acctcctcgc actgtcatca tgaaggtggg taataaaaca acggcccttg atccggggag    9600
gtaccagtcc cgtcgaggtc tcgttgcagt caagaggggt attgcgggta atgaagttga    9660
tcttgctgat ggagattacc aagtggtacc tcttctgccg acttgcaaag atataaacat    9720
ggtgaaggtg gcttgcaacg tactactcag caagttcata gtagggccac caggttccgg    9780
gaagaccacc tggctactaa gtcaagttca ggacgatgat gtcatttaca cacccactca    9840
tcagaccatg tttgacatag ttagtgctct caaagtttgc aggtattcca ttccaggagc    9900
ctcgggactc cctttcccac cgcctgccag gtccgggccg tgggttaggc tcattgccag    9960
cgggcacgtc cctggccgag tatcatacct cgatgaggcc ggatattgca atcatctgga   10020
cattcttaga ctgctttcca aaacaccccct tgtgtgtttg ggtgaccttc agcaacttca   10080
cccagtcggc tttgattcct attgttatgt gttcgatcag atgcctcaga agcagttgac   10140
caccatttac agatttggcc ccaacatctg cgcagccatc cagccttgtt acagggagaa   10200
acttgaatct aaggctagga acaccagggt ggtttttacc acccggcctg tggcctttgg   10260
ccaggtgctg acaccatatc acaaagatcg cgtcggctcc gcgattacca tagactcatc   10320 ccaggggggcc acctttgaca ttgtaacatt gcatctacca tcgccaaagt ccctaaataa   10380
gtcccgggca cttgtggcca tcacacgggc aagacacggg ttgttcattt atgaccctca   10440
caaccagctc cgggagtttt tcaacctaac ccctgagcgc actgattgta accttgtgtt   10500
cagccgtgga gatgagctgg tggtcctgaa tgcagataat gcagtcacaa ccgtggcgaa   10560
ggccttagag acaggtccaa ctcaatttcg agtgtcagac ccgaggtgca agtctctctt   10620
agccgcttgc tcggccagtc tggaagggag ctgcatgccg ctaccgcaag tggcgcataa   10680
cctggggttt tacttctccc cagacagtcc agtatttgca cctctgccaa aagagttggc   10740
gccacattgg ccagtggtta cccatcagaa taatcgggcg tggcctgatc gacttgtcgc   10800
tagtatgcgt ccaattgacg cccgctacag caagccgatg gtcggtgcag ggtatgtggt   10860
```

```
cggaccgtcc accttccttg gtactcctgg agtggtgtca tactatctca cactatacat   10920 cagggggtgag ccccaggcct tgccagaaac acttgtttca acaggacgta tagccacaga  10980
ttgtcgggag tatctcgacg cggctgagga agaggcagca aaagaacttc cccacgcgtt   11040
cattggcgat gtcaaaggca ccacagttgg ggggtgtcat cacattacat caaaatacct   11100
acctaggtcc ctgcctaaag actctgttgc cgtagttgga gtaagttcgc ctggcagggc   11160
tgctaaagcc gtatgcaccc tcaccgatgt gtacctccct gaactccggc catatctgca   11220
acctgagacg gcatcaaaat gctggaaact caaattagac ttcagggacg tccgactaat   11280
ggtctggaaa ggagccaccg cctactttca attggaaggg ctcacatggt cggcgctgcc   11340
tgactatgcc aggtttattc agctgcccaa aaacgctgtt gtatacatcg atccgtgcat   11400
aggaccggca acagccaatc gtaaagtcgt acgaaccaca gattggcggg ccgacctggc   11460
agtgacgccg tatgattacg gtgcccggaa cattttgaca acagcctggt tcgaggacct   11520
cgggccgcag tggaagattc tggggttgca gccctttagg cgggcgtttg gctttgaaaa   11580
cactgaggat tgggcaatcc ttgcatgctg catgagtgac ggcaaggact acactgacta   11640
taactggaat tgcgttcgac aacgcccaca cgctatccat ggacgcgctc gtgaccatac   11700
gtaccacttt gccctggca ctgaattgca agtggagctc ggtaaacccc ggctgccacc    11760
tgagcaagta ccgtgaattc ggagtgatgc aatggggtca ctgtggagta aaatcagcca   11820
gctgttcgtg gacgccttca ctgaattcct tgttagtgtg gttgatattg tcatcttcct   11880
tgccatattg tttgggttca ccgtcgcagg atggttactg gtctttcttc tcagagtggt   11940
ttgctccgcg cttctccgtt cgcgctctgc cattcactct tccgaactat cgaaggtcct   12000
atgagggctt actacctaat tgcagaccgg atgttccaca atttgcattt aagcacccctt  12060 tgggtatgtt ttggcacatg cgggtttccc acctaattga tcagatgtc tctcgccgca    12120 tctaccagac catggaacat tcaggtcaag cggcctggaa gcacgtggtc agtgaggcta   12180
ctcttacaaa attgtcagaa ctcgacatag ttctccactt ccaacacctg gccgcagtgg   12240
aggcggactc ttgtcgcttc ctcagctcac gacttgtgat gctgaaaaat cttgccgttg   12300
gcaatgtgag cttgcagtac aacaccacgt tgaaccgcgt tgagctcatc ctccccacac   12360
caggtacgag gcccaaattg accgatttca dacaatggct catcagtgtg cacgcttcca   12420 tttttttcctc tgtagcctca tcagttactt tgttcatagt gctttggctt cgaattccag   12480
ccgtacgcta tgttttttggt ttccattggc ccatggcaac acgtcattcg agctgaccat  12540
taattacact atatgcatgc cctgtcttac cagccaagcg gctcaacaaa ggctcgaacc   12600
cggtcgtaac atgtggtgca aaataggaca caccacgtgc gaggagcgtg accatgatga   12660
gttgtcaatg tccatcccgt ccgggtacga caacctcaaa cttgaaggtt attacgcttg   12720
gctggctttt ttgtcctttt cctacgcggc ccaattccat ccggagttgt ttggaatagg   12780
gaatgtgtcg cgcgtctttg tggataaacg acaccagttc attgtgccg agcatgacgg    12840 agataattca accgtatcta ccggacacaa catctccgca tcatatgcgg catattatca   12900
ccaccaaata gacgggggca attggttcca tttggaatgg ctgcggccgc tcttttcctc   12960
ttggctagtg ctcaacatat catgggttttct gaggcgttcg cctgcaagcc ctgtttctcg  13020
acgcatctat cagatattaa gaccaatacg accgcggctg ccggtttcat ggtccttcaa   13080
gacatcagtt gcctccgacc tcacagggtc tcagcatcgc aagagaacat tcccttcgga   13140
aagtcgtcac aatgtcgtga agccgtcggt actccccagt acattacgat gactgctaat   13200
gtgaccgacg aatcatattt gtacaacgcg gacttgctaa tgctttccgc gtgcctttc    13260
```

```
cacgcctcag aaatgagcga gaaaggcttc aaagttatct ttggaaacgt ctccggcgtt   13320
gtttcagctt gtgtcaattt cacagattat gtggcccatg taacccaaca tacccaacag   13380
catcatctgg taattgatca cattcggtta ctgcatttcc tgacaccatc tgcaatgagg   13440
tgggctacaa ccattgcttg tttgttcgcc attctcttag cgatatgaga tgttctcaca   13500
aattggggcg tttcttgact ccgcactctt gcttctggtg gctttttttg ctgtgtaccg   13560
gcttgtcctg gtcctttgcc gatggcaacg gcaacagctc gacacgccaa tacatatata   13620
acttgacgat atgcgagctg aatgggaccg tctggttgtc cagtcatttt gattgggcag   13680
tcgagacctt tgtgctttac ccggtggcca ctcatatcct ctcactgggt tttctcacaa   13740
caagccattt ttttgatgcg ctcggtctcg gcgctgtgtc cactacggga tttcttggcg   13800
ggcggtatgt acttagcagc gtgtacggcg cctgcgcctt cgcagcgctt gtatgttttg   13860
tcatccgtgc tgctaaaaat tgcatggctt gccgttatgc ccgcacccgg ttcaccaact   13920
tcatcgtgga cgaccggggg aagatccatc gatggaagtc cccaatagtg gtagagaaat   13980
taggcaaagc tgacatcggc ggcgaccttg tcaccatcaa acatgttgtc ctcgaaggag   14040
tcaaagctca acctttgacg aggacatcgg cggagcaatg ggaagcctag atgattttg   14100
caatgatcct accgccgcac agaagcttgt gctggcattt agtatcacat acacacctat   14160
aatgatatac gccctcaagg tgtcacgcgg ccggctccta ggactgttac atcctgat   14220
atttctgaac tgttctttca cgttcggata catgacatac gtgcactttc aatccactaa   14280
ccgtgtcgcg cttactatgg gggcggtcgt tgccctttg tggggcattt acagctttat   14340
agaatcatgg aagtttgtca cttccagatg caggttgtgt tgcctaggcc ggcgatacat   14400
tctggcccct gcccaccacg tagaaagtgc tgcaggcctc cattcaatcc cagcgtctgg   14460
taaccgagca tacgctgtga aaagcccgg actaacatca gtgaacggca ctctagtacc   14520
aggacttcgg agcctcgtgt tgggcggcaa acgagctgtt aaacgaggag tggttaacct   14580
cgtcaagtat ggccggtaaa aaccagagcc agaagaaaaa gaaaaacaca gctcctatgg   14640
ggagtggcca gccagtcaat caactgtgcc aattgctggg cacaatgata aagtcccagc   14700
gccagcggcc taggggagga caggccaaaa tgaaaaagcc tgagaagcca catttcccc   14760
tagctgctga agatgacatc cggcaccatt tcacccagac cgagcgttcc ctttgcttgc   14820
aatcgatcca cacggcctcc aatcaaggcg caggaactgc gtcgctttca ccagcggga   14880
aggtcagttt tcaggttgag ttcatgctgc cggtcgctca tacggtgcgc ctgattcgcg   14940
taacttccac atccgccagt cagggtgcaa gttaatttga tagttaggtg aatggccgcg   15000
attggcgtgt ggcctctgag tcacctattc aattagggcg atcacatggg ggttagactt   15060
aattggcgag aaccatgtga ccgaaattaa aaaaaaaaaa aaaaaaaaaa aaaaaa       15116
```

<210> SEQ ID NO 14
<211> LENGTH: 15111
<212> TYPE: DNA
<213> ORGANISM: Porcine reproductive and respiratory syndrome virus

<400> SEQUENCE: 14

```
atgatgtgta gggtattccc cctacataca cgacacttct agtgtttgtg taccttggag     60
gcgtgggtac agccccgccc cacccttgg cccctgttct agcccaacag gtatccttct    120
ctctcggggc gagtgcgccg cctgctgctc ccttgcagcg ggaaggacct cccgagtatt    180
tccggagagc acctgcttta cgggatctcc acccttaac catgtctggg acgttctccc    240
```

```
ggtgcatgtg caccccggct gcccgggtat tttggaacgc cggccaagtc ttttgcacac    300
ggtgtctcag tgcgcggtct cttctctctc cagagcttca ggacactgac ctcggtgcag    360
ttggcttgtt ttacaagcct agggacaagc ttcactggaa agtccctatc ggcatccctc    420
aggtggaatg tactccatcc gggtgctgtt ggctctcagc tgttttccct ttggcgcgta    480
tgacctccgg caatcacaac ttcctccaac gacttgtgaa ggttgctgat gttttgtacc    540
gtgacggttg cttggcacct cgacaccttc gtgaactcca agtttacgag cgcggctgca    600
actggtaccc gatcacgggg cccgtgcccg ggatgggttt gtttgcgaac tccatgcacg    660
tatccgacca gccgttccct ggtgccaccc atgtgttgac taactcgcct ttgcctcaac    720
aggcttgtcg gcagccgttc tgtccatttg aggaggctca ttctagcgtg tacaggtgga    780
agaaatttgt ggttttcacg gactcctccc tcaacggtcg atctcgcatg atgtggacgc    840
cggaatccga tgattcagcc gccctggagg tactaccgcc tgagttagaa cgtcaggtcg    900
aaatcctcat tcggagtttt cctgctcatc accctgtcga cctggccgac tgggagctca    960
ctgagtcccc tgagaacggt ttttccttca acacgtctca ttcttgcggt caccttgtcc   1020
agaaccccga cgtgtttgat ggcaagtgct ggctctcctg cttttttgggc cagtcggtcg   1080 aagtgcgctg ccatgaggaa catctagctg acgccttcgg ttaccaaacc aagtggggcg   1140
tgcatggtaa gtacctccag cgcaggcttc aagttcgcgg cattcgtgct gtagtcgatc   1200
ctgatggtcc cattcacgtt gaagcgctgt cttgccccca gtcttggatc aggcacctga   1260
ctctggatga tgatgtcacc ccaggattcg ttcgcctgac atcccttcgc attgtgccga   1320
acacagagcc taccacttcc cggatctttc ggtttggagc gcataagtgg tatgcgcctg   1380
ccggcaaacg ggctcgtgct aagcgtgccg ctaaaagtga aaggattcg gctcccaccc   1440 ccaaggttgc cctgccggtc cccacctgtg gaattaccac ctactctcca ccgacagacg   1500
ggtcttgtgg ttggcatgtc cttgccgcca taatgaaccg gatgataaat ggtgacttca   1560
cgtcccctct gactcagtac aacagaccag aggatgattg gcttctgat tatgatcttg   1620 ttcaggcgat tcaatgtcta cgactgcctg ctaccgtggt tcggaatcgc gcctgtccta   1680
acgccaagta ccttataaaa cttaacggag ttcactggga ggtagaggtg aggtctggaa   1740
tggctcctcg ctcccttttct cgtgaatgtg tggttggcgt ttgctctgaa ggctgtgtcg   1800
caccgcctta ccagcagac gggctaccta aacgtgcact cgaggccttg gcgtctgctt   1860
acagactacc ctccgattgt gttagctctg gtattgctga cttttcttgct aatccacctc   1920 ctcaggaatt ctggaccctc gacaaaatgt tgacctcccc gtcaccagag cggtccggct   1980
tctctagttt gtataaatta ctattagagg ttgttccgca aaaatgcggt gccacggaag   2040
gggctttcat ctatgctgtt gagaggatgt tgaaggattg tccgagctcc aaacaggcca   2100
tggcccttct ggcaaaaatt aaagttccat cctcaaaggc cccgtctgtg tccctggacg   2160
agtgtttccc tacggatgtt ttagccgact tcgagccagc atctcaggaa aggccccaaa   2220
gttccggcgc tgctgttgtc ctgtgttcac cggatgcaaa agagttcgag gaagcagccc   2280
cggaagaagt tcaagagagt ggccacaagg ccgtccactc tgcactcctt gccgagggtc   2340
ctaacaatga gcaggtacag gtggttgccg gtgagcaact gaagctcggc ggttgtggtt   2400
tggcagtcgg gaatgctcat gaaggtgctc tggtctcagc tggtctaatt aacctggtag   2460
gcgggaattt gtccccctca gaccccatga agaaaacat gctcaatagc cgggaagacg   2520
aaccactgga tttgtcccaa ccagcaccag cttccacaac gacccttgtg agagagcaaa   2580 caccccgacaa cccaggttct gatgccggtg ccctcccgt caccgttcga gaatttgtcc   2640
```

```
cgacggggcc tatactctgt catgttgagc actgcggcac ggagtcgggc gacagcagtt    2700
cgcctttgga tctatctgat gcgcaaaccc tggaccagcc tttaaatcta tccctggccg    2760
cttggccagt gagggccacc gcgtctgacc ctggctgggt ccacggtagg cgcgagcctg    2820
tctttgtaaa gcctcgaaat gctttctctg atggcgattc agcccttcag ttcggggagc    2880
tttctgaatc cagctctgtc atcgagtttg accggacaaa agatgctccg gtggttgacg    2940
cccctgtcga cttgacgact tcgaacgagg ccctctctgt agtcgatcct ttcgaatttg    3000
ccgaactcaa gcgcccgcgt ttctccgcac aagccttaat tgaccgaggc ggtccacttg    3060
ccgatgtcca tgcaaaaata aagaaccggg tatatgaaca gtgcctccaa gcttgtgagc    3120
ccggtagtcg tgcaaccccA gccaccaggg agtggctcga caaaatgtgg gatagggtgg    3180
acatgaaaac ttggcgctgc acctcgcagt tccaagctgg tcgcattctt gcgtccctca    3240
aattcctccc tgacatgatt caagacacac cgcctcctgt tcccaggaag aaccgagcta    3300
gtgacaatgc cggcctgaag caactggtgg cacagtggga taggaaattg agtgtgaccc    3360 ccccccaaa accggttggg ccagtgcttg accagatcgt ccctccgcct acggatatcc    3420
agcaagaaga tgtcaccccc tccgatgggc cacccatgc gccggatttt cctagtcgag    3480
tgagcacggg cgggagttgg aaaggcctta tgctttccgg caccgtctc gcggggtcta    3540 tcagccagcg cctatgaca tgggttttg aagttttctc ccacctccca gcttttatgc    3600
tcacactttt ctcgccgcgg ggctctatgg ctccaggtga ttggttgttt gcaggtgtcg    3660
ttttacttgc tctcttgctc tgtcgttctt acccgatact cggatgcctt cccttattgg    3720
gtgtcttttc tggttctttg cggcgtgttc gtctgggtgt ttttggttct tggatggctt    3780
ttgctgtatt tttattctcg actccatcca acccagtcgg ttcttcttgt gaccacgatt    3840
cgccggagtg tcatgctgag cttttggctc ttgagcagcg ccaactttgg gaacctgtgc    3900
gcggccttgt ggtcggcccc tcaggcctct tatgtgtcat tcttggcaag ttactcggtg    3960
ggtcacgtta tctctggcat gttctcctac gtttatgcat gcttgcagat ttggcccttt    4020
ctcttgttta tgtggtgtcc caggggcgtt gtcacaagtg ttggggaaag tgtataagga    4080
cagctcctgc ggaggtggct cttaatgtat tcctttctc gcgcgccacc cgtgtctctc    4140
ttgtatcctt gtgtgatcga ttccaaacgc caaaggggt tgatcctgtg cacttggcaa    4200
cgggttggcg cgggtgctgg cgtggtgaga gccccatcca tcaaccacac caaaagccca    4260
tagcttatgc caatttggat gaaaagaaaa tgtctgccca aacggtggtt gctgtcccat    4320
acgatcccag tcaggctatc aaatgcctga agttctgca ggcgggaggg gccatcgtgg    4380
accagcctac acctgaggtc gttcgtgtgt ccgagatccc cttctcagcc ccattttcc    4440 caaaagttcc agtcaaccca gattgcaggg ttgtggtaga tcggacact tttgtggctg    4500 cggttcgctg cggttactcg acagcacaac tggttctggg ccggggcaac tttgccaagt    4560
taaatcagac cccccccagg aactctatct ccaccaaaac gactggtggg gcctcttaca    4620
cccttgctgt ggctcaagtg tctgcgtgga ctcttgttca tttcatcctc ggtctttggt    4680
tcacatcacc tcaagtgtgt ggccgaggaa ccgctgaccc atggtgttca aatcctttt    4740 catatcctac ctatggcccc ggagttgtgt gctcctctcg actttgtgtg tctgccgacg    4800
gggtcaccct gccattgttc tcagccgtgg cacaactctc cggtagagag gtgggatt    4860 ttatttggt gctcgtctcc ttgactgctt tggcccaccg catggctctt aaggcagaca    4920
tgttagtggt cttttcggct ttttgtgctt acgcctggcc catgagctcc tggttaatct    4980
```

```
gcttctttcc tatactcttg aagtgggtta cccttcaccc tcttactatg ctttgggtgc   5040
actcattctt ggtgttttgt ctgccagcag ccggcatcct ctcactaggg ataactggcc   5100
ttctttgggc aattggccgc tttacccagg ttgccggaat tattacacct tatgacatcc   5160
accagtacac ctctgggcca cgtggtgcag ctgctgtggc cacagcccca gaaggcactt   5220
atatggccgc cgtccggaga gctgctttaa ctgggcgaac tttaatcttc accccgtctg   5280
cagttggatc ccttctcgaa ggtgctttca ggactcataa accctgcctt aacaccgtga   5340
atgttgtagg ctcttccctt ggttccggag gggttttcac cattgatggc agaagaactg   5400
tcgtcactgc tgcccatgtg ttgaacggcg acacagctag agtcaccggc gactcctaca   5460
accgcatgca cactttcaag accaatggtg attatgcctg gtcccatgct gatgactggc   5520
agggcgttgc ccctgtggtc aaggttgcga aggggtaccg cggtcgtgcc tactggcaaa   5580
catcaactgg tgtcgaaccc ggtatcattg gggaagggt cgccttctgt tttactaact   5640
gcggcgattc ggggtcaccc gtcatctcag aatctggtga tcttattgga atccacaccg   5700
gttcaaacaa acttggttct ggtcttgtga caacccctga aggggagacc tgcaccatca   5760
aagaaaccaa gctctctgac ctttccagac attttgcagg cccaagcgtt cctcttgggg   5820
acattaaatt gagtccggcc atcatccctg atgtaacatc cattccgagt gacttggcat   5880
cgctcctagc ctccgtccct gtagtggaag gcggcctctc gaccgttcaa cttttgtgtg   5940
tcttttttcct tctctggcgc atgatgggcc atgcctggac acccattgtt gccgtgggct   6000
tcttttgct gaatgaaatt cttccagcag ttttggtccg agccgtgttt tcttttgcac   6060
tctttgtgct tgcatgggcc accccctggt ctgcacaggt gttgatgatt agactcctca   6120
cggcatctct caaccgcaac aagctttctc tggcgttcta cgcactcggg ggtgtcgtcg   6180
gtttggcagc tgaaatcggg acttttgctg cagattgtc tgaattgtct caagctcttt   6240
cgacatactg cttcttacct agggtccttg ctatgaccag ttgtgttccc accatcatca   6300
ttggtggact ccatacccctc ggtgtgattc tgtggttatt caaataccgg tgcctccaca   6360
acatgctggt tggtgatggg agtttttcaa gcgccttctt cctacggtat tttgcagagg   6420
gtaatctcag aaaaggtgtt tcacagtcct gtggcatgaa taacgagtcc ctaacggctg   6480
ctttagcttg caagttgtca caggctgacc ttgatttttt gtccagctta acgaacttca   6540
agtgctttgt atctgcttca aacatgaaaa atgctgccgg ccagtacatt gaagcagcgt   6600
atgccaaggc cctgcgccaa gagttggcct ctctagttca gattgacaaa atgaaaggag   6660
ttttgtccaa gctcgaggcc tttgctgaaa cagccacccc gtcccttgac ataggtgacg   6720
tgattgttct gcttgggcaa catcctcacg gatccatcct cgatattaat gtggggactg   6780
aaaggaaaac tgtgtccgtg caagagaccc ggagcctagg cggctccaaa ttcagtgttt   6840
gtactgtcgt gtccaacaca cccgtggacg ccttgaccgg catcccactc cagacaccaa   6900
cccctctttt tgagaatggt ccgcgtcatc gcagcgagga agacgatctt aaagtcgaga   6960
ggatgaagaa acactgtgta tccctcggct ccacaacat caatggcaaa gtttactgca   7020
aaatttggga caagtctacc ggtgacacct tttacacgga tgattccgg tacacccaag   7080
accatgcttt tcaggacagg tcagccgact acagagacag ggactatgag ggtgtgcaaa   7140
ccaccccccca acagggattt gatccaaagt ctgaaaccc tgttggcact gttgtgatcg   7200
gcggtattac gtataacagg tatctgatca aggtaagga ggttctggtc cccaagcctg   7260
acaactgcct tgaagctgcc aagctgtccc ttgagcaagc tctcgctggg atgggccaaa   7320
cttgcgacct tacagctgcc gaggtggaaa agctaaagcg catcattagt caactccaag   7380
```

```
gtttgaccac tgaacaggct ttaaactgtt agccgccagc ggcttgaccc gctgtggccg   7440
cggcggccta gttgtgactg aaacggcggt aaaaattata aaataccaca gcagaacttt   7500
caccttaggc cctttagacc taaaagtcac ttccgaggtg gaggtaaaga atcaactga    7560 gcagggccac gctgttgtgg caaacttatg ttccggtgtc atcttgatga acctcaccc    7620 accgtccctt gtcgacgttc ttctgaaacc cggacttgac acaatacccg gcattcaacc   7680
agggcatggg gccgggaata tgggcgtgga cggttctatt tgggattttg aaaccgcacc   7740
cacaaaggca gaactcgagt tatccaagca ataatccaa gcatgtgaag ttaggcgcgg    7800
ggacgccccg aacctccaac tcccttacaa gctctatcct gttaggggggg atcctgagcg  7860 gcataaaggc cgccttatca ataccaggtt tggagattta ccttacaaaa ctcctcaaga   7920
caccaagtcc gcaatccacg cggcttgttg cctgcacccc aacggggccc ccgtgtctga   7980
tggtaaatcc acactaggta ccactcttca acatggtttc gagctttatg tccctactgt   8040
gccctatagt gtcatggagt accttgattc acgccctgac accccttta tgtgtactaa    8100 acatggcact tccaaggctg ctgcagagga cctccaaaaa tacgacctat ccacccaagg   8160
atttgtcctg cctggggtcc tacgcctagt acgcagattc atctttggcc atattggtaa   8220
ggcgccgcca ttgttcctcc catcaaccta tcccgccaag aactctatgg cagggatcaa   8280
tggccagagg ttcccaacaa aggacgttca gagcatacct gaaattgatg aaatgtgtgc   8340
ccgcgctgtc aaggagaatt ggcaaactgt gacaccttgc accctcaaga aacagtactg   8400
ttccaagccc aaaaccagga ccatcctggg caccaacaac tttattgcct tggctcacag   8460
atcggcgctc agtggtgtca cccaggcatt catgaagaag gcttggaagt ccccaattgc   8520
cttggggaaa aacaaattca aggagctgca ttgcactgtc gccggcaggt gtcttgaggc   8580
cgacttggcc tcctgtgacc gcagcacccc cgccattgta agatggtttg ttgccaacct   8640
cctgtatgaa cttgcaggat gtgaagagta cttgcctagc tatgtgctta attgctgcca   8700
tgacctcgtg gcaacacagg atggtgcctt cacaaaacgc ggtggcctgt cgtccgggga   8760
ccccgtcacc agtgtgtcca caccgtata ttcactggta atttatgccc agcacatggt    8820
attgtcggcc ttgaaaatgg gtcatgaaat tggtcttaag ttcctcgagg aacagctcaa   8880
gttcgaggac ctccttgaaa ttcagcctat gttggtatac tctgatgatc ttgtcttgta   8940
cgctgaaaga cccacatttc ccaattacca ctggtgggtc gagcaccttg acctgatgct   9000
gggtttcaga acggacccaa agaaaaccgt cataactgat aaacccagct cctcggctg    9060 cagaattgag gcagggcgac agctagtccc caatcgcgac cgcatcctgg ctgctcttgc   9120
atatcacatg aaggcgcaga acgcctcaga gtattatgcg tctgctgccg caatcctgat   9180
ggattcatgt gcttgcattg accatgaccc tgagtggtat gaggacctca tctgcggtat   9240
tgcccggtgc gcccgccagg atggttatag cttcccaggt ccggcatttt tcatgtccat   9300
gtgggagaag ctgagaagtc ataatgaagg gaagaaattc cgccactgcg gcatctgcga   9360
cgccaaagcc gactatgcgt ccgcctgtgg gcttgatttg tgtttgttcc attcgcactt   9420 tcatcaaacac tgccctgtca ctctgagctg cggtcaccat gccggttcaa aggaatgttc   9480
gcagtgtcag tcacctgttg gggctggcag atcccctctt gatgccgtgc taaaacaaat   9540
tccatacaaa cctcctcgta ctgtcatcat gaaggtgggt aataaaacaa cggccctcga   9600
tccggggagg taccagtccc gtcgaggtct cgttgcagtc aagagggta ttgcaggcaa    9660 tgaagttgat cttctgatg gggactacca agtggtgcct cttttgccga cttgcaaaga   9720
```

```
cataaacatg gtgaaggtgg cttgcaatgt actactcagc aagttcatag tagggccacc    9780
aggttccgga aagaccacct ggctactgag tcaagtccag gacgatgatg tcatttacac    9840
acccacccat cagactatgt ttgatatagt cagtgctctc aaagtttgca ggtattccat    9900
tccaggagcc tcaggactcc ctttcccacc acctgccagg tccgggccgt gggttaggct    9960
tattgccagc gggcacgtcc ctggccgagt atcatacctc gatgaggctg gatattgtaa   10020
tcatctggac attcttagac tgcttttcaa acacccctt gtgtgtttgg gtgaccttca    10080
gcaacttcac cctgtcggct ttgattccta ctgttatgtg ttcgatcaga tgcctcagaa   10140
gcagctgacc actatttaca gatttggccc taacatctgc gcagccatcc agccttgtta   10200
cagggagaaa cttgaatcta aggctaggaa cactagggtg gttttacca cccggcctgt    10260
ggcctttggt caggtgctga caccatacca taaagatcgc atcggctctg cgataaccat   10320
agattcatcc caggggggcca cctttgatat tgtgacattg catctaccat cgccaaagtc   10380
cctaaataaa tcccgagcac ttgtagccat cactcgggca agacgcgggt tgttcattta   10440
tgaccctcat aaccagctcc aggagttttt caacttaacc cctgagcgca ctgattgtaa   10500
ccttgtgttc agccgtgggg atgagctggt agttctgaat gcggataatg cagtcacaac   10560
tgtagcgaag gcccttgaga caggtccatc tcgatttcga gtatcagacc cgaggtgcaa   10620
gtctctctta gccgcttgtt cggccagtct ggaagggagc tgtatgccac taccgcaagt   10680
ggcacataac ctgggggtttt actttttccc ggacagtcca acatttgcac ctctgccaaa   10740
agagttggcg ccacattggc cagtggttac ccaccagaat aatcgggcgt ggcctgatcg   10800
acttgtcgct agtatgcgcc caattgatgc ccgctacagc aagccaatgg tcggtgcagg   10860
gtatgtggtc gggccgtcca cctttcttgg tactcctggt gtggtgtcat actatctcac   10920
actatacatc aggggtgagc cccaggcctt gccagaaaca ctcgtttcaa cagggcgtat   10980
agccacagat tgtcgggagt atctcgacgc ggctgaggaa gaggcagcaa aagaactccc   11040
ccacgcattc attggcgatg tcaaaggtac cacggttggg gggtgtcatc acattacatc   11100
aaaataccta cctaggtccc tgcctaagga ctctgttgcc gtagttggag taagttcgcc   11160
cggcagggct gctaaagccg tgtgcactct caccgatgtg tacctccccg aactccggcc   11220
atatctgcaa cctgagacgg catcaaaatg ctggaaactc aaattagact tcagggacgt   11280
ccgactaatg gtctgaaaag gagccaccgc ctatttccag ttggaagggc ttacatggtc   11340
ggcgctgccc gactatgcca ggtttattca gctgcccaag gatgccgttg tatacattga   11400
tccgtgtata ggaccggcaa cagccaaccg taaggtcgtg cgaaccacag actggcgggc   11460
cgacctggca gtgacaccgt atgattacgg tgcccagaac attttgacaa cagcctggtt   11520
cgaggacctc gggccgcagt ggaagatttt ggggttgcag cccttaggc gagcatttgg    11580
cttttgaaaac actgaggatt gggcaatcct tgcacgccgt atgaatgacg gcaaggacta   11640
cactgactat aactgaaact gtgttcgaga acgcccacac gccatctacg ggcgtgctcg   11700
tgaccatacg tatcattttg ccctggcac agaattgcag gtagagctag gtaaaccccg    11760
gctgccgcct gggcaagtgc cgtgaattcg gggtgatgca atggggtcac tgtggagtaa   11820
aatcagccag ctgttcgtgg acgccttcac tgagttcctt gttagtgtgg ttgatattgc   11880
cattttcctt gccatactgt ttgggttcac cgtcgcagga tggttactgg tcttttcttct   11940
cagagtggtt tgctccgcgc ttctccgttc gcgctctgcc attcactctc ccgaactatc   12000
gaaggtccta tgaaggcttg ttgcccaact gcagaccgga tgtcccacaa tttgcagtca   12060
agcacccatt gggtatgttt tggcacatgc gagtttccca cttgattgat gagatggtct   12120
```

```
ctcgtcgcat ttaccagacc atggaacatt caggtcaagc ggcctggaag caggtggttg   12180
gtgaggccac tctcacgaag ctgtcagggc tcgatatagt tactcatttc caacacctgg   12240
ccgcagtgga ggcggattct tgccgctttc tcagctcacg actcgtgatg ctaaaaaatc   12300
ttgccgttgg caatgtgagc ctacagtaca acaccacgtt ggaccgcgtt gagctcatct   12360
tccccacgcc aggtacgagg cccaagttga ccgatttcag acaatggctc atcagtgtgc   12420
acgcttccat ttttcctct gtggcttcat ctgttacctt gttcatagtg ctttggcttc     12480
gaattccagc tctacgctat gttttggtt ccattggcc cacggcaaca catcattcga      12540
gctgaccatc aactacacca tatgcatgcc ctgttctacc agtcaagcgg ctcgccaaag   12600
gctcgagccc ggtcgtaaca tgtggtgcaa aatagggcat gacaggtgtg aggagcgtga   12660
ccatgatgag ttgttaatgt ccatcccgtc cgggtacgac aacctcaaac ttgagggtta   12720
ttatgcttgg ctggcttttt tgtccttttc ctacgcggcc caattccatc cggagttgtt   12780 cgggatatggg aatgtgtcgc gcgtcttcgt ggacaagcga caccagttca tttgtgccga  12840
gcatgatgga cacaattcaa ccgtatctac cggacacaac atctccgcat tatatgcggc   12900
atattaccac caccaaatag acgggggcaa ttggttccat ttggaatggc tgcggccact   12960
cttttcttcc tggctggtgc tcaacatatc atggtttctg aggcgttcgc ctgtaagccc   13020
tgtttctcga cgcatctatc agatattgag accaacacga ccgcggctgc cggtttcatg   13080
gtccttcagg acatcaattg tttccgacct cacggggtct cagcagcgca agagaaaatt   13140
tccttcggaa agtcgtccca atgtcgtgaa gccgtcggta ctccccagta catcacgata   13200
acggctaacg tgaccgacga atcatacttg tacaacgcgg acctgctgat gctttctgcg   13260
tgccttttct acgcctcaga aatgagcgag aaaggcttca agtcatctt tgggaatgtc    13320 tctggcgttg tttctgcttg tgtcaatttc acagattatg tgcccatgt gacccaacat    13380 acccagcagc atcatctggt aattgatcac attcggttgc tgcatttcct gacaccatct   13440
gcaatgaggt gggctacaac cattgcttgt ttgttcgcca ttctcttggc aatatgagat   13500
gttctcacaa attggggcgt ttcttgactc cgcactcttg cttctggtgg cttttttgc    13560 tgtgtaccgg cttgtcctgg tcctttgccg atggcaacgg cgacagctcg ataccaat    13620 acatatataa cttgacgata tgcgagctga atgggaccga ctggttgtcc agccattttg   13680
gttgggcagt cgagaccttt tgtgctttacc cggttgccac tcatatcctc tcactgggtt   13740
ttctcacaac aagccatttt tttgacgcgc tcggtctcgg cgctgtatcc actgcaggat   13800
ttgttggcgg gcggtacgta ctctgcagcg tctacgcgcg ttgtgctttc gcagcgttcg   13860
tatgttttgt catccgtgct gctaaaaatt gcatggcctg ccgctatgcc cgtacccggt   13920
ttaccaactt cattgtggac gaccggggga gagttcatcg atggaagtct ccaatagtgg   13980
tagaaaaatt gggcaaagcc gaagtcgatg gcaacctcgt caccatcaaa catgtcgtcc   14040
tcgaaggggt taaagctcaa cccttgacga ggacttcggc tgagcaatgg gaggcctaga   14100 cgattttgc aacgatccta tcgccgcaca aaagctcgtg ctagccttta gcatcacata    14160
cacacctata atgatatacg cccttaaggt gtcacgcggc cgactcctgg ggctgttgca   14220
catcctaata tttctgaact gttccttac attcggatac atgacatatg tgcatttca    14280 atccaccaac cgtgtcgcac ttaccctggg ggctgttgtc gcccttctgt ggggtgttta   14340
cagcttcaca gagtcatgga agtttatcac ttccagatgc agattgtgtt gccttggccg   14400
gcgatacatt ctggccccctg cccatcacgt agaaagtgct gcaggtctcc attcaatctc   14460
```

-continued

```
agcgtctggt aaccgagcat acgctgtgag aaagcccgga ctaacatcag tgaacggcac   14520
tctagtacca ggacttcgga gcctcgtgct gggcggcaaa cgagctgtta acgaggagt    14580 ggttaacctc gtcaagtatg gccggtaaaa accagagcca aagaaaaag aaaagtacag    14640 ctccgatggg gaatggccag ccagtcaatc aactgtgcca gttgctgggt gcaatgataa   14700
agtcccagcg ccagcaacct aggggaggac aggccaaaaa gaaaaagcct gagaagccac   14760
attttcccct ggctgctgaa gatgacatcc ggcaccacct cacccagact gaacgctccc   14820
tctgcttgca atcgatccag acggctttca atcaaggcgc aggaactgcg tcgctttcat   14880
ccagcgggaa ggtcagtttt caggttgagt ttatgctgcc ggttgctcat acagtgcgcc   14940
tgattcgcgt gacttctaca tccgccagtc agggtgcaag ttaatttgac agtcaggtga   15000
atggccgcga ttggcgtgtg gcctctgagt cacctattca attagggcga tcacatgggg   15060
gtcatactta atcaggcagg aaccatgtga ccgaaattaa aaaaaaaaa a             15111
```

<210> SEQ ID NO 15
<211> LENGTH: 15182
<212> TYPE: DNA
<213> ORGANISM: Porcine reproductive and respiratory syndrome virus

<400> SEQUENCE: 15

```
tttctccacc cctttaacca tgtctgggat acttgatcgg tgcacgtgta cccccaatgc     60
cagggtgttt atggcggagg gccaagtcta ctgcacacga tgcctcagtg cacggtctct    120
ccttcccctg aacctccaag tttctgagct cggggtgcta ggcctattct acaggcccga    180
agagccactc cggtggacgt tgccacgtgc attccccact gttgagtgct ccccgccgg     240 ggcctgctgg ctctctgcaa tctttccaat cgcacgaatg accagtggaa acctgaactt    300
ccaacaaaga atgatacggg tcgcagctga gctttacaga gccggccagc tcacccctgc    360
agtcttgaag gctctacaag tttatgaacg gggttgccgc tggtacccca ttgttggacc    420
tgcccctgga gtgccgtttt acgccaattc cctacatgtg agtgataaac ctttcccggg    480
agcaactcac gtgttgacca acctgccgct cccgcagaga cccaagcctg aagacttttg    540 ccccttttgag tgtgctatgg ctactgtcta tgacattggt catgacgccg tcatgtatgt    600
ggccgaaagg aaaatctcct gggcccctcg tggcggggat gaagtgaaat ttgaagctgt    660
ccccggggag ttgaggttga ttgcgaaccg gctccgcacc tccttcccgc ccaccacac    720 agtggacatg tctaagttcg ccttcacagc ccctgggtgt ggtgtttcta tgcgggttga    780
acgccaacac ggctgccttc ccgctgacac tgtccctgaa gcaactgct ggtggagctt     840 gtttgactcg cttccactgg aagttcagaa caaagaaatt cgccatgcta accaatttgg    900
ctaccagacc aagcatggtg tctctggcaa gtacctacag cggaggctgc aagttaatgg    960
tctccgagca gtaactgacc taaacggacc tatcgtcgta cagtacttct ccgttaagga   1020
gagttggatc cgccatttga aactggcggg agaacccagc tactctgggt ttgaggacct   1080
cctcagaata agggttgagc ctaacacgtc gccattggct gacaaggaag aaaaatttt    1140 ccggtttggc agtcacaagt ggtacggcgc tggaagaga gcaagaaaag cacgctcttg    1200
tgcgactgcc acagtcgctg gccgcgcttt gtccgttcgt gaaacccggc aggccaagga   1260
gcacgaggtt gccggcgcca acaaggctga gcacctcaaa cactactccc cgcctgccga   1320
agggaattgt ggttggcatt gcatttccgc catcgccaac cggatggtga attccaaatt   1380
tgaaaccacc cttcccgaaa gagtgagacc tccagatgac tgggctactg acaggatct    1440 tgtgaatgcc atccaaatcc tcagactccc tgcggcctta gacaggaacg gtgcttgtac   1500
```

```
tagcgccaag tacgtactta agctggaagg tgagcattgg actgtcactg tggcccctgg    1560
gatgtcccct tctttgctcc ctcttgaatg tgttcagggc tgttgtgggc acaagggcgg    1620
tcttggttcc ccagatgcag tcgaggtctc cggatttgac cctgcctgcc ttgaccggct    1680
ggctgaggtg atgcacctgc ctagcagtgc tatcccagcc gctctggccg aaatgtctgg    1740
cgattccgat cgttcggctt ctccggtcac caccgtgtgg actgtttcgc agttctttgc    1800
ccgtcacagc ggagggaatc accctgatca agtgcgctta gggaaaatta tcagcctttg    1860
tcaggtgatt gaggactgct gctgttccca gaacaaaacc aaccgggtca ccccggagga    1920
ggtcgcagca aagattgacc tgtacctccg tggtgcaaca aatcttgaag aatgcttggc    1980
caggcttgag aaagcgcgcc cgccacgcgt aatcgacacc ttctttgatt gggatgttgt    2040
gctccctggg gttgaggcgg caacccagac gatcaagctg ccccaggtca ccagtgtcg    2100
tgctctggtc cctgttgtga ctcaaaagtc cttggacgac aactcggtcc ccctgaccgc    2160
cttttcactg gctaactact actaccgtgc gcaaggtgac gaagttcgtc accgtgaaag    2220
actaaccgcc gtgctctcca gttggaaaaa ggttgttcga gaagaatatg gctcatgcc    2280
aaccgagcct ggtccacggc ccacactgcc acgcgggctc gacgaactca agaccagat    2340
ggaggaggac ttgctgaagc tggctaacgc ccagacgact tcggacatga tggcctgggc    2400
agtcgagcag gttgacctaa aaacttgggt caagaactac ccgcggtgga caccaccacc    2460
ccctccgcca aaagttcagc ctcgaaaaac gaagcctgtc aagagcttgc cggagagaaa    2520
gcctgtcccc gccccgcgca ggaaggttgg gtccgattgt ggcagcccgg tttcattagg    2580
cggcgatgtc tctaacagtt gggaagattt ggctgttagt agcccctttg atctcccgac    2640
cccacctgag ccggcaacac cttcaagtga gctggtgatt gtgtcctcac cgcaatgcat    2700
cttcaggccg gcgacaccct tgagtgagcc ggctccaatt cccgcacctc gcggaactgt    2760
gtctcgaccg gtgacaccct tgagtgagcc gatccctgtg cccgcaccgc ggcgtaagtt    2820
tcagcaggtg aaaagattga gttcggcggc ggcaatccca ccgtaccaga acgagcccct    2880
ggatttgtct gcttcctcac agactgaaca tgaggcctct cccccagcac cgccgcagag    2940
cgggggcgtt ccgggagtag aggggcatga agctgaggaa accctgagtg aaatctcgga    3000
catgtcgggt aacattaaac ctgcgtccgt gtcatcaagc agctccttgt ccagcgtgag    3060
aatcacacgc ccaaaatact cagctcaagc catcatcgac tcgggcgggc cctgcagtgg    3120
gcatctccaa gaggtaaagg aaacatgcct tagtgtcatg cgcgaggcat gtgatgcgac    3180
taagcttgat gaccctgcta cgcaggaatg gctttctcgc atgtgggatc gggtggacat    3240
gctgacttgg cgcaacacgt ctgtttacca ggcgatttgc accttagatg gcaggttaaa    3300
gttcctccca aaaatgatac tcgagacacc gccgcctat ccgtgtgagt ttgtgatgat    3360
gcctcacacg cctgcacctt ccgtaggtgc ggagagcgac cttaccattg gctcagttgc    3420
tactgaagat gttccacgca tcctcgagaa aatagaaaat gtcggcgaga tggccaacca    3480
gggacccttg gccttctccg aggataaacc ggtagatgac caacttgtca cgacccccg    3540
gatatcgtcg cggaggcctg acgagagcac atcagctccg tccgcaggca caggtggcgc    3600
cggctctttt accgatttgc cgccttcaga tggcgcggat acggacgggg gggggccgtt    3660
tcggacggca aaaagaaaag ctgaaaggct ctttgaccaa ctgagccgtc aggttttgga    3720
cctcgtctcc catctccctg ttttcttctc acgccttttc tacccctggcg gtggttattc    3780
tccgggtgat tggggttttg cagcttttac tctattgtgc ctcttttat gttacagtta    3840
```

```
cccagcctttt  ggtattgctc  ccctcttggg  tgtgttttct  gggtcttctc  ggcgcgttcg   3900
aatgggggtt   tttggctgct  ggttggcttt  tgctgttggt  ctgttcaagc  ctgtgtccga   3960
cccagtcggc   gctgcttgtg  agtttgactc  gccagagtgt  agaaacatcc  ttcattcttt   4020
tgagcttctc   aaaccttggg  accctgttcg  cagccttgtt  gtgggccccg  tcggtctcgg   4080
tcttgccatt   cttggcaggt  tactgggcgg  ggcacgctgc  atctggcact  ttttgcttag   4140
gcttggcatt   gttgcagact  gtatcttggc  tggagcttac  gtgctttctc  aaggtaggtg   4200
taaaaagtgc   tggggatctt  gtataagaac  tgctcctaat  gaggtcgctt  ttaacgtgtt   4260
tcctttcaca   cgtgcgacca  ggtcgtcact  tatcgacctg  tgcgatcggt  tttgtgcgcc   4320
aaaaggaatg   gaccccatttt ttctcgccac  tgggtggcgc  gggtgctggg  ccggccgaag   4380
ccccattgag   caaccctctg  aaaaacccat  cgcgtttgcc  caattggatg  aaaagaagat   4440
tacggctagg   actgtggtcg  cccagcctta  tgaccccaac  caagccgtaa  agtgcttgcg   4500
ggtattgcag   gcgggtgggg  cgatggtggc  taaggcggtc  ccaaaagtgg  ttaaggtttc   4560
cgctgttcca   ttccgagctc  ccttctttcc  cactggagtg  aaagttgacc  ctgattgcag   4620
ggtcgtggtt   gaccctgaca  cttttcactgc agctctccgg  tctggctact  ccaccacaaa   4680
cctcgtcctt   ggtgtagggg  actttgccca  gctaaatgga  ttaaaaatca  ggcaaatttc   4740
caagccttca   gggggaggcc  cacatctcat  ggctgccctg  catgttgcct  gctcgatggc   4800
tctgcacatg   cttgctggga  tttatgtgac  tgcggtgggt  tcttgcggca  ccggcaccaa   4860
cgacccgtgg   tgcgctaacc  cgtttgccgt  ccctggctac  ggacctggct  ctctctgtac   4920
gtccagattg   tgcatttccc  aacacggcct  taccctgccc  ttgtcagcac  ttgtggcggg   4980
attcggtatt   caagaaattg  ccttggtcgt  tttgattttt  gtttccatcg  gaggcatggc   5040
tcataggtta   agctgtaagg  ctgacatgct  gtgtgttttg  cttgcaattg  ccagctatgt   5100
ttgggtacct   cttacctggt  tgctttgtgt  gtttccttgc  tggttgcgct  gttttcttt   5160
gcacccctc    accatcctat  ggttggtgtt  tttcttgatt  tctgtgaata  tgccttcagg   5220
aatcttggcc   atggtgttgt  tggtttctct  ttggcttctt  ggtcgttata  ctaatgttgc   5280
tggccttgtc   acccctacg   acattcatca  ttacaccagt  ggcccccgcg  tgttgccgc   5340
cttggctacc   gcaccagatg  ggacctactt  ggccgctgtc  cgccgcgctg  cgttgactgg   5400
ccgcaccatg   ctgtttaccc  cgtcccagct  tgggtctctt  cttgagggtg  ccttcagaac   5460
tcgaaagccc   tcactgaaca  ccgtcaatgt  gatcgggtcc  tccatgggct  ctggcggggt   5520
gtttaccatc   gacgggaaag  tcaagtgcgt  aactgccgca  catgtcctta  cgggcaattc   5580
agctcgggtt   tccggggtcg  gcttcaatca  aatgcttgac  tttgacgtaa  agggagattt   5640
cgctatcgct   gattgcccga  attggcaagg  ggctgccccc  aagacccaat  ctgcacgga    5700
tggatggact   ggccgtgcct  attggctaac  atcctctggc  gtcgaacccg  gcgtcattgg   5760
aaaaggattc   gccttctgct  tcaccgcatg  tggcgattcc  gggtccccag  tgatcaccga   5820
ggccggtgag   cttgtcggcg  ttcacacggg  atcgaataaa  caaggggggg  gcattgttac   5880
gcgcccctca   ggccagtttt  gtaatgtggc  acccatcaag  ctaagcgaat  taagtgaatt   5940
ctttgctggg   cctaaggtcc  cgctcggtga  tgtgaaggtc  ggcagccaca  taattaaaga   6000
cataagcgag   gtgccttcag  atctttgtgc  cttgcttgct  gccaaacctg  aactggaagg   6060
aggcctctcc   accgtccaac  ttctttgtgt  gttttttctc  ctgtggagaa  tgatgggaca   6120
tgcctggacg   cccttggttg  ctgtgagttt  ctttatttg   aatgaggttc  tccctgccgt   6180
cctggtccgg   agtgttttct  cctttggaat  gtttgtgcta  tcctggctca  cgccatggtc   6240
```

```
tgcgcaagtt ctgatgatca ggcttctgac agcagctctt aacaggaaca gatggtcact    6300
tgcctttttc agcctcggtg cagtgaccgg ttttgtcgca gatcttgcgg ccactcaggg    6360
gcatccgttg caggcagtga tgaatttgag cacctatgca ttcctgcctc ggatgatggt    6420
tgtgacctca ccagtcccag tgatcacgtg tggtgtcgtg cacctacttg ccatcatttt    6480
gtacttgttt aagtaccgtg gcctgcacca tatccttgtt ggcgatggag tgttctctgc    6540
ggctttcttc ttgagatact ttgccgaggg aaagttgagg aaggggtgt cgcaatcctg    6600 cggaatgaat catgagtctc tgactggtgc cctcgctatg agactcaatg acgaggactt    6660
ggatttcctt atgaaatgga ctgattttaa gtgctttgtt tctgcgtcca acatgaggaa    6720
tgcagcgggt caatttatcg aggctgccta tgctaaagca cttagagtag aactggccca    6780
gttggtacag gttgataaag ttcgaggtac tttggccaaa cttgaagctt ttgctgatac    6840
cgtggctcct caactctcgc ccggtgacat tgttgtcgct ctcggccaca cgcctgttgg    6900
cagtatcttc gacctaaagg ttggtagcac caagcatacc ctccaagcca ttgagaccag    6960
agtccttgct gggtccaaaa tgaccgtggc gcgcgtcgtc gacccgaccc ccacgccccc    7020
acccgcaccc gtgcccatcc ccctcccacc gaaagttctg gagaatggcc caacgcttg    7080 gggggatgag gaccgtttga ataagaagaa gaggcgcagg atggaagccc tcggcatcta    7140
tgttatgggc gggaaaaagt accagaaatt ttgggacaag aattccggtg atgtgtttta    7200
tgaggaggtc cataataaca cagatgagtg ggagtgtctc agagttggcg accctgccga    7260 ctttgacccct gagaagggaa ctctgtgtgg acatgtcacc attgaaaata aggcttacca    7320
tgtttacacc tccccatctg gtaagaagtt cttggtcccc gtcaacccag agaatggaag    7380
agttcaatgg gaagctgcaa agctttccgt ggagcaggcc ctaggtatga tgaatgtcga    7440
cggcgaactg actgccaaag aactggagaa actgaaaaga ataattgaca aactccaggg    7500
cctgactaag gagcagtgtt taaactgcta gccgccagcg acttgacccg ctgtggtcgc    7560
ggcggcttgg ttgttactga acagcggta aaaatagtca aatttcacaa ccggaccttc    7620
accctgggac ctgtgaattt aaaagtggcc agtgaggttg agctaaaaga cgcggttgag    7680
cacaaccaac acccggttgc gagaccgatc gatggtggag ttgtgctctt gcgttccgcg    7740
gttccttcgc ttatagacgt cttgatctcc ggtgctgatg catctcccaa gttacttgcc    7800
catcacgggc cggaaacac tgggatcgat ggcacgctct gggattttga gtccgaagcc    7860 actaagagg aagtcgcact cagtgcgcaa ataatacagg cttgtgacat taggcgcggc    7920
gacgctcctg aaattggtct cccttacaag ctgtacctg ttaggggtaa ccctgagcgg    7980
gtgaaaggag ttctgcagaa tacaaggttt ggagacatac cttacaaaac ccccagtgac    8040
actggaagcc cagtgcacgc ggctgcctgc ttacgccca cgccactcc ggtgactgat    8100 gggcgctccg tcttggccac gaccatgccc cccgggtttg agttatatgt accgaccata    8160
ccagcgtctg tccttgatta ccttgactct aggcctgact gccctaaaca gctgacagag    8220
cacggctgcg aagatgccgc actgaaagac ctctctaaat atgacttgtc cacccaaggc    8280
tttgttttac ctggagttct tcgccttgtg cggaaatacc tgtttgccca tgtaggtaag    8340
tgcccacccg ttcatcggcc ttctacttac cctgctaaga attctatggc tggaataaat    8400
gggaacaggt tcccaaccaa ggacattcag agcgtccctg aaatcgacgt tctgtgcgca    8460
caggctgtgc gagaaaactg gcaaactgtc accccttgta ctcttaagaa acagtattgc    8520
gggaagaaga agactaggac catactcggc accaataact tcatcgcact agcccaccga    8580
```

```
gcagtgttga gtggtgttac ccagggcttc atgaaaaagg cgtttaactc gcccatcgcc   8640
ctcggaaaga acaagtttaa ggagctacag actccggtcc tgggcaggtg ccttgaagct   8700
gatctcgcat cctgcgatcg atccacgcct gcaattgtcc gctggtttgc cgccaacctt   8760
ctttatgaac ttgcctgtgc tgaagagcat ctaccgtcgt acgtgctgaa ctgctgccac   8820
gacttactgg tcacgcagtc cggcgcagtg actaagagag gtggcctgtc gtctggcgac   8880
ccgatcacct ctgtgtctaa caccatttat agtttggtga tctatgcaca gcatatggtg   8940
cttagttact tcaaaagtgg tcaccccat ggccttctgt tcttacaaga ccagctaaag   9000
tttgaggaca tgctcaaggt tcaacccctg atcgtctatt cggacgacct cgtgctgtat   9060
gccgagtctc ccaccatgcc aaactatcac tggtgggttg aacatctgaa tttgatgctg   9120
gggtttcaga cggacccaaa gaagacagca ataacagact cgccatcatt tctaggctgt   9180
agaataataa atgggcgcca gctagtcccc aaccgtgaca ggatcctcgc ggccctcgcc   9240
tatcacatga aggcgagtaa tgtttctgaa tactatgcct cagcggctgc aatactcatg   9300
gacagctgtg cttgtttgga gtatgatcct gaatggtttg aagaacttgt agttggaata   9360
gcgcagtgcg cccgcaagga cggctacagt tttcccggca cgccgttctt catgtccatg   9420
tgggaaaaac tcaggtccaa ttatgagggg aagaagtcga gagtgtgcgg gtactgcggg   9480
gccccggccc cgtacgctac tgcctgtggc ctcgacgtct gcatttacca cacccacttc   9540
caccagcatt gtccagtcac aatctggtgt ggccatccag cgggtctgg ttcttgtagt   9600
gagtgcaaat cccctgtagg gaaaggcaca agccctttag acgaggtgct ggaacaagtc   9660
ccgtataagc ccccacggac cgttatcatg catgtggagc agggtctcac ccccttgat   9720
ccaggtagat accaaactcg ccgcggacta gtctctgtca ggcgtggaat taggggaaat   9780
gaagttgaac taccagacgg tgattatgct agcaccgcct tgctccctac ctgcaaagag   9840
atcaacatgg tcgctgtcgc ttccaatgta ctgcgcagca ggttcatcat cggcccaccc   9900
ggtgctggga aaacatactg gctccttcaa caggtccagg atggtgatgt tatttacaca   9960
ccaactcacc agaccatgct tgacatgatt agggctttgg ggacgtgccg gttcaacgtc  10020
ccggcaggca caacgctgca attccccgtc ccctcccgca ccggtccgtg ggttcgcatc  10080
ctagccggcg gttggtgtcc tggcaagaat tccttcctag atgaagcagc gtattgcaat  10140
cacctcgatg tttgaggct tcttagtaaa actaccctca cctgtctagg agacttcaag  10200
caactccacc cagtgggttt tgattctcat tgctatgttt ttgacatcat gcctcaaact  10260
caactgaaga ccatctggag gtttggacag aatatctgtg atgccgttca gccagattac  10320
agggacaaac tcatgtccat ggtcaacaca acccgtgtga cctacgtgga aaaacctgtc  10380
aggtatgggc aggtcctcac cccctaccac agggaccgag aggacgacgc catcactatt  10440
gactccagtc aaggcgccac attcgatgtg gttacattgc atttgcccac taaagattca  10500
ctcaacagga aaagagccct tgttgccatc accagggcaa gacacgctat ctttgtgtat  10560
gacccacaca ggcagctgca gggcttgttt gatcttcctg caaaaggcac acccgtcaac  10620
ctcgcagtgc accgcgacgg gcagctgatc gtgctggata gaaataacaa agaatgcacg  10680
gtcgctcagg ctctaggcaa cggggataaa tttagggcca cagataagcg tgttgtagat  10740
tctctccgcg ccatttgtgc tgatctagaa gggtcgagct ctccgctccc caaggtcgca  10800
cacaacttgg gatttatt ctcacctgat ttaacacagt tgctaaaact cccagtagaa  10860
cttgcacctc actggccgt ggtgacaacc agaacaatg aaaagtggcc agatcggctg  10920
gttgccagcc ttcgccctat ccataaatac agccgcgcgt gcatcggtgc cggctatatg  10980
```

```
gtgggccctt cggtgtttct aggcactcct ggggtcgtgt catactatct cacaaaattt    11040
gttaagggcg aggctcaatt gcttccggag acggttttca gcaccggccg aattgaggta    11100
gactgccggg aatatcttga tgatcgggag cgagaagttg ctgcgtccct cccacacgct    11160
ttcattggca acgtcaaagg cactaccgtt ggaggatgtc atcatgtcac ctccagatac    11220
ctcccacgcg tccttcccaa ggaatcagtt gcggtagtcg gggtttcaag ccccggaaaa    11280
gccgcgaaag cattgtgcac actgacagat gtgtacctcc cagatcttga cgcctatctc    11340
cacccggaga cccagtccaa gtgctggaaa atgatgttgg acttcaaaga agttcgacta    11400
atggtctgga aagacaaaac agcctatttc caacttgaag gtcgctattt cacctggtat    11460
cagcttgcca gctatgcctc gtacatccgt gttcctgtca actctacggt gtacttggac    11520
ccctgcatgg gccccgccct ttgcaacagg agagtcgtcg ggtccaccca ctgggggggct    11580 gacctcgcgg tcacccctta tgattacggc gctaaaatta tcctgtctag cgcgtaccat    11640
ggtgaaatgc cccccggata caaaattctg gcgtgcgcgg agttctcgtt ggatgaccca    11700
gttaagtaca acatacctg ggggtttgaa tcggatacag cgtatctgta tgagttcacc    11760
ggaaacggtg aggactggga ggattacaat gatgcgtttc gtgcgcgcca ggaagggaaa    11820
atttataagg ccactgccac cagcttgaag ttttatttc ccccgggccc tgtcattgaa    11880
ccaactttag gcctgaattg aaatgaaatg gggtccatgc aaagcctttt ttacaaaatt    11940
ggccaacttt ttgtggatgc tttcacggag ttcttggtgt ccattgttga tatcactata    12000
tttttggcca ttttgtttgg cttccaccatc gccggttggc tggtggtctt ttgcatcaga    12060
ttggtttgct ccgcgatact ccgtacgcgc tctgccattc actctgagca attacagaag    12120
atcttatgag gcctttcttt cccagtgcca agtggacatt cccacctggg gaactaaaca    12180
tcctttgggg atgctttggc accataaggt gtcaaccctg attgatgaaa tggtgtcgcg    12240
tcgaatgtac cgcatcatgg aaaaagcagg gcaggctgcc tggaaacagg tggtgagcga    12300
ggctacgctg tctcgcatta gtagtttgga tgtggtggct cattttcagc atctagccgc    12360
cattgaagcc gagacctgta aatatttggc ctcccggctg cccatgctac acaacctgcg    12420
catgacaggt tcaaatgtaa ccatagtgta taatagcact ttgaatcagg tgtttgctat    12480
ttttccaacc cctggttccc ggccaaagct taatgatttt cagcaatggt taatagctgt    12540
acattcctcc atatttcct ctgttgcaac ttcttgtact cttttttgttg tgctgtggtt    12600 gcgggttcca atactacgta ctgcttttgg tttccgctgg ttaggggcaa ttttttctttc    12660 gaactcacag tgaattacac ggtgtgtcca ccttgcctca cccggcaagc agccgcagag    12720
atctacgaac ccggtaggtc tctttggtgc aggataggt atgaccgatg tgaggaggat    12780
gatcatgacg agctagggtt tatggtaccg cctggcctct ccagcgaagg ccacttgact    12840
agtgtttacg cctggttggc gttcttgtcc ttcagctaca cggcccagtt ccatcccgag    12900
atattcggga tagggaatgt gagtcgagtt tatgttgaca tcaaacatca actcatctgc    12960
gccgaacatg acgggcagaa caccaccttg cctcgtcatg acaacatttc agccgtgttt    13020
cagacctatt accaacatca agtcgacggc ggcaattggt ttcacctaga atggcttcgt    13080
cccttctttt cctcgtggtt ggtttttaaat gtctcttggt ttctcaggcg ttcgcctgca    13140
aaccatgttt cagttcgagt cttgcagata ttaagaccaa caccaccgca gcggcaagct    13200
ttgctgtcct ccaagacatc agttgcctta ggcatcgcga ctcggcctct gaggcgattc    13260
gcaaaatccc tcagtgccgt acggcgatag ggacacccgt gtatgttacc atcacagcca    13320
```

```
atgtgacaga tgagaattat ttacattctt ctgatctcct catgctttct tcttgccttt    13380
tctatgcttc tgagatgagt gaaaagggat ttaaggtggt atttggcaat gtgtcaggca    13440
tcgtggctgt gtgtgtcaat tttaccagct acgtccaaca tgtcaaggag tttacccaac    13500
gctccctggt ggtcgaccat gtgcggttgc tccatttcat gacacctgag accatgaggt    13560
gggcaactgt tttagcctgt cttttgcca ttctgttggc aatttgaatg tttaagtatg     13620
ttggagaaat gcttgaccgc gggctgttac tcgcaattgc tttctttgtg gtgtatcgtg    13680
ccgttctgtt ttgctgtgct cgtcaacgcc agcaacgaca gcagctccca tctacagctg    13740
atttacaact gacgctatg tgagctgaat ggcacagatt ggctagctaa caaatttgat     13800
tgggcagtgg agagttttgt catctttccc gttttgactc acattgtctc ctatggtgcc    13860
ctcactacta gccatttcct tgacacagtc gctttagtca ctgtgtctac cgccgggttt    13920
gttcacgggc ggtatgtcct aagtagcatc tacgcggtct gtgccctggc tgcgttgact    13980
tgcttcgtca ttaggtttgc aaagaattgc atgtcctggc gctacgcgtg taccagatat    14040
accaactttc ttctggacac taagggcaga ctctatcgtt ggcggtcgcc tgtcatcata    14100
gagaaaaggg gcaaagttga ggtcgaaggt catctgatcg acctcaaaag agttgtgctt    14160
gatggttccg tggcaacccc tataaccaga gtttcagcgg aacaatgggg tcgtccttag    14220
atgacttctg tcatgatagc acggctccac aaaaggtgct tttggcgttt tctattacct    14280
acacgccagt gatgatatat gccctaaagg tgagtcgcgg ccgactgcta gggcttctgc    14340 acctttgat cttcctgaat tgtgctttca ccttcgggta catgactttc gcgcactttc     14400
agagtacaaa taaggtcgcg ctcactatgg agcagtagt tgcactcctt tgggggtgt      14460 actcagccat agaaacctgg aaattcatca cctccagatg ccgtttgtgc ttgctaggcc    14520
gcaagtacat tctggcccct gcccaccacg ttgaaagtgc cgcaggcttt catccgattg    14580
cggcaaatga taaccacgca tttgtcgtcc ggcgtcccgg ctccactacg gtcaacggca    14640
cattggtgcc cggggttaaaa agcctcgtgt tgggtggcag aaaagctgtt aaacaggag    14700 tggtaaacct tgtcaaatat gccaaataac aacggcaagc agcagaatag aaagaagggg    14760
gatggccagc cagtcaatca gctgtgccag atgctgggta agatcatcgc tcagcaaaac    14820
cagtccagag gcaagggacc gggaaagaaa aataagaaga aaacccgga gagccccat      14880 tttcctctag cgactgaaga tgatgtcaga catcactttta cccctagtga gcggcaattg    14940
tgtctgtcgt caatccagac cgcctttaat caaggcgctg ggacttgcac cctgtcagat    15000
tcagggagga taagttacac tgtggagttt agtttgccta cgcatcatac tgtgcgcctg    15060
attcgcgtca cagcatcacc ctcagcatga tgggctggca ttcttgaggc atctcagtgt    15120
ttgaattgga agaatgtgtg gtgaatggca ctgattgaca ttgtgcctct aagcactata    15180
tt                                                                   15182

<210> SEQ ID NO 16
<211> LENGTH: 383
<212> TYPE: PRT
<213> ORGANISM: Porcine reproductive and respiratory syndrome virus

<400> SEQUENCE: 16

Met Ser Gly Thr Phe Ser Arg Cys Met Cys Thr Pro Ala Ala Arg Val
1               5                   10                  15

Phe Trp Asn Ala Gly Gln Val Tyr Cys Thr Arg Cys Leu Ser Ala Arg
            20                  25                  30

Ser Leu Leu Pro Pro Glu Leu Gln Asp Ile Asp Leu Ala Ala Ile Gly
```

```
                35                  40                  45

Leu Phe Tyr Lys Pro Lys Asp Lys Leu His Trp Lys Val Pro Ile Gly
 50                  55                  60

Ile Pro Gln Val Glu Cys Thr Pro Ser Gly Cys Cys Trp Leu Ser Gly
 65                  70                  75                  80

Ile Phe Pro Leu Ala Arg Met Thr Ser Gly Asn His Asn Phe Leu Gln
                 85                  90                  95

Arg Leu Val Lys Val Ala Asp Val Leu Tyr Arg Asp Gly Cys Leu Thr
                100                 105                 110

Ser Arg His Leu Arg Glu Leu Gln Val Tyr Glu Arg Gly Cys Ser Trp
            115                 120                 125

Tyr Pro Ile Thr Gly Pro Val Pro Gly Met Gly Leu Tyr Ala Asn Ser
        130                 135                 140

Met His Val Ser Asp Gln Pro Phe Pro Gly Ala Thr His Val Leu Thr
145                 150                 155                 160

Asn Ser Pro Leu Pro Gln Gln Ala Cys Arg Gln Pro Phe Cys Pro Phe
                165                 170                 175

Glu Glu Ala His Ser Ser Val Tyr Arg Trp Lys Lys Phe Val Val Phe
            180                 185                 190

Thr Asp Ser Ser Pro Asn Gly Arg Met Met Trp Thr Pro Glu Ser Asp
        195                 200                 205

Asp Ser Ala Asp Leu Glu Ala Leu Pro Pro Glu Leu Glu Arg Gln Val
210                 215                 220

Glu Ile Leu Ile Arg Ser Phe Pro Ala His His Pro Val Ser Leu Ala
225                 230                 235                 240

Asp Trp Glu Leu Ala Glu Ser Pro Glu Asn Gly Phe Ser Phe Ser Thr
                245                 250                 255

Tyr His Ser Gly Gly Tyr Leu Val Gln Asn Pro Asp Val Phe Asp Ser
            260                 265                 270

Lys Cys Trp Leu Ser Cys Phe Leu Asp Gln Pro Ile Glu Val Arg Leu
        275                 280                 285

Tyr Glu Asp Tyr Leu Ala Asn Ala Phe Gly Tyr Gln Thr Lys Trp Gly
    290                 295                 300

Val Ser Gly Lys Tyr Leu Gln Arg Arg Leu Gln Val Asn Gly Ile Arg
305                 310                 315                 320

Ala Val Ile Asp Pro Asp Gly Pro Ile His Val Glu Ala Leu Ser Cys
                325                 330                 335

Pro Gln Ser Trp Ile Arg His Leu Thr Leu Asp Asp Asp Val Thr Pro
            340                 345                 350

Gly Phe Val Arg Leu Thr Ser Leu Arg Ile Val Pro Asn Thr Glu Pro
        355                 360                 365

Thr Thr Leu Arg Ile Phe Arg Phe Gly Ala His Lys Trp Tyr Gly
    370                 375                 380

<210> SEQ ID NO 17
<211> LENGTH: 382
<212> TYPE: PRT
<213> ORGANISM: Porcine reproductive and respiratory syndrome virus

<400> SEQUENCE: 17

Met Ser Gly Thr Phe Ser Arg Cys Met Cys Thr Pro Ala Ala Arg Val
 1               5                  10                  15

Phe Trp Asn Ala Gly Gln Val Tyr Cys Thr Arg Cys Leu Ser Ala Arg
                20                  25                  30
```

```
Ser Leu Leu Pro Pro Glu Leu Gln Asp Ile Asp Leu Ala Ala Ile Gly
         35                  40                  45

Leu Phe Tyr Lys Pro Lys Asp Lys Leu His Trp Lys Val Pro Ile Gly
 50                  55                  60

Ile Pro Gln Val Glu Cys Thr Pro Ser Gly Cys Cys Trp Leu Ser Gly
 65                  70                  75                  80

Ile Phe Pro Leu Ala Arg Met Thr Ser Gly Asn His Asn Phe Leu Gln
                 85                  90                  95

Arg Leu Val Lys Val Ala Asp Val Leu Tyr Arg Asp Gly Cys Leu Thr
                100                 105                 110

Ser Arg His Leu Arg Glu Leu Gln Val Tyr Glu Arg Gly Cys Ser Trp
            115                 120                 125

Tyr Pro Ile Thr Gly Pro Val Pro Gly Met Gly Leu Tyr Ala Asn Ser
130                 135                 140

Met His Val Ser Asp Gln Pro Phe Pro Gly Ala Thr His Val Leu Thr
145                 150                 155                 160

Asn Ser Pro Leu Pro Gln Gln Ala Cys Arg Gln Pro Phe Cys Pro Phe
                165                 170                 175

Glu Glu Ala His Ser Ser Val Tyr Arg Trp Lys Lys Phe Val Val Phe
                180                 185                 190

Thr Asp Ser Ser Pro Asn Gly Met Met Trp Thr Pro Glu Ser Asp Asp
            195                 200                 205

Ser Ala Asp Leu Glu Ala Leu Pro Pro Glu Leu Glu Arg Gln Val Glu
            210                 215                 220

Ile Leu Ile Arg Ser Phe Pro Ala His His Pro Val Ser Leu Ala Asp
225                 230                 235                 240

Trp Glu Leu Ala Glu Ser Pro Glu Asn Gly Phe Ser Phe Ser Thr Tyr
                245                 250                 255

His Ser Gly Gly Tyr Leu Val Gln Asn Pro Asp Val Phe Asp Ser Lys
            260                 265                 270

Cys Trp Leu Ser Cys Phe Leu Asp Gln Pro Ile Glu Val Arg Leu Tyr
        275                 280                 285

Glu Asp Tyr Leu Ala Asn Ala Phe Gly Tyr Gln Thr Lys Trp Gly Val
290                 295                 300

Ser Gly Lys Tyr Leu Gln Arg Arg Leu Gln Val Asn Gly Ile Arg Ala
305                 310                 315                 320

Val Ile Asp Pro Asp Gly Pro Ile His Val Glu Ala Leu Ser Cys Pro
                325                 330                 335

Gln Ser Trp Ile Arg His Leu Thr Leu Asp Asp Asp Val Thr Pro Gly
            340                 345                 350

Phe Val Arg Leu Thr Ser Leu Arg Ile Val Pro Asn Thr Glu Pro Thr
            355                 360                 365

Thr Leu Arg Ile Phe Arg Phe Gly Ala His Lys Trp Tyr Gly
370                 375                 380

<210> SEQ ID NO 18
<211> LENGTH: 381
<212> TYPE: PRT
<213> ORGANISM: Porcine reproductive and respiratory syndrome virus

<400> SEQUENCE: 18

Met Ser Gly Thr Phe Ser Arg Cys Met Cys Thr Pro Ala Ala Arg Val
 1               5                  10                  15

Phe Trp Asn Ala Gly Gln Val Tyr Cys Thr Arg Cys Leu Ser Ala Arg
                 20                  25                  30
```

```
Ser Leu Leu Pro Pro Glu Leu Gln Asp Ile Asp Leu Ala Ala Ile Gly
        35                  40                  45

Leu Phe Tyr Lys Pro Lys Asp Lys Leu His Trp Lys Val Pro Ile Gly
 50                  55                  60

Ile Pro Gln Val Glu Cys Thr Pro Ser Gly Cys Cys Trp Leu Ser Gly
 65                  70                  75                  80

Ile Phe Pro Leu Ala Arg Met Thr Ser Gly Asn His Asn Phe Leu Gln
                 85                  90                  95

Arg Leu Val Lys Val Ala Asp Val Leu Tyr Arg Asp Gly Cys Leu Thr
             100                 105                 110

Ser Arg His Leu Arg Glu Leu Gln Val Tyr Glu Arg Gly Cys Ser Trp
         115                 120                 125

Tyr Pro Ile Thr Gly Pro Val Pro Gly Met Gly Leu Tyr Ala Asn Ser
     130                 135                 140

Met His Val Ser Asp Gln Pro Phe Pro Gly Ala Thr His Val Leu Thr
145                 150                 155                 160

Asn Ser Pro Leu Pro Gln Gln Ala Cys Arg Gln Pro Phe Cys Pro Phe
                165                 170                 175

Glu Glu Ala His Ser Ser Val Tyr Arg Trp Lys Lys Phe Val Val Phe
            180                 185                 190

Thr Asp Ser Ser Pro Asn Met Met Trp Thr Pro Glu Ser Asp Asp Ser
        195                 200                 205

Ala Asp Leu Glu Ala Leu Pro Pro Glu Leu Glu Arg Gln Val Glu Ile
    210                 215                 220

Leu Ile Arg Ser Phe Pro Ala His His Pro Val Ser Leu Ala Asp Trp
225                 230                 235                 240

Glu Leu Ala Glu Ser Pro Glu Asn Gly Phe Ser Phe Ser Thr Tyr His
                245                 250                 255

Ser Gly Gly Tyr Leu Val Gln Asn Pro Asp Val Phe Asp Ser Lys Cys
            260                 265                 270

Trp Leu Ser Cys Phe Leu Asp Gln Pro Ile Glu Val Arg Leu Tyr Glu
        275                 280                 285

Asp Tyr Leu Ala Asn Ala Phe Gly Tyr Gln Thr Lys Trp Gly Val Ser
    290                 295                 300

Gly Lys Tyr Leu Gln Arg Arg Leu Gln Val Asn Gly Ile Arg Ala Val
305                 310                 315                 320

Ile Asp Pro Asp Gly Pro Ile His Val Glu Ala Leu Ser Cys Pro Gln
                325                 330                 335

Ser Trp Ile Arg His Leu Thr Leu Asp Asp Asp Val Thr Pro Gly Phe
            340                 345                 350

Val Arg Leu Thr Ser Leu Arg Ile Val Pro Asn Thr Glu Pro Thr Thr
        355                 360                 365

Leu Arg Ile Phe Arg Phe Gly Ala His Lys Trp Tyr Gly
    370                 375                 380

<210> SEQ ID NO 19
<211> LENGTH: 380
<212> TYPE: PRT
<213> ORGANISM: Porcine reproductive and respiratory syndrome virus

<400> SEQUENCE: 19

Met Ser Gly Thr Phe Ser Arg Cys Met Cys Thr Pro Ala Ala Arg Val
1               5                  10                  15

Phe Trp Asn Ala Gly Gln Val Tyr Cys Thr Arg Cys Leu Ser Ala Arg
```

```
            20                  25                  30
Ser Leu Leu Pro Pro Glu Leu Gln Asp Ile Asp Leu Ala Ala Ile Gly
        35                  40                  45

Leu Phe Tyr Lys Pro Lys Asp Lys Leu His Trp Lys Val Pro Ile Gly
 50                  55                  60

Ile Pro Gln Val Glu Cys Thr Pro Ser Gly Cys Cys Trp Leu Ser Gly
 65                  70                  75                  80

Ile Phe Pro Leu Ala Arg Met Thr Ser Gly Asn His Asn Phe Leu Gln
                 85                  90                  95

Arg Leu Val Lys Val Ala Asp Val Leu Tyr Arg Asp Gly Cys Leu Thr
            100                 105                 110

Ser Arg His Leu Arg Glu Leu Gln Val Tyr Glu Arg Gly Cys Ser Trp
        115                 120                 125

Tyr Pro Ile Thr Gly Pro Val Pro Gly Met Gly Leu Tyr Ala Asn Ser
    130                 135                 140

Met His Val Ser Asp Gln Pro Phe Pro Gly Ala Thr His Val Leu Thr
145                 150                 155                 160

Asn Ser Pro Leu Pro Gln Gln Ala Cys Arg Gln Pro Phe Cys Pro Phe
                165                 170                 175

Glu Glu Ala His Ser Ser Val Tyr Arg Trp Lys Lys Phe Val Val Phe
            180                 185                 190

Thr Asp Ser Ser Pro Met Met Trp Thr Pro Glu Ser Asp Asp Ser Ala
        195                 200                 205

Asp Leu Glu Ala Leu Pro Pro Glu Leu Glu Arg Gln Val Glu Ile Leu
    210                 215                 220

Ile Arg Ser Phe Pro Ala His His Pro Val Ser Leu Ala Asp Trp Glu
225                 230                 235                 240

Leu Ala Glu Ser Pro Glu Asn Gly Phe Ser Phe Ser Thr Tyr His Ser
                245                 250                 255

Gly Gly Tyr Leu Val Gln Asn Pro Asp Val Phe Asp Ser Lys Cys Trp
            260                 265                 270

Leu Ser Cys Phe Leu Asp Gln Pro Ile Glu Val Arg Leu Tyr Glu Asp
        275                 280                 285

Tyr Leu Ala Asn Ala Phe Gly Tyr Gln Thr Lys Trp Gly Val Ser Gly
    290                 295                 300

Lys Tyr Leu Gln Arg Arg Leu Gln Val Asn Gly Ile Arg Ala Val Ile
305                 310                 315                 320

Asp Pro Asp Gly Pro Ile His Val Glu Ala Leu Ser Cys Pro Gln Ser
                325                 330                 335

Trp Ile Arg His Leu Thr Leu Asp Asp Asp Val Thr Pro Gly Phe Val
            340                 345                 350

Arg Leu Thr Ser Leu Arg Ile Val Pro Asn Thr Glu Pro Thr Thr Leu
        355                 360                 365

Arg Ile Phe Arg Phe Gly Ala His Lys Trp Tyr Gly
    370                 375                 380

<210> SEQ ID NO 20
<211> LENGTH: 379
<212> TYPE: PRT
<213> ORGANISM: Porcine reproductive and respiratory syndrome virus

<400> SEQUENCE: 20

Met Ser Gly Thr Phe Ser Arg Cys Met Cys Thr Pro Ala Ala Arg Val
 1               5                  10                  15
```

```
Phe Trp Asn Ala Gly Gln Val Tyr Cys Thr Arg Cys Leu Ser Ala Arg
                20                  25                  30

Ser Leu Leu Pro Pro Glu Leu Gln Asp Ile Asp Leu Ala Ala Ile Gly
        35                  40                  45

Leu Phe Tyr Lys Pro Lys Asp Lys Leu His Trp Lys Val Pro Ile Gly
    50                  55                  60

Ile Pro Gln Val Glu Cys Thr Pro Ser Gly Cys Cys Trp Leu Ser Gly
65                  70                  75                  80

Ile Phe Pro Leu Ala Arg Met Thr Ser Gly Asn His Asn Phe Leu Gln
                85                  90                  95

Arg Leu Val Lys Val Ala Asp Val Leu Tyr Arg Asp Gly Cys Leu Thr
            100                 105                 110

Ser Arg His Leu Arg Glu Leu Gln Val Tyr Glu Arg Gly Cys Ser Trp
        115                 120                 125

Tyr Pro Ile Thr Gly Pro Val Pro Gly Met Gly Leu Tyr Ala Asn Ser
    130                 135                 140

Met His Val Ser Asp Gln Pro Phe Pro Gly Ala Thr His Val Leu Thr
145                 150                 155                 160

Asn Ser Pro Leu Pro Gln Gln Ala Cys Arg Gln Pro Phe Cys Pro Phe
                165                 170                 175

Glu Glu Ala His Ser Ser Val Tyr Arg Trp Lys Lys Phe Val Val Phe
            180                 185                 190

Thr Asp Ser Ser Met Met Trp Thr Pro Glu Ser Asp Ser Ala Asp
        195                 200                 205

Leu Glu Ala Leu Pro Pro Glu Leu Glu Arg Gln Val Glu Ile Leu Ile
210                 215                 220

Arg Ser Phe Pro Ala His His Pro Val Ser Leu Ala Asp Trp Glu Leu
225                 230                 235                 240

Ala Glu Ser Pro Glu Asn Gly Phe Ser Phe Ser Thr Tyr His Ser Gly
                245                 250                 255

Gly Tyr Leu Val Gln Asn Pro Asp Val Phe Asp Ser Lys Cys Trp Leu
            260                 265                 270

Ser Cys Phe Leu Asp Gln Pro Ile Glu Val Arg Leu Tyr Glu Asp Tyr
        275                 280                 285

Leu Ala Asn Ala Phe Gly Tyr Gln Thr Lys Trp Gly Val Ser Gly Lys
    290                 295                 300

Tyr Leu Gln Arg Arg Leu Gln Val Asn Gly Ile Arg Ala Val Ile Asp
305                 310                 315                 320

Pro Asp Gly Pro Ile His Val Glu Ala Leu Ser Cys Pro Gln Ser Trp
                325                 330                 335

Ile Arg His Leu Thr Leu Asp Asp Val Thr Pro Gly Phe Val Arg
            340                 345                 350

Leu Thr Ser Leu Arg Ile Val Pro Asn Thr Glu Pro Thr Thr Leu Arg
        355                 360                 365

Ile Phe Arg Phe Gly Ala His Lys Trp Tyr Gly
    370                 375

<210> SEQ ID NO 21
<211> LENGTH: 203
<212> TYPE: PRT
<213> ORGANISM: Porcine reproductive and respiratory syndrome virus

<400> SEQUENCE: 21

Ser Ser Val Tyr Arg Trp Lys Lys Phe Val Val Phe Thr Asp Ser Ser
1               5                   10                  15
```

```
Pro Asn Gly Arg Met Met Trp Thr Pro Glu Ser Asp Asp Ser Ala Asp
            20                  25                  30

Leu Glu Ala Leu Pro Pro Glu Leu Glu Arg Gln Val Glu Ile Leu Ile
        35                  40                  45

Arg Ser Phe Pro Ala His His Pro Val Ser Leu Ala Asp Trp Glu Leu
    50                  55                  60

Ala Glu Ser Pro Glu Asn Gly Phe Ser Phe Ser Thr Tyr His Ser Gly
65                  70                  75                  80

Gly Tyr Leu Val Gln Asn Pro Asp Val Phe Asp Ser Lys Cys Trp Leu
                85                  90                  95

Ser Cys Phe Leu Asp Gln Pro Ile Glu Val Arg Leu Tyr Glu Asp Tyr
            100                 105                 110

Leu Ala Asn Ala Phe Gly Tyr Gln Thr Lys Trp Gly Val Ser Gly Lys
        115                 120                 125

Tyr Leu Gln Arg Arg Leu Gln Val Asn Gly Ile Arg Ala Val Ile Asp
130                 135                 140

Pro Asp Gly Pro Ile His Val Glu Ala Leu Ser Cys Pro Gln Ser Trp
145                 150                 155                 160

Ile Arg His Leu Thr Leu Asp Asp Asp Val Thr Pro Gly Phe Val Arg
                165                 170                 175

Leu Thr Ser Leu Arg Ile Val Pro Asn Thr Glu Pro Thr Thr Leu Arg
            180                 185                 190

Ile Phe Arg Phe Gly Ala His Lys Trp Tyr Gly
        195                 200

<210> SEQ ID NO 22
<211> LENGTH: 202
<212> TYPE: PRT
<213> ORGANISM: Porcine reproductive and respiratory syndrome virus

<400> SEQUENCE: 22

Ser Ser Val Tyr Arg Trp Lys Lys Phe Val Val Phe Thr Asp Ser Ser
1               5                   10                  15

Pro Asn Gly Met Met Trp Thr Pro Glu Ser Asp Asp Ser Ala Asp Leu
            20                  25                  30

Glu Ala Leu Pro Pro Glu Leu Glu Arg Gln Val Glu Ile Leu Ile Arg
        35                  40                  45

Ser Phe Pro Ala His His Pro Val Ser Leu Ala Asp Trp Glu Leu Ala
    50                  55                  60

Glu Ser Pro Glu Asn Gly Phe Ser Phe Ser Thr Tyr His Ser Gly Gly
65                  70                  75                  80

Tyr Leu Val Gln Asn Pro Asp Val Phe Asp Ser Lys Cys Trp Leu Ser
                85                  90                  95

Cys Phe Leu Asp Gln Pro Ile Glu Val Arg Leu Tyr Glu Asp Tyr Leu
            100                 105                 110

Ala Asn Ala Phe Gly Tyr Gln Thr Lys Trp Gly Val Ser Gly Lys Tyr
        115                 120                 125

Leu Gln Arg Arg Leu Gln Val Asn Gly Ile Arg Ala Val Ile Asp Pro
130                 135                 140

Asp Gly Pro Ile His Val Glu Ala Leu Ser Cys Pro Gln Ser Trp Ile
145                 150                 155                 160

Arg His Leu Thr Leu Asp Asp Asp Val Thr Pro Gly Phe Val Arg Leu
                165                 170                 175

Thr Ser Leu Arg Ile Val Pro Asn Thr Glu Pro Thr Thr Leu Arg Ile
```

```
              180                 185                 190

Phe Arg Phe Gly Ala His Lys Trp Tyr Gly
        195                 200

<210> SEQ ID NO 23
<211> LENGTH: 201
<212> TYPE: PRT
<213> ORGANISM: Porcine reproductive and respiratory syndrome virus

<400> SEQUENCE: 23

Ser Ser Val Tyr Arg Trp Lys Lys Phe Val Val Phe Thr Asp Ser Ser
1               5                   10                  15

Pro Asn Met Met Trp Thr Pro Glu Ser Asp Ser Ala Asp Leu Glu
            20                  25                  30

Ala Leu Pro Pro Glu Leu Glu Arg Gln Val Glu Ile Leu Ile Arg Ser
        35                  40                  45

Phe Pro Ala His His Pro Val Ser Leu Ala Asp Trp Glu Leu Ala Glu
    50                  55                  60

Ser Pro Glu Asn Gly Phe Ser Phe Ser Thr Tyr His Ser Gly Gly Tyr
65                  70                  75                  80

Leu Val Gln Asn Pro Asp Val Phe Asp Ser Lys Cys Trp Leu Ser Cys
                85                  90                  95

Phe Leu Asp Gln Pro Ile Glu Val Arg Leu Tyr Glu Asp Tyr Leu Ala
            100                 105                 110

Asn Ala Phe Gly Tyr Gln Thr Lys Trp Gly Val Ser Gly Lys Tyr Leu
        115                 120                 125

Gln Arg Arg Leu Gln Val Asn Gly Ile Arg Ala Val Ile Asp Pro Asp
    130                 135                 140

Gly Pro Ile His Val Glu Ala Leu Ser Cys Pro Gln Ser Trp Ile Arg
145                 150                 155                 160

His Leu Thr Leu Asp Asp Asp Val Thr Pro Gly Phe Val Arg Leu Thr
                165                 170                 175

Ser Leu Arg Ile Val Pro Asn Thr Glu Pro Thr Thr Leu Arg Ile Phe
            180                 185                 190

Arg Phe Gly Ala His Lys Trp Tyr Gly
        195                 200

<210> SEQ ID NO 24
<211> LENGTH: 200
<212> TYPE: PRT
<213> ORGANISM: Porcine reproductive and respiratory syndrome virus

<400> SEQUENCE: 24

Ser Ser Val Tyr Arg Trp Lys Lys Phe Val Val Phe Thr Asp Ser Ser
1               5                   10                  15

Pro Met Met Trp Thr Pro Glu Ser Asp Ser Ala Asp Leu Glu Ala
            20                  25                  30

Leu Pro Pro Glu Leu Glu Arg Gln Val Glu Ile Leu Ile Arg Ser Phe
        35                  40                  45

Pro Ala His His Pro Val Ser Leu Ala Asp Trp Glu Leu Ala Glu Ser
    50                  55                  60

Pro Glu Asn Gly Phe Ser Phe Ser Thr Tyr His Ser Gly Gly Tyr Leu
65                  70                  75                  80

Val Gln Asn Pro Asp Val Phe Asp Ser Lys Cys Trp Leu Ser Cys Phe
                85                  90                  95

Leu Asp Gln Pro Ile Glu Val Arg Leu Tyr Glu Asp Tyr Leu Ala Asn
```

```
                    100                 105                 110
Ala Phe Gly Tyr Gln Thr Lys Trp Gly Val Ser Gly Lys Tyr Leu Gln
            115                 120                 125

Arg Arg Leu Gln Val Asn Gly Ile Arg Ala Val Ile Asp Pro Asp Gly
            130                 135                 140

Pro Ile His Val Glu Ala Leu Ser Cys Pro Gln Ser Trp Ile Arg His
145                 150                 155                 160

Leu Thr Leu Asp Asp Val Thr Pro Gly Phe Val Arg Leu Thr Ser
                    165                 170                 175

Leu Arg Ile Val Pro Asn Thr Glu Pro Thr Thr Leu Arg Ile Phe Arg
            180                 185                 190

Phe Gly Ala His Lys Trp Tyr Gly
            195                 200

<210> SEQ ID NO 25
<211> LENGTH: 199
<212> TYPE: PRT
<213> ORGANISM: Porcine reproductive and respiratory syndrome virus

<400> SEQUENCE: 25

Ser Ser Val Tyr Arg Trp Lys Lys Phe Val Phe Thr Asp Ser Ser
1               5                   10                  15

Met Met Trp Thr Pro Glu Ser Asp Ser Ala Asp Leu Glu Ala Leu
                20                  25                  30

Pro Pro Glu Leu Glu Arg Gln Val Glu Ile Leu Ile Arg Ser Phe Pro
            35                  40                  45

Ala His His Pro Val Ser Leu Ala Asp Trp Glu Leu Ala Glu Ser Pro
50                  55                  60

Glu Asn Gly Phe Ser Phe Ser Thr Tyr His Ser Gly Gly Tyr Leu Val
65                  70                  75                  80

Gln Asn Pro Asp Val Phe Asp Ser Lys Cys Trp Leu Ser Cys Phe Leu
                85                  90                  95

Asp Gln Pro Ile Glu Val Arg Leu Tyr Glu Asp Tyr Leu Ala Asn Ala
            100                 105                 110

Phe Gly Tyr Gln Thr Lys Trp Gly Val Ser Gly Lys Tyr Leu Gln Arg
            115                 120                 125

Arg Leu Gln Val Asn Gly Ile Arg Ala Val Ile Asp Pro Asp Gly Pro
            130                 135                 140

Ile His Val Glu Ala Leu Ser Cys Pro Gln Ser Trp Ile Arg His Leu
145                 150                 155                 160

Thr Leu Asp Asp Val Thr Pro Gly Phe Val Arg Leu Thr Ser Leu
                    165                 170                 175

Arg Ile Val Pro Asn Thr Glu Pro Thr Thr Leu Arg Ile Phe Arg Phe
            180                 185                 190

Gly Ala His Lys Trp Tyr Gly
            195

<210> SEQ ID NO 26
<211> LENGTH: 50
<212> TYPE: PRT
<213> ORGANISM: Porcine reproductive and respiratory syndrome virus

<400> SEQUENCE: 26

Ser Ser Val Tyr Arg Trp Lys Lys Phe Val Phe Thr Asp Ser Ser
1               5                   10                  15

Pro Asn Gly Arg Met Met Trp Thr Pro Glu Ser Asp Asp Ser Ala Asp
```

```
            20                  25                  30

Leu Glu Ala Leu Pro Pro Glu Leu Glu Arg Gln Val Glu Ile Leu Ile
        35                  40                  45

Arg Ser
    50

<210> SEQ ID NO 27
<211> LENGTH: 49
<212> TYPE: PRT
<213> ORGANISM: Porcine reproductive and respiratory syndrome virus

<400> SEQUENCE: 27

Ser Ser Val Tyr Arg Trp Lys Lys Phe Val Val Phe Thr Asp Ser Ser
1               5                   10                  15

Pro Asn Gly Met Met Trp Thr Pro Glu Ser Asp Asp Ser Ala Asp Leu
            20                  25                  30

Glu Ala Leu Pro Pro Glu Leu Glu Arg Gln Val Glu Ile Leu Ile Arg
        35                  40                  45

Ser

<210> SEQ ID NO 28
<211> LENGTH: 48
<212> TYPE: PRT
<213> ORGANISM: Porcine reproductive and respiratory syndrome virus

<400> SEQUENCE: 28

Ser Ser Val Tyr Arg Trp Lys Lys Phe Val Val Phe Thr Asp Ser Ser
1               5                   10                  15

Pro Asn Met Met Trp Thr Pro Glu Ser Asp Asp Ser Ala Asp Leu Glu
            20                  25                  30

Ala Leu Pro Pro Glu Leu Glu Arg Gln Val Glu Ile Leu Ile Arg Ser
        35                  40                  45

<210> SEQ ID NO 29
<211> LENGTH: 47
<212> TYPE: PRT
<213> ORGANISM: Porcine reproductive and respiratory syndrome virus

<400> SEQUENCE: 29

Ser Ser Val Tyr Arg Trp Lys Lys Phe Val Val Phe Thr Asp Ser Ser
1               5                   10                  15

Pro Met Met Trp Thr Pro Glu Ser Asp Asp Ser Ala Asp Leu Glu Ala
            20                  25                  30

Leu Pro Pro Glu Leu Glu Arg Gln Val Glu Ile Leu Ile Arg Ser
        35                  40                  45

<210> SEQ ID NO 30
<211> LENGTH: 46
<212> TYPE: PRT
<213> ORGANISM: Porcine reproductive and respiratory syndrome virus

<400> SEQUENCE: 30

Ser Ser Val Tyr Arg Trp Lys Lys Phe Val Val Phe Thr Asp Ser Ser
1               5                   10                  15

Met Met Trp Thr Pro Glu Ser Asp Asp Ser Ala Asp Leu Glu Ala Leu
            20                  25                  30

Pro Pro Glu Leu Glu Arg Gln Val Glu Ile Leu Ile Arg Ser
        35                  40                  45
```

<210> SEQ ID NO 31
<211> LENGTH: 15110
<212> TYPE: DNA
<213> ORGANISM: Porcine reproductive and respiratory syndrome virus

<400> SEQUENCE: 31

```
atgatgtgta gggtattccc cctacataca cgacactact agtgtttgtg taccttggag      60
gcgtgggtac agccccgccc caccccttgg ccctgttct agcccaacag gtatccttct      120
ctctcggggc gagtgtgccg cctgctgctc ccttgcagcg ggaaggacct cccgagtatt     180
cccggagagc acctgcttta cgggatctcc accctttaac catgtctggg acgttctccc    240
ggtgcatgtg cacccggct gctcgggtat tttggaacgc cggccaagtc tattgcacac     300
ggtgtctcag tgcgcggtct cttctccctc cggaacttca ggacattgac ctcgccgcaa   360
ttggcttgtt ttacaagcct aaagacaagc ttcactggaa agtccctatc ggcatccctc  420
aggtggagtg tactccatcc gggtgttgtt ggctctcagg catttttccc ttagcgcgca  480
tgacctccgg caatacaac ttcctacaac gacttgtgaa agttgccgat gtgttgtacc   540
gtgatggttg cttaacttct cgacaccttc gtgaactcca agtttacgag cgtggctgca  600
gctggtaccc aatcacgggg ccagtgcccg gatgggtttt gtacgcaaat tccatgcacg  660
tatctgacca gccgttccct ggtgccaccc atgtgttgac gaactcgcct ttgcctcaac  720
aagcttgtcg gcagccgttc tgcccatttg aggaggctca ttctagcgtg tacaggtgga  780
aaaaatttgt ggtcttcacg gactcctccc ccaacggtcg gatgatgtgg acgccggaat  840
ccgatgattc agccgaccta gaggcgctac cgcctgagct agaacgtcag gtcgaaatcc  900
tcattcggag ttttcctgcc catcaccctg tcagcctggc cgactgggag ctcgctgagt  960
cccctgagaa cggtttttcc ttcagcacgt accattctgg tggttatctt gtccaaaacc 1020
ccgacgtgtt tgacagcaag tgctggctct cctgtttctt ggatcagccg atcgaagtgc 1080
gcctctatga ggattatctg ctaacgctt tcggttacca aaccaagtgg ggcgtgtctg  1140
gtaagtacct ccagcgcagg cttcaagtca acggtattcg tgctgtaatc gatcctgatg  1200
gccccattca cgttgaagcg ctgtcttgcc ccaatcttg gatcaggcac ctgactctgg  1260
acgatgacgt caccccagga ttcgttcgcc taacatccct ccgcattgtg ccgaacacag  1320
agcccactac tctccgaatc tttcggtttg gagcgcataa gtggtatggc gctgccggca  1380
aacgggctcg tgccaagcgt gccgctaaaa gtgagaaggg tccggctccc actcccaagg  1440
ttgccccgcc agcccccacc tgcggaattg ttacctactc tccaccaaca gacgggtctt  1500
gcggttggca cgtccttgcc gccataatga accgaatgat gaacggtgac ttcatgtccc  1560
ctctggccca gtacaacaga ccagaggatg attgggcttc tgattacgat cttgcccagg  1620
cgattcaatg tctgcggttg cctgctacca tagttcggaa tcgtgcctgt cccaacgcca  1680
agtacctcat aaaactcaac ggagtccact gggaggtaga ggtgaggtca gggatggccc  1740
ctcgctccct tccccgcgag tgcgtagtcg cgtttgttc cgaaggctgt gccgcatcgc  1800
cttacccaga aaacgggcta cctaaacgag cgtttgaggc cttggcgtct gcttacagac  1860
taccttccga ttgtgtcagt tctggtattg ctgactttct tgctaacccc cctcaggaat  1920
tctggactct tgacaaaatg ttgacctccc cgtcaccgga gcggtctggt tttttccagtc 1980
tgtacaaatt gctattagag gttgtcccgc agaaatgcgg agccacggaa ggggctttca  2040
cctatgctgt tgagagaatg ctgaaggatt gcccgagctc cgaacaggcc atggccttc  2100
tggcaaaaat taaagttcca tcctcaaagg ccccgtctgt gtccctggac gagtgtttcc  2160
```

```
ctacggatgt tcagccgat tcgaaccag catctcagga gaggtcccaa aattccagcg    2220
ctgctgttgt cctgcattca ccgaatgcaa aagagttcga ggaagcagct ccaggggaag    2280
ttcaggaggg tggccacaag gccgtccact ctgcactccc tgccgggggt cctaacaata    2340
agcaggcaca gctggttgcc ggtgagcaac tgaagctcgg cggttgtggt tcggtagttg    2400
ggaatgcaca tgaaggtgtt ctggtcccac ctggtccaat taatttgaca agcggggatt    2460
taccctcctc aggctccatg aaagaagata tgctcaatag ccgggaggac gaaccactgg    2520
atttgtccca accagcaaca gctgtcacaa cgactcttat gggagagcta acacccgact    2580
acctaggttc tgatactggt gccctccccg tcaccgtccg aaaatttgtc ccgacggggc    2640
ctatactccg tcatgttgag cactgcagca cggggtcggg cgatagcagt tcgcctttgg    2700
atctgtctgg tgcgcaaacc ccggaccagc ctttaaatct gtccctgccg gcttggccag    2760
tgaggaccac cgcgtctgat cctggctggg tccacggtag acgcgagcct gtctttgtaa    2820
agcctcgaga tgttttctct gatggcgatt cagcccttca gttcggggag ctttctgaat    2880
ccagctctgt catcgagttt gatcgggcaa agatgctca ggtggctgac gcccctgtcg    2940
gtctgacgac ttcggacgag gccctctccg cagtcgatcc tttcgagttt ccgaactca    3000
agcgcccacg tttctccgca caagccttaa ttgaccgagg cggcccactt gccgatgtcc    3060
atgcaaaaat aaagaaccgg gtatatgaac agtgcctcca agcttgtgag cccggtagtc    3120
gcgcaacccc agctaccagg gagtggctcg acaaaatgtg ggagagagtg acatgaaaa    3180
cctggcgctg cacctcacag ttccaagctg gtcacattct tgcgtccctc aaattcctcc    3240
ctgacatgat tcaagacaca ccgcctcctg ttcccaggaa gaaccgagcc agtgataaag    3300
ctggcctgaa acaactagtg gcacagtggg ataggagatt gagttcaacc cccccccaa    3360
aaccggttgg gccggtactt gaccgggtcg atcctccgcc tacgggtacc cggcaagaag    3420
acgtcacccc ctccgatggg ccaccccatg cgccggatgg tcgagtgagt acgggtggga    3480
gttggaaagg cctatgcttt tccggcaccc gtctcacggg gtccatcagt catcgcctca    3540
tgacatgggt ttttgaagtt gtctcccatc tcccagcttt tatgctcaca ctttctcgc    3600
cgcgggctc tatggctcca ggcgattggg tttttgcagg tgttgtttta cttgctctcc    3660
tgctctgtcg ttcttaccca atattcgggt gccttccctt attgggtgtc ttttctggta    3720
ctgtgcggcg tgttcgtctg ggtgtttttg gctcttggat ggcttttgct gtatttttat    3780
tctcgactcc atccaaccca gtcggttctt cttgtaacca cgattcgccg gagtgtcatg    3840
ctgagcttct ggctcttgag cagcgccaac tttgggaacc tgtgcgcggc cttgtggtcg    3900
gcccatcggg cctcttatgt gtcattcttg gcaagttact cggtgggtca cgttatctct    3960
ggcatgttct cctacgtcta tgcctgcttg cagatttggc cctttctctt gtttatgtgg    4020
tgtcccaggg gcgttgtcac aagtgttggg gaaagtgtat aaggacagct cctgctgagg    4080
tggcttttaa tgtatttcct ttctcgcgcg ccacccgtag ttctcttgta tccttatgtg    4140
atcgattcca aacgccaaaa ggagttgatc ccgtgcactt ggcgacaggt tggcgcgggt    4200
gctggcgtgg tgagagtcct atccatcaac cacaccaaaa gcccatagct tacgccaatt    4260
tggatgaaaa aagatatctc gcccaaacgt tgttgctgt cccatacgat cccaatcagg    4320
ctatcaaatg tctgaaagtt ctgcaggcgg gaggggctat cgtggatcag cctacgcctg    4380
aggtcgttcg tgtgtccgag atccccttct cagccccatt tttcccaaaa gttccagtca    4440
acccagattg tagggtcgtg gtggattcgg acactttgt ggctgcggtt cgttgtggtt    4500
attcgacatc acaactggtc ctgggccagg gcaactttgc caagttaaat caaacccccc    4560
```

```
ccaggaactc tatctccacc aaagcgactg gtggggcctc ttatactttt gctgtggctc    4620
aagtgtctgt gtggacccct gttcatttcg tcctcggtct ttggctcacg tcacctcaag    4680
tgtgtggtcg aggaaccgct gacccatggt gttcaagtcc attttcatat cctacctatg    4740
gccccggggt tgtgtgctcc tctcgacttt gtgtgtctgc tgacggggtc acccttccat    4800
tgttctcagc cgtggcacaa ctctctggta gggaggtggg gattttttatt ttagtgctcg    4860 tctccttta t tgccttggcc caccgcatgg ctcttaaggc agacatgtta gtagtctttt    4920
tggctctttg tgcttatgcc tgggccatga gctcctggtt gatctgcttc tttcctatac    4980
tcttgaggtg ggttacccct caccctctca ctatgctttg ggtgcattca ttcttgatgt    5040
tttgtctccc agcagccggc gtcctctcac tggggataac tggcctcctc tgggcaatcg    5100
gccgctttac tcaggttgcc ggaatcatta caccttatga tatccaccag tacacctctg    5160
ggccacgtgg tgcagccgct gtggccacag ccccagaagg cacttacatg gccgccgtcc    5220
ggagagctgc tttaaccggg cggactttaa tcttcacccc gtccgcagtt ggatcccttc    5280
tcgaaggtgc tttcaggact cataaaccct gccttaacac cgtgaatgtc gtaggctcct    5340
cccttggttc cggaggggtt ttcaccattg acggaaaaaa aattgtcgtc actgctgccc    5400
atgtgctgaa cggcgacaca gctagagtca ccggtgattc ctacaaccgc atgcacactt    5460
tcaagactaa tggtgactat gcctggtccc atgctgataa ctggcagggc gctgccctg    5520 tggtcaaggt tgcgaaaggg tatcgcggtc gtgcctactg gcaaacatca actggtgtcg    5580
agcctggtgt tattgggaat gggttcgcct tctgtttcac caactgcggc gattcggggt    5640
cacccgttat ctcagaatct ggtgatctta tcggaatcca caccggttca aacaaacttg    5700
gttctggtct tgtgacaacc cctgaagggg agacctgtac catcagagaa accaagcttt    5760
ctgacctttc cagacatttc gcaggcccaa gcgttcctct tggggacatc aaattgagtc    5820
cggccatcat ccctgatgtg acatccattc cgagtgactt ggcatcgctc ctagcttccg    5880
tccctgtaat ggaaggcggc ctctcgaccg ttcaacttttt gtgtgtcttt ttcctcctct    5940
ggcgcatgat gggccatgcc tggacgccca ttgttgccgt gggcttcttt ttgctgaatg    6000
aaattcttcc agcagttttg gttcgagccg tgttttcttt tgcactcttt gtgcttgcat    6060
gggccacccc ctggtctgca caagtgttga tgattagact tctcacggca tctctcaacc    6120
gcaacaaact ttctcttgcg ttctacgcac tcggaggtgt tgttggtttg gctgctgaaa    6180
tcgggacttt tgctggtaaa ttgtctgaat tgtctcaagc tctttcgaca tactgtttct    6240
tacctagggt ccttgctatg accagctgtg ttcccatcat catcattggt ggactccatg    6300
ccctcggtgt gattctgtgg ttattcaaat accggtgcct ccacaacatg ctggttggtg    6360
atggaagctt ttcaagcgct ttcttcctac ggtattttgc agagggcaat ctcaggagag    6420
gtgtttcaca gtcctgtggc atgagtaacg agtccctgac ggctgctttg gcttgcaagt    6480
tgtcacaggc tgaccttgat ttttttgtcca gcttaacgaa cttcaagtgc tttgtatctg    6540
cttcaaacat gaaaaatgct gccggccagt acattgaagc agcttatgcc agggccctgc    6600
gtcaagagtt ggcctctttta gtccagattg acaaaaatgaa aggagttttg tccaagctag    6660
aggcctttgc tgaaacggcc actccgtccc tcgacgtagg tgacgtgatt gttctacttg    6720
gacaacatcc tcacggatcc gttctcgata ttaatgtggg gactgaaagg aaaactgtat    6780
ccgtgcaaga gacccggagc ctaggcggct ccaagttcag tgtttgtact gttgtgtcaa    6840
acacacccgt ggacgcctta gccggtattc cactccagac accaacccc cttttcgaga    6900
```

-continued

| | |
|---|---|
| atggcccgcg tcatcgcagc gaggaggacg atcttaaagt cgagaggatg aagaaacact | 6960 |
| gcgtgtccct cggcttccac aacattaacg gtaaagttta ctgcaagatt tgggacaagt | 7020 |
| ctaccggtga cgccttttac actgatgatt cccggtacac ccaagactat gcttttcagg | 7080 |
| acaggtcagc tgactataga gacagggact acgagggtgt gcaaaccgcc ccccaacagg | 7140 |
| gatttgatcc aaagtctgaa acccctgttg gtaccgttgt gatcggcggt attacgtaca | 7200 |
| acaggtattt ggtcaaaggt aaggaggttc tggttcccaa gcctgacaac tgccttgaag | 7260 |
| ctgccaagct gtcccttgag caagctctcg ctgggatggg ccaaacttgt gaccttacag | 7320 |
| ctgccgaggt ggaaaagcta aagcgcatca ttggtcaact tcaaggattg accactgagc | 7380 |
| aggctttaaa ctgttagccg ccagcggctt gacccgctgt ggccgcggcg gcctagttgt | 7440 |
| aactgaaacg gcgtaaaaaa ttgtcaaata ccacagcaga acttttacct taggctcttt | 7500 |
| agacctaaaa gtcacttccg aggtggaggt gaagaagtca accgagcagg gccacgctgt | 7560 |
| tgtggcaaac ttgtgttctg gtgtcgtctt gatgagacct cacccaccgt cccttgtcga | 7620 |
| cgttcttctg aaacccggac ttgacataac acccggcatt caaccagggc atggggccgg | 7680 |
| gaatatgggc gtggacggtt ccatttggga ttttgaaacc gcacccacaa aggctgaact | 7740 |
| cgagttatcc aagcaaataa ttcaagcatg tgaagtcagg cgcggggatg ccccgaacct | 7800 |
| ccagctccct tacaagctct atcctgttag aggggatcct gagcggcata aaggccacct | 7860 |
| catcaatacc aggtttggag acttacctta caaaactcct caagacacca agtccgcaat | 7920 |
| ccacgcggct tgttgcctgc accccaacgg ggccccgtg tctgatggta atccacact | 7980 |
| aggtaccact cttcaacatg gcttcgagct ttatgtccct actgtgccct atagtgtcat | 8040 |
| ggagtacctt gattcacgcc cagacacccc ttttatgtgc actaaacacg gcacttccaa | 8100 |
| ggctgctgca gaggacctcc aaaaatacga cctatccacc caaggatttg tcctgcctgg | 8160 |
| ggtcctacgc ctagtgcgca ggttcatctt tggccacatt ggcaaggcac cgccattgtt | 8220 |
| cctcccatca acttatcccg ccaagaactc catggcaggt attaatgtc agaggttccc | 8280 |
| aacaaaggat gttcaaagta tacctgaaat tgatgaaatg tgtgcccgcg ccgtcaagga | 8340 |
| gaattggcaa actgtgacac cttgcaccct caagaaacag tattgttcta ggcccaaaac | 8400 |
| caggaccatc ctgggcacta acaacttcat agccttggct catagatcgg cgctcagtgg | 8460 |
| tgttacccag gcattcatga agaaggcttg gaagtcccca atagccttag ggaaaaacaa | 8520 |
| attcaaggag ctgcattgca ctgtcgctgg caggtgcctc gaggccgact ggcttcctg | 8580 |
| tgaccgcagc acccctgcca ttgtgaggtg gttcactacc cacctcctat atgaacttgc | 8640 |
| aggatgtgaa gaatatctac ctagctatgt gcttaactgt tgccatgacc ttgtggcgac | 8700 |
| gcaggatggt gcttttcacaa aacgcggtgg cctgtcgtct ggagacccag tcaccagtgt | 8760 |
| gtccaacact gtgtactcac tggtgattta tgcccagcac atggtactat ctgccctgaa | 8820 |
| aatgggtcat gaaattggcc tcaagttcct cgaagaacaa ctcaaatttg aggaccttct | 8880 |
| tgaaatccag cctatgttag tatactctga tgatcttgtc ttgtacgcag aaaagcccac | 8940 |
| cttccccaac tatcattggt gggtcgagca tcttgacctg atgttgggct ttaaaacgga | 9000 |
| cccaaagaaa accgtcataa ctgataaacc cagtttcctc gggtgcagaa tcgaagcagg | 9060 |
| gcgacagcta gtccccaatc gcgaccgcat cctggctgct cttgcatatc acatgaaggc | 9120 |
| gcagaacgcc tcagagtatt atgcgtctgc tgccgcaatc ctgatggatt catgtgcttg | 9180 |
| cattgaccac gatcctgaat ggtatgagga cctcatctgt ggcattgccc gatgcgctcg | 9240 |
| cctggacggt tatagctttc caggtccggc attttttcatg tccatgtggg agaagctgag | 9300 |

```
gagtcataat gaagggaaga aattccgcca ctgcggcatc tgcgacgcca aagccgacta    9360
cgcggctgct tgtgggcttg atttgtgttt gtttcattcg cactttcacc aacactgccc    9420
tgtcactctg agctgcggtc accatgccgg ttcgaaggaa tgttcgcagt gtcagtcacc    9480
tgttggggcc ggcagatccc ctcttgatgc tgtgctggaa caaattccat acaaacctcc    9540
tcgcactgtc atcatgaagg tgggtaataa acaacggcc cttgatccgg ggaggtacca     9600
gtcccgtcga ggtctcgttg cagtcaagag gggtattgcg ggtaatgaag ttgatcttgc    9660
tgatggagat taccaagtgg tacctcttct gccgacttgc aaagatataa acatggtgaa    9720
ggtggcttgc aacgtactac tcagcaagtt catagtaggg ccaccaggtt ccgggaagac    9780
cacctggcta ctaagtcaag ttcaggacga tgatgtcatt tacacaccca ctcatcagac    9840
catgtttgac atagttagtg ctctcaaagt ttgcaggtat tccattccag gagcctcggg    9900
actccctttc ccaccgcctg ccaggtccgg gccgtgggtt aggctcattg ccagcgggca    9960
cgtccctggc cgagtatcat acctcgatga ggccggatat tgcaatcatc tggacattct    10020
tagactgctt tccaaaacac cccttgtgtg tttgggtgac cttcagcaac ttcacccagt    10080
cggctttgat tcctattgtt atgtgttcga tcagatgcct cagaagcagt tgaccaccat    10140
ttacagattt ggccccaaca tctgcgcagc catccagcct tgttacaggg agaaacttga    10200
atctaaggct aggaacacca gggtggtttt taccacccgg cctgtggcct ttggccaggt    10260
gctgacacca tatcacaaag atcgcgtcgg ctccgcgatt accatagact catcccaggg    10320
ggccaccttt gacattgtaa cattgcatct accatcgcca aagtccctaa ataagtcccg    10380
ggcacttgtg gccatcacac gggcaagaca cgggttgttc atttatgacc ctcacaacca    10440
gctccgggag ttttcaacc taaccctga gcgcactgat tgtaaccttg tgttcagccg      10500
tggagatgag ctggtggtcc tgaatgcaga taatgcagtc acaaccgtgg cgaaggcctt    10560
agagacaggt ccaactcaat ttcgagtgtc agacccgagg tgcaagtctc tcttagccgc    10620
ttgctcggcc agtctggaag ggagctgcat gccgctaccg caagtggcgc ataacctggg    10680
gttttacttc tccccagaca gtccagtatt tgcacctctg ccaaaagagt ggcgccaca    10740 ttggccagtg gttacccatc agaataatcg ggcgtggcct gatcgacttg tcgctagtat    10800
gcgtccaatt gacgcccgct acagcaagcc gatggtcggt gcagggtatg tggtcggacc    10860
gtccaccttc cttggtactc ctggagtggt gtcatactat ctcacactat acatcagggg    10920
tgagccccag gccttgccag aaacacttgt ttcaacagga cgtatagcca cagattgtcg    10980
ggagtatctc gacgcggctg aggaagaggc agcaaaagaa cttccccacg cgttcattgg    11040
cgatgtcaaa ggcaccacag ttgggggtg tcatcacatt acatcaaaat acctacctag     11100
gtccctgcct aaagactctg ttgccgtagt tggagtaagt tcgcctggca gggctgctaa    11160
agccgtatgc accctcaccg atgtgtacct ccctgaactc cggccatatc tgcaacctga    11220
gacggcatca aaatgctgga aactcaaatt agacttcagg gacgtccgac taatggtctg    11280
gaaaggagcc accgcctact ttcaattgga agggctcaca tggtcggcgc tgcctgacta    11340
tgccaggttt attcagctgc ccaaaaacgc tgttgtatac atcgatccgt gcataggacc    11400
ggcaacagcc aatcgtaaag tcgtacgaac cacagattgg cgggccgacc tggcagtgac    11460
gccgtatgat tacggtgccc ggaacatttt gacaacagcc tggttcgagg acctcgggcc    11520
gcagtggaag attctggggt tgcagcccett aggcgggcg tttggctttg aaaacactga    11580
ggattgggca atccttgcat gctgcatgag tgacggcaag gactacactg actataactg    11640
```

```
gaattgcgtt cgacaacgcc cacacgctat ccatggacgc gctcgtgacc atacgtacca    11700
ctttgcccct ggcactgaat tgcaagtgga gctcggtaaa ccccggctgc cacctgagca    11760
agtaccgtga attcggagtg atgcaatggg gtcactgtgg agtaaaatca gccagctgtt    11820
cgtggacgcc ttcactgaat tccttgttag tgtggttgat attgtcatct tccttgccat    11880
attgtttggg ttcaccgtcg caggatggtt actggtcttt cttctcagag tggtttgctc    11940
cgcgcttctc cgttcgcgct ctgccattca ctcttccgaa ctatcgaagg tcctatgagg    12000
gcttactacc taattgcaga ccggatgttc cacaatttgc atttaagcac cctttgggta    12060
tgttttggca catgcgggtt tcccacctaa ttgatcagat ggtctctcgc cgcatctacc    12120
agaccatgga acattcaggt caagcggcct ggaagcacgt ggtcagtgag gctactctta    12180
caaaattgtc agaactcgac atagttctcc acttccaaca cctggccgca gtggaggcgg    12240
actcttgtcg cttcctcagc tcacgacttg tgatgctgaa aaatcttgcc gttggcaatg    12300
tgagcttgca gtacaacacc acgttgaacc gcgttgagct catcctcccc acaccaggta    12360
cgaggcccaa attgaccgat ttcagacaat ggctcatcag tgtgcacgct tccattttt    12420
cctctgtagc ctcatcagtt actttgttca tagtgctttg gcttcgaatt ccagccgtac    12480
gctatgtttt tggtttccat ggcccatgg caacacgtca ttcgagctga ccattaatta    12540
cactatatgc atgccctgtc ttaccagcca agcggctcaa caaaggctcg aacccggtcg    12600
taacatgtgg tgcaaaatag gacacaccac gtgcgaggag cgtgaccatg atgagttgtc    12660
aatgtccatc ccgtccgggt acgacaacct caaacttgaa ggttattacg cttggctggc    12720
ttttttgtcc ttttcctacg cggcccaatt ccatccggag ttgtttggaa tagggaatgt    12780
gtcgcgcgtc tttgtggata acgacacca gttcatttgt gccgagcatg acggagataa    12840
ttcaaccgta tctaccggac acaacatctc cgcatcatat gcggcatatt atcaccacca    12900
aatagacggg ggcaattggt tccatttgga atggctgcgg ccgctctttt cctcttggct    12960
agtgctcaac atatcatggt ttctgaggcg ttcgcctgca agccctgttt ctcgacgcat    13020
ctatcagata ttaagaccaa tacgaccgcg gctgccggtt tcatggtcct tcaagacatc    13080
agttgcctcc gacctcacag ggtctcagca tcgcaagaga acattccctt cggaaagtcg    13140
tcacaatgtc gtgaagccgt cggtactccc cagtacatta cgatgactgc taatgtgacc    13200
gacgaatcat atttgtacaa cgcggacttg ctaatgcttt ccgcgtgcct tttccacgcc    13260
tcagaaatga gcgagaaagg cttcaaagtt atctttggaa acgtctccgg cgttgtttca    13320
gcttgtgtca atttcacaga ttatgtggcc catgtaaccc aacataccca acagcatcat    13380
ctggtaattg atcacattcg gttactgcat ttcctgacac catctgcaat gaggtgggct    13440
acaaccattg cttgtttgtt cgccattctc ttagcgatat gagatgttct cacaaattgg    13500
ggcgtttctt gactccgcac tcttgcttct ggtggctttt tttgctgtgt accggcttgt    13560
cctggtcctt tgccgatggc aacggcaaca gctcgacacg ccaatacata tataacttga    13620
cgatatgcga gctgaatggg accgtctggt tgtccagtca ttttgattgg gcagtcgaga    13680
cctttgtgct ttaccggtg gccactcata tcctctcact gggttttctc acaacaagcc    13740
attttttga tgcgctcggt ctcggcgctg tgtccactac gggatttctt ggcgggcggt    13800
atgtacttag cagcgtgtac ggcgcctgcg ccttcgcagc gcttgtatgt tttgtcatcc    13860
gtgctgctaa aaattgcatg gcttgccgtt atgcccgcac ccggttcacc aacttcatcg    13920
tggacgaccg ggggaagatc catcgatgga agtcccaat agtggtagag aaattaggca    13980
aagctgacat cggcggcgac cttgtcacca tcaaacatgt tgtcctcgaa ggagtcaaag    14040
```

```
ctcaaccttt gacgaggaca tcggcggagc aatgggaagc ctagatgatt tttgcaatga    14100
tcctaccgcc gcacagaagc ttgtgctggc atttagtatc acatacacac ctataatgat    14160
atacgccctc aaggtgtcac gcggccggct cctaggactg ttacatatcc tgatatttct    14220
gaactgttct ttcacgttcg gatacatgac atacgtgcac tttcaatcca ctaaccgtgt    14280
cgcgcttact atggggggcgg tcgttgccct tttgtggggc atttacagct ttatagaatc    14340
atggaagttt gtcacttcca gatgcaggtt gtgttgccta ggccggcgat acattctggc    14400
ccctgcccac cacgtagaaa gtgctgcagg cctccattca atcccagcgt ctggtaaccg    14460
agcatacgct gtgagaaagc ccggactaac atcagtgaac ggcactctag taccaggact    14520
tcggagcctc gtgttgggcg gcaaacgagc tgttaaacga ggagtggtta acctcgtcaa    14580
gtatggccgg taaaaaccag agccagaaga aaagaaaaaa cacagctcct atggggagtg    14640
gccagccagt caatcaactg tgccaattgc tgggcacaat gataaagtcc cagcgccagc    14700
ggcctagggg aggacaggcc aaaatgaaaa agcctgagaa gccacatttc cccctagctg    14760
ctgaagatga catccggcac catttcaccc agaccgagcg ttcccttttgc ttgcaatcga    14820 tccagacggc cttcaatcaa ggcgcaggaa ctgcgtcgct ttcatccagc gggaaggtca    14880
gttttcaggt tgagttcatg ctgccggtcg ctcatacggt gcgcctgatt cgcgtaactt    14940
ccacatccgc cagtcagggt gcaagttaat ttgatagtta ggtgaatggc cgcgattggc    15000
gtgtggcctc tgagtcacct attcaattag ggcgatcaca tgggggttag acttaattgg    15060
cgagaaccat gtgaccgaaa ttaaaaaaaa aaaaaaaaaa aaaaaaaaa                15110
```

<210> SEQ ID NO 32
<211> LENGTH: 15107
<212> TYPE: DNA
<213> ORGANISM: Porcine reproductive and respiratory syndrome virus

<400> SEQUENCE: 32

```
atgatgtgta gggtattccc cctacataca cgacactact agtgtttgtg taccttggag     60
gcgtgggtac agccccgccc cacccccttgg ccccctgttct agcccaacag gtatccttct    120
ctctcggggc gagtgtgccg cctgctgctc ccttgcagcg ggaaggacct cccgagtatt    180
cccggagagc acctgcttta cgggatctcc acccttttaac catgtctggg acgttctccc    240
ggtgcatgtg caccccggct gctcgggtat tttggaacgc cggccaagtc tattgcacac    300
ggtgtctcag tgcgcggtct cttctcccctc cggaacttca ggacattgac ctcgccgcaa    360
ttggcttgtt ttacaagcct aaagacaagc ttcactggaa agtccctatc ggcatccctc    420
aggtggagtg tactccatcc gggtgttgtt ggctctcagg catttttccccc ttagcgcgca    480 tgacctccgg caatcacaac ttcctacaac gacttgtgaa agttgccgat gtgttgtacc    540
gtgatggttg cttaacttct cgacaccttc gtgaactcca agtttacgag cgtggctgca    600
gctggtaccc aatcacgggg ccagtgcccg ggatgggttt gtacgcaaat tccatgcacg    660
tatctgacca gccgttccct ggtgccaccc atgtgttgac gaactcgcct ttgcctcaac    720
aagcttgtcg gcagccgttc tgcccatttg aggaggctca ttctagcgtg tacaggtgga    780
aaaaatttgt ggtcttcacg gactcctccc ccaacggtat gatgtggacg ccggaatccg    840
atgattcagc cgacctagag gcgctaccgc ctgagctaga acgtcaggtc gaaatcctca    900
ttcggagttt tcctgcccat cacccctgtca gcctggccga ctgggagctc gctgagtccc    960
ctgagaacgg ttttttcctc agcacgtacc attctggtgg ttatcttgtc caaaaccccg    1020
```

-continued

```
acgtgtttga cagcaagtgc tggctctcct gtttcttgga tcagccgatc gaagtgcgcc    1080
tctatgagga ttatctggct aacgctttcg gttaccaaac caagtggggc gtgtctggta    1140
agtacctcca gcgcaggctt caagtcaacg gtattcgtgc tgtaatcgat cctgatggcc    1200
ccattcacgt tgaagcgctg tcttgccccc aatcttggat caggcacctg actctggacg    1260
atgacgtcac cccaggattc gttcgcctaa catccctccg cattgtgccg aacacagagc    1320
ccactactct ccgaatcttt cggtttggag cgcataagtg gtatgcgct gccggcaaac    1380
gggctcgtgc caagcgtgcc gctaaaagtg agaagggtcc ggctcccact cccaaggttg    1440
ccccgccagc ccccacctgc ggaattgtta cctactctcc accaacagac gggtcttgcg    1500
gttggcacgt ccttgccgcc ataatgaacc gaatgatgaa cggtgacttc atgtcccctc    1560
tggcccagta caacagacca gaggatgatt gggcttctga ttacgatctt gcccaggcga    1620
ttcaatgtct gcggttgcct gctaccatag ttcggaatcg tgcctgtccc aacgccaagt    1680
acctcataaa actcaacgga gtccactggg aggtagaggt gaggtcaggg atggcccctc    1740
gctcccttcc ccgcgagtgc gtagtcgcg tttgttccga aggctgtgcc gcatcgcctt    1800
acccagaaaa cgggctacct aaacgagcgt tgaggccttt ggcgtctgct tacagactac    1860
cttccgattg tgtcagttct ggtattgctg actttcttgc taaccccccct caggaattct    1920
ggactcttga caaaatgttg acctccccgt caccggagcg gtctggtttt tccagtctgt    1980
acaaattgct attagaggtt gtcccgcaga atgcgcgagc cacggaaggg gctttcacct    2040
atgctgttga gagaatgctg aaggattgcc cgagctccga acaggccatg gcccttctgg    2100
caaaaattaa agttccatcc tcaaaggccc cgtctgtgtc cctggacgag tgtttcccta    2160
cggatgtttc agccgatttc gaaccagcat ctcaggagag gtcccaaaat tccagcgctg    2220
ctgttgtcct gcattcaccg aatgcaaaag agttcgagga agcagctcca ggggaagttc    2280
aggagggtgg ccacaaggcc gtccactctg cactccctgc cggggggtcct aacaataagc    2340
aggcacagct ggttgccggt gagcaactga agctcggcgg ttgtggttcg gtagttggga    2400
atgcacatga aggtgttctg gtcccacctg gtccaattaa tttgacaagc ggggatttac    2460
cctcctcagg ctccatgaaa gaagatatgc tcaatagccg ggaggacgaa ccactggatt    2520
tgtcccaacc agcaacagct gtcacaacga ctcttatggg agagctaaca cccgactacc    2580
taggttctga tactggtgcc ctccccgtca ccgtccgaaa atttgtcccg acggggccta    2640
tactccgtca tgttgagcac tgcagcacgg ggtcgggcga tagcagttcg cctttggatc    2700
tgtctggtgc gcaaacccng gaccagcctt taaatctgtc cctggcggct tggccagtga    2760
ggaccaccgc gtctgatcct ggctgggtcc acggtagacg cgagcctgtc tttgtaaagc    2820
ctcgagatgt tttctctgat ggcgattcag cccttcagtt cggggagctt tctgaatcca    2880
gctctgtcat cgagtttgat cgggcaaaag atgctcaggt ggctgacgcc cctgtcggtc    2940
tgacgacttc ggacgaggcc ctctccgcag tcgatccttt cgagttttcc gaactcaagc    3000
gcccacgttt ctccgcacaa gccttaattg accgaggcgg cccacttgcc gatgtccatg    3060
caaaaataaa gaaccgggta tatgaacagt gcctccaagc ttgtgagccc ggtagtcgcg    3120
caaccccagc taccagggag tggctcgaca aaatgtggga gagagtggac atgaaaacct    3180
ggcgctgcac ctcacagttc aagctggtc acattcttgc gtccctcaaa ttcctccctg    3240
acatgattca agacacaccg cctcctgttc ccaggaagaa ccgagccagt gataaagctg    3300
gcctgaaaca actagtggca cagtgggata ggagattgag ttcaaccccc ccccaaaac    3360
cggttgggcc ggtacttgac cgggtcgatc ctccgcctac gggtacccgg caagaagacg    3420
```

```
tcaccccctc cgatgggcca ccccatgcgc cggatggtcg agtgagtacg ggtgggagtt    3480
ggaaaggcct tatgctttcc ggcacccgtc tcacggggtc catcagtcat cgcctcatga    3540
catgggtttt tgaagttgtc tcccatctcc cagcttttat gctcacactt ttctcgccgc    3600
ggggctctat ggctccaggc gattgggttt ttgcaggtgt tgttttactt gctctcctgc    3660
tctgtcgttc ttacccaata ttcgggtgcc ttcccttatt gggtgtcttt tctggtactg    3720
tgcggcgtgt tcgtctgggt gttttttggct cttggatggc ttttgctgta ttttttattct   3780 cgactccatc caacccagtc ggttcttctt gtaaccacga ttcgccggag tgtcatgctg    3840
agcttctggc tcttgagcag cgccaacttt gggaacctgt gcgcggcctt gtggtcggcc    3900
catcgggcct cttatgtgtc attcttggca agttactcgg tgggtcacgt tatctctggc    3960
atgttctcct acgtctatgc ctgcttgcag atttggccct ttctcttgtt tatgtggtgt    4020
cccaggggcg ttgtcacaag tgttggggaa agtgtataag gacagctcct gctgaggtgg    4080
cttttaatgt atttcctttc tcgcgcgcca cccgtagttc tcttgtatcc ttatgtgatc    4140
gattccaaac gccaaaagga gttgatcccg tgcacttggc gacaggttgg cgcgggtgct    4200
ggcgtggtga gagtcctatc catcaaccac accaaaagcc catagcttac gccaatttgg    4260
atgaaaagaa gatatctgcc caaacggttg ttgctgtccc atacgatccc aatcaggcta    4320
tcaaatgtct gaaagttctg caggcgggag gggctatcgt ggatcagcct acgcctgagg    4380
tcgttcgtgt gtccgagatc cccttctcag ccccattttt cccaaaagtt ccagtcaacc    4440
cagattgtag ggtcgtggtg gattcggaca cttttgtggc tgcggttcgt tgtggttatt    4500
cgacatcaca actggtcctg ggccagggca actttgccaa gttaaatcaa accccccca    4560 ggaactctat ctccaccaaa gcgactggtg gggcctctta tacttttgct gtggctcaag    4620
tgtctgtgtg gacccttgtt catttcgtcc tcggtctttg gctcacgtca cctcaagtgt    4680
gtggtcgagg aaccgctgac ccatggtgtt caagtccatt ttcatatcct acctatggcc    4740
ccggggttgt gtgctcctct cgactttgtg tgtctgctga cggggtcacc cttccattgt    4800
tctcagccgt ggcacaactc tctggtaggg aggtggggat ttttatttta gtgctcgtct    4860
cctttattgc cttggcccac cgcatggctc ttaaggcaga catgttagta gtcttttgg    4920 ctctttgtgc ttatgcctgg cccatgagct cctggttgat ctgcttcttt cctatactct    4980
tgaggtgggt taccccttcac cctctcacta tgctttgggt gcattcattc ttgatgtttt    5040
gtctcccagc agccggcgtc ctctcactgg ggataactgg cctcctctgg gcaatcggcc    5100
gctttactca ggttgccgga atcattacac cttatgatat ccaccagtac acctctgggc    5160
cacgtggtgc agccgctgtg gccacagccc cagaaggcac ttacatggcc gccgtccgga    5220
gagctgcttt aaccgggcgg actttaatct tcacccccgtc cgcagttgga tcccttctcg    5280
aaggtgcttt caggactcat aaaccctgcc ttaacaccgt gaatgtcgta ggctcctccc    5340
ttggttccgg aggggttttc accattgacg gaaaaaaaat tgtcgtcact gctgcccatg    5400
tgctgaacgg cgacacagct agagtcaccg gtgattccta caaccgcatg cacactttca    5460
agactaatgg tgactatgcc tggtcccatg ctgataactg gcaggcgcgct gcccctgtgg    5520 tcaaggttgc gaaagggtat cgcggtcgtg cctactggca aacatcaact ggtgtcgagc    5580
ctggtgttat tgggaatggg ttcgccttct gtttcaccaa ctgcggcgat tcggggtcac    5640
ccgttatctc agaatctggt gatcttatcg gaatccacac cggttcaaac aaacttggtt    5700 ctggtctgt gacaaccct gaaggggaga cctgtaccat cagagaaacc aagctttctg    5760
```

```
accttttccag acatttcgca ggcccaagcg ttcctcttgg ggacatcaaa ttgagtccgg    5820
ccatcatccc tgatgtgaca tccattccga gtgacttggc atcgctccta gcttccgtcc    5880
ctgtaatgga aggcggcctc tcgaccgttc aacttttgtg tgtcttttc ctcctctggc     5940 gcatgatggg ccatgcctgg acgcccattg ttgccgtggg cttcttttg ctgaatgaaa     6000 ttcttccagc agttttggtt cgagccgtgt tttcttttgc actctttgtg cttgcatggg    6060
ccaccccctg gtctgcacaa gtgttgatga ttagacttct cacggcatct ctcaaccgca    6120
acaaactttc tcttgcgttc tacgcactcg gaggtgttgt tggtttggct gctgaaatcg    6180
ggacttttgc tggtaaattg tctgaattgt ctcaagctct ttcgacatac tgtttcttac    6240
ctagggtcct tgctatgacc agctgtgttc ccatcatcat cattggtgga ctccatgccc    6300
tcggtgtgat tctgtggtta ttcaaatacc ggtgcctcca caacatgctg gttggtgatg    6360
gaagcttttc aagcgctttc ttcctacggt attttgcaga gggcaatctc aggagaggtg    6420
tttcacagtc ctgtggcatg agtaacgagt ccctgacggc tgctttggct tgcaagttgt    6480
cacaggctga ccttgatttt ttgtccagct taacgaactt caagtgcttt gtatctgctt    6540
caaacatgaa aaatgctgcc ggccagtaca ttgaagcagc ttatgccagg gccctgcgtc    6600
aagagttggc ctctttagtc cagattgaca aaatgaaagg agttttgtcc aagctagagg    6660
cctttgctga acggccact ccgtccctcg acgtaggtga cgtgattgtt ctacttggac      6720
aacatcctca cggatccgtt ctcgatatta atgtggggac tgaaaggaaa actgtatccg    6780
tgcaagagac ccggagccta ggcggctcca agttcagtgt ttgtactgtt gtgtcaaaca    6840
cacccgtgga cgccttagcc ggtattccac tccagacacc aacccccctt ttcgagaatg    6900
gcccgcgtca tcgcagcgag gaggacgatc ttaaagtcga gaggatgaag aaacactgcg    6960
tgtccctcgg cttccacaac attaacggta agtttactg caagatttgg gacaagtcta     7020
ccggtgacgc cttttacact gatgattccc ggtacaccca agactatgct tttcaggaca    7080
ggtcagctga ctatagagac agggactacg agggtgtgca aaccgccccc caacagggat    7140
ttgatccaaa gtctgaaacc cctgttggta ccgttgtgat cggcggtatt acgtacaaca    7200
ggtatttggt caaaggtaag gaggttctgg ttcccaagcc tgacaactgc cttgaagctg    7260
ccaagctgtc ccttgagcaa gctctcgctg ggatgggcca aacttgtgac cttacagctg    7320
ccgaggtgga aaagctaaag cgcatcattg gtcaacttca aggattgacc actgagcagg    7380
ctttaaactg ttagccgcca gcggcttgac ccgctgtggc cgcggcggcc tagttgtaac    7440
tgaaacggcg gtaaaaattg tcaaatacca cagcagaact tttaccttag gctctttaga    7500
cctaaaagtc acttccgagg tggaggtgaa gaagtcaacc gagcagggcc acgctgttgt    7560
ggcaaacttg tgttctggtg tcgtcttgat gagacctcac ccaccgtccc ttgtcgacgt    7620
tcttctgaaa cccggacttg acataacacc cggcattcaa ccagggcatg gggccgggaa    7680
tatgggcgtg gacggttcca tttgggattt tgaaaccgca cccacaaagg ctgaactcga    7740
gttatccaag caaataattc aagcatgtga agtcaggcgc ggggatgccc cgaacctcca    7800
gctcccttac aagctctatc ctgttagagg ggatcctgag cggcataaag gccacctcat    7860
caataccagg tttggagact taccttacaa aactcctcaa gacaccaagt ccgcaatcca    7920
cgcggcttgt tgcctgcacc ccaacggggc ccccgtgtct gatggtaaat ccacactagg    7980
taccactctt caacatggct tcgagcttta tgtccctact gtgccctata gtgtcatgga    8040
gtaccttgat tcacgcccag acaccccttt tatgtgcact aaaacgcgca cttccaaggc    8100
tgctgcagag gacctccaaa aatacgacct atccacccaa ggatttgtcc tgcctggggt    8160
```

```
cctacgccta gtgcgcaggt tcatctttgg ccacattggc aaggcaccgc cattgttcct   8220
cccatcaact tatcccgcca agaactccat ggcaggtatt aatggtcaga ggttcccaac   8280
aaaggatgtt caaagtatac ctgaaattga tgaaatgtgt gcccgcgccg tcaaggagaa   8340
ttggcaaact gtgacacctt gcaccctcaa gaaacagtat tgttctaggc ccaaaaccag   8400
gaccatcctg ggcactaaca acttcatagc cttggctcat agatcggcgc tcagtggtgt   8460
tacccaggca ttcatgaaga aggcttggaa gtccccaata gccttaggga aaaacaaatt   8520
caaggagctg cattgcactg tcgctggcag gtgcctcgag gccgacttgg cttcctgtga   8580
ccgcagcacc cctgccattg tgaggtggtt cactacccac ctcctatatg aacttgcagg   8640
atgtgaagaa tatctaccta gctatgtgct taactgttgc catgaccttg tggcgacgca   8700
ggatggtgct ttcacaaaac gcggtggcct gtcgtctgga gacccagtca ccagtgtgtc   8760
caacactgtg tactcactgg tgatttatgc ccagcacatg gtactatctg ccctgaaaat   8820
gggtcatgaa attggcctca gttcctcga agaacaactc aaatttgagg accttcttga   8880
aatccagcct atgttagtat actctgatga tcttgtcttg tacgcagaaa agcccacctt   8940
ccccaactat cattggtggg tcgagcatct tgacctgatg ttgggcttta aaacggaccc   9000
aaagaaaacc gtcataactg ataaacccag tttcctcggg tgcagaatcg aagcagggcg   9060
acagctagtc cccaatcgcg accgcatcct ggctgctctt gcatatcaca tgaaggcgca   9120
gaacgcctca gagtattatg cgtctgctgc cgcaatcctg atggattcat gtgcttgcat   9180
tgaccacgat cctgaatggt atgaggacct catctgtggc attgcccgat gcgctcgcct   9240
ggacggttat agctttccag gtccggcatt tttcatgtcc atgtgggaga agctgaggag   9300
tcataatgaa gggaagaaat tccgccactg cggcatctgc gacgccaaag ccgactacgc   9360
ggctgcttgt gggcttgatt tgtgtttgtt tcattcgcac tttcaccaac actgccctgt   9420
cactctgagc tgcggtcacc atgccggttc gaaggaatgt tcgcagtgtc agtcacctgt   9480
tggggccggc agatcccctc ttgatgctgt gctggaacaa attccataca aacctcctcg   9540
cactgtcatc atgaaggtgg gtaataaaac aacggccctt gatccgggga ggtaccagtc   9600
ccgtcgaggt ctcgttgcag tcaagagggg tattgcgggt aatgaagttg atcttgctga   9660
tggagattac caagtggtac ctcttctgcc gacttgcaaa gatataaaca tggtgaaggt   9720
ggcttgcaac gtactactca gcaagttcat agtagggcca ccaggttccg ggaagaccac   9780
ctggctacta agtcaagttc aggacgatga tgtcatttac acacccactc atcagaccat   9840
gtttgacata gttagtgctc tcaaagtttg caggtattcc attccaggag cctcgggact   9900 cccctttccca ccgcctgcca ggtccgggcc gtgggttagg ctcattgcca gcgggcacgt   9960
ccctggccga gtatcatacc tcgatgaggc cggatattgc aatcatctgg acattcttag  10020
actgctttcc aaaacacccc ttgtgtgttt gggtgacctt cagcaacttc acccagtcgg  10080
ctttgattcc tattgttatg tgttcgatca gatgcctcag aagcagttga ccaccattta  10140
cagatttggc cccaacatct cgcgcagcca tccagccttg tacagggaga acttgaatc  10200 taaggctagg aacaccaggg tggtttttac caccgcct gtggcctttg gccaggtgct  10260
gacaccatat cacaaagatc gcgtcggctc cgcgattacc atagactcat cccagggggc  10320
cacctttgac attgtaacat tgcatctacc atcgccaaag tccctaaata agtcccggc  10380 acttgtggcc atcacacggg caagacacgg gttgttcatt tatgaccctc acaaccagct  10440
ccgggagttt ttcaacctaa cccctgagcg cactgattgt aaccttgtgt tcagccgtgg  10500
```

```
agatgagctg gtggtcctga atgcagataa tgcagtcaca accgtggcga aggccttaga    10560
gacaggtcca actcaatttc gagtgtcaga cccgaggtgc aagtctctct tagccgcttg    10620
ctcggccagt ctggaaggga gctgcatgcc gctaccgcaa gtggcgcata acctggggtt    10680
ttacttctcc ccagacagtc cagtatttgc acctctgcca aaagagttgg cgccacattg    10740
gccagtggtt acccatcaga ataatcgggc gtggcctgat cgacttgtcg ctagtatgcg    10800
tccaattgac gcccgctaca gcaagccgat ggtcggtgca gggtatgtgg tcggaccgtc    10860
caccttcctt ggtactcctg gagtggtgtc atactatctc acactataca tcagggggtga    10920 gccccaggcc ttgccagaaa cacttgtttc aacaggacgt atagccacag attgtcggga    10980
gtatctcgac gcggctgagg aagaggcagc aaaagaactt ccccacgcgt tcattggcga    11040
tgtcaaaggc accacagttg gggggtgtca tcacattaca tcaaaatacc tacctaggtc    11100
cctgcctaaa gactctgttg ccgtagttgg agtaagttcg cctggcaggg ctgctaaagc    11160
cgtatgcacc ctcaccgatg tgtacctccc tgaactccgg ccatatctgc aacctgagac    11220
ggcatcaaaa tgctggaaac tcaaattaga cttcagggac gtccgactaa tggtctggaa    11280
aggagccacc gcctactttc aattggaagg gctcacatgg tcggcgctgc ctgactatgc    11340
caggtttatt cagctgccca aaaacgctgt tgtatacatc gatccgtgca taggaccggc    11400
aacagccaat cgtaaagtcg tacgaaccac agattggcgg gccgacctgg cagtgacgcc    11460
gtatgattac ggtgcccgga acattttgac aacagcctgg ttcgaggacc tcgggccgca    11520
gtggaagatt ctggggttgc agccctttag gcgggcgttt ggctttgaaa acactgagga    11580
ttgggcaatc cttgcatgct gcatgagtga cggcaaggac tacactgact ataactggaa    11640
ttgcgttcga caacgcccac acgctatcca tggacgcgct cgtgaccata cgtaccactt    11700
tgcccctggc actgaattgc aagtggagct cggtaaaccc cggctgccac ctgagcaagt    11760
accgtgaatt cggagtgatg caatgggtc actgtggagt aaaatcagcc agctgttcgt    11820
ggacgccttc actgaattcc ttgttagtgt ggttgatatt gtcatcttcc ttgccatatt    11880
gtttgggttc accgtcgcag gatggttact ggtctttctt ctcagagtgg tttgctccgc    11940
gcttctccgt tcgcgctctg ccattcactc ttccgaacta tcgaaggtcc tatgagggct    12000
tactacctaa ttgcagaccg gatgttccac aatttgcatt taagcaccct ttgggtatgt    12060
tttggcacat gcgggtttcc cacctaattg atcagatggt ctctcgccgc atctaccaga    12120
ccatggaaca ttcaggtcaa gcggcctgga agcacgtggt cagtgaggct actcttacaa    12180
aattgtcaga actcgacata gttctccact tccaacacct ggccgcagtg gaggcggact    12240
cttgtcgctt cctcagctca cgacttgtga tgctgaaaaa tcttgccgtt ggcaatgtga    12300
gcttgcagta caacaccacg ttgaaccgcg ttgagctcat cctccccaca ccaggtacga    12360
ggcccaaatt gaccgatttc agacaatggc tcatcagtgt gcacgcttcc atttttttcct    12420 ctgtagcctc atcagttact tgttcatag tgctttggct tcgaattcca gccgtacgct    12480 atgttttttgg tttccattgg cccatggcaa cacgtcattc gagctgacca ttaattacac    12540
tatatgcatg ccctgtctta ccagccaagc ggctcaacaa aggctcgaac ccggtcgtaa    12600
catgtggtgc aaaataggac acaccacgtg cgaggagcgt gaccatgatg agttgtcaat    12660
gtccatcccg tccgggtacg acaacctcaa acttgaaggt tattacgctt ggctggcttt    12720
tttgtccttt tcctacgcgg cccaattcca tccggagttg tttggaatag ggaatgtgtc    12780
gcgcgtcttt gtgataaac gacaccagtt catttgtgcc gagcatgacg gagataattc    12840
aaccgtatct accggacaca acatctccgc atcatatgcg gcatattatc accaccaaat    12900
```

```
agacggggc aattggttcc atttggaatg gctgcggccg ctcttttcct cttggctagt    12960
gctcaacata tcatggtttc tgaggcgttc gcctgcaagc cctgtttctc gacgcatcta    13020
tcagatatta agaccaatac gaccgcggct gccggtttca tggtccttca agacatcagt    13080
tgcctccgac ctcacagggt ctcagcatcg caagagaaca ttcccttcgg aaagtcgtca    13140
caatgtcgtg aagccgtcgg tactccccag tacattacga tgactgctaa tgtgaccgac    13200
gaatcatatt tgtacaacgc ggacttgcta atgctttccg cgtgcctttt ccacgcctca    13260
gaaatgagcg agaaaggctt caaagttatc tttggaaacg tctccggcgt tgtttcagct    13320
tgtgtcaatt tcacagatta tgtggcccat gtaacccaac ataccaaca gcatcatctg     13380
gtaattgatc acattcggtt actgcatttc ctgacaccat ctgcaatgag gtgggctaca    13440
accattgctt gtttgttcgc cattctctta gcgatgagg atgttctcac aaattggggc     13500
gtttcttgac tccgcactct tgcttctggt ggcttttttt gctgtgtacc ggcttgtcct    13560
ggtcctttgc cgatgcaac ggcaacagct cgacacgcca atacatatat aacttgacga     13620
tatgcgagct gaatgggacc gtctggttgt ccagtcattt tgattgggca gtcgagacct    13680
ttgtgcttta cccggtggcc actcatatcc tctcactggg ttttctcaca caagccatt     13740
tttttgatgc gctcggtctc ggcgctgtgt ccactacggg atttcttggc gggcggtatg    13800
tacttagcag cgtgtacggc gcctgcgcct tcgcagcgct tgtatgtttt gtcatccgtg    13860
ctgctaaaaa ttgcatggct tgccgttatg cccgcacccg gttcaccaac ttcatcgtgg    13920
acgaccgggg gaagatccat cgatggaagt ccccaatagt ggtagagaaa ttaggcaaag    13980
ctgacatcgg cggcgacctt gtcaccatca aacatgttgt cctcgaagga gtcaaagctc    14040
aacctttgac gaggacatcg gcggagcaat gggaagccta gatgattttt gcaatgatcc    14100
taccgccgca cagaagcttg tgctggcatt tagtatcaca tacacaccta taatgatata    14160
cgccctcaag gtgtcacgcg gccggctcct aggactgtta cacatcctga tatttctgaa    14220
ctgttctttc acgttcggat acatgacata cgtgcacttt caatccacta accgtgtcgc    14280
gcttactatg ggggcggtcg ttgcccttt gtggggcatt tacagcttta tagaatcatg    14340
gaagtttgtc acttccagat gcaggttgtg ttgcctaggc cggcgataca ttctggcccc    14400
tgcccaccac gtagaaagtg ctgcaggcct ccattcaatc ccagcgtctg gtaaccgagc    14460
atacgctgtg agaaagcccg gactaacatc agtgaacggc actctagtac caggacttcg    14520
gagcctcgtg ttgggcggca aacgagctgt taaacgagga gtggttaacc tcgtcaagta    14580
tggccggtaa aaaccagagc cagaagaaaa agaaaaacac agctcctatg gggagtggcc    14640
agccagtcaa tcaactgtgc caattgctgg gcacaatgat aaagtcccag cgccagcggc    14700
ctaggggagg acaggccaaa atgaaaaagc ctgagaagcc acatttcccc ctagctgctg    14760
aagatgacat ccggcaccat ttcacccaga ccgagcgttc cctttgcttg caatcgatcc    14820
agacggcctt caatcaaggc gcaggaactg cgtcgctttc atccagcggg aaggtcagtt    14880
ttcaggttga gttcatgctg ccggtcgctc atacggtgcg cctgattcgc gtaacttcca    14940
catccgccag tcagggtgca agttaatttg atagttaggt gaatggccgc gattggcgtg    15000
tggcctctga gtcaccctatt caattagggc gatcacatgg gggttagact taattggcga    15060
gaaccatgtg accgaaatta aaaaaaaaaa aaaaaaaaa aaaaaaa                   15107

<210> SEQ ID NO 33
<211> LENGTH: 15104
<212> TYPE: DNA
```

<213> ORGANISM: Porcine reproductive and respiratory syndrome virus

<400> SEQUENCE: 33

| | | | | | |
|---|---|---|---|---|---|
| atgatgtgta | gggtattccc | cctacataca | cgacactact | agtgtttgtg | taccttggag | 60 |
| gcgtgggtac | agccccgccc | cacccctttgg | cccctgttct | agcccaacag | gtatccttct | 120 |
| ctctcggggc | gagtgtgccg | cctgctgctc | ccttgcagcg | ggaaggacct | cccgagtatt | 180 |
| cccggagagc | acctgcttta | cgggatctcc | acccttttaac | catgtctggg | acgttctccc | 240 |
| ggtgcatgtg | caccccggct | gctcgggtat | tttggaacgc | cggccaagtc | tattgcacac | 300 |
| ggtgtctcag | tgcgcggtct | cttctccctc | cggaacttca | ggacattgac | ctcgccgcaa | 360 |
| ttggcttgtt | ttacaagcct | aaagacaagc | ttcactggaa | agtccctatc | ggcatccctc | 420 |
| aggtggagtg | tactccatcc | gggtgttgtt | ggctctcagg | cattttcccc | ttagcgcgca | 480 |
| tgacctccgg | caatcacaac | ttcctacaac | gacttgtgaa | agttgccgat | gtgttgtacc | 540 |
| gtgatggttg | cttaacttct | cgacaccttc | gtgaactcca | agtttacgag | cgtggctgca | 600 |
| gctggtaccc | aatcacgggg | ccagtgcccg | ggatgggttt | gtacgcaaat | tccatgcacg | 660 |
| tatctgacca | gccgttccct | ggtgccaccc | atgtgttgac | gaactcgcct | ttgcctcaac | 720 |
| aagcttgtcg | gcagccgttc | tgcccatttg | aggaggctca | ttctagcgtg | tacaggtgga | 780 |
| aaaaatttgt | ggtcttcacg | gactcctccc | ccaacatgat | gtggacgccg | gaatccgatg | 840 |
| attcagccga | cctagaggcg | ctaccgcctg | agctagaacg | tcaggtcgaa | atcctcattc | 900 |
| ggagttttcc | tgcccatcac | cctgtcagcc | tggccgactg | ggagctcgct | gagtcccctg | 960 |
| agaacgtttt | ttccttcagc | acgtaccatt | ctggtggtta | tcttgtccaa | accccgacg | 1020 |
| tgtttgacag | caagtgctgg | ctctcctgtt | tcttggatca | gccgatcgaa | gtgcgcctct | 1080 |
| atgaggatta | tctggctaac | gctttcggtt | accaaaccaa | gtggggcgtg | tctggtaagt | 1140 |
| acctccagcg | caggcttcaa | gtcaacggta | ttcgtgctgt | aatcgatcct | gatggcccca | 1200 |
| ttcacgttga | agcgctgtct | tgcccccaat | cttggatcag | gcacctgact | ctggacgatg | 1260 |
| acgtcacccc | aggattcgtt | cgcctaacat | ccctccgcat | tgtgccgaac | acagagccca | 1320 |
| ctactctccg | aatcttttcgg | tttggagcgc | ataagtggta | tggcgctgcc | ggcaaacggg | 1380 |
| ctcgtgccaa | gcgtgccgct | aaaagtgaga | agggtccggc | tcccactccc | aaggttgccc | 1440 |
| cgccagcccc | cacctgcgga | attgttacct | actctccacc | aacagacggg | tcttgcggtt | 1500 |
| ggcacgtcct | tgccgccata | atgaaccgaa | tgatgaacgg | tgacttcatg | tcccctctgg | 1560 |
| cccagtacaa | cagaccagag | gatgattggg | cttctgatta | cgatcttgcc | caggcgattc | 1620 |
| aatgtctgcg | gttgcctgct | accatagttc | ggaatcgtgc | ctgtcccaac | gccaagtacc | 1680 |
| tcataaaact | caacggagtc | cactgggagg | tagaggtgag | gtcagggatg | gcccctcgct | 1740 |
| cccttccccg | cgagtgcgta | gtcggcgttt | gttccgaagg | ctgtgccgca | tcgccttacc | 1800 |
| cagaaaacgg | gctacctaaa | cgagcgtttg | aggcctggc | gtctgcttac | agactacctt | 1860 |
| ccgattgtgt | cagttctggt | attgctgact | ttcttgctaa | ccccctcag | gaattctgga | 1920 |
| ctcttgacaa | aatgttgacc | tccccgtcac | cggagcggtc | tggttttttcc | agtctgtaca | 1980 |
| aattgctatt | agaggttgtc | ccgcagaaat | gcggagccac | ggaaggggct | ttcacctatg | 2040 |
| ctgttgagag | aatgctgaag | gattgcccga | gctccgaaca | ggccatggcc | cttctggcaa | 2100 |
| aaattaaagt | tccatcctca | aaggcccgt | ctgtgtccct | ggacgagtgt | ttccctacgg | 2160 |
| atgtttcagc | cgatttcgaa | ccagcatctc | aggagaggtc | ccaaaattcc | agcgctgctg | 2220 |
| ttgtcctgca | ttcaccgaat | gcaaaagagt | tcgaggaagc | agctccaggg | gaagttcagg | 2280 |

```
agggtggcca caaggccgtc cactctgcac tccctgccgg gggtcctaac aataagcagg    2340
cacagctggt tgccggtgag caactgaagc tcggcggttg tggttcggta gttgggaatg    2400
cacatgaagg tgttctggtc ccacctggtc caattaattt gacaagcggg gatttaccct    2460
cctcaggctc catgaaagaa gatatgctca atagccggga ggacgaacca ctggatttgt    2520
cccaaccagc aacagctgtc acaacgactc ttatgggaga gctaacaccc gactacctag    2580
gttctgatac tggtgccctc cccgtcaccg tccgaaaatt tgtcccgacg gggcctatac    2640
tccgtcatgt tgagcactgc agcacggggt cgggcgatag cagttcgcct ttggatctgt    2700
ctggtgcgca aaccccggac cagcctttaa atctgtccct ggcggcttgg ccagtgagga    2760
ccaccgcgtc tgatcctggc tgggtccacg gtagacgcga gcctgtcttt gtaaagcctc    2820
gagatgtttt ctctgatggc gattcagccc ttcagttcgg ggagctttct gaatccagct    2880
ctgtcatcga gtttgatcgg gcaaaagatg ctcaggtggc tgacgcccct gtcggtctga    2940
cgacttcgga cgaggccctc tccgcagtcg atcctttcga gttttccgaa ctcaagcgcc    3000
cacgtttctc cgcacaagcc ttaattgacc gaggcggccc acttgccgat gtccatgcaa    3060
aaataaagaa ccgggtatat gaacagtgcc tccaagcttg tgagcccggt agtcgcgcaa    3120
ccccagctac cagggagtgg ctcgacaaaa tgtgggagag agtggacatg aaaacctggc    3180
gctgcacctc acagttccaa gctggtcaca ttcttgcgtc cctcaaattc ctccctgaca    3240
tgattcaaga cacaccgcct cctgttccca ggaagaaccg agccagtgat aaagctggcc    3300
tgaaacaact agtggcacag tgggatagga gattgagttc aacccccccc ccaaaaccgg    3360
ttgggccggt acttgaccgg gtcgatcctc cgcctacggg tacccggcaa gaagacgtca    3420 cccccctccga tgggccaccc catgcgccgg atggtcgagt gagtacgggt gggagttgga    3480
aaggccttat gctttccggc acccgtctca cggggtccat cagtcatcgc ctcatgacat    3540 gggttttga agttgtctcc catctcccag cttttatgct cacactttc tcgccgcggg    3600 gctctatggc tccaggcgat tgggttttg caggtgttgt tttacttgct ctcctgctct    3660
gtcgttctta cccaatattc gggtgccttc ccttattggg tgtctttct ggtactgtgc    3720 ggcgtgttcg tctgggtgtt tttggctctt ggatggcttt tgctgtattt ttattctcga    3780
ctccatccaa cccagtcggt tcttcttgta accacgattc gccggagtgt catgctgagc    3840
ttctggctct tgagcagcgc caactttggg aacctgtgcg cggccttgtg gtcggcccat    3900
cgggcctctt atgtgtcatt cttggcaagt tactcggtgg gtcacgttat ctctggcatg    3960
ttctcctacg tctatgcctg cttgcagatt tggcccttc tcttgtttat gtggtgtccc    4020 agggcgttg tcacaagtgt tggggaaagt gtataaggac agctcctgct gaggtggctt    4080
ttaatgtatt tccttttctcg cgcgccaccc gtagttctct tgtatccta tgtgatcgat    4140 tccaaacgcc aaaaggagtt gatcccgtgc acttggcgac aggttggcgc gggtgctggc    4200
gtggtgagag tcctatccat caaccacacc aaaagcccat agcttacgcc aatttggatg    4260
aaaagaagat atctgcccaa acggttgttg ctgtcccata cgatcccaat caggctatca    4320
aatgtctgaa agttctgcag gcgggagggg ctatcgtgga tcagcctacg cctgaggtcg    4380
ttcgtgtgtc cgagatcccc ttctcagccc cattttccc aaaagttcca gtcaacccag    4440
attgtagggt cgtggtggat tcggacactt tgtggctgc ggttcgttgt ggttattcga    4500
catcacaact ggtcctgggc cagggcaact ttgccaagtt aaatcaaacc ccccccagga    4560
actctatctc caccaaagcg actggtgggg cctcttatac ttttgctgtg gctcaagtgt    4620
```

```
ctgtgtggac ccttgttcat ttcgtcctcg gtctttggct cacgtcacct caagtgtgtg    4680
gtcgaggaac cgctgaccca tggtgttcaa gtccattttc atatcctacc tatggccccg    4740
gggttgtgtg ctcctctcga ctttgtgtgt ctgctgacgg ggtcacccct ccattgttct    4800
cagccgtggc acaactctct ggtagggagg tggggatttt tattttagtg ctcgtctcct    4860
ttattgcctt ggcccaccgc atggctctta aggcagacat gttagtagtc ttttttggctc   4920
tttgtgctta tgcctggccc atgagctcct ggttgatctg cttctttcct atactcttga    4980
ggtgggttac ccttcaccct ctcactatgc tttgggtgca ttcattcttg atgtttttgtc   5040
tcccagcagc cggcgtcctc tcactgggga taactggcct cctctgggca atcgccgct     5100
ttactcaggt tgccggaatc attacacctt atgatatcca ccagtacacc tctgggccac    5160
gtggtgcagc cgctgtggcc acagcccag aaggcactta catggccgcc gtccggagag     5220
ctgctttaac cgggcggact ttaatcttca ccccgtccgc agttggatcc cttctcgaag    5280
gtgctttcag gactcataaa ccctgcctta acaccgtgaa tgtcgtaggc tcctcccttg    5340
gttccggagg ggttttcacc attgacggaa aaaaaattgt cgtcactgct gcccatgtgc    5400
tgaacggcga cacagctaga gtcaccggtg attcctacaa ccgcatgcac actttcaaga    5460
ctaatggtga ctatgcctgg tcccatgctg ataactggca gggcgctgcc cctgtggtca    5520
aggttgcgaa agggtatcgc ggtcgtgcct actggcaaac atcaactggt gtcgagcctg    5580
gtgttattgg gaatgggttc gccttctgtt tcaccaactg cggcgattcg gggtcacccg    5640
ttatctcaga atctggtgat cttatcggaa tccacaccgg ttcaaacaaa cttggttctg    5700
gtcttgtgac aaccccctgaa ggggagacct gtaccatcag agaaaccaag ctttctgacc    5760
tttccagaca tttcgcaggc ccaagcgttc ctcttgggga catcaaattg agtccggcca    5820
tcatccctga tgtgacatcc attccgagtg acttggcatc gctcctagct tccgtccctg    5880
taatggaagg cggcctctcg accgttcaac ttttgtgtgt cttttttcctc ctctggcgca    5940
tgatgggcca tgcctggacg cccattgttg ccgtgggctt cttttttgctg aatgaaattc    6000
ttccagcagt tttggttcga gccgtgtttt cttttgcact ctttgtgctt gcatgggcca    6060
cccccctggtc tgcacaagtg ttgatgatta gacttctcac ggcatctctc aaccgcaaca    6120
aactttctct tgcgttctac gcactcggag gtgttgttgg tttggctgct gaaatcggga    6180
cttttgctgg taaattgtct gaattgtctc aagctctttc gacatactgt ttcttaccta    6240
gggtccttgc tatgaccagc tgtgttccca tcatcatcat tggtggactc catgccctcg    6300
gtgtgattct gtggttattc aaataccggt gcctccacaa catgctggtt ggtgatggaa    6360
gcttttcaag cgctttcttc ctacggtatt ttgcagaggg caatctcagg agaggtgttt    6420
cacagtcctg tggcatgagt aacgagtccc tgacggctgc tttggcttgc aagttgtcac    6480
aggctgacct tgattttttg tccagcttaa cgaacttcaa gtgctttgta tctgcttcaa    6540
acatgaaaaa tgctgccggc cagtacattg aagcagctta tgccagggcc ctgcgtcaag    6600
agttggcctc tttagtccag attgacaaaa tgaaaggagt tttgtccaag ctagaggcct    6660
ttgctgaaac ggccactccg tccctcgacg taggtgacgt gattgttcta cttggacaac    6720
atcctcacgg atccgttctc gatattaatg tgggactga aaggaaaact gtatccgtgc     6780
aagagacccg gagcctaggc ggctccaagt tcagtgtttg tactgttgtg tcaaacacac    6840
ccgtggacgc cttagccggt attccactcc agacaccaac ccccctttcc gagaatggcc    6900
cgcgtcatcg cagcgaggag gacgatctta agtcgagag gatgaagaaa cactgcgtgt     6960
ccctcggctt ccacaacatt aacggtaaag tttactgcaa gatttgggac aagtctaccg    7020
```

```
gtgacgcctt ttacactgat gattcccggt acacccaaga ctatgctttt caggacaggt      7080
cagctgacta tagagacagg gactacgagg gtgtgcaaac cgcccccaa cagggatttg       7140 atccaaagtc tgaaacccct gttggtaccg ttgtgatcgg cggtattacg tacaacaggt      7200
atttggtcaa aggtaaggag gttctggttc ccaagcctga caactgcctt gaagctgcca      7260
agctgtccct tgagcaagct ctcgctggga tgggccaaac ttgtgacctt acagctgccg      7320
aggtggaaaa gctaaagcgc atcattggtc aacttcaagg attgaccact gagcaggctt      7380
taaactgtta gccgccagcg gcttgacccg ctgtggccgc ggcggcctag ttgtaactga      7440
aacggcggta aaaattgtca aataccacag cagaactttt accttaggct ctttagacct      7500
aaaagtcact tccgaggtgg aggtgaagaa gtcaaccgag cagggccacg ctgttgtggc      7560
aaacttgtgt tctggtgtcg tcttgatgag acctcaccca ccgtcccttg tcgacgttct      7620
tctgaaaccc ggacttgaca taacacccgg cattaaccca gggcatgggg ccgggaatat      7680
gggcgtggac ggttccattt gggattttga accgcaccc acaaaggctg aactcgagtt       7740
atccaagcaa ataattcaag catgtgaagt caggcgcggg gatgccccga acctccagct      7800
cccttacaag ctctatcctg ttagagggga tcctgagcgg cataaaggcc acctcatcaa      7860
taccaggttt ggagacttac cttacaaaac tcctcaagac accaagtccg caatccacgc      7920
ggcttgttgc ctgcacccca acggggcccc cgtgtctgat ggtaaatcca cactaggtac      7980
cactcttcaa catggcttcg agctttatgt ccctactgtg ccctatagtg tcatggagta      8040
ccttgattca cgcccagaca ccccttttat gtgcactaaa cacggcactt ccaaggctgc      8100
tgcagaggac ctccaaaaat acgacctatc cacccaagga tttgtcctgc ctgggggtcct    8160 acgcctagtg cgcaggttca tctttggcca cattggcaag gcaccgccat tgttcctccc      8220
atcaacttat cccgccaaga actccatggc aggtattaat ggtcagaggt tcccaacaaa      8280
ggatgttcaa agtatacctg aaattgatga aatgtgtgcc cgcgccgtca aggagaattg      8340
gcaaactgtg acaccttgca ccctcaagaa acagtattgt tctaggccca aaaccaggac      8400
catcctgggc actaacaact tcatagcctt ggctcataga tcggcgctca gtggtgttac      8460
ccaggcattc atgaagaagg cttggaagtc cccaatagcc ttagggaaaa acaaattcaa      8520
ggagctgcat tgcactgtcg ctggcaggtg cctcgaggcc gacttggctt cctgtgaccg      8580
cagcacccct gccattgtga ggtggttcac tacccacctc ctatatgaac ttgcaggatg      8640
tgaagaatat ctacctagct atgtgcttaa ctgttgccat gaccttgtgg cgacgcagga      8700
tggtgctttc acaaaacgcg gtggcctgtc gtctggagac ccagtcacca gtgtgtccaa      8760
cactgtgtac tcactggtga tttatgccca gcacatggta ctatctgccc tgaaaatggg      8820
tcatgaaatt ggcctcaagt tcctcgaaga acaactcaaa tttgaggacc ttcttgaaat      8880
ccagcctatg ttagtatact ctgatgatct tgtcttgtac gcagaaaagc ccaccttccc      8940
caactatcat tggtgggtcg agcatcttga cctgatgttg ggctttaaaa cggacccaaa      9000
gaaaaccgtc ataactgata aacccagttt cctcgggtgc agaatcgaag cagggcgaca      9060
gctagtcccc aatcgcgacc gcatcctggc tgctcttgca tatcacatga aggcgcagaa      9120
cgcctcagag tattatgcgt ctgctgccgc aatcctgatg gattcatgtg cttgcattga      9180
ccacgatcct gaatggtatg aggacctcat ctgtggcatt gcccgatgcg ctcgcctgga      9240
cggttatagc tttccaggtc cggcattttt catgtccatg tgggagaagc tgaggagtca      9300
taatgaaggg aagaaattcc gccactgcgg catctgcgac gccaaagccg actacgcggc      9360
```

-continued

| | | | | | |
|---|---|---|---|---|---|
| tgcttgtggg | cttgatttgt | gtttgtttca | ttcgcactTt | caccaacact | gccctgtcac | 9420 |
| tctgagctgc | ggtcaccatg | ccggttcgaa | ggaatgttcg | cagtgtcagt | cacctgttgg | 9480 |
| ggccggcaga | tccectcttg | atgctgtgct | ggaacaaatt | ccatacaaac | ctcctcgcac | 9540 |
| tgtcatcatg | aaggtgggta | ataaaacaac | ggcccttgat | ccggggaggt | accagtcccg | 9600 |
| tcgaggtctc | gttgcagtca | agaggggtat | tgcgggtaat | gaagttgatc | ttgctgatgg | 9660 |
| agattaccaa | gtggtacctc | ttctgccgac | ttgcaaagat | ataaacatgg | tgaaggtggc | 9720 |
| ttgcaacgta | ctactcagca | agttcatagt | agggccacca | ggttccggga | agaccacctg | 9780 |
| gctactaagt | caagttcagg | acgatgatgt | catttacaca | cccactcatc | agaccatgtt | 9840 |
| tgacatagtt | agtgctctca | agtttgcag | gtattccatt | ccaggagcct | cgggactccc | 9900 |
| tttcccaccg | cctgccaggt | ccgggccgtg | ggttaggctc | attgccagcg | ggcacgtccc | 9960 |
| tggccgagta | tcatacctcg | atgaggccgg | atattgcaat | catctggaca | ttcttagact | 10020 |
| gctttccaaa | acacccctTg | tgtgtttggg | tgaccttcag | caacttcacc | cagtcggctt | 10080 |
| tgattcctat | tgttatgtgt | tcgatcagat | gcctcagaag | cagttgacca | ccatttacag | 10140 |
| atttggcccc | aacatctgcg | cagccatcca | gccttgttac | agggagaaac | ttgaatctaa | 10200 |
| ggctaggaac | accagggtgg | ttttaccac | ccggcctgtg | gcctttggcc | aggtgctgac | 10260 |
| accatatcac | aaagatcgcg | tcggctccgc | gattaccata | gactcatccc | aggggccac | 10320 |
| cttTgacatt | gtaacattgc | atctaccatc | gccaaagtcc | ctaaataagt | cccgggcact | 10380 |
| tgtggccatc | acacgggcaa | gacacggggt | gttcatTtat | gaccctcaca | accagctccg | 10440 |
| ggagttTttc | aacctaaccc | ctgagcgcac | tgattgtaac | cttgtgttca | gccgtggaga | 10500 |
| tgagctggtg | gtcctgaatg | cagataatgc | agtcacaacc | gtggcgaagg | ccttagagac | 10560 |
| aggtccaact | caatttcgag | tgtcagaccc | gaggtgcaag | tctctcttag | ccgcttgctc | 10620 |
| ggccagtctg | gaagggagct | gcatgccgct | accgcaagtg | gcgcataacc | tggggtttta | 10680 |
| cttctcccca | gacagtccag | tatttgcacc | tctgccaaaa | gagttggcgc | acattggcc | 10740 |
| agtggttacc | catcagaata | atcgggcgtg | gcctgatcga | cttgtcgcta | gtatgcgtcc | 10800 |
| aattgacgcc | cgctacagca | agccgatggt | cggtgcaggg | tatgtggtcg | accgtccac | 10860 |
| cttccttggt | actcctggag | tggtgtcata | ctatctcaca | ctatacatca | ggggtgagcc | 10920 |
| ccaggccttg | ccagaaacac | ttgtTtcaac | aggacgtata | gccacagatt | gtcgggagta | 10980 |
| tctcgacgcg | gctgaggaag | aggcagcaaa | agaacttccc | cacgcgttca | ttggcgatgt | 11040 |
| caaaggcacc | acagttgggg | ggtgtcatca | cattacatca | aaatacctac | ctaggtccct | 11100 |
| gcctaaagac | tctgttgccg | tagttggagt | aagttcgcct | ggcagggctg | ctaaagccgt | 11160 |
| atgcacccte | accgatgtgt | acctccctga | actccggcca | tatctgcaac | ctgagacggc | 11220 |
| atcaaaatgc | tggaaactca | aattagactt | cagggacgtc | cgactaatgg | tctgaaaagg | 11280 |
| agccaccgcc | tactttcaat | tggaagggct | cacatggtcg | cgcgctgcctg | actatgccag | 11340 |
| gtTtattcag | ctgcccaaaa | acgctgttgt | atacatcgat | ccgtgcatag | gaccggcaac | 11400 |
| agccaatcgt | aaagtcgtac | gaaccacaga | ttggcgggcc | gacctggcag | tgacgccgta | 11460 |
| tgattacggg | gcccggaaca | tTtTgacaac | agcctggttc | gaggacctcg | gccgcagtg | 11520 |
| gaagatTctg | ggggttgcagc | cctttaggcg | ggcgtTtggc | ttTgaaaaca | ctgaggattg | 11580 |
| ggcaatccTt | gcatgctgca | tgagtgacgg | caaggactac | actgactata | actggaattg | 11640 |
| cgTtcgacaa | cgcccacacg | ctatccatgg | acgcgctcgt | gaccatacgt | accactTtgc | 11700 |
| ccctggcact | gaattgcaag | tggagctcgg | taaaccccgg | ctgccacctg | agcaagtacc | 11760 |

```
gtgaattcgg agtgatgcaa tggggtcact gtggagtaaa atcagccagc tgttcgtgga   11820
cgccttcact gaattccttg ttagtgtggt tgatattgtc atcttccttg ccatattgtt   11880
tgggttcacc gtcgcaggat ggttactggt cttcttctc agagtggttt gctccgcgct   11940
tctccgttcg cgctctgcca ttcactcttc cgaactatcg aaggtcctat gagggcttac   12000
tacctaattg cagaccggat gttccacaat ttgcatttaa gcacccttg ggtatgtttt   12060
ggcacatgcg ggttcccac ctaattgatc agatggtctc tcgccgcatc taccagacca   12120
tggaacattc aggtcaagcg gcctggaagc acgtggtcag tgaggctact cttacaaaat   12180
tgtcagaact cgacatagtt ctccacttcc aacacctggc cgcagtggag gcggactctt   12240
gtcgcttcct cagctcacga cttgtgatgc tgaaaaatct tgccgttggc aatgtgagct   12300
tgcagtacaa caccacgttg aaccgcgttg agctcatcct ccccacacca ggtacgaggc   12360
ccaaattgac cgatttcaga caatggctca tcagtgtgca cgcttccatt ttttcctctg   12420
tagcctcatc agttactttg ttcatagtgc tttggcttcg aattccagcc gtacgctatg   12480
tttttggttt ccattggccc atggcaacac gtcattcgag ctgaccatta attacactat   12540
atgcatgccc tgtcttacca gccaagcggc tcaacaaagg ctcgaacccg gtcgtaacat   12600
gtggtgcaaa ataggacaca ccacgtgcga ggagcgtgac catgatgagt tgtcaatgtc   12660
catcccgtcc gggtacgaca acctcaaact tgaaggttat tacgcttggc tggcttttt   12720
gtccttttcc tacgcggccc aattccatcc ggagttgttt ggaatagggga atgtgtcgcg   12780
cgtcttgtg gataaacgac accagttcat ttgtgccgag catgacggag ataattcaac   12840
cgtatctacc ggacacaaca tctccgcatc atatgcggca tattatcacc accaaataga   12900
cgggggcaat tggttccatt tggaatggct gcggccgctc ttttcctctt ggctagtgct   12960
caacatatca tggtttctga ggcgttcgcc tgcaagccct gtttctcgac gcatctatca   13020
gatattaaga ccaatacgac cgcggctgcc ggtttcatgg tccttcaaga catcagttgc   13080
ctccgacctc acagggtctc agcatcgcaa agaacattc ccttcggaaa gtcgtcacaa   13140
tgtcgtgaag ccgtcggtac tccccagtac attacgatga ctgctaatgt gaccgacgaa   13200
tcatatttgt acaacgcgga cttgctaatg ctttccgcgt gccttttcca cgcctcagaa   13260
atgagcgaga aaggcttcaa agttatcttt ggaaacgtct ccggcgttgt ttcagcttgt   13320
gtcaatttca cagattatgt ggcccatgta acccaacata cccaacagca tcatctggta   13380
attgatcaca ttcggttact gcatttcctg acaccatctg caatgaggtg ggctacaacc   13440
attgcttgtt tgttcgccat tctcttagcg atatgagatg ttctcacaaa ttggggcgtt   13500
tcttgactcc gcactcttgc ttctggtggc tttttttgct gtgtaccggc ttgtcctggt   13560
cctttgccga tggcaacggc aacagctcga cacgccaata catatataac ttgacgtat   13620
gcgagctgaa tgggaccgtc tggttgtcca gtcatttga ttgggcagtc gagacctttg   13680
tgctttaccc ggtggccact catatcctct cactgggttt tctcacaaca agccattttt   13740
ttgatgcgct cggtctcggc gctgtgtcca ctacgggatt tcttggcggg cggtatgtac   13800
ttagcagcgt gtacggcgcc tgcgccttcg cagcgcttgt atgttttgtc atccgtgctg   13860
ctaaaaattg catggcttgc cgttatgccc gcacccggtt caccaacttc atcgtggacg   13920
accgggggaa gatccatcga tggaagtccc caatagtggt agagaaatta ggcaaagctg   13980
acatcggcgg cgaccttgtc accatcaaac atgttgtcct cgaaggagtc aaagctcaac   14040
cttgacgag gacatcggcg gagcaatggg aagcctagat gattttgca atgatcctac   14100
```

```
cgccgcacag aagcttgtgc tggcatttag tatcacatac acacctataa tgatatacgc    14160
cctcaaggtg tcacgcggcc ggctcctagg actgttacac atcctgatat ttctgaactg    14220
ttctttcacg ttcggataca tgacatacgt gcactttcaa tccactaacc gtgtcgcgct    14280
tactatgggg gcggtcgttg ccctttttgtg gggcatttac agctttatag aatcatggaa    14340
gtttgtcact tccagatgca ggttgtgttg cctaggccgg cgatacattc tggcccctgc    14400
ccaccacgta gaaagtgctg caggcctcca ttcaatccca gcgtctggta accgagcata    14460
cgctgtgaga aagcccggac taacatcagt gaacggcact ctagtaccag gacttcggag    14520
cctcgtgttg ggcggcaaac gagctgttaa cgaggagtg gttaacctcg tcaagtatgg    14580
ccggtaaaaa ccagagccag aagaaaaaga aaaacacagc tcctatgggg agtggccagc    14640
cagtcaatca actgtgccaa ttgctgggca caatgataaa gtcccagcgc cagcggccta    14700
ggggaggaca ggccaaaatg aaaaagcctg agaagccaca tttcccccta gctgctgaag    14760
atgacatccg gcaccatttc acccagaccg agcgttccct ttgcttgcaa tcgatccaga    14820
cggccttcaa tcaaggcgca ggaactgcgt cgctttcatc cagcgggaag gtcagttttc    14880
aggttgagtt catgctgccg gtcgctcata cggtgcgcct gattcgcgta acttccacat    14940
ccgccagtca gggtgcaagt taatttgata gttaggtgaa tggccgcgat tggcgtgtgg    15000
cctctgagtc acctattcaa ttagggcgat cacatggggg ttagacttaa ttggcgagaa    15060
ccatgtgacc gaaattaaaa aaaaaaaaaa aaaaaaaaa aaaa                      15104

<210> SEQ ID NO 34
<211> LENGTH: 15101
<212> TYPE: DNA
<213> ORGANISM: Porcine reproductive and respiratory syndrome virus

<400> SEQUENCE: 34
atgatgtgta gggtattccc cctacataca cgacactact agtgtttgtg taccttggag      60
gcgtgggtac agccccgccc caccccttgg ccctgttct agcccaacag gtatccttct     120
ctctcggggc gagtgtgccg cctgctgctc ccttgcagcg ggaaggacct cccgagtatt     180
cccggagagc acctgcttta cgggatctcc accctttaac catgtctggg acgttctccc     240
ggtgcatgtg caccccggct gctcgggtat tttggaacgc cggccaagtc tattgcacac     300
ggtgtctcag tgcgcggtct cttctcccctc cggaacttca ggacattgac ctcgccgcaa     360
ttggcttgtt ttacaagcct aaagacaagc ttcactggaa agtccctatc ggcatccctc     420
aggtggagtg tactccatcc gggtgttgtt ggctctcagg catttttccc ttagcgcgca     480
tgacctccgg caatcacaac ttcctacaac gacttgtgaa agttgccgat gtgttgtacc     540
gtgatggttg cttaacttct cgacaccttc gtgaactcca gtttacgag cgtggctgca     600 gctggtaccc aatcacgggg ccagtgcccg ggatgggttt gtacgcaaat tccatgcacg     660
tatctgacca gccgttccct ggtgccaccc atgtgttgac gaactcgcct ttgcctcaac     720
aagcttgtcg gcagccgttc tgcccatttg aggaggctca ttctagcgtg tacaggtgga     780
aaaaatttgt ggtcttcacg gactcctccc ccatgatgtg gacgccggaa tccgatgatt     840
cagccgacct agaggcgcta ccgcctgagc tagaacgtca ggtcgaaatc ctcattcgga     900
gttttcctgc ccatcaccct gtcagcctgg ccgactggga gctcgctgag tcccctgaga     960
acggtttttc cttcagcacg taccattctg tggttatct tgtccaaaac ccgacgtgt    1020 ttgacagcaa gtgctggctc tcctgttttt tggatcagcc gatcgaagtg cgcctctatg    1080
aggattatct ggctaacgct ttcggttacc aaaccaagtg gggcgtgtct ggtaagtacc    1140
```

```
tccagcgcag gcttcaagtc aacggtattc gtgctgtaat cgatcctgat ggccccattc    1200
acgttgaagc gctgtcttgc ccccaatctt ggatcaggca cctgactctg gacgatgacg    1260 tcacccagg attcgttcgc ctaacatccc tccgcattgt gccgaacaca gagcccacta     1320
ctctccgaat ctttcggttt ggagcgcata agtggtatgg cgctgccggc aaacgggctc    1380
gtgccaagcg tgccgctaaa agtgagaagg gtccggctcc cactcccaag gttgccccgc    1440 cagccccac ctgcggaatt gttacctact ctccaccaac agacgggtct tgcggttggc     1500
acgtccttgc cgccataatg aaccgaatga tgaacggtga cttcatgtcc cctctggccc    1560
agtacaacag accagaggat gattgggctt ctgattacga tcttgcccag gcgattcaat    1620
gtctgcggtt gcctgctacc atagttcgga atcgtgcctg tcccaacgcc aagtacctca    1680
taaaactcaa cggagtccac tgggaggtag aggtgaggtc agggatggcc cctcgctccc    1740
ttccccgcga gtgcgtagtc ggcgtttgtt ccgaaggctg tgccgcatcg ccttacccag    1800
aaaacgggct acctaaacga gcgtttgagg ccttggcgtc tgcttacaga ctaccttccg    1860
attgtgtcag ttctggtatt gctgactttc ttgctaaccc ccctcaggaa ttctggactc    1920
ttgacaaaat gttgacctcc ccgtcaccgg agcggtctgg tttttccagt ctgtacaaat    1980
tgctattaga ggttgtcccg cagaaatgcg gagccacgga aggggctttc acctatgctg    2040
ttgagagaat gctgaaggat tgcccgagct ccgaacaggc catggccctt ctggcaaaaa    2100
ttaaagttcc atcctcaaag gccccgtctg tgtccctgga cgagtgtttc cctacggatg    2160
tttcagccga tttcgaacca gcatctcagg agaggtccca aaattccagc gctgctgttg    2220
tcctgcattc accgaatgca aaagagttcg aggaagcagc tccaggggaa gttcaggagg    2280
gtggccacaa ggccgtccac tctgcactcc ctgccggggg tcctaacaat aagcaggcac    2340
agctggttgc cggtgagcaa ctgaagctcg gcggttgtgg ttcggtagtt gggaatgcac    2400
atgaaggtgt tctggtccca cctggtccaa ttaatttgac aagcggggat ttaccctcct    2460
caggctccat gaaagaagat atgctcaata gccgggagga cgaaccactg gatttgtccc    2520
aaccagcaac agctgtcaca acgactctta tgggagagct aacacccgac tacctaggtt    2580
ctgatactgg tgccctcccc gtcaccgtcc gaaaatttgt cccgacgggg cctatactcc    2640
gtcatgttga gcactgcagc acggggtcgg gcgatagcag ttcgccttg gatctgtctg     2700 gtgcgcaaac cccggaccag cctttaaatc tgtccctggc ggcttggcca gtgaggacca    2760
ccgcgtctga tcctggctgg gtccacggta gacgcgagcc tgtctttgta aagcctcgag    2820
atgttttctc tgatggcgat tcagcccttc agttcgggga gctttctgaa tccagctctg    2880
tcatcgagtt tgatcgggca aaagatgctc aggtggctga cgcccctgtc ggtctgacga    2940
cttcggacga ggccctctcc gcagtcgatc ctttcgagtt ttccgaactc aagcgcccac    3000
gtttctccgc acaagcctta attgaccgag gcggcccact tgccgatgtc catgcaaaaa    3060
taaagaaccg ggtatatgaa cagtgcctcc aagcttgtga gcccggtagt cgcgcaaccc    3120
cagctaccag ggagtggctc gacaaaatgt gggagagagt ggacatgaaa acctggcgct    3180
gcacctcaca gttccaagct ggtcacattc ttgcgtccct caaattcctc cctgacatga    3240
ttcaagacac accgcctcct gttcccagga agaaccgagc cagtgataaa gctggcctga    3300
aacaactagt ggcacagtgg gataggagat tgagttcaac ccccccccca aaaccggttg    3360
ggccggtact tgaccgggtc gatcctccgc ctacgggtac ccggcaagaa gacgtcaccc    3420
cctccgatgg gccacccat gcgccggatg gtcgagtgag tacgggtggg agttggaaag      3480
```

```
gccttatgct ttccggcacc cgtctcacgg ggtccatcag tcatcgcctc atgacatggg   3540
tttttgaagt tgtctcccat ctcccagctt ttatgctcac acttttctcg ccgcggggct   3600
ctatggctcc aggcgattgg gttttttgcag gtgttgttttt acttgctctc ctgctctgtc   3660
gttcttaccc aatattcggg tgccttccct tattgggtgt cttttctggt actgtgcggc   3720
gtgttcgtct gggtgttttt ggctcttgga tggcttttgc tgtattttta ttctcgactc   3780
catccaaccc agtcggttct tcttgtaacc acgattcgcc ggagtgtcat gctgagcttc   3840
tggctcttga gcagcgccaa ctttgggaac ctgtgcgcgg ccttgtggtc ggcccatcgg   3900
gcctcttatg tgtcattctt ggcaagttac tcggtgggtc acgttatctc tggcatgttc   3960
tcctacgtct atgcctgctt gcagatttgg ccctttctct tgtttatgtg gtgtcccagg   4020
ggcgttgtca caagtgttgg ggaaagtgta aaggacagc tcctgctgag gtggcttttta   4080
atgtatttcc tttctcgcgc gccacccgta gttctcttgt atccttatgt gatcgattcc   4140
aaacgccaaa aggagttgat cccgtgcact tggcgacagg ttggcgcggg tgctggcgtg   4200
gtgagagtcc tatccatcaa ccacaccaaa agcccatagc ttacgccaat ttggatgaaa   4260
agaagatatc tgcccaaacg gttgttgctg tcccatacga tcccaatcag gctatcaaat   4320
gtctgaaagt tctgcaggcg ggaggggcta tcgtggatca gcctacgcct gaggtcgttc   4380
gtgtgtccga gatcccttc tcagccccat ttttcccaaa agttccagtc aacccagatt   4440
gtagggtcgt ggtggattcg gacacttttg tggctgcgt tcgttgtggt tattcgacat   4500
cacaactggt cctgggccag ggcaactttg ccaagttaaa tcaaaccccc cccaggaact   4560
ctatctccac caaagcgact ggtggggcct cttatacttt tgctgtggct caagtgtctg   4620
tgtggaccct tgttcatttc gtcctcggtc tttggctcac gtcacctcaa gtgtgtggtc   4680
gaggaaccgc tgacccatgg tgttcaagtc cattttcata tcctacctat ggccccgggg   4740
ttgtgtgctc ctctcgactt tgtgtgtctg ctgacggggt cacccttcca ttgttctcag   4800
ccgtggcaca actctctggt agggaggtgg ggattttttat tttagtgctc gtctcctttta   4860
ttgccttggc ccaccgcatg gctcttaagg cagacatgtt agtagtcttt ttggctcttt   4920
gtgcttatgc ctggcccatg agctcctggt tgatctgctt cttttcctata ctcttgaggt   4980
gggttaccct tcaccctctc actatgcttt gggtgcattc attcttgatg ttttgtctcc   5040
cagcagccgg cgtcctctca ctggggataa ctggcctcct ctgggcaatc ggccgcttta   5100
ctcaggttgc cggaatcatt acaccttatg atatccacca gtacacctct gggccacgtg   5160
gtgcagccgc tgtggccaca gccccagaag gcacttacat ggccgccgtc cggagagctg   5220
ctttaaccgg gcggacttta atcttcaccc cgtccgcagt tggatcccctt ctcgaaggtg   5280
cttttcaggac tcataaaccc tgccttaaca ccgtgaatgt cgtaggctcc tcccttggtt   5340
ccggaggggt tttcaccatt gacggaaaaa aaattgtcgt cactgctgcc catgtgctga   5400
acggcgacac agctagagtc accggtgatt cctacaaccg catgcacact ttcaagacta   5460
atggtgacta tgcctggtcc catgctgata actggcaggg cgctgcccct gtggtcaagg   5520
ttgcgaaagg gtatcgcggt cgtgcctact ggcaaacatc aactggtgtc gagcctggtg   5580
ttattgggaa tgggttcgcc ttctgtttca ccaactgcgg cgattcgggg tcacccgtta   5640
tctcagaatc tggtgatctt atcggaatcc acaccggttc aaacaaactt ggttctggtc   5700
ttgtgacaac ccctgaaggg gagacctgta ccatcagaga aaccaagctt tctgaccttt   5760
ccagacattt cgcaggccca agcgttcctc ttggggacat caaattgagt ccggccatca   5820
tccctgatgt gacatccatt ccgagtgact tggcatcgct cctagcttcc gtccctgtaa   5880
```

```
tggaaggcgg cctctcgacc gttcaacttt tgtgtgtctt tttcctcctc tggcgcatga    5940
tgggccatgc ctggacgccc attgttgccg tgggcttctt tttgctgaat gaaattcttc    6000
cagcagtttt ggttcgagcc gtgttttctt ttgcactctt tgtgcttgca tgggccaccc    6060
cctggtctgc acaagtgttg atgattagac ttctcacggc atctctcaac cgcaacaaac    6120
tttctcttgc gttctacgca ctcggaggtg ttgttggttt ggctgctgaa atcgggactt    6180
ttgctggtaa attgtctgaa ttgtctcaag ctctttcgac atactgtttc ttacctaggg    6240
tccttgctat gaccagctgt gttcccatca tcatcattgg tggactccat gccctcggtg    6300
tgattctgtg gttattcaaa taccggtgcc tccacaacat gctggttggt gatggaagct    6360
tttcaagcgc tttcttccta cggtatttg cagagggcaa tctcaggaga ggtgtttcac    6420
agtcctgtgg catgagtaac gagtccctga cggctgcttt ggcttgcaag ttgtcacagg    6480
ctgaccttga ttttttgtcc agcttaacga acttcaagtg ctttgtatct gcttcaaaca    6540
tgaaaaatgc tgccggccag tacattgaag cagcttatgc cagggccctg cgtcaagagt    6600
tggcctcttt agtccagatt gacaaaatga aggagtttt gtccaagcta gaggcctttg    6660
ctgaaacggc cactccgtcc ctcgacgtag gtgacgtgat tgttctactt ggacaacatc    6720
ctcacggatc cgttctcgat attaatgtgg ggactgaaag gaaaactgta ccgtgcaag    6780
agacccggag cctaggcggc tccaagttca gtgtttgtac tgttgtgtca aacacacccg    6840
tggacgcctt agccggtatt ccactccaga caccaaccc ccttttcgag aatggcccgc    6900
gtcatcgcag cgaggaggac gatcttaaag tcgagaggat gaagaaacac tgcgtgtccc    6960
tcggcttcca caacattaac ggtaaagttt actgcaagat ttgggacaag tctaccggtg    7020
acgcctttta cactgatgat tcccggtaca cccaagacta tgcttttcag gacaggtcag    7080
ctgactatag agacagggac tacgagggtg tgcaaaccgc cccccaacag ggatttgatc    7140
caaagtctga aacccctgtt ggtaccgttg tgatcggcgg tattacgtac aacaggtatt    7200
tggtcaaagg taaggaggtt ctggttccca agcctgacaa ctgccttgaa gctgccaagc    7260
tgtcccttga gcaagctctc gctgggatgg gccaaacttg tgaccttaca gctgccgagg    7320
tggaaaagct aaagcgcatc attggtcaac ttcaaggatt gaccactgag caggctttaa    7380
actgttagcc gccagcggct tgacccgctg tggccgcggc ggcctagttg taactgaaac    7440
ggcggtaaaa attgtcaaat accacagcag aactttacc ttaggctctt tagacctaaa    7500
agtcacttcc gaggtggagg tgaagaagtc aaccgagcag ggccacgctg ttgtggcaaa    7560
cttgtgttct ggtgtcgtct tgatgagacc tcacccaccg tcccttgtcg acgttcttct    7620
gaaacccgga cttgacataa cacccggcat tcaaccaggg catgggccg ggaatatggg    7680
cgtgacggt tccatttggg attttgaaac cgcacccaca aaggctgaac tcgagttatc    7740
caagcaaata attcaagcat gtgaagtcag cgcgcgggat gccccgaacc tccagctccc    7800
ttacaagctc tatcctgtta gaggggatcc tgagcggcat aaaggccacc tcatcaatac    7860
caggtttgga gacttaccntt acaaaactcc tcaagacacc aagtccgcaa tccacgcggc    7920
ttgttgcctg caccccaacg gggcccccgt gtctgatggt aaatccacac taggtaccac    7980
tcttcaacat ggcttcgagc tttatgtccc tactgtgccc tatagtgtca tggagtacct    8040
tgattcacgc ccagacaccc ctttttatgtg cactaaacac ggcacttcca aggctgctgc    8100
agaggacctc caaaaatacg acctatccac ccaaggattt gtcctgcctg gggtcctacg    8160
cctagtgcgc aggttcatct ttggccacat tggcaaggca ccgccattgt tcctcccatc    8220
```

```
aacttatccc gccaagaact ccatggcagg tattaatggt cagaggttcc caacaaagga    8280
tgttcaaagt atacctgaaa ttgatgaaat gtgtgcccgc gccgtcaagg agaattggca    8340
aactgtgaca ccttgcaccc tcaagaaaca gtattgttct aggcccaaaa ccaggaccat    8400
cctgggcact aacaacttca tagccttggc tcatagatcg cgctcagtg gtgttaccca    8460 ggcattcatg aagaaggctt ggaagtcccc aatagcctta gggaaaaaca aattcaagga    8520
gctgcattgc actgtcgctg gcaggtgcct cgaggccgac ttggcttcct gtgaccgcag    8580 caccctgcc attgtgaggt ggttcactac ccacctccta tatgaacttg caggatgtga    8640
agaatatcta cctagctatg tgcttaactg ttgccatgac cttgtggcga cgcaggatgg    8700
tgctttcaca aaacgcggtg gcctgtcgtc tggagaccca gtcaccagtg tgtccaacac    8760
tgtgtactca ctggtgattt atgcccagca catggtacta tctgccctga aaatgggtca    8820
tgaaattggc ctcaagttcc tcgaagaaca actcaaattt gaggaccttc ttgaaatcca    8880
gcctatgtta gtatactctg atgatcttgt cttgtacgca gaaaagccca ccttccccaa    8940
ctatcattgg tgggtcgagc atcttgacct gatgttgggc tttaaaacgg acccaaagaa    9000
aaccgtcata actgataaac ccagtttcct cgggtgcaga atcgaagcag gcgacagct    9060 agtccccaat cgcgaccgca tcctggctgc tcttgcatat cacatgaagg cgcagaacgc    9120
ctcagagtat tatgcgtctg ctgccgcaat cctgatggat tcatgtgctt gcattgacca    9180
cgatcctgaa tggtatgagg acctcatctg tggcattgcc cgatgcgctc gcctggacgg    9240
ttatagcttt ccaggtccgg cattttcat gtccatgtgg gagaagctga ggagtcataa    9300
tgaagggaag aaattccgcc actgcggcat ctgcgacgcc aaagccgact acgcggctgc    9360
ttgtgggctt gatttgtgtt tgtttcattc gcactttcac caacactgcc ctgtcactct    9420
gagctgcggt caccatgccg gttcgaagga atgttcgcag tgtcagtcac ctgttggggc    9480
cggcagatcc cctcttgatg ctgtgctgga acaaattcca tacaaacctc ctcgcactgt    9540
catcatgaag gtgggtaata aaacaacggc ccttgatccg gggaggtacc agtcccgtcg    9600
aggtctcgtt gcagtcaaga ggggtattgc gggtaatgaa gttgatcttg ctgatggaga    9660
ttaccaagtg gtacctcttc tgccgacttg caaagatata acatggtga aggtggcttg    9720 caacgtacta ctcagcaagt tcatagtagg gccaccaggt tccgggaaga ccacctggct    9780
actaagtcaa gttcaggacg atgatgtcat ttacacaccc actcatcaga ccatgtttga    9840
catagttagt gctctcaaag tttgcaggta ttccattcca ggagcctcgg gactcccttt    9900
cccaccgcct gccaggtccg ggccgtgggt taggctcatt gccagcgggc acgtccctgg    9960
ccgagtatca tacctcgatg aggccggata ttgcaatcat ctggacattc ttagactgct   10020
ttccaaaaca ccccttgtgt gtttgggtga ccttcagcaa cttcacccag tcggctttga   10080
ttcctattgt tatgtgttcg atcagatgcc tcagaagcag ttgaccacca tttacagatt   10140
tggccccaac atctgcgcag ccatccagcc ttgttacagg gagaaacttg aatctaaggc   10200
taggaacacc agggtggttt ttaccacccg gcctgtggcc tttggccagg tgctgacacc   10260
atatcacaaa gatcgcgtcg gctccgcgat taccatagac tcatcccagg ggccaccttt   10320
tgacattgta acattgcatc taccatcgcc aaagtcccta aataagtccc gggcacttgt   10380
ggccatcaca cgggcaagac acgggttgtt catttatgac cctcacaacc agctccggga   10440 gttttttcaac ctaaccctg agcgcactga ttgtaacctt gtgttcagcc gtggagatga   10500
gctggtggtc ctgaatgcag ataatgcagt cacaaccgtg gcgaaggcct tagagacagg   10560
tccaactcaa tttcgagtgt cagacccgag gtgcaagtct ctcttagccg cttgctcggc   10620
```

```
cagtctggaa gggagctgca tgccgctacc gcaagtggcg cataacctgg ggttttactt    10680
ctccccagac agtccagtat ttgcacctct gccaaaagag ttggcgccac attggccagt    10740
ggttacccat cagaataatc gggcgtggcc tgatcgactt gtcgctagta tgcgtccaat    10800
tgacgcccgc tacagcaagc cgatggtcgg tgcagggtat gtggtcggac cgtccacctt    10860
ccttggtact cctggagtgg tgtcatacta tctcacacta tacatcaggg gtgagcccca    10920
ggccttgcca gaaacacttg tttcaacagg acgtatagcc acagattgtc gggagtatct    10980
cgacgcggct gaggaagagg cagcaaaaga acttccccac gcgttcattg gcgatgtcaa    11040
aggcaccaca gttgggggt gtcatcacat tacatcaaaa tacctaccta ggtccctgcc    11100
taaagactct gttgccgtag ttggagtaag ttcgcctggc agggctgcta aagccgtatg    11160
caccctcacc gatgtgtacc tccctgaact ccggccatat ctgcaacctg agacggcatc    11220
aaaatgctgg aaactcaaat tagacttcag ggacgtccga ctaatggtct ggaaaggagc    11280
caccgcctac tttcaattgg aagggctcac atggtcggcg ctgcctgact atgccaggtt    11340
tattcagctg cccaaaaacg ctgttgtata catcgatccg tgcataggac cggcaacagc    11400
caatcgtaaa gtcgtacgaa ccacagattg gcgggccgac ctggcagtga cgccgtatga    11460
ttacggtgcc cggaacattt tgacaacagc ctggttcgag gacctcgggc cgcagtggaa    11520
gattctgggg ttgcagccct ttaggcgggc gtttggcttt gaaaacactg aggattgggc    11580
aatccttgca tgctgcatga gtgacggcaa ggactacact gactataact ggaattgcgt    11640
tcgacaacgc ccacacgcta tccatggacg cgctcgtgac catacgtacc actttgcccc    11700
tggcactgaa ttgcaagtgg agctcggtaa accccggctg ccacctgagc aagtaccgtg    11760
aattcggagt gatgcaatgg ggtcactgtg gagtaaaatc agccagctgt tcgtggacgc    11820
cttcactgaa ttccttgtta gtgtggttga tattgtcatc ttccttgcca tattgtttgg    11880
gttcaccgtc gcaggatggt tactggtctt tcttctcaga gtggtttgct ccgcgcttct    11940
ccgttcgcgc tctgccattc actcttccga actatcgaag gtcctatgag ggcttactac    12000
ctaattgcag accggatgtt ccacaatttg catttaagca ccctttgggt atgttttggc    12060
acatgcgggt ttcccaccta attgatcaga tggtctctcg ccgcatctac cagaccatgg    12120
aacattcagg tcaagcggcc tggaagcacg tggtcagtga ggctactctt acaaaattgt    12180
cagaactcga catagttctc cacttccaac acctggccgc agtggaggcg gactcttgtc    12240
gcttcctcag ctcacgactt gtgatgctga aaaatcttgc cgttggcaat gtgagcttgc    12300
agtacaacac cacgttgaac cgcgttgagc tcatcctccc cacaccaggt acgaggccca    12360
aattgaccga tttcagacaa tggctcatca gtgtgcacgc ttccattttt tcctctgtag    12420
cctcatcagt tactttgttc atagtgcttt ggcttcgaat tccagccgta cgctatgttt    12480 ttggttttcca ttggcccatg gcaacacgtc attcgagctg accattaatt acactatatg    12540
catgccctgt cttaccagcc aagcggctca acaaaggctc gaaccccggtc gtaacatgtg    12600 gtgcaaaata ggacacacca cgtgcgagga gcgtgaccat gatgagttgt caatgtccat    12660
cccgtccggg tacgacaacc tcaaacttga aggttattac gcttggctgg cttttttgtc    12720
cttttcctac gcggcccaat tccatccgga gttgttggaa atagggaatg tgtcgcgcgt    12780
ctttgtggat aaacgacacc agttcatttg tgccgagcat gacggagata attcaaccgt    12840
atctaccgga cacaacatct ccgcatcata tgcggcatat tatcaccacc aaatagacgg    12900
gggcaattgg ttccatttgg aatggctgcg gccgctcttt cctcttggc tagtgctcaa    12960
```

```
catatcatgg tttctgaggc gttcgcctgc aagccctgtt tctcgacgca tctatcagat    13020
attaagacca atacgaccgc ggctgccggt tcatggtcc ttcaagacat cagttgcctc     13080
cgacctcaca gggtctcagc atcgcaagag aacattccct tcggaaagtc gtcacaatgt    13140
cgtgaagccg tcggtactcc ccagtacatt acgatgactg ctaatgtgac cgacgaatca    13200
tatttgtaca acgcggactt gctaatgctt tccgcgtgcc ttttccacgc ctcagaaatg    13260
agcgagaaag gcttcaaagt tatctttgga acgtctccg gcgttgtttc agcttgtgtc     13320
aatttcacag attatgtggc ccatgtaacc caacataccc aacagcatca tctggtaatt    13380
gatcacattc ggttactgca tttcctgaca ccatctgcaa tgaggtgggc tacaaccatt    13440
gcttgtttgt tcgccattct cttagcgata tgagatgttc tcacaaattg gggcgtttct    13500
tgactccgca ctcttgcttc tggtggcttt ttttgctgtg taccggcttg tcctggtcct    13560
ttgccgatgg caacggcaac agctcgacac gccaatacat atataacttg acgatatgcg    13620
agctgaatgg gaccgtctgg ttgtccagtc attttgattg ggcagtcgag acctttgtgc    13680
tttacccggt ggccactcat atcctctcac tgggttttct cacaacaagc cattttttg    13740 atgcgctcgg tctcggcgct gtgtccacta cgggatttct tggcgggcgg tatgtactta    13800
gcagcgtgta cggcgcctgc gccttcgcag cgcttgtatg ttttgtcatc cgtgctgcta    13860
aaaattgcat ggcttgccgt tatgcccgca cccggttcac caacttcatc gtggacgacc    13920
gggggaagat ccatcgatgg aagtcccaa tagtggtaga gaaattaggc aaagctgaca    13980
tcggcggcga ccttgtcacc atcaaacatg ttgtcctcga aggagtcaaa gctcaacctt    14040
tgacgaggac atcggcggag caatgggaag cctagatgat ttttgcaatg atcctaccgc    14100
cgcacagaag cttgtgctgg catttagtat cacatacaca cctataatga tatacgccct    14160
caaggtgtca cgcggccggc tcctaggact gttacacatc ctgatatttc tgaactgttc    14220
tttcacgttc ggatacatga catacgtgca cttcaatcc actaaccgtg tcgcgcttac    14280 tatggggcg gtcgttgccc ttttgtgggg catttacagc tttatagaat catgaaagtt    14340
tgtcacttcc agatgcaggt tgtgttgcct aggccggcga tacattctgg cccctgccca    14400
ccacgtagaa agtgctgcag gcctccattc aatcccagcg tctggtaacc gagcatacgc    14460
tgtgagaaag cccggactaa catcagtgaa cggcactcta gtaccaggac ttcggagcct    14520
cgtgttgggc ggcaaacgag ctgttaaacg aggagtggtt aacctcgtca gtatggccg     14580 gtaaaaacca gagccagaag aaaaagaaaa acacagctcc tatggggagt ggccagccag    14640
tcaatcaact gtgccaattg ctgggcacaa tgataaagtc ccagcgccag cggcctaggg    14700
gaggacaggc caaaatgaaa aagcctgaga agccacattt cccccctagct gctgaagatg    14760 acatccggca ccatttccacc cagaccgagc gttcccttg cttgcaatcg atccagacgc    14820
ccttcaatca aggcgcagga actgcgtcgc tttcatccag cgggaaggtc agttttcagg    14880
ttgagttcat gctgccggtc gctcatacgg tgcgcctgat tcgcgtaact tccacatccg    14940
ccagtcaggg tgcaagttaa tttgatagtt aggtgaatgg ccgcgattgg cgtgtggcct    15000
ctgagtcacc tattcaatta gggcgatcac atggggtta gacttaattg gcgagaacca    15060
tgtgaccgaa attaaaaaaa aaaaaaaaa aaaaaaaaa a                          15101
```

<210> SEQ ID NO 35
<211> LENGTH: 15098
<212> TYPE: DNA
<213> ORGANISM: Porcine reproductive and respiratory syndrome virus

<400> SEQUENCE: 35

```
atgatgtgta gggtattccc cctacataca cgacactact agtgtttgtg taccttggag    60
gcgtgggtac agccccgccc caccccttgg ccctgttct agcccaacag gtatccttct    120
ctctcgggc gagtgtgccg cctgctgctc ccttgcagcg ggaaggacct cccgagtatt    180
cccgagagc acctgcttta cgggatctcc acccttaac catgtctggg acgttctccc    240
ggtgcatgtg caccccggct gctcgggtat tttggaacgc cggccaagtc tattgcacac    300
ggtgtctcag tgcgcggtct cttctccctc cggaacttca ggacattgac ctcgccgcaa    360
ttggcttgtt ttacaagcct aaagacaagc ttcactggaa agtccctatc ggcatccctc    420
aggtggagtg tactccatcc gggtgttgtt ggctctcagg cattttcccc ttagcgcgca    480
tgacctccgg caatcacaac ttcctacaac gacttgtgaa agttgccgat gtgttgtacc    540
gtgatggttc cttaacttct cgacaccttc gtgaactcca gtttacgag cgtggctgca    600
gctggtaccc aatcacgggg ccagtgcccg ggatgggttt gtacgcaaat tccatgcacg    660
tatctgacca gccgttccct ggtgccaccc atgtgttgac gaactcgcct ttgcctcaac    720
aagcttgtcg gcagccgttc tgcccatttg aggaggctca ttctagcgtg tacaggtgga    780
aaaaatttgt ggtcttcacg gactcctcca tgatgtggac gccggaatcc gatgattcag    840
ccgacctaga ggcgctaccg cctgagctag aacgtcaggt cgaaatcctc attcggagtt    900
ttcctgccca tcaccctgtc agcctggccg actgggagct cgctgagtcc cctgagaacg    960
gttttttcctt cagcacgtac cattctggtg gttatcttgt ccaaaacccc gacgtgtttg   1020
acagcaagtg ctggctctcc tgtttcttgg atcagccgat cgaagtgcgc ctctatgagg   1080
attatctggc taacgctttc ggttaccaaa ccaagtgggg cgtgtctggt aagtacctcc   1140
agcgcaggct tcaagtcaac ggtattcgtg ctgtaatcga tcctgatggc cccattcacg   1200
ttgaagcgct gtcttgcccc caatcttgga tcaggcacct gactctggac gatgacgtca   1260
cccccaggatt cgttcgccta acatccctcc gcattgtgcc gaacacagag cccactactc   1320
tccgaatctt tcggtttgga gcgcataagt ggtatggcgc tgccggcaaa cgggctcgtg   1380
ccaagcgtgc cgctaaaagt gagaagggtc cggctcccac tcccaaggtt gccccgccag   1440
cccccacctg cggaattgtt acctactctc caccaacaga cgggtcttgc ggttggcacg   1500
tccttgccgc cataatgaac cgaatgatga acgtgactt catgtcccct ctggcccagt   1560
acaacagacc agaggatgat tgggcttctg attacgatct tgcccaggcg attcaatgtc   1620
tgcggttgcc tgctaccata gttcggaatc gtgcctgtcc caacgccaag tacctcataa   1680
aactcaacgg agtccactgg gaggtagagg tgaggtcagg gatggcccct cgctcccttc   1740
cccgcgagtg cgtagtcggc gtttgttccg aaggctgtgc cgcatcgcct acccagaaa   1800
acgggctacc taaacgagcg tttgaggcct tggcgtctgc ttacagacta ccttccgatt   1860
gtgtcagttc tggtattgct gactttcttg ctaacccccc tcaggaattc tggactcttg   1920
acaaaatgtt gacctccccg tcaccggagc ggtctggttt ttccagtctg tacaaattgc   1980
tattagaggt tgtcccgcag aaatgcggag ccacggaagg ggctttcacc tatgctgttg   2040
agagaatgct gaaggattgc ccgagctccg aacaggccat ggcccttctg gcaaaaatta   2100
aagttccatc ctcaaaggcc ccgtctgtgt ccctggacga gtgtttccct acggatgttt   2160
cagccgattt cgaaccagca tctcaggaga ggtcccaaaa ttccagcgct gctgttgtcc   2220
tgcattcacc gaatgcaaaa gagttcgagg aagcagctcc aggggaagtt caggagggtg   2280
gccacaaggc cgtccactct gcactccctg ccggggtcc taacaataag caggcacagc   2340
```

```
tggttgccgg tgagcaactg aagctcggcg gttgtggttc ggtagttggg aatgcacatg    2400
aaggtgttct ggtcccacct ggtccaatta atttgacaag cggggattta ccctcctcag    2460
gctccatgaa agaagatatg ctcaatagcc gggaggacga accactggat ttgtcccaac    2520
cagcaacagc tgtcacaacg actcttatgg gagagctaac acccgactac ctaggttctg    2580
atactggtgc cctccccgtc accgtccgaa aatttgtccc gacggggcct atactccgtc    2640
atgttgagca ctgcagcacg gggtcgggcg atagcagttc gcctttggat ctgtctggtg    2700
cgcaaacccc ggaccagcct ttaaatctgt ccctggcggc ttggccagtg aggaccaccg    2760
cgtctgatcc tggctgggtc cacggtagac gcgagcctgt ctttgtaaag cctcgagatg    2820
ttttctctga tggcgattca gcccttcagt tcggggagct ttctgaatcc agctctgtca    2880
tcgagtttga tcgggcaaaa gatgctcagg tggctgacgc ccctgtcggt ctgacgactt    2940
cggacgaggc cctctccgca gtcgatcctt tcgagttttc cgaactcaag cgcccacgtt    3000
tctccgcaca agccttaatt gaccgaggcg gcccacttgc cgatgtccat gcaaaaataa    3060
agaaccgggt atatgaacag tgcctccaag cttgtgagcc cggtagtcgc gcaacccag    3120 ctaccaggga gtggctcgac aaaatgtggg agagagtgga catgaaaacc tggcgctgca    3180
cctcacagtt ccaagctggt cacattcttg cgtccctcaa attcctccct gacatgattc    3240
aagacacacc gcctcctgtt cccaggaaga accgagccag tgataaagct ggcctgaaac    3300
aactagtggc acagtgggat aggagattga gttcaacccc cccccaaaa ccggttgggc    3360 cggtacttga ccgggtcgat cctccgccta cgggtacccg gcaagaagac gtcaccccct    3420
ccgatgggcc accccatgcg ccggatggtc gagtgagtac gggtgggagt tggaaaggcc    3480
ttatgctttc cggcacccgt ctcacggggt ccatcagtca tcgcctcatg acatgggttt    3540
ttgaagttgt ctcccatctc ccagctttta tgctcacact tttctcgccg cggggctcta    3600
tggctccagg cgattgggtt tttgcaggtg ttgttttact tgctctcctg ctctgtcgtt    3660
cttacccaat attcgggtgc cttcccttat tgggtgtctt ttctggtact gtgcggcgtg    3720
ttcgtctggg tgttttttggc tcttggatgg cttttgctgt attttttattc tcgactccat    3780 ccaacccagt cggttcttct tgtaaccacg attcgccgga gtgtcatgct gagcttctgg    3840
ctcttgagca gcgccaactt tgggaacctg tgcgcggcct tgtggtcggc ccatcgggcc    3900
tcttatgtgt cattcttggc aagttactcg gtgggtcacg ttatctctgg catgttctcc    3960
tacgtctatg cctgcttgca gatttggccc tttctcttgt ttatgtggtg tcccaggggc    4020
gttgtcacaa gtgttgggga agtgtataa ggacagctcc tgctgaggtg gcttttaatg    4080
tatttccttt ctcgcgcgcc acccgtagtt ctcttgtatc cttatgtgat cgattccaaa    4140
cgccaaaagg agttgatccc gtgcacttgg cgacaggttg gcgcgggtgc tggcgtggtg    4200
agagtcctat ccatcaacca caccaaaagc ccatagctta cgccaatttg gatgaaaaga    4260
agatatctgc ccaaacggtt gttgctgtcc catacgatcc caatcaggct atcaaatgtc    4320
tgaaagttct gcaggcggga ggggctatcg tggatcagcc tacgcctgag gtcgttcgtg    4380
tgtccgagat ccccttctca gccccatttt tcccaaaagt tccagtcaac ccagattgta    4440
gggtcgtggt ggattcggac acttttgtgg ctgcggttcg ttgtggttat tcgacatcac    4500
aactggtcct gggccagggc aactttgcca agttaaatca aaccccccc aggaactcta    4560 tctccaccaa agcgactggt ggggcctctt atactttgc tgtggctcaa gtgtctgtgt    4620 ggaccccttgt tcatttcgtc ctcggtcttt ggctcacgtc acctcaagtg tgtggtcgag    4680
gaaccgctga cccatggtgt tcaagtccat tttcatatcc tacctatggc cccggggttg    4740
```

```
tgtgctcctc tcgactttgt gtgtctgctg acggggtcac ccttccattg ttctcagccg    4800
tggcacaact ctctggtagg gaggtgggga ttttattt agtgctcgtc tcctttattg      4860
ccttggccca ccgcatggct cttaaggcag acatgttagt agtcttttg gctctttgtg     4920 cttatgcctg gcccatgagc tcctggttga tctgcttctt tcctatactc ttgaggtggg    4980
ttacccttca ccctctcact atgctttggg tgcattcatt cttgatgttt tgtctcccag    5040
cagccggcgt cctctcactg gggataactg gcctcctctg gcaatcggc cgctttactc     5100 aggttgccgg aatcattaca ccttatgata tccaccagta cacctctggg ccacgtggtg    5160
cagccgctgt ggcacagcc ccagaaggca cttacatggc cgccgtccgg agagctgctt     5220
taaccgggcg gactttaatc ttcaccccgt ccgcagttgg atcccttctc gaaggtgctt    5280
tcaggactca taaaccctgc cttaacaccg tgaatgtcgt aggctcctcc cttggttccg    5340
gaggggtttt caccattgac ggaaaaaaaa ttgtcgtcac tgctgcccat gtgctgaacg    5400
gcgacacagc tagagtcacc ggtgattcct acaaccgcat gcacactttc aagactaatg    5460
gtgactatgc ctggtcccat gctgataact ggcagggcgc tgcccctgtg gtcaaggttg    5520
cgaaagggta tcgcggtcgt gcctactggc aaacatcaac tggtgtcgag cctggtgtta    5580
ttgggaatgg gttcgccttc tgtttcacca actgcggcga ttcggggtca cccgttatct    5640
cagaatctgg tgatcttatc ggaatccaca ccggttcaaa caaacttggt tctggtcttg    5700
tgacaacccc tgaagggag acctgtacca tcagagaaac caagctttct gacctttcca    5760
gacatttcgc aggcccaagc gttcctcttg gggacatcaa attgagtccg gccatcatcc    5820
ctgatgtgac atccattccg agtgacttgg catcgctcct agcttccgtc cctgtaatgg    5880
aaggcggcct ctcgaccgtt caactttgt gtgtctttt cctcctctgg cgcatgatgg      5940
gccatgcctg gacgcccatt gttgccgtgg gcttcttttt gctgaatgaa attcttccag    6000 cagtttggt tcgagccgtg ttttcttttg cactctttgt gcttgcatgg gccaccccct     6060
ggtctgcaca agtgttgatg attagacttc tcacggcatc tctcaaccgc aacaaacttt    6120
ctcttgcgtt ctacgcactc ggaggtgttg ttggtttggc tgctgaaatc gggactttg     6180 ctggtaaatt gtctgaattg tctcaagctc tttcgacata ctgtttctta cctagggtcc    6240
ttgctatgac cagctgtgtt cccatcatca tcattggtgg actccatgcc ctcggtgtga    6300
ttctgtggtt attcaaatac cggtgcctcc acaacatgct ggttggtgat ggaagctttt    6360
caagcgcttt cttcctacgg tattttgcag agggcaatct caggagaggt gtttcacagt    6420
cctgtggcat gagtaacgag tccctgacgg ctgctttggc ttgcaagttg tcacaggctc    6480
accttgattt tttgtccagc ttaacgaact tcaagtgctt tgtatctgct tcaaacatga    6540
aaaatgctgc cggccagtac attgaagcag cttatgccag ggccctgcgt caagagttgg    6600
cctctttagt ccagattgac aaaatgaaag gagttttgtc caagctagag gcctttgctg    6660
aaacggccac tccgtccctc gacgtaggtg acgtgattgt tctacttgga caacatcctc    6720
acggatccgt tctcgatatt aatgtgggga ctgaaaggaa aactgtatcc gtgcaagaga    6780
cccggagcct aggcggctcc aagttcagtg tttgtactgt tgtgtcaaac acaccgtgg     6840 acgccttagc cggtattcca ctccagacac caacccccct tttcgagaat ggcccgcgtc    6900
atcgcagcga ggaggacgat cttaaagtcg agaggatgaa gaaacactgc gtgtccctcg    6960
gcttccacaa cattaacggt aaagtttact gcaagatttg ggacaagtct accggtgacg    7020
ccttttacac tgatgattcc cggtacaccc aagactatgc ttttcaggac aggtcagctg    7080
```

```
actatagaga cagggactac gagggtgtgc aaaccgcccc ccaacaggga tttgatccaa    7140
agtctgaaac ccctgttggt accgttgtga tcggcggtat tacgtacaac aggtatttgg    7200
tcaaaggtaa ggaggttctg gttcccaagc ctgacaactg ccttgaagct gccaagctgt    7260
cccttgagca agctctcgct gggatgggcc aaacttgtga ccttacagct gccgaggtgg    7320
aaaagctaaa gcgcatcatt ggtcaacttc aaggattgac cactgagcag gctttaaact    7380
gttagccgcc agcggcttga cccgctgtgg ccgcggcggc ctagttgtaa ctgaaacggc    7440
ggtaaaaatt gtcaaatacc acagcagaac ttttaccttta ggctctttag acctaaaagt    7500
cacttccgag gtggaggtga agaagtcaac cgagcagggc cacgctgttg tggcaaactt    7560
gtgttctggt gtcgtcttga tgagacctca cccaccgtcc cttgtcgacg ttcttctgaa    7620
acccggactt gacataacac ccggcattca accagggcat ggggccggga atatgggcgt    7680
ggacggttcc atttgggatt ttgaaaccgc acccacaaag gctgaactcg agttatccaa    7740
gcaaataatt caagcatgtg aagtcaggcg cggggatgcc ccgaacctcc agctcccta    7800 caagctctat cctgttagag gggatcctga gcggcataaa ggccacctca tcaataccag    7860
gtttggagac ttaccttaca aaactcctca agacaccaag tccgcaatcc acgcggcttg    7920
ttgcctgcac cccaacgggg ccccgtgtc tgatggtaaa tccacactag gtaccactct    7980
tcaacatggc ttcgagcttt atgtccctac tgtgccctat agtgtcatgg agtaccttga    8040
ttcacgccca gacaccccttt ttatgtgcac taaacacggc acttccaagg ctgctgcaga    8100
ggacctccaa aaatacgacc tatccaccca aggatttgtc ctgcctgggg tcctacgcct    8160
agtgcgcagg ttcatctttg gccacattgg caaggcaccg ccattgttcc tcccatcaac    8220
ttatcccgcc aagaactcca tggcaggtat taatggtcag aggttcccaa caaaggatgt    8280
tcaaagtata cctgaaattg atgaaatgtg tgcccgcgcc gtcaaggaga attggcaaac    8340
tgtgacacct tgcacccctca agaaacagta ttgttctagg cccaaaacca ggaccatcct    8400
gggcactaac aacttcatag ccttggctca tagatcggcg ctcagtggtg ttacccaggc    8460
attcatgaag aaggcttgga agtccccaat agccttaggg aaaaacaaat tcaaggagct    8520
gcattgcact gtcgctggca ggtgcctcga ggccgacttg gcttcctgtg accgcagcac    8580
ccctgccatt gtgaggtggt tcactaccca cctcctatat gaacttgcag gatgtgaaga    8640
atatctacct agctatgtgc ttaactgttg ccatgacctt gtggcgacgc aggatggtgc    8700
tttcacaaaa cgcggtggcc tgtcgtctgg agacccagtc accagtgtgt ccaacactgt    8760
gtactcactg gtgatttatg cccagcacat ggtactatct gccctgaaaa tgggtcatga    8820
aattggcctc aagttcctcg aagaacaact caaatttgag gaccttcttg aaatccagcc    8880
tatgttagta tactctgatg atcttgtctt gtacgcagaa aagcccacct tccccaacta    8940
tcattggtgg gtcgagcatc ttgacctgat gttgggcttt aaaacggacc aaagaaaac    9000 cgtcataact gataaaccca gtttcctcgg gtgcagaatc gaagcagggc gacagctagt    9060
ccccaatcgc gaccgcatcc tggctgctct tgcatatcac atgaaggcgc agaacgcctc    9120
agagtattat gcgtctgctg ccgcaatcct gatggattca tgtgcttgca ttgaccacga    9180
tcctgaatgg tatgaggacc tcatctgtgg cattgcccga tgcgctcgcc tggacggtta    9240 tagcttttcca ggtccggcat ttttcatgtc catgtgggag aagctgagga gtcataatga    9300
agggaagaaa ttccgccact gcggcatctg cgacgccaaa gccgactacg cggctgcttg    9360
tgggcttgat ttgtgtttgt ttcattcgca cttttcaccaa cactgccctg tcactctgag    9420
ctgcggtcac catgccggtt cgaaggaatg ttcgcagtgt cagtcacctg ttggggccgg    9480
```

```
cagatcccct cttgatgctg tgctggaaca aattccatac aaacctcctc gcactgtcat   9540
catgaaggtg ggtaataaaa caacggccct tgatccgggg aggtaccagt cccgtcgagg   9600
tctcgttgca gtcaagaggg gtattgcggg taatgaagtt gatcttgctg atggagatta   9660
ccaagtggta cctcttctgc cgacttgcaa agatataaac atggtgaagg tggcttgcaa   9720
cgtactactc agcaagttca tagtagggcc accaggttcc gggaagacca cctggctact   9780
aagtcaagtt caggacgatg atgtcattta cacacccact catcagacca tgtttgacat   9840
agttagtgct ctcaaagttt gcaggtattc cattccagga gcctcgggac tcccttcccc   9900
accgcctgcc aggtccgggc cgtgggttag gctcattgcc agcgggcacg tccctggccg   9960
agtatcatac ctcgatgagg ccggatattg caatcatctg gacattctta gactgctttc  10020
caaaacaccc cttgtgtgtt tgggtgacct tcagcaactt cacccagtcg gctttgattc  10080
ctattgttat gtgttcgatc agatgcctca gaagcagttg accaccattt acagatttgg  10140
ccccaacatc tgcgcagcca tccagccttg ttacagggag aaacttgaat ctaaggctag  10200
gaacaccagg gtggttttta ccacccggcc tgtggccttt ggccaggtgc tgacaccata  10260
tcacaaagat cgcgtcggct ccgcgattac catagactca tcccaggggg ccacctttga  10320
cattgtaaca ttgcatctac catcgccaaa gtccctaaat aagtcccggg cacttgtggc  10380
catcacacgg gcaagacacg ggttgttcat ttatgaccct cacaaccagc tccgggagtt  10440
tttcaaccta acccctgagc gcactgattg taaccttgtg ttcagccgtg gagatgagct  10500
ggtggtcctg aatgcagata atgcagtcac aaccgtggcg aaggccttag agacaggtcc  10560
aactcaattt cgagtgtcag acccgaggtg caagtctctc ttagccgctt gctcggccag  10620
tctggaaggg agctgcatgc cgctaccgca agtggcgcat aacctggggt tttacttctc  10680
cccagacagt ccagtatttg cacctctgcc aaaagagttg gcgccacatt ggccagtggt  10740
tacccatcag aataatcggg cgtggcctga tcgacttgtc gctagtatgc gtccaattga  10800
cgcccgctac agcaagccga tggtcggtgc agggtatgtg gtcggaccgt ccaccttcct  10860
tggtactcct ggagtggtgt catactatct cacactatac atcagggggtg agccccaggc  10920
cttgccagaa acacttgttt caacaggacg tatagccaca gattgtcggg agtatctcga  10980
cgcggctgag gaagaggcag caaaagaact tccccacgcg ttcattggcg atgtcaaagg  11040
caccacagtt gggggggtgtc atcacattac atcaaaatac ctaccctaggt ccctgcctaa  11100
agactctgtt gccgtagttg gagtaagttc gcctggcagg gctgctaaag ccgtatgcac  11160
cctcaccgat gtgtacctcc ctgaactccg gccatatctg caacctgaga cggcatcaaa  11220
atgctggaaa ctcaaattag acttcaggga cgtccgacta atggtctgga aaggagccac  11280
cgcctacttt caattggaag ggctcacatg gtcggcgctg cctgactatg ccaggtttat  11340
tcagctgccc aaaaacgctg ttgtatacat cgatccgtgc ataggaccgg caacagccaa  11400
tcgtaaagtc gtacgaacca cagattggcg ggccgacctg gcagtgacgc cgtatgatta  11460
cggtgcccgg aacattttga caacagcctg gttcgaggac ctcgggccgc agtggaagat  11520
tctggggttg cagccctttta ggcgggcgtt tggctttgaa aacactgagg attgggcaat  11580
ccttgcatgc tgcatgagtg acggcaagga ctacactgac tataactgga attgcgttcg  11640
acaacgccca cacgctatcc atggacgcgc tcgtgaccat acgtaccact ttgcccctgg  11700
cactgaattg caagtggagc tcggtaaacc ccggctgcca cctgagcaag taccgtgaat  11760
tcggagtgat gcaatggggt cactgtggag taaaatcagc cagctgttcg tggacgcctt  11820
```

```
cactgaattc cttgttagtg tggttgatat tgtcatcttc cttgccatat tgtttgggtt   11880
caccgtcgca ggatggttac tggtcttttct tctcagagtg gtttgctccg cgcttctccg   11940
ttcgcgctct gccattcact cttccgaact atcgaaggtc ctatgagggc ttactaccta   12000
attgcagacc ggatgttcca caatttgcat ttaagcaccc tttgggtatg ttttggcaca   12060
tgcgggtttc ccacctaatt gatcagatgg tctctcgccg catctaccag accatggaac   12120
attcaggtca agcggcctgg aagcacgtgg tcagtgaggc tactcttaca aaattgtcag   12180
aactcgacat agttctccac ttccaacacc tggccgcagt ggaggcggac tcttgtcgct   12240
tcctcagctc acgacttgtg atgctgaaaa atcttgccgt tggcaatgtg agcttgcagt   12300
acaacaccac gttgaaccgc gttgagctca tcctccccac accaggtacg aggcccaaat   12360
tgaccgattt cagacaatgg ctcatcagtg tgcacgcttc cattttttcc tctgtagcct   12420
catcagttac tttgttcata gtgctttggc ttcgaattcc agccgtacgc tatgttttg    12480 gtttccattg gcccatggca acacgtcatt cgagctgacc attaattaca ctatatgcat   12540
gccctgtctt accagccaag cggctcaaca aaggctcgaa cccggtcgta acatgtggtg   12600
caaaatagga cacaccacgt gcgaggagcg tgaccatgat gagttgtcaa tgtccatccc   12660
gtccgggtac gacaacctca aacttgaagg ttattacgct tggctggctt ttttgtcctt   12720
ttcctacgcg gcccaattcc atccggagtt gtttggaata gggaatgtgt cgcgcgtctt   12780
tgtggataaa cgacaccagt tcatttgtgc cgagcatgac ggagataatt caaccgtatc   12840
taccggacac aacatctccg catcatatgc ggcatattat caccaccaaa tagacggggg   12900
caattggttc catttggaat ggctgcggcc gctcttttcc tcttggctag tgctcaacat   12960
atcatggttt ctgaggcgtt cgcctgcaag ccctgtttct cgacgcatct atcagatatt   13020
aagaccaata cgaccgcggc tgccggtttc atggtccttc aagacatcag ttgcctccga   13080
cctcacaggg tctcagcatc gcaagagaac attcccttcg gaaagtcgtc acaatgtcgt   13140
gaagccgtcg gtactcccca gtacattacg atgactgcta atgtgaccga cgaatcatat   13200
ttgtacaacg cggacttgct aatgcttttcc gcgtgccttt tccacgcctc agaaatgagc   13260
gagaaaggct tcaaagttat cttttggaaac gtctccggcg ttgtttcagc ttgtgtcaat   13320
ttcacagatt atgtggccca tgtaacccaa catacccaac agcatcatct ggtaattgat   13380
cacattcggt tactgcattt cctgacacca tctgcaatga ggtgggctac aaccattgct   13440
tgtttgttcg ccattctctt agcgatatga gatgttctca caaattgggg cgtttcttga   13500
ctccgcactc ttgcttctgg tggctttttt tgctgtgtac cggcttgtcc tggtcctttg   13560
ccgatggcaa cggcaacagc tcgacacgcc aatacatata taacttgacg atatgcgagc   13620
tgaatgggac cgtctggttg tccagtcatt ttgattgggc agtcgagacc tttgtgcttt   13680
acccggtggc cactcatatc ctctcactgg gtttttctcac aacaagccat ttttttgatg   13740
cgctcggtct cggcgctgtg tccactacgg gatttcttgg cgggcggtat gtacttagca   13800
gcgtgtacgg cgcctgcgcc ttcgcagcgc ttgtatgttt tgtcatccgt gctgctaaaa   13860
attgcatggc ttgccgttat gcccgcaccc ggttcaccaa cttcatcgtg gacgaccggg   13920
ggaagatcca tcgatggaag tccccaatag tggtagagaa attaggcaaa gctgacatcg   13980
gcggcgacct tgtcaccatc aaacatgttg tcctcgaagg agtcaaagct caacctttga   14040
cgaggacatc ggcggagcaa tgggaagcct agatgatttt tgcaatgatc ctaccgccgc   14100
acagaagctt gtgctggcat ttagtatcac atacacacct ataatgatat acgccctcaa   14160
ggtgtcacgc ggccggctcc taggactgtt acacatcctg atatttctga actgttcttt   14220
```

-continued

```
cacgttcgga tacatgacat acgtgcactt tcaatccact aaccgtgtcg cgcttactat   14280
gggggcggtc gttgcccttt tgtggggcat ttacagcttt atagaatcat ggaagtttgt   14340
cacttccaga tgcaggttgt gttgcctagg ccggcgatac attctggccc ctgcccacca   14400
cgtagaaagt gctgcaggcc tccattcaat cccagcgtct ggtaaccgag catacgctgt   14460
gagaaagccc ggactaacat cagtgaacgg cactctagta ccaggacttc ggagcctcgt   14520
gttgggcggc aaacgagctg ttaaacgagg agtggttaac ctcgtcaagt atggccggta   14580
aaaaccagag ccagaagaaa agaaaaaaca cagctcctat ggggagtggc cagccagtca   14640
atcaactgtg ccaattgctg ggcacaatga taaagtccca gcgccagcgg cctaggggag   14700
gacaggccaa aatgaaaaag cctgagaagc cacatttccc cctagctgct gaagatgaca   14760
tccggcacca tttcacccag accgagcgtt cctttgctt gcaatcgatc cagacggcct   14820
tcaatcaagg cgcaggaact gcgtcgcttt catccagcgg gaaggtcagt tttcaggttg   14880
agttcatgct gccggtcgct catacggtgc gcctgattcg cgtaacttcc acatccgcca   14940
gtcagggtgc aagttaattt gatagttagg tgaatggccg cgattggcgt gtggcctctg   15000
agtcacctat tcaattaggg cgatcacatg ggggttagac ttaattggcg agaaccatgt   15060
gaccgaaatt aaaaaaaaaa aaaaaaaaaa aaaaaaaa                           15098
```

```
<210> SEQ ID NO 36
<211> LENGTH: 50
<212> TYPE: PRT
<213> ORGANISM: Porcine reproductive and respiratory syndrome virus
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (20)..(21)
<223> OTHER INFORMATION: Any amino acid
<220> FEATURE:
<221> NAME/KEY: MOD_RES
<222> LOCATION: (24)..(26)
<223> OTHER INFORMATION: Any amino acid
<220> FEATURE:
<221> NAME/KEY: MOD_RES
<222> LOCATION: (28)..(29)
<223> OTHER INFORMATION: Any amino acid
<220> FEATURE:
<221> NAME/KEY: MOD_RES
<222> LOCATION: (31)..(32)
<223> OTHER INFORMATION: Any amino acid
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (38)..(39)
```

```
<223> OTHER INFORMATION: Any amino acid
<220> FEATURE:
<221> NAME/KEY: MOD_RES
<222> LOCATION: (41)..(46)
<223> OTHER INFORMATION: Any amino acid
<220> FEATURE:
<221> NAME/KEY: MOD_RES
<222> LOCATION: (48)..(48)
<223> OTHER INFORMATION: Any amino acid

<400> SEQUENCE: 36

Ser Xaa Xaa Tyr Xaa Xaa Xaa Xaa Val Xaa Phe Xaa Asp Xaa Xaa
 1               5                   10                  15

Xaa Xaa Gly Xaa Xaa Met Trp Xaa Xaa Xaa Ser Xaa Xaa Ser Xaa Xaa
             20                  25                  30

Leu Glu Xaa Leu Pro Xaa Xaa Leu Xaa Xaa Xaa Xaa Xaa Xaa Leu Xaa
         35                  40                  45

Arg Ser
     50

<210> SEQ ID NO 37
<211> LENGTH: 49
<212> TYPE: PRT
<213> ORGANISM: Porcine reproductive and respiratory syndrome virus
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (23)..(25)
<223> OTHER INFORMATION: Any amino acid
<220> FEATURE:
<221> NAME/KEY: MOD_RES
<222> LOCATION: (27)..(28)
<223> OTHER INFORMATION: Any amino acid
<220> FEATURE:
<221> NAME/KEY: MOD_RES
<222> LOCATION: (30)..(31)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (37)..(38)
<223> OTHER INFORMATION: Any amino acid
<220> FEATURE:
<221> NAME/KEY: MOD_RES
<222> LOCATION: (40)..(45)
<223> OTHER INFORMATION: Any amino acid
<220> FEATURE:
<221> NAME/KEY: MOD_RES
```

```
<222> LOCATION: (47)..(47)
<223> OTHER INFORMATION: Any amino acid

<400> SEQUENCE: 37

Ser Xaa Xaa Tyr Xaa Xaa Xaa Xaa Val Xaa Phe Xaa Asp Xaa Xaa
1               5                   10                  15

Xaa Xaa Gly Xaa Met Trp Xaa Xaa Xaa Ser Xaa Xaa Ser Xaa Xaa Leu
            20                  25                  30

Glu Xaa Leu Pro Xaa Xaa Leu Xaa Xaa Xaa Xaa Xaa Xaa Leu Xaa Arg
        35                  40                  45

Ser

<210> SEQ ID NO 38
<211> LENGTH: 48
<212> TYPE: PRT
<213> ORGANISM: Porcine reproductive and respiratory syndrome virus
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(19)
<223> OTHER INFORMATION: Any amino acid
<220> FEATURE:
<221> NAME/KEY: MOD_RES
<222> LOCATION: (22)..(24)
<223> OTHER INFORMATION: Any amino acid
<220> FEATURE:
<221> NAME/KEY: MOD_RES
<222> LOCATION: (26)..(27)
<223> OTHER INFORMATION: Any amino acid
<220> FEATURE:
<221> NAME/KEY: MOD_RES
<222> LOCATION: (29)..(30)
<223> OTHER INFORMATION: Any amino acid
<220> FEATURE:
<221> NAME/KEY: MOD_RES
<222> LOCATION: (33)..(33)
<223> OTHER INFORMATION: Any amino acid
<220> FEATURE:
<221> NAME/KEY: MOD_RES
<222> LOCATION: (36)..(37)
<223> OTHER INFORMATION: Any amino acid
<220> FEATURE:
<221> NAME/KEY: MOD_RES
<222> LOCATION: (39)..(44)
<223> OTHER INFORMATION: Any amino acid
<220> FEATURE:
<221> NAME/KEY: MOD_RES
<222> LOCATION: (46)..(46)
<223> OTHER INFORMATION: Any amino acid

<400> SEQUENCE: 38

Ser Xaa Xaa Tyr Xaa Xaa Xaa Xaa Val Xaa Phe Xaa Asp Xaa Xaa
1               5                   10                  15

Xaa Xaa Xaa Met Trp Xaa Xaa Xaa Ser Xaa Xaa Ser Xaa Xaa Leu Glu
            20                  25                  30

Xaa Leu Pro Xaa Xaa Leu Xaa Xaa Xaa Xaa Xaa Xaa Leu Xaa Arg Ser
```

```
              35                  40                  45

<210> SEQ ID NO 39
<211> LENGTH: 47
<212> TYPE: PRT
<213> ORGANISM: Porcine reproductive and respiratory syndrome virus
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (21)..(23)
<223> OTHER INFORMATION: Any amino acid
<220> FEATURE:
<221> NAME/KEY: MOD_RES
<222> LOCATION: (25)..(26)
<223> OTHER INFORMATION: Any amino acid
<220> FEATURE:
<221> NAME/KEY: MOD_RES
<222> LOCATION: (28)..(29)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FE

```
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(17)
<223> OTHER INFORMATION: Any amino acid
<220> FEATURE:
<221> NAME/KEY: MOD_RES
<222> LOCATION: (20)..(22)
<223> OTHER INFORMATION: Any amino acid
<220> FEATURE:
<221> NAME/KEY: MOD_RES
<222> LOCATION: (24)..(25)
<223> OTHER INFORMATION: Any amino acid
<220> FEATURE:
<221> NAME/KEY: MOD_RES
<222> LOCATION: (27)..(28)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (34)..(35)
<223> OTHER INFORMATION: Any amino acid
<220> FEATURE:
<221> NAME/KEY: MOD_RES
<222> LOCATION: (37)..(42)
<223> OTHER INFORMATION: Any amino acid
<220> FEATURE:
<221> NAME/KEY: MOD_RES
<222> LOCATION: (44)..(44)
<223> OTHER INFORMATION: Any amino acid

<400> SEQUENCE: 40

Ser Xaa Xaa Tyr Xaa Xaa Xaa Xaa Xaa Val Xaa Phe Xaa Asp Xaa Xaa
1               5                   10                  15

Xaa Met Trp Xaa Xaa Xaa Ser Xaa Xaa Ser Xaa Xaa Leu Glu Xaa Leu
            20                  25                  30

Pro Xaa Xaa Leu Xaa Xaa Xaa Xaa Xaa Xaa Leu Xaa Arg Ser
        35                  40                  45

<210> SEQ ID NO 41
<211> LENGTH: 45
<212> TYPE: PRT
<213> ORGANISM: Porcine reproductive and respiratory syndrome virus
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(16)
<223> OTHER INFORMATION: Any amino acid
<220> FEATURE:
```

```
<221> NAME/KEY: MOD_RES
<222> LOCATION: (19)..(21)
<223> OTHER INFORMATION: Any amino acid
<220> FEATURE:
<221> NAME/KEY: MOD_RES
<222> LOCATION: (23)..(24)
<223> OTHER INFORMATION: Any amino acid
<220> FEATURE:
<221> NAME/KEY: MOD_RES
<222> LOCATION: (26)..(27)
<223> OTHER INFORMATION: Any amino acid
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (33)..(34)
<223> OTHER INFORMATION: Any amino acid
<220> FEATURE:
<221> NAME/KEY: MOD_RES
<222> LOCATION: (36)..(41)
<223> OTHER INFORMATION: Any amino acid
<220> FEATURE:
<221> NAME/KEY: MOD_RES
<222> LOCATION: (43)..(43)
<223> OTHER INFORMATION: Any amino acid

<400> SEQUENCE: 41

Ser Xaa Xaa Tyr Xaa Xaa Xaa Xaa Val Xaa Phe Xaa Asp Xaa Xaa
1               5                   10                  15

Met Trp Xaa Xaa Xaa Ser Xaa Xaa Ser Xaa Xaa Leu Glu Xaa Leu Pro
            20                  25                  30

Xaa Xaa Leu Xaa Xaa Xaa Xaa Xaa Xaa Leu Xaa Arg Ser
        35                  40                  45

<210> SEQ ID NO 42
<211> LENGTH: 46
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (16)..(19)
<223> OTHER INFORMATION: Any amino acid
<220> FEATURE:
<221> NAME/KEY: MOD_RES
<222> LOCATION: (25)..(28)
<223> OTHER INFORMATION: Any amino acid
<220> FEATURE:
<221> NAME/KEY: MOD_RES
<222> LOCATION: (30)..(35)
<223> OTHER INFORMATION: Any amino acid
<220> FEATURE:
<221> NAME/KEY: MOD_RES
<222> LOCATION: (37)..(37)
<223> OTHER INFORMATION: Any amino acid
<220> FEATURE:
<221> NAME/KEY: MOD_RES
<222> LOCATION: (39)..(39)
<223> OTHER INFORMATION: Any amino acid
<220> FEATURE:
<221> NAME/KEY: MOD_RES
<222> LOCATION: (41)..(45)
```

-continued

```
<223> OTHER INFORMATION: Any amino acid

<400> SEQUENCE: 42

Ala Xaa Val Tyr Asp Ile Gly Xaa Xaa Ala Val Met Xaa Val Ala Xaa
1               5                   10                  15

Xaa Xaa Xaa Ser Trp Ala Gly Gly Xaa Xaa Xaa Xaa Phe Xaa Xaa Xaa
            20                  25                  30

Xaa Xaa Xaa Leu Xaa Leu Xaa Ala Xaa Xaa Xaa Xaa Xaa Ser
        35                  40                  45

<210> SEQ ID NO 43
<211> LENGTH: 45
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (16)..(19)
<223> OTHER INFORMATION: Any amino acid
<220> FEATURE:
<221> NAME/KEY: MOD_RES
<222> LOCATION: (24)..(27)
<223> OTHER INFORMATION: Any amino acid
<220> FEATURE:
<221> NAME/KEY: MOD_RES
<222> LOCATION: (29)..(34)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (40)..(44)
<223> OTHER INFORMATION: Any amino acid

<400> SEQUENCE: 43

Ala Xaa Val Tyr Asp Ile Gly Xaa Xaa Ala Val Met Xaa Val Ala Xaa
1               5                   10                  15

Xaa Xaa Xaa Ser Trp Gly Gly Xaa Xaa Xaa Phe Xaa Xaa Xaa Xaa
            20                  25                  30

Xaa Xaa Leu Xaa Leu Xaa Ala Xaa Xaa Xaa Xaa Xaa Ser
        35                  40                  45

<210> SEQ ID NO 44
<211> LENGTH: 44
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (8)..(9)
<223> OTHER INFORMATION: Any amino acid
```

-continued

```
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (16)..(19)
<223> OTHER INFORMATION: Any amino acid
<220> FEATURE:
<221> NAME/KEY: MOD_RES
<222> LOCATION: (23)..(26)
<223> OTHER INFORMATION: Any amino acid
<220> FEATURE:
<221> NAME/KEY: MOD_RES
<222> LOCATION: (28)..(33)
<223> OTHER INFORMATION: Any amino acid
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (37)..(37)
<223> OTHER INFORMATION: Any amino acid
<220> FEATURE:
<221> NAME/KEY: MOD_RES
<222> LOCATION: (39)..(43)
<223> OTHER INFORMATION: Any amino acid

<400> SEQUENCE: 44

Ala Xaa Val Tyr Asp Ile Gly Xaa Xaa Ala Val Met Xaa Val Ala Xaa
 1               5                  10                  15

Xaa Xaa Xaa Ser Gly Gly Xaa Xaa Xaa Xaa Phe Xaa Xaa Xaa Xaa Xaa
                20                  25                  30

Xaa Leu Xaa Leu Xaa Ala Xaa Xaa Xaa Xaa Xaa Ser
            35                  40

<210> SEQ ID NO 45
<211> LENGTH: 43
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (16)..(19)
<223> OTHER INFORMATION: Any amino acid
<220> FEATURE:
<221> NAME/KEY: MOD_RES
<222> LOCATION: (22)..(25)
<223> OTHER INFORMATION: Any amino acid
<220> FEATURE:
<221> NAME/KEY: MOD_RES
<222> LOCATION: (27)..(32)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
```

```
<222> LOCATION: (38)..(42)
<223> OTHER INFORMATION: Any amino acid

<400> SEQUENCE: 45

Ala Xaa Val Tyr Asp Ile Gly Xaa Xaa Ala Val Met Xaa Val Ala Xaa
1               5                   10                  15

Xaa Xaa Xaa Gly Gly Xaa Xaa Xaa Phe Xaa Xaa Xaa Xaa Xaa
            20                  25                  30

Leu Xaa Leu Xaa Ala Xaa Xaa Xaa Xaa Xaa Ser
        35                  40

<210> SEQ ID NO 46
<211> LENGTH: 42
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (16)..(18)
<223> OTHER INFORMATION: Any amino acid
<220> FEATURE:
<221> NAME/KEY: MOD_RES
<222> LOCATION: (21)..(24)
<223> OTHER INFORMATION: Any amino acid
<220> FEATURE:
<221> NAME/KEY: MOD_RES
<222> LOCATION: (26)..(31)
<223> OTHER INFORMATION: Any amino acid
<220> FEATURE:
<221> NAME/KEY: MOD_RES
<222> LOCATION: (33)..(33)
<223> OTHER INFORMATION: Any amino acid
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (37)..(41)
<223> OTHER INFORMATION: Any amino acid

<400> SEQUENCE: 46

Ala Xaa Val Tyr Asp Ile Gly Xaa Xaa Ala Val Met Xaa Val Ala Xaa
1               5                   10                  15

Xaa Xaa Gly Gly Xaa Xaa Xaa Xaa Phe Xaa Xaa Xaa Xaa Xaa Xaa Leu
            20                  25                  30

Xaa Leu Xaa Ala Xaa Xaa Xaa Xaa Xaa Ser
        35                  40

<210> SEQ ID NO 47
<211> LENGTH: 41
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (8)..(9)
```

```
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (16)..(17)
<223> OTHER INFORMATION: Any amino acid
<220> FEATURE:
<221> NAME/KEY: MOD_RES
<222> LOCATION: (20)..(23)
<223> OTHER INFORMATION: Any amino acid
<220> FEATURE:
<221> NAME/KEY: MOD_RES
<222> LOCATION: (25)..(30)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (36)..(40)
<223> OTHER INFORMATION: Any amino acid

<400> SEQUENCE: 47

Ala Xaa Val Tyr Asp Ile Gly Xaa Xaa Ala Val Met Xaa Val Ala Xaa
1               5                   10                  15

Xaa Gly Gly Xaa Xaa Xaa Xaa Phe Xaa Xaa Xaa Xaa Xaa Xaa Leu Xaa
            20                  25                  30

Leu Xaa Ala Xaa Xaa Xaa Xaa Xaa Ser
        35                  40

<210> SEQ ID NO 48
<211> LENGTH: 50
<212> TYPE: PRT
<213> ORGANISM: Porcine reproductive and respiratory syndrome virus
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (35)..(35)
<223> OTHER INFORMATION: Any amino acid

<400> SEQUENCE: 48

Ser Ser Val Tyr Arg Trp Lys Lys Phe Val Val Phe Thr Asp Ser Ser
1               5                   10                  15

Xaa Asn Gly Arg Met Met Trp Thr Pro Glu Ser Asp Asp Ser Ala Xaa
            20                  25                  30

Leu Glu Xaa Leu Pro Pro Glu Leu Glu Arg Gln Val Glu Ile Leu Ile
        35                  40                  45

Arg Ser
    50

<210> SEQ ID NO 49
<211> LENGTH: 49
<212> TYPE: PRT
<213> ORGANISM: Porcine reproductive and respiratory syndrome virus
<220> FEATURE:
```

<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (34)..(34)
<223> OTHER INFORMATION: Any amino acid

<400> SEQUENCE: 49

Ser Ser Val Tyr Arg Trp Lys Lys Phe Val Val Phe Thr Asp Ser Ser
1               5                   10                  15

Xaa Asn Gly Met Met Trp Thr Pro Glu Ser Asp Asp Ser Ala Xaa Leu
            20                  25                  30

Glu Xaa Leu Pro Pro Glu Leu Glu Arg Gln Val Glu Ile Leu Ile Arg
        35                  40                  45

Ser

<210> SEQ ID NO 50
<211> LENGTH: 48
<212> TYPE: PRT
<213> ORGANISM: Porcine reproductive and respiratory syndrome virus
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (33)..(33)
<223> OTHER INFORMATION: Any amino acid

<400> SEQUENCE: 50

Ser Ser Val Tyr Arg Trp Lys Lys Phe Val Val Phe Thr Asp Ser Ser
1               5                   10                  15

Xaa Asn Met Met Trp Thr Pro Glu Ser Asp Asp Ser Ala Xaa Leu Glu
            20                  25                  30

Xaa Leu Pro Pro Glu Leu Glu Arg Gln Val Glu Ile Leu Ile Arg Ser
        35                  40                  45

<210> SEQ ID NO 51
<211> LENGTH: 47
<212> TYPE: PRT
<213> ORGANISM: Porcine reproductive and respiratory syndrome virus
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (29)..(29)
<223> OTHER INFORMATION: Any amino acid
<220> FEATURE:
<221> NAME/KEY: MOD_RES
<222> LOCATION: (32)..(32)
<223> OTHER INFORMATION: Any amino acid

<400> SEQUENCE: 51

Ser Ser Val Tyr Arg Trp Lys Lys Phe Val Val Phe Thr Asp Ser Ser
1               5                   10                  15

Xaa Met Met Trp Thr Pro Glu Ser Asp Asp Ser Ala Xaa Leu Glu Xaa
            20                  25                  30

```
Leu Pro Pro Glu Leu Glu Arg Gln Val Glu Ile Leu Ile Arg Ser
        35                  40                  45

<210> SEQ ID NO 52
<211> LENGTH: 46
<212> TYPE: PRT
<213> ORGANISM: Porcine reproductive and respiratory syndrome virus
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (31)..(31)
<223> OTHER INFORMATION: Any amino acid

<400> SEQUENCE: 52

Ser Ser Val Tyr Arg Trp Lys Lys Phe Val Val Phe Thr Asp Ser Ser
1               5                   10                  15

Met Met Trp Thr Pro Glu Ser Asp Asp Ser Ala Xaa Leu Glu Xaa Leu
            20                  25                  30

Pro Pro Glu Leu Glu Arg Gln Val Glu Ile Leu Ile Arg Ser
        35                  40                  45

<210> SEQ ID NO 53
<211> LENGTH: 45
<212> TYPE: PRT
<213> ORGANISM: Porcine reproductive and respiratory syndrome virus
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (30)..(30)
<223> OTHER INFORMATION: Any amino acid

<400> SEQUENCE: 53

Ser Ser Val Tyr Arg Trp Lys Lys Phe Val Val Phe Thr Asp Ser Met
1               5                   10                  15

Met Trp Thr Pro Glu Ser Asp Asp Ser Ala Xaa Leu Glu Xaa Leu Pro
            20                  25                  30

Pro Glu Leu Glu Arg Gln Val Glu Ile Leu Ile Arg Ser
        35                  40                  45

<210> SEQ ID NO 54
<211> LENGTH: 46
<212> TYPE: PRT
<213> ORGANISM: Porcine reproductive and respiratory syndrome virus
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (16)..(17)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (34)..(34)
<223> OTHER INFORMATION: Any amino acid
```

```
<220> FEATURE:
<221> NAME/KEY: MOD_RES
<222> LOCATION: (39)..(39)
<223> OTHER INFORMATION: Any amino acid
<220> FEATURE:
<221> NAME/KEY: MOD_RES
<222> LOCATION: (44)..(44)
<223> OTHER INFORMATION: Any amino acid

<400> SEQUENCE: 54

Ala Thr Val Tyr Asp Ile Gly Xaa Xaa Ala Val Met Tyr Val Ala Xaa
1               5                   10                  15

Xaa Lys Val Ser Trp Ala Gly Gly Xaa Glu Val Lys Phe Glu Xaa Val
            20                  25                  30

Pro Xaa Glu Leu Lys Leu Xaa Ala Asn Arg Leu Xaa Thr Ser
        35                  40                  45

<210> SEQ ID NO 55
<211> LENGTH: 45
<212> TYPE: PRT
<213> ORGANISM: Porcine reproductive and respiratory syndrome virus
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (16)..(17)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (33)..(33)
<223> OTHER INFORMATION: Any amino acid
<220> FEATURE:
<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (43)..(43)
<223> OTHER INFORMATION: Any amino acid

<400> SEQUENCE: 55

Ala Thr Val Tyr Asp Ile Gly Xaa Xaa Ala Val Met Tyr Val Ala Xaa
1               5                   10                  15

Xaa Lys Val Ser Trp Gly Gly Xaa Glu Val Lys Phe Glu Xaa Val Pro
            20                  25                  30

Xaa Glu Leu Lys Leu Xaa Ala Asn Arg Leu Xaa Thr Ser
        35                  40                  45

<210> SEQ ID NO 56
<211> LENGTH: 44
<212> TYPE: PRT
<213> ORGANISM: Porcine reproductive and respiratory syndrome virus
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (16)..(17)
<223> OTHER INFORMATION: Any amino acid
<220> FEATURE:
```

```
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (29)..(29)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (37)..(37)
<223> OTHER INFORMATION: Any amino acid
<220> FEATURE:
<221> NAME/KEY: MOD_RES
<222> LOCATION: (42)..(42)
<223> OTHER INFORMATION: Any amino acid

<400> SEQUENCE: 56

Ala Thr Val Tyr Asp Ile Gly Xaa Xaa Ala Val Met Tyr Val Ala Xaa
1               5                   10                  15

Xaa Lys Val Ser Gly Gly Xaa Glu Val Lys Phe Glu Xaa Val Pro Xaa
            20                  25                  30

Glu Leu Lys Leu Xaa Ala Asn Arg Leu Xaa Thr Ser
        35                  40

<210> SEQ ID NO 57
<211> LENGTH: 43
<212> TYPE: PRT
<213> ORGANISM: Porcine reproductive and respiratory syndrome virus
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (16)..(17)
<223> OTHER INFORMATION: Any amino acid
<220> FEATURE:
<221> NAME/KEY: MOD_RES
<222> LOCATION: (22)..(22)
<223> OTHER INFORMATION: Any amino acid
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (41)..(41)
<223> OTHER INFORMATION: Any amino acid

<400> SEQUENCE: 57

Ala Thr Val Tyr Asp Ile Gly Xaa Xaa Ala Val Met Tyr Val Ala Xaa
1               5                   10                  15

Xaa Lys Val Gly Gly Xaa Glu Val Lys Phe Glu Xaa Val Pro Xaa Glu
            20                  25                  30

Leu Lys Leu Xaa Ala Asn Arg Leu Xaa Thr Ser
        35                  40

<210> SEQ ID NO 58
<211> LENGTH: 42
```

```
<212> TYPE: PRT
<213> ORGANISM: Porcine reproductive and respiratory syndrome virus
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (16)..(17)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (40)..(40)
<223> OTHER INFORMATION: Any amino acid

<400> SEQUENCE: 58

Ala Thr Val Tyr Asp Ile Gly Xaa Xaa Ala Val Met Tyr Val Ala Xaa
1               5                   10                  15

Xaa Lys Gly Gly Xaa Glu Val Lys Phe Glu Xaa Val Pro Xaa Glu Leu
            20                  25                  30

Lys Leu Xaa Ala Asn Arg Leu Xaa Thr Ser
        35                  40

<210> SEQ ID NO 59
<211> LENGTH: 41
<212> TYPE: PRT
<213> ORGANISM: Porcine reproductive and respiratory syndrome virus
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (16)..(17)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (29)..(29)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (39)..(39)
<223> OTHER INFORMATION: Any amino acid

<400> SEQUENCE: 59

Ala Thr Val Tyr Asp Ile Gly Xaa Xaa Ala Val Met Tyr Val Ala Xaa
```

```
                1               5                  10                  15
Xaa Gly Gly Xaa Glu Val Lys Phe Glu Xaa Val Pro Xaa Glu Leu Lys
            20                  25                  30
Leu Xaa Ala Asn Arg Leu Xaa Thr Ser
        35                  40
```

<210> SEQ ID NO 60
<211> LENGTH: 4
<212> TYPE: PRT
<213> ORGANISM: Porcine reproductive and respiratory syndrome virus
<220> FEATURE:
<221> NAME/KEY: MOD_RES
<222> LOCATION: (2)..(3)
<223> OTHER INFORMATION: Any amino acid

<400> SEQUENCE: 60

Ser Xaa Xaa Tyr
1

<210> SEQ ID NO 61
<211> LENGTH: 4
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any amino acid

<400> SEQUENCE: 61

Ala Xaa Val Tyr
1

<210> SEQ ID NO 62
<211> LENGTH: 3
<212> TYPE: PRT
<213> ORGANISM: Porcine reproductive and respiratory syndrome virus

<400> SEQUENCE: 62

Ser Phe Pro
1

<210> SEQ ID NO 63
<211> LENGTH: 4
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any amino acid

<400> SEQUENCE: 63

Arg Xaa Met Trp
1

<210> SEQ ID NO 64
<211> LENGTH: 3
<212> TYPE: PRT
<213> ORGANISM: Porcine reproductive and respiratory syndrome virus

<400> SEQUENCE: 64

Arg Gly Gly
1

<210> SEQ ID NO 65
<211> LENGTH: 3
<212> TYPE: PRT

```
<213> ORGANISM: Porcine reproductive and respiratory syndrome virus

<400> SEQUENCE: 65

Arg Met Met
1

<210> SEQ ID NO 66
<211> LENGTH: 3
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any amino acid

<400> SEQUENCE: 66

Arg Xaa Arg
1

<210> SEQ ID NO 67
<211> LENGTH: 3
<212> TYPE: PRT
<213> ORGANISM: Porcine reproductive and respiratory syndrome virus

<400> SEQUENCE: 67

Ala Pro Arg
1

<210> SEQ ID NO 68
<211> LENGTH: 4
<212> TYPE: PRT
<213> ORGANISM: Porcine reproductive and respiratory syndrome virus
<220> FEATURE:
<221> NAME/KEY: MOD_RES
<222> LOCATION: (3)..(3)
<223> OTHER INFORMATION: Any amino acid

<400> SEQUENCE: 68

Gly Arg Xaa Arg
1

<210> SEQ ID NO 69
<211> LENGTH: 4
<212> TYPE: PRT
<213> ORGANISM: Porcine reproductive and respiratory syndrome virus

<400> SEQUENCE: 69

Trp Ala Pro Arg
1

<210> SEQ ID NO 70
<211> LENGTH: 3
<212> TYPE: PRT
<213> ORGANISM: Porcine reproductive and respiratory syndrome virus

<400> SEQUENCE: 70

Trp Tyr Gly
1

<210> SEQ ID NO 71
<211> LENGTH: 3
<212> TYPE: PRT
<213> ORGANISM: Porcine reproductive and respiratory syndrome virus

<400> SEQUENCE: 71

Ala Gly Arg
```

```
<210> SEQ ID NO 72
<211> LENGTH: 3
<212> TYPE: PRT
<213> ORGANISM: Porcine reproductive and respiratory syndrome virus

<400> SEQUENCE: 72

Ala Ala Gly
1

<210> SEQ ID NO 73
<211> LENGTH: 4
<212> TYPE: PRT
<213> ORGANISM: Porcine reproductive and respiratory syndrome virus

<400> SEQUENCE: 73

Glu Cys Ala Met
1

<210> SEQ ID NO 74
<211> LENGTH: 5
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any amino acid

<400> SEQUENCE: 74

Ala Xaa Val Tyr Asp
1               5

<210> SEQ ID NO 75
<211> LENGTH: 4
<212> TYPE: PRT
<213> ORGANISM: Porcine reproductive and respiratory syndrome virus

<400> SEQUENCE: 75

Glu Glu Ala His
1

<210> SEQ ID NO 76
<211> LENGTH: 5
<212> TYPE: PRT
<213> ORGANISM: Porcine reproductive and respiratory syndrome virus
<220> FEATURE:
<221> NAME/KEY: MOD_RES
<222> LOCATION: (2)..(2)
<223> OTHER INFORMATION: Any amino acid

<400> SEQUENCE: 76

Ser Xaa Val Tyr Arg
1               5

<210> SEQ ID NO 77
<211> LENGTH: 2
<212> TYPE: PRT
<213> ORGANISM: Porcine reproductive and respiratory syndrome virus

<400> SEQUENCE: 77

Pro Arg
1

<210> SEQ ID NO 78
<211> LENGTH: 3
```

```
<212> TYPE: PRT
<213> ORGANISM: Porcine reproductive and respiratory syndrome virus

<400> SEQUENCE: 78

Arg Pro Arg
1

<210> SEQ ID NO 79
<211> LENGTH: 4
<212> TYPE: PRT
<213> ORGANISM: Porcine reproductive and respiratory syndrome virus

<400> SEQUENCE: 79

Gly Arg Pro Arg
1

<210> SEQ ID NO 80
<211> LENGTH: 5
<212> TYPE: PRT
<213> ORGANISM: Porcine reproductive and respiratory syndrome virus

<400> SEQUENCE: 80

Asn Gly Arg Pro Arg
1               5

<210> SEQ ID NO 81
<211> LENGTH: 6
<212> TYPE: PRT
<213> ORGANISM: Porcine reproductive and respiratory syndrome virus

<400> SEQUENCE: 81

Pro Asn Gly Arg Pro Arg
1               5

<210> SEQ ID NO 82
<211> LENGTH: 389
<212> TYPE: PRT
<213> ORGANISM: Porcine reproductive and respiratory syndrome virus

<400> SEQUENCE: 82

Met Ser Gly Thr Phe Ser Arg Cys Met Cys Thr Pro Ala Ala Arg Val
1               5                   10                  15

Phe Trp Asn Ala Gly Gln Val Tyr Cys Thr Arg Cys Leu Ser Ala Arg
                20                  25                  30

Ser Leu Leu Pro Pro Glu Leu Gln Asp Ile Asp Leu Ala Ala Ile Gly
            35                  40                  45

Leu Phe Tyr Lys Pro Lys Asp Lys Leu His Trp Lys Val Pro Ile Gly
        50                  55                  60

Ile Pro Gln Val Glu Cys Thr Pro Ser Gly Cys Cys Trp Leu Ser Gly
65                  70                  75                  80

Ile Phe Pro Leu Ala Arg Met Thr Ser Gly Asn His Asn Phe Leu Gln
                85                  90                  95

Arg Leu Val Lys Val Ala Asp Val Leu Tyr Arg Asp Gly Cys Leu Thr
                100                 105                 110

Ser Arg His Leu Arg Glu Leu Gln Val Tyr Glu Arg Gly Cys Ser Trp
            115                 120                 125

Tyr Pro Ile Thr Gly Pro Val Pro Gly Met Gly Leu Tyr Ala Asn Ser
        130                 135                 140

Met His Val Ser Asp Gln Pro Phe Pro Gly Ala Thr His Val Leu Thr
145                 150                 155                 160
```

-continued

```
Asn Ser Pro Leu Pro Gln Gln Ala Cys Arg Gln Pro Phe Cys Pro Phe
                165                 170                 175

Glu Glu Ala His Ser Ser Val Tyr Arg Trp Lys Lys Phe Val Val Phe
            180                 185                 190

Thr Asp Ser Ser Pro Asn Gly Arg Pro Arg Met Met Trp Thr Pro Glu
        195                 200                 205

Ser Asp Asp Ser Ala Asp Leu Glu Ala Leu Pro Pro Glu Leu Glu Arg
    210                 215                 220

Gln Val Glu Ile Leu Ile Arg Ser Phe Pro Ala His His Pro Val Ser
225                 230                 235                 240

Leu Ala Asp Trp Glu Leu Ala Glu Ser Pro Glu Asn Gly Phe Ser Phe
                245                 250                 255

Ser Thr Tyr His Ser Gly Gly Tyr Leu Val Gln Asn Pro Asp Val Phe
            260                 265                 270

Asp Ser Lys Cys Trp Leu Ser Cys Phe Leu Asp Gln Pro Ile Glu Val
        275                 280                 285

Arg Leu Tyr Glu Asp Tyr Leu Ala Asn Ala Phe Gly Tyr Gln Thr Lys
    290                 295                 300

Trp Gly Val Ser Gly Lys Tyr Leu Gln Arg Arg Leu Gln Val Asn Gly
305                 310                 315                 320

Ile Arg Ala Val Ile Asp Pro Asp Gly Pro Ile His Val Glu Ala Leu
                325                 330                 335

Ser Cys Pro Gln Ser Trp Ile Arg His Leu Thr Leu Asp Asp Asp Val
            340                 345                 350

Thr Pro Gly Phe Val Arg Leu Thr Ser Leu Arg Ile Val Pro Asn Thr
        355                 360                 365

Glu Pro Thr Thr Leu Arg Ile Phe Arg Phe Gly Ala His Lys Trp Tyr
    370                 375                 380

Gly Ala Ala Gly Lys
385

<210> SEQ ID NO 83
<211> LENGTH: 203
<212> TYPE: PRT
<213> ORGANISM: Porcine reproductive and respiratory syndrome virus

<400> SEQUENCE: 83

Ala Asp Val Tyr Asp Ile Gly Arg Gly Ala Val Met Tyr Val Ala Gly
1               5                   10                  15

Gly Lys Val Ser Trp Ala Pro Arg Gly Gly Asn Glu Val Lys Phe Glu
            20                  25                  30

Pro Val Pro Lys Glu Leu Lys Leu Val Ala Asn Arg Leu His Thr Ser
        35                  40                  45

Phe Pro Pro His His Val Val Asp Met Ser Lys Phe Thr Phe Ile Thr
    50                  55                  60

Pro Gly Ser Gly Val Ser Met Arg Val Glu Tyr Gln Tyr Gly Cys Leu
65                  70                  75                  80

Pro Ala Asp Thr Val Pro Glu Gly Asn Cys Trp Trp Arg Leu Leu Asp
                85                  90                  95

Ser Leu Pro Pro Glu Val Gln Tyr Lys Glu Ile Arg His Ala Asn Gln
            100                 105                 110

Phe Gly Tyr Gln Thr Lys His Gly Val Pro Gly Lys Tyr Leu Gln Arg
        115                 120                 125

Arg Leu Gln Val Asn Gly Leu Arg Ala Val Thr Asp Thr His Gly Pro
    130                 135                 140
```

```
Ile Val Ile Gln Tyr Phe Ser Val Lys Glu Ser Trp Ile Arg His Leu
145                 150                 155                 160

Lys Leu Val Glu Glu Pro Ser Leu Pro Gly Phe Glu Asp Leu Leu Arg
                165                 170                 175

Ile Arg Val Glu Pro Asn Thr Ser Pro Leu Ala Gly Lys Asp Glu Lys
            180                 185                 190

Ile Phe Arg Phe Gly Ser His Lys Trp Tyr Gly
        195                 200

<210> SEQ ID NO 84
<211> LENGTH: 203
<212> TYPE: PRT
<213> ORGANISM: Porcine reproductive and respiratory syndrome virus

<400> SEQUENCE: 84

Ala Thr Val Tyr Asp Ile Gly His Asp Ala Val Met Tyr Val Ala Glu
1               5                   10                  15

Arg Lys Val Ser Trp Ala Pro Arg Gly Gly Asp Glu Val Lys Phe Glu
                20                  25                  30

Ala Val Pro Gly Glu Leu Lys Leu Ile Ala Asn Arg Leu Arg Thr Ser
                35                  40                  45

Phe Pro Pro His His Thr Val Asp Met Ser Lys Phe Ala Phe Thr Ala
    50                  55                  60

Pro Gly Cys Gly Val Ser Met Arg Val Glu Arg Gln His Gly Cys Leu
65                  70                  75                  80

Pro Ala Asp Thr Val Pro Glu Gly Asn Cys Trp Trp Ser Leu Phe Asp
                85                  90                  95

Leu Leu Pro Leu Glu Val Gln Asn Lys Glu Ile Arg His Ala Asn Gln
                100                 105                 110

Phe Gly Tyr Gln Thr Lys His Gly Val Ser Gly Lys Tyr Leu Gln Arg
            115                 120                 125

Arg Leu Gln Val Asn Gly Leu Arg Ala Val Thr Asp Leu Asn Gly Pro
        130                 135                 140

Ile Val Val Gln Tyr Phe Ser Val Lys Glu Ser Trp Ile Arg His Leu
145                 150                 155                 160

Lys Leu Ala Gly Glu Pro Ser Tyr Ser Gly Phe Glu Asp Leu Leu Arg
                165                 170                 175

Ile Arg Val Glu Pro Asn Thr Ser Pro Leu Ala Asp Lys Glu Glu Lys
            180                 185                 190

Ile Phe Arg Phe Gly Ser His Lys Trp Tyr Gly
        195                 200
```